(12) United States Patent
Nalagatla et al.

(10) Patent No.: US 11,058,426 B2
(45) Date of Patent: Jul. 13, 2021

(54) STAPLE CARTRIDGE ASSEMBLY COMPRISING VARIOUS TISSUE COMPRESSION GAPS AND STAPLE FORMING GAPS

(71) Applicant: Ethicon Endo-Surgery, LLC, Guaynabo, PR (US)

(72) Inventors: Anil K. Nalagatla, Mason, OH (US); Brian DiNardo, Cincinnati, OH (US); Disha V. Labhasetwar, Cincinnati, OH (US); Chester O. Baxter, III, Loveland, OH (US); Jeffrey S. Swayze, West Chester, OH (US); Frederick E. Shelton, IV, Hillsboro, OH (US); Jerome R. Morgan, Cincinnati, OH (US); Jason L. Harris, Lebanon, OH (US)

(73) Assignee: Cilag GmbH International, Zug (CH)

(*) Notice: Subject to any disclaimer, the term of this patent is extended or adjusted under 35 U.S.C. 154(b) by 1191 days.

(21) Appl. No.: 14/836,163

(22) Filed: Aug. 26, 2015

(65) Prior Publication Data

US 2017/0056002 A1  Mar. 2, 2017

(51) Int. Cl.
*A61B 17/10* (2006.01)
*A61B 17/068* (2006.01)
(Continued)

(52) U.S. Cl.
CPC ........ *A61B 17/105* (2013.01); *A61B 17/0469* (2013.01); *A61B 17/064* (2013.01);
(Continued)

(58) Field of Classification Search
CPC ............ A61B 17/105; A61B 17/07207; A61B 17/068; A61B 2017/07278;
(Continued)

(56) References Cited

U.S. PATENT DOCUMENTS

| 66,052 A | 6/1867 | Smith |
| 662,587 A | 11/1900 | Blake |

(Continued)

FOREIGN PATENT DOCUMENTS

| AU | 2008207624 A1 | 3/2009 |
| AU | 2010214687 A1 | 9/2010 |

(Continued)

OTHER PUBLICATIONS

"Biomedical Coatings," Fort Wayne Metals, Research Products Corporation, obtained online at www.fwmetals.com on Jun. 21, 2010 (1 page).

(Continued)

*Primary Examiner* — Nathaniel C Chukwurah
*Assistant Examiner* — Mobeen Ahmed

(57) ABSTRACT

An end effector including an anvil and a staple cartridge assembly is disclosed. The staple cartridge assembly comprises a deck having steps defined thereon for compressing tissue positioned between the anvil and the staple cartridge assembly to different pressures. The staple cartridge assembly further comprises staples having different unformed heights removably stored therein. The staples are deformed against the anvil to different formed heights.

20 Claims, 66 Drawing Sheets

(51) Int. Cl.
*A61B 17/064* (2006.01)
*A61B 17/072* (2006.01)
*A61B 17/115* (2006.01)
*A61L 31/02* (2006.01)
*A61L 31/10* (2006.01)
*A61L 31/14* (2006.01)
*A61B 17/32* (2006.01)
*A61B 17/04* (2006.01)
*A61B 17/00* (2006.01)
*A61B 17/11* (2006.01)
*A61B 90/00* (2016.01)
*A61B 17/06* (2006.01)
*A61B 17/29* (2006.01)

(52) U.S. Cl.
CPC ........ *A61B 17/068* (2013.01); *A61B 17/0644* (2013.01); *A61B 17/072* (2013.01); *A61B 17/07207* (2013.01); *A61B 17/07292* (2013.01); *A61B 17/115* (2013.01); *A61B 17/1155* (2013.01); *A61B 17/32* (2013.01); *A61L 31/022* (2013.01); *A61L 31/10* (2013.01); *A61L 31/148* (2013.01); *A61B 17/00491* (2013.01); *A61B 17/0401* (2013.01); *A61B 2017/00004* (2013.01); *A61B 2017/00398* (2013.01); *A61B 2017/00526* (2013.01); *A61B 2017/00831* (2013.01); *A61B 2017/00889* (2013.01); *A61B 2017/00893* (2013.01); *A61B 2017/00964* (2013.01); *A61B 2017/0464* (2013.01); *A61B 2017/0472* (2013.01); *A61B 2017/06042* (2013.01); *A61B 2017/0645* (2013.01); *A61B 2017/07214* (2013.01); *A61B 2017/07221* (2013.01); *A61B 2017/07228* (2013.01); *A61B 2017/07235* (2013.01); *A61B 2017/07242* (2013.01); *A61B 2017/07264* (2013.01); *A61B 2017/07271* (2013.01); *A61B 2017/07278* (2013.01); *A61B 2017/1142* (2013.01); *A61B 2017/2929* (2013.01); *A61B 2017/320052* (2013.01); *A61B 2090/037* (2016.02); *A61B 2090/038* (2016.02); *A61B 2090/08021* (2016.02)

(58) Field of Classification Search
CPC .......... A61B 2017/07242; A61B 2017/07235; A61B 17/07292
See application file for complete search history.

(56) References Cited

U.S. PATENT DOCUMENTS

| | | |
|---|---|---|
| 670,748 A | 3/1901 | Weddeler |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,318,379 A | 5/1943 | Davis et al. |
| 2,441,096 A | 5/1948 | Happe |
| 2,475,322 A | 7/1949 | Horton et al. |
| 2,526,902 A | 10/1950 | Rublee |
| 2,578,686 A | 12/1951 | Fish |
| 2,674,149 A | 4/1954 | Benson |
| 2,711,461 A | 6/1955 | Happe |
| 2,804,848 A | 9/1957 | O'Farrell et al. |
| 2,808,482 A | 10/1957 | Zanichkowsky et al. |
| 2,853,074 A | 9/1958 | Olson |
| 2,886,358 A | 5/1959 | Munchbach |
| 2,959,974 A | 11/1960 | Emrick |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,166,072 A | 1/1965 | Sullivan, Jr. |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,275,211 A | 9/1966 | Hirsch et al. |
| 3,317,103 A | 5/1967 | Cullen et al. |
| 3,499,591 A | 3/1970 | Green |
| 3,551,987 A | 1/1971 | Wilkinson |
| 3,583,393 A | 6/1971 | Takahashi |
| 3,662,939 A | 5/1972 | Bryan |
| 3,717,294 A | 2/1973 | Green |
| 3,799,151 A | 3/1974 | Fukaumi et al. |
| 3,940,844 A | 3/1976 | Colby et al. |
| RE28,932 E | 8/1976 | Noiles et al. |
| 4,014,244 A | 3/1977 | Larson |
| 4,060,089 A | 11/1977 | Noiles |
| 4,106,446 A | 8/1978 | Yamada et al. |
| 4,108,211 A | 8/1978 | Tanaka |
| 4,111,206 A | 9/1978 | Vishnevsky et al. |
| 4,129,059 A | 12/1978 | Van Eck |
| 4,169,990 A | 10/1979 | Lerdman |
| 4,180,285 A | 12/1979 | Reneau |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,275,813 A | 6/1981 | Noiles |
| 4,289,133 A | 9/1981 | Rothfuss |
| 4,296,654 A | 10/1981 | Mercer |
| 4,304,236 A | 12/1981 | Conta et al. |
| 4,305,539 A | 12/1981 | Korolkov et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,454,887 A | 6/1984 | Kruger |
| 4,467,805 A | 8/1984 | Fukuda |

(56) References Cited

U.S. PATENT DOCUMENTS

| | | |
|---|---|---|
| 4,473,077 A | 9/1984 | Noiles et al. |
| 4,475,679 A | 10/1984 | Fleury, Jr. |
| 4,485,816 A | 12/1984 | Krumme |
| 4,486,928 A | 12/1984 | Tucker et al. |
| 4,488,523 A | 12/1984 | Shichman |
| 4,489,875 A | 12/1984 | Crawford et al. |
| 4,499,895 A | 2/1985 | Takayama |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,589,416 A | 5/1986 | Green |
| 4,591,085 A | 5/1986 | Di Giovanni |
| 4,597,753 A | 7/1986 | Turley |
| 4,600,037 A | 7/1986 | Flatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,441 S | 10/1986 | Korthoff et al. |
| D286,442 S | 10/1986 | Korthoff et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,652,820 A | 3/1987 | Maresca |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,787,387 A | 11/1988 | Burbank, III et al. |
| 4,790,225 A | 12/1988 | Moody et al. |
| 4,802,478 A | 2/1989 | Powell |
| 4,805,617 A | 2/1989 | Bedi et al. |
| 4,805,823 A | 2/1989 | Rothfuss |
| 4,809,695 A | 3/1989 | Gwathmey et al. |
| 4,815,460 A | 3/1989 | Porat et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |
| 4,873,977 A | 10/1989 | Avant et al. |
| 4,874,122 A | 10/1989 | Froelich et al. |
| 4,880,015 A | 11/1989 | Nierman |
| 4,887,601 A | 12/1989 | Richards |
| 4,887,756 A | 12/1989 | Puchy |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A * | 7/1990 | Pruitt .................. A61B 17/072 227/175.1 |
| 4,944,443 A | 7/1990 | Oddsen et al. |
| 4,951,860 A | 8/1990 | Peters et al. |
| 4,955,898 A | 9/1990 | Matsutani et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,671 A | 6/1991 | Tu et al. |
| 5,027,834 A * | 7/1991 | Pruitt .................. A61B 17/072 128/898 |
| 5,031,814 A | 7/1991 | Tompkins et al. |
| 5,035,040 A | 7/1991 | Kerrigan et al. |
| 5,038,109 A | 8/1991 | Goble et al. |
| 5,040,715 A | 8/1991 | Green et al. |
| 5,042,707 A | 8/1991 | Taheri |

(56) References Cited

U.S. PATENT DOCUMENTS

| | | |
|---|---|---|
| 5,053,047 A | 10/1991 | Yoon |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,009 A | 2/1992 | Green |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,108,368 A | 4/1992 | Hammerslag et al. |
| 5,111,987 A | 5/1992 | Moeinzadeh et al. |
| 5,116,349 A | 5/1992 | Aranyi |
| D327,323 S | 6/1992 | Hunt |
| 5,122,156 A * | 6/1992 | Granger ............... A61B 17/115 227/179.1 |
| 5,125,876 A | 6/1992 | Hirota |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,200,280 A | 4/1993 | Karasa |
| 5,201,746 A | 4/1993 | Shichman |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,303,539 A | 4/1994 | Neamtu |
| 5,304,204 A | 4/1994 | Bregen |
| D347,474 S | 5/1994 | Olson |
| 5,307,976 A | 5/1994 | Olson et al. |
| 5,308,576 A | 5/1994 | Green et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller et al. |
| 5,314,466 A | 5/1994 | Stern et al. |
| 5,318,221 A | 6/1994 | Green et al. |
| D348,930 S | 7/1994 | Olson |
| 5,329,923 A | 7/1994 | Lundquist |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,229 A | 8/1994 | Noda |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,305 A | 11/1994 | Kerrigan |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |

(56) References Cited

U.S. PATENT DOCUMENTS

| | | |
|---|---|---|
| 5,368,592 A | 11/1994 | Stern et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,978 A | 2/1995 | Velez et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,403,043 A | 4/1995 | Smet |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,409,498 A | 4/1995 | Braddock et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |

(56) References Cited

U.S. PATENT DOCUMENTS

| | | |
|---|---|---|
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,541 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| D381,077 S | 7/1997 | Hunt |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,238 A | 8/1997 | Suzuki et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,665,100 A | 9/1997 | Yoon |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |

(56) References Cited

U.S. PATENT DOCUMENTS

| | | |
|---|---|---|
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,706 A | 2/1998 | Roger |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,958 A | 8/1998 | Yoon |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,893,863 A | 4/1999 | Yoon |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,647 A | 5/1999 | Ouchi |
| 5,904,693 A | 5/1999 | Dicesare et al. |
| 5,904,702 A | 5/1999 | Ek et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |

(56) References Cited

U.S. PATENT DOCUMENTS

| | | |
|---|---|---|
| 5,916,225 A | 6/1999 | Kugel |
| 5,918,791 A | 7/1999 | Sorrentino et al. |
| 5,919,198 A | 7/1999 | Graves, Jr. et al. |
| 5,919,202 A | 7/1999 | Yoon |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,947,984 A | 9/1999 | Whipple |
| 5,947,996 A | 9/1999 | Logeman |
| 5,948,030 A | 9/1999 | Miller et al. |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| D416,089 S | 11/1999 | Barton et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,010,054 A | 1/2000 | Johnson et al. |
| 6,010,513 A | 1/2000 | Tormala et al. |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,050,172 A | 4/2000 | Corves et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,097 A | 5/2000 | Oi et al. |
| 6,063,098 A | 5/2000 | Houser et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,286 A | 6/2000 | Cuschieri et al. |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,153,292 A | 11/2000 | Bell et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,179,194 B1 | 1/2001 | Morton |
| 6,179,195 B1 | 1/2001 | Adams et al. |
| 6,179,776 B1 | 1/2001 | Adams et al. |
| 6,179,849 B1 | 1/2001 | Yencho et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,206,904 B1 | 3/2001 | Ouchi |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,117 B1 | 6/2001 | Blatter |
| 6,249,076 B1 | 6/2001 | Madden et al. |
| 6,250,532 B1 | 6/2001 | Green et al. |

(56) References Cited

U.S. PATENT DOCUMENTS

| | | |
|---|---|---|
| 6,258,107 B1 | 7/2001 | Balazs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |
| 6,322,284 B1 | 11/2001 | Bonardo et al. |
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,383,958 B1 | 5/2002 | Swanson et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,429,611 B1 | 8/2002 | Li |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,447,518 B1 | 9/2002 | Krause et al. |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,478,210 B2 | 11/2002 | Adams et al. |
| 6,482,200 B2 | 11/2002 | Shippert |
| 6,485,490 B2 | 11/2002 | Wampler et al. |
| 6,485,503 B2 | 11/2002 | Jacobs et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,512,360 B1 | 1/2003 | Goto et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,782 B2 | 3/2003 | Hogg et al. |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,588,643 B2 | 7/2003 | Bolduc et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |

(56) References Cited

U.S. PATENT DOCUMENTS

| | | |
|---|---|---|
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,109 B2 | 4/2004 | Solingen |
| 6,726,697 B2 | 4/2004 | Nicholas et al. |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,762,339 B1 | 7/2004 | Klun et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,072 B1 | 8/2004 | Truckai et al. |
| 6,773,409 B2 | 8/2004 | Truckai et al. |
| 6,773,437 B2 | 8/2004 | Ogilvie et al. |
| 6,773,438 B1 | 8/2004 | Knodel et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,850,817 B1 | 2/2005 | Green |
| 6,858,005 B2 | 2/2005 | Ohline et al. |
| RE38,708 E | 3/2005 | Bolanos et al. |
| D502,994 S | 3/2005 | Blake, III |
| 6,861,142 B1 | 3/2005 | Wilkie et al. |
| 6,863,668 B2 | 3/2005 | Gillespie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,899,538 B2 | 5/2005 | Matoba |
| 6,905,057 B2 | 6/2005 | Swayze et al. |
| 6,905,497 B2 | 6/2005 | Truckai et al. |
| 6,908,472 B2 | 6/2005 | Wiener et al. |
| 6,911,033 B2 | 6/2005 | de Guillebon et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| D509,297 S | 9/2005 | Wells |
| D509,589 S | 9/2005 | Wells |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |

(56) References Cited

U.S. PATENT DOCUMENTS

| | | |
|---|---|---|
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,981,983 B1 | 1/2006 | Rosenblatt et al. |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,731 B2 | 1/2006 | Haytayan |
| 6,990,796 B2 | 1/2006 | Schnipke et al. |
| 6,994,708 B2 | 2/2006 | Manzo |
| 6,995,729 B2 | 2/2006 | Govari et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,023,159 B2 | 4/2006 | Gorti et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,119,534 B2 | 10/2006 | Butzmann |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,824 B2 | 1/2007 | Rosenman |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,172,593 B2 | 2/2007 | Trieu et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |

(56) References Cited

U.S. PATENT DOCUMENTS

| | | |
|---|---|---|
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,213,736 B2 | 5/2007 | Wales et al. |
| 7,214,224 B2 | 5/2007 | Goble |
| 7,214,232 B2 | 5/2007 | Bowman et al. |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,267,682 B1 | 9/2007 | Bender et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,367,973 B2 | 5/2008 | Manzo et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,417 B2 | 6/2008 | Cucin |
| 7,386,730 B2 | 6/2008 | Uchikubo |
| 7,388,217 B2 | 6/2008 | Buschbeck et al. |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,400,752 B2 | 7/2008 | Zacharias |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |

(56) References Cited

U.S. PATENT DOCUMENTS

| | | | |
|---|---|---|---|
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,566 B2 | 3/2009 | Jacobs et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,543,730 B1 | 6/2009 | Marczyk |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| D605,762 S | 12/2009 | Nalagatla et al. |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,457 B2 | 1/2010 | Stefanchik et al. |
| 7,648,519 B2 | 1/2010 | Lee et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,288 B2 | 2/2010 | Bauman et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,686,201 B2 | 3/2010 | Csiky |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,106 B2 | 4/2010 | Schenberger et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,624 B2 | 6/2010 | Bettuchi |
| 7,744,627 B2 | 6/2010 | Orban, III et al. |

(56) References Cited

U.S. PATENT DOCUMENTS

| | | |
|---|---|---|
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,776,037 B2 | 8/2010 | Odom |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,884 B2 | 10/2010 | Lee et al. |
| 7,819,886 B2 | 10/2010 | Whitfield et al. |
| 7,819,896 B2 | 10/2010 | Racenet |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,838,789 B2 | 11/2010 | Stoffers et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,850,623 B2 | 12/2010 | Griffin et al. |
| 7,850,642 B2 | 12/2010 | Moll et al. |
| 7,850,982 B2 | 12/2010 | Stopek et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,563 B2 | 2/2011 | Cummins |
| 7,891,531 B1 | 2/2011 | Ward |
| 7,891,532 B2 | 2/2011 | Mastri et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,896,895 B2 | 3/2011 | Boudreaux et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,893 B2 | 3/2011 | Kuhns et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,867 B2 | 4/2011 | Dana et al. |
| 7,918,873 B2 | 4/2011 | Cummins |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,931,660 B2 | 4/2011 | Aranyi et al. |
| 7,931,695 B2 | 4/2011 | Ringeisen |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,301 B2 | 5/2011 | Sater |
| 7,942,303 B2 | 5/2011 | Shah |
| 7,942,890 B2 | 5/2011 | D'Agostino et al. |
| 7,944,175 B2 | 5/2011 | Mori et al. |
| 7,946,453 B2 | 5/2011 | Voegele et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |

(56) References Cited

U.S. PATENT DOCUMENTS

| | | |
|---|---|---|
| 7,954,688 B2 | 6/2011 | Argentine et al. |
| 7,955,257 B2 | 6/2011 | Frasier et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,963 B2 | 6/2011 | Francischelli et al. |
| 7,963,964 B2 | 6/2011 | Santilli et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,839 B2 | 6/2011 | Flock et al. |
| 7,972,298 B2 | 7/2011 | Wallace et al. |
| 7,976,563 B2 | 7/2011 | Summerer |
| 7,980,443 B2 | 7/2011 | Scheib et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,511 B2 | 8/2011 | Brock et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,021,377 B2 | 9/2011 | Eskuri |
| 8,025,199 B2 | 9/2011 | Whitman et al. |
| 8,028,883 B2 | 10/2011 | Stopek |
| 8,028,884 B2 | 10/2011 | Snithn et al. |
| 8,028,885 B2 | 10/2011 | Smith et al. |
| 8,033,438 B2 | 10/2011 | Scirica |
| 8,033,442 B2 | 10/2011 | Racenet et al. |
| 8,034,077 B2 | 10/2011 | Smith et al. |
| 8,034,363 B2 | 10/2011 | Li et al. |
| 8,035,487 B2 | 10/2011 | Malackowski |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,047,236 B2 | 11/2011 | Perry |
| 8,048,503 B2 | 11/2011 | Farnsworth et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,061,576 B2 | 11/2011 | Cappola |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,070,033 B2 | 12/2011 | Milliman et al. |
| 8,070,035 B2 | 12/2011 | Holsten et al. |
| 8,070,036 B1 * | 12/2011 | Knodel .............. A61B 17/0644 227/178.1 |
| 8,070,743 B2 | 12/2011 | Kagan et al. |
| 8,075,571 B2 | 12/2011 | Vitali et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,085,013 B2 | 12/2011 | Wei et al. |
| 8,087,563 B2 | 1/2012 | Milliman et al. |
| 8,091,756 B2 | 1/2012 | Viola |
| 8,092,443 B2 | 1/2012 | Bischoff |
| 8,092,932 B2 | 1/2012 | Phillips et al. |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,872 B2 | 1/2012 | Patel |
| 8,102,278 B2 | 1/2012 | Deck et al. |
| 8,105,350 B2 | 1/2012 | Lee et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,766 B2 | 2/2012 | Bauman et al. |
| 8,123,767 B2 | 2/2012 | Bauman et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,136,713 B2 | 3/2012 | Hathaway et al. |
| 8,140,417 B2 | 3/2012 | Shibata |
| 8,141,762 B2 | 3/2012 | Bedi et al. |
| 8,141,763 B2 | 3/2012 | Milliman |
| 8,146,790 B2 | 4/2012 | Milliman |
| 8,147,485 B2 | 4/2012 | Wham et al. |
| 8,152,041 B2 | 4/2012 | Kostrzewski |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,180,458 B2 | 5/2012 | Kane et al. |
| 8,181,840 B2 | 5/2012 | Milliman |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,202,549 B2 | 6/2012 | Stucky et al. |

(56) References Cited

U.S. PATENT DOCUMENTS

| | | |
|---|---|---|
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,206,291 B2 | 6/2012 | Fischvogt et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,123 B2 | 7/2012 | Gross et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,225,980 B1 | 7/2012 | Rivera |
| 8,226,715 B2 | 7/2012 | Hwang et al. |
| 8,227,946 B2 | 7/2012 | Kim |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,257,634 B2 | 9/2012 | Scirica |
| 8,261,958 B1 | 9/2012 | Knodel |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,281,974 B2 | 10/2012 | Hessler et al. |
| 8,285,367 B2 | 10/2012 | Hyde et al. |
| 8,286,845 B2 | 10/2012 | Perry et al. |
| 8,286,846 B2 | 10/2012 | Smith et al. |
| 8,287,561 B2 | 10/2012 | Nunez et al. |
| 8,292,147 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,323,314 B2 | 12/2012 | Blier |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,348,123 B2 | 1/2013 | Scirica et al. |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,787 B2 | 2/2013 | Brown et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,382,761 B2 | 2/2013 | Holsten et al. |
| 8,387,848 B2 | 3/2013 | Johnson et al. |
| 8,388,633 B2 | 3/2013 | Rousseau et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,973 B1 | 3/2013 | Hausen |
| 8,398,633 B2 | 3/2013 | Mueller |
| 8,398,673 B2 | 3/2013 | Hinchliffe et al. |
| 8,403,138 B2 | 3/2013 | Weisshaupt et al. |
| 8,403,197 B2 | 3/2013 | Vidal et al. |
| 8,403,198 B2 | 3/2013 | Sorrentino et al. |
| 8,403,945 B2 | 3/2013 | Whitfield et al. |
| 8,403,950 B2 | 3/2013 | Palmer et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,222 B2 | 4/2013 | Whitfield et al. |
| 8,409,223 B2 | 4/2013 | Sorrentino et al. |
| 8,413,870 B2 | 4/2013 | Pastorelli et al. |
| 8,413,871 B2 | 4/2013 | Racenet et al. |

(56) References Cited

U.S. PATENT DOCUMENTS

| | | |
|---|---|---|
| 8,413,872 B2 | 4/2013 | Patel |
| 8,414,577 B2 | 4/2013 | Boudreaux et al. |
| 8,418,908 B1 | 4/2013 | Beardsley |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,430,292 B2 | 4/2013 | Patel et al. |
| 8,430,892 B2 | 4/2013 | Bindra et al. |
| 8,430,898 B2 | 4/2013 | Wiener et al. |
| 8,439,246 B1 | 5/2013 | Knodel |
| 8,444,036 B2 | 5/2013 | Shelton, IV |
| 8,444,100 B2 | 5/2013 | Takahashi et al. |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,502 B2 | 6/2013 | Zergiebel |
| 8,469,973 B2 | 6/2013 | Meade et al. |
| 8,470,355 B2 | 6/2013 | Skalla et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,475,491 B2 | 7/2013 | Milo |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,762 B2 | 8/2013 | Sholev et al. |
| 8,505,227 B2 | 8/2013 | Barrett et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,042 B2 | 9/2013 | Masiakos et al. |
| 8,523,043 B2 | 9/2013 | Ullrich et al. |
| 8,523,881 B2 | 9/2013 | Cabin et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,556,151 B2 | 10/2013 | Viola |
| 8,556,918 B2 | 10/2013 | Bauman et al. |
| 8,556,935 B1 | 10/2013 | Knodel et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,568,425 B2 | 10/2013 | Ross et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,263 B2 | 11/2013 | Mueller |
| 8,579,176 B2 | 11/2013 | Smith et al. |
| 8,579,178 B2 | 11/2013 | Holsten et al. |
| 8,579,937 B2 | 11/2013 | Gresham |
| 8,579,938 B2 | 11/2013 | Heinrich et al. |
| 8,584,919 B2 | 11/2013 | Hueil et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,613,384 B2 | 12/2013 | Pastorelli et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,544 B2 | 1/2014 | Farascioni |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,647,350 B2 | 2/2014 | Mohan et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,814 B2 | 2/2014 | Werneth et al. |
| 8,662,370 B2 | 3/2014 | Takei |
| 8,663,192 B2 | 3/2014 | Hester et al. |
| 8,663,224 B2 | 3/2014 | Overes et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |

(56) References Cited

U.S. PATENT DOCUMENTS

| | | |
|---|---|---|
| 8,672,951 B2 | 3/2014 | Smith et al. |
| 8,678,263 B2 | 3/2014 | Viola |
| 8,679,093 B2 | 3/2014 | Farra |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,250 B2 | 4/2014 | Bettuchi et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,701,960 B1 | 4/2014 | Manoux et al. |
| 8,708,210 B2 | 4/2014 | Zemlok et al. |
| 8,708,211 B2 | 4/2014 | Zemlok et al. |
| 8,708,213 B2 | 4/2014 | Shelton, IV et al. |
| 8,714,429 B2 | 5/2014 | Demmy |
| 8,715,226 B2 | 5/2014 | Webster et al. |
| 8,720,766 B2 | 5/2014 | Hess et al. |
| 8,721,630 B2 | 5/2014 | Ortiz et al. |
| 8,721,646 B2 | 5/2014 | Fox |
| 8,721,666 B2 | 5/2014 | Schroeder et al. |
| 8,727,197 B2 | 5/2014 | Hess et al. |
| 8,728,119 B2 | 5/2014 | Cummins |
| 8,728,120 B2 | 5/2014 | Blier |
| 8,733,612 B2 | 5/2014 | Ma |
| 8,733,613 B2 | 5/2014 | Huitema et al. |
| 8,733,614 B2 | 5/2014 | Ross et al. |
| 8,734,478 B2 | 5/2014 | Widenhouse et al. |
| D706,927 S | 6/2014 | Cheney et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,287 B2 | 6/2014 | Mak et al. |
| 8,757,465 B2 | 6/2014 | Woodard, Jr. et al. |
| 8,757,467 B2 | 6/2014 | Racenet et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,312 B1 | 7/2014 | Knodel et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,795,308 B2 | 8/2014 | Valin |
| 8,800,837 B2 | 8/2014 | Zemlok |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,801,732 B2 | 8/2014 | Harris et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,808,294 B2 | 8/2014 | Fox et al. |
| 8,808,311 B2 | 8/2014 | Heinrich et al. |
| 8,808,325 B2 | 8/2014 | Hess et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,632 B2 | 9/2014 | Swensgard |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,844,789 B2 | 9/2014 | Shelton, IV et al. |
| 8,851,354 B2 | 10/2014 | Swensgard et al. |
| 8,852,185 B2 | 10/2014 | Twomey |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,049 B2 | 10/2014 | Amid et al. |
| 8,870,050 B2 | 10/2014 | Hodgkinson |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,888,792 B2 | 11/2014 | Harris et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,905,287 B2 | 12/2014 | Racenet et al. |
| 8,905,977 B2 | 12/2014 | Shelton et al. |
| 8,911,426 B2 | 12/2014 | Coppeta et al. |
| 8,911,471 B2 | 12/2014 | Spivey et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,939,974 B2 | 1/2015 | Boudreaux et al. |
| 8,945,163 B2 | 2/2015 | Voegele et al. |
| 8,955,732 B2 | 2/2015 | Zemlok et al. |
| 8,956,390 B2 | 2/2015 | Shah et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,967,443 B2 | 3/2015 | McCuen |
| 8,967,446 B2 | 3/2015 | Beardsley et al. |

(56) References Cited

U.S. PATENT DOCUMENTS

| | | |
|---|---|---|
| 8,967,448 B2 | 3/2015 | Carter et al. |
| 8,968,276 B2 | 3/2015 | Zemlok et al. |
| 8,968,337 B2 | 3/2015 | Whitfield et al. |
| 8,968,355 B2 | 3/2015 | Malkowski et al. |
| 8,968,358 B2 | 3/2015 | Reschke |
| 8,973,803 B2 | 3/2015 | Hall et al. |
| 8,973,804 B2 | 3/2015 | Hess et al. |
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,890 B2 | 3/2015 | Boudreaux |
| 8,982,195 B2 | 3/2015 | Claus et al. |
| 8,985,428 B2 | 3/2015 | Natarajan et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,422 B2 | 3/2015 | Spivey et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,061 B2 | 4/2015 | Williams et al. |
| 8,998,935 B2 | 4/2015 | Hart |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,608 B2 | 4/2015 | Casasanta, Jr. et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,017,331 B2 | 4/2015 | Fox |
| 9,023,014 B2 | 5/2015 | Chowaniec et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,038,881 B1 | 5/2015 | Schaller et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,120 B2 | 6/2015 | Swarup et al. |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,060,769 B2 | 6/2015 | Coleman et al. |
| 9,060,770 B2 | 6/2015 | Shelton, IV et al. |
| 9,060,894 B2 | 6/2015 | Wubbeling |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,095,339 B2 | 8/2015 | Moore et al. |
| 9,095,362 B2 | 8/2015 | Dachs, II et al. |
| 9,096,033 B2 | 8/2015 | Holop et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,870 B2 | 8/2015 | Viola |
| 9,113,874 B2 | 8/2015 | Shelton, IV et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,125,649 B2 | 9/2015 | Bruewer et al. |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,138,225 B2 | 9/2015 | Huang et al. |
| 9,138,226 B2 | 9/2015 | Racenet et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,155,536 B1 | 10/2015 | Hausen et al. |
| 9,168,038 B2 | 10/2015 | Shelton, IV et al. |
| 9,168,039 B1 | 10/2015 | Knodel |
| 9,179,911 B2 | 11/2015 | Morgan et al. |
| 9,179,912 B2 | 11/2015 | Yates et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,143 B2 | 11/2015 | Timm et al. |
| 9,192,377 B1 | 11/2015 | Schaller |
| 9,192,380 B2 | 11/2015 | (Tarinelli) Racenet et al. |
| 9,192,384 B2 | 11/2015 | Bettuchi |
| 9,198,661 B2 | 12/2015 | Swensgard |
| 9,198,662 B2 | 12/2015 | Barton et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,923 B2 | 12/2015 | Manzo et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,019 B2 | 12/2015 | Schmid et al. |
| 9,216,020 B2 | 12/2015 | Zhang et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,559 B2 | 12/2015 | Worrell et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,237,891 B2 | 1/2016 | Shelton, IV |
| 9,237,892 B2 | 1/2016 | Hodgkinson |
| 9,241,714 B2 | 1/2016 | Timm et al. |
| 9,241,758 B2 | 1/2016 | Franer et al. |
| 9,254,131 B2 | 2/2016 | Soltz et al. |
| 9,265,500 B2 | 2/2016 | Sorrentino et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,463 B2 | 3/2016 | Viola et al. |
| 9,295,464 B2 | 3/2016 | Shelton, IV et al. |
| 9,295,466 B2 | 3/2016 | Hodgkinson et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |

(56) References Cited

U.S. PATENT DOCUMENTS

| | | |
|---|---|---|
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,314,246 B2 | 4/2016 | Shelton, IV et al. |
| 9,314,247 B2 | 4/2016 | Shelton, IV et al. |
| 9,314,594 B2 | 4/2016 | Kirschenman |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,082 B2 | 5/2016 | Wei et al. |
| 9,345,477 B2 | 5/2016 | Anim et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,351,731 B2 | 5/2016 | Carter et al. |
| 9,358,003 B2 | 6/2016 | Hall et al. |
| 9,358,005 B2 | 6/2016 | Shelton, IV et al. |
| 9,358,015 B2 | 6/2016 | Sorrentino et al. |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,229 B2 | 6/2016 | D'Agostino et al. |
| 9,364,230 B2 | 6/2016 | Shelton, IV et al. |
| 9,364,233 B2 | 6/2016 | Alexander, III et al. |
| 9,370,341 B2 | 6/2016 | Ceniccola et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,393,015 B2 | 7/2016 | Laurent et al. |
| 9,393,018 B2 | 7/2016 | Wang et al. |
| 9,398,911 B2 | 7/2016 | Auld |
| 9,402,604 B2 | 8/2016 | Williams et al. |
| 9,402,626 B2 | 8/2016 | Ortiz et al. |
| 9,402,628 B2 | 8/2016 | Beardsley |
| 9,408,604 B2 | 8/2016 | Shelton, IV et al. |
| 9,408,606 B2 | 8/2016 | Shelton, IV |
| 9,408,622 B2 | 8/2016 | Stulen et al. |
| 9,414,838 B2 | 8/2016 | Shelton, IV et al. |
| 9,414,848 B2 | 8/2016 | Edwards et al. |
| 9,414,880 B2 | 8/2016 | Monson et al. |
| 9,421,013 B2 | 8/2016 | Patel et al. |
| 9,421,014 B2 | 8/2016 | Ingmanson et al. |
| 9,427,223 B2 | 8/2016 | Park et al. |
| 9,427,232 B2 | 8/2016 | Gupta et al. |
| 9,433,411 B2 | 9/2016 | Racenet et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,651 B2 | 9/2016 | Smith et al. |
| 9,445,808 B2 | 9/2016 | Woodard, Jr. et al. |
| 9,445,813 B2 | 9/2016 | Shelton, IV et al. |
| 9,451,956 B2 | 9/2016 | Balbierz et al. |
| 9,451,958 B2 | 9/2016 | Shelton, IV et al. |
| 9,463,260 B2 | 10/2016 | Stopek |
| 9,468,438 B2 | 10/2016 | Baber et al. |
| 9,480,476 B2 | 11/2016 | Aldridge et al. |
| 9,480,492 B2 | 11/2016 | Aranyi et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,189 B2 | 11/2016 | Williams et al. |
| 9,498,211 B2 | 11/2016 | Cohn et al. |
| 9,498,215 B2 | 11/2016 | Duque et al. |
| 9,498,219 B2 | 11/2016 | Moore et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,522,029 B2 | 12/2016 | Yates et al. |
| 9,526,564 B2 | 12/2016 | Rusin |
| 9,539,020 B2 | 1/2017 | Conlon et al. |
| 9,545,258 B2 | 1/2017 | Smith et al. |
| 9,549,732 B2 | 1/2017 | Yates et al. |
| 9,549,735 B2 | 1/2017 | Shelton, IV et al. |
| 9,554,794 B2 | 1/2017 | Baber et al. |
| 9,554,796 B2 | 1/2017 | Kostrzewski |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,572,574 B2 | 2/2017 | Shelton, IV et al. |
| 9,572,577 B2 | 2/2017 | Lloyd et al. |
| 9,574,644 B2 | 2/2017 | Parihar |
| 9,585,657 B2 | 3/2017 | Shelton, IV et al. |
| 9,585,658 B2 | 3/2017 | Shelton, IV |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,074 B2 | 3/2017 | Felder et al. |
| 9,597,075 B2 | 3/2017 | Shelton, IV et al. |
| 9,597,080 B2 | 3/2017 | Milliman et al. |
| 9,597,104 B2 | 3/2017 | Nicholas et al. |
| 9,603,595 B2 | 3/2017 | Shelton, IV et al. |
| 9,603,598 B2 | 3/2017 | Shelton, IV et al. |
| 9,603,991 B2 | 3/2017 | Shelton, IV et al. |
| 9,610,080 B2 | 4/2017 | Whitfield et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,629 B2 | 4/2017 | Leimbach et al. |
| 9,629,814 B2 | 4/2017 | Widenhouse et al. |
| 9,636,113 B2 | 5/2017 | Wenchell |
| 9,642,620 B2 | 5/2017 | Baxter, III et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,624 B2 | 5/2017 | Shelton, IV et al. |
| 9,656,024 B2 | 5/2017 | Eggert et al. |
| 9,658,011 B2 | 5/2017 | Gomez |
| 9,662,110 B2 | 5/2017 | Huang et al. |
| 9,662,131 B2 | 5/2017 | Omori et al. |
| 9,668,729 B2 | 6/2017 | Williams et al. |
| 9,668,732 B2 | 6/2017 | Patel et al. |
| 9,675,344 B2 | 6/2017 | Combrowski et al. |
| 9,675,351 B2 | 6/2017 | Hodgkinson et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,681,870 B2 | 6/2017 | Baxter, III et al. |
| 9,681,873 B2 | 6/2017 | Smith et al. |
| 9,687,230 B2 | 6/2017 | Leimbach et al. |
| 9,687,231 B2 | 6/2017 | Baxter, III et al. |

(56) References Cited

U.S. PATENT DOCUMENTS

| | | |
|---|---|---|
| 9,687,232 B2 | 6/2017 | Shelton, IV et al. |
| 9,687,236 B2 | 6/2017 | Leimbach et al. |
| 9,687,237 B2 | 6/2017 | Schmid et al. |
| 9,690,362 B2 | 6/2017 | Leimbach et al. |
| 9,693,772 B2 | 7/2017 | Ingmanson et al. |
| 9,693,777 B2 | 7/2017 | Schellin et al. |
| 9,693,819 B2 | 7/2017 | Francischelli et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,317 B2 | 7/2017 | Aronhalt et al. |
| 9,700,319 B2 | 7/2017 | Motooka et al. |
| 9,700,321 B2 | 7/2017 | Shelton, IV et al. |
| 9,706,991 B2 | 7/2017 | Hess et al. |
| 9,706,993 B2 | 7/2017 | Hessler et al. |
| 9,707,043 B2 | 7/2017 | Bozung |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,096 B2 | 8/2017 | Thompson et al. |
| 9,724,098 B2 | 8/2017 | Baxter, III et al. |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,733,663 B2 | 8/2017 | Leimbach et al. |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,928 B2 | 8/2017 | Shelton, IV et al. |
| 9,743,929 B2 | 8/2017 | Leimbach et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,130 B2 | 9/2017 | Shelton, IV |
| 9,763,662 B2 | 9/2017 | Shelton, IV et al. |
| 9,770,245 B2 | 9/2017 | Swayze et al. |
| 9,770,317 B2 | 9/2017 | Nering |
| 9,775,608 B2 | 10/2017 | Aronhalt et al. |
| 9,775,609 B2 | 10/2017 | Shelton, IV et al. |
| 9,775,613 B2 | 10/2017 | Shelton, IV et al. |
| 9,775,614 B2 | 10/2017 | Shelton, IV et al. |
| 9,782,169 B2 | 10/2017 | Kimsey et al. |
| 9,788,834 B2 | 10/2017 | Schmid et al. |
| 9,788,836 B2 | 10/2017 | Overmyer et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,384 B2 | 10/2017 | Weaner et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,820,738 B2 | 11/2017 | Lytle, IV et al. |
| 9,820,741 B2 | 11/2017 | Kostrzewski |
| 9,820,770 B2 | 11/2017 | Palermo |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,833,236 B2 | 12/2017 | Shelton, IV et al. |
| 9,833,238 B2 | 12/2017 | Baxter, III et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schell In et al. |
| 9,839,423 B2 | 12/2017 | Vendely et al. |
| 9,839,425 B2 | 12/2017 | Zergiebel et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,848,898 B2 | 12/2017 | Friedman et al. |
| 9,855,040 B2 | 1/2018 | Kostrzewski |
| 9,855,041 B2 | 1/2018 | Nering et al. |
| 9,861,359 B2 | 1/2018 | Shelton, IV et al. |
| 9,861,361 B2 | 1/2018 | Aronhalt et al. |
| 9,867,612 B2 | 1/2018 | Parihar et al. |
| 9,867,613 B2 | 1/2018 | Marczyk et al. |
| 9,867,616 B2 | 1/2018 | Marczyk |
| 9,867,618 B2 | 1/2018 | Hall et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,877,721 B2 | 1/2018 | Schellin et al. |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,342 B2 | 2/2018 | Shelton, IV et al. |
| 9,901,343 B2 | 2/2018 | Vold et al. |
| 9,907,620 B2 | 3/2018 | Shelton, IV et al. |
| 9,913,642 B2 | 3/2018 | Leimbach et al. |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,918,704 B2 | 3/2018 | Shelton, IV et al. |
| 9,918,716 B2 | 3/2018 | Baxter, III et al. |
| 9,918,717 B2 | 3/2018 | Czernik |
| 9,918,778 B2 | 3/2018 | Walberg et al. |
| 9,924,942 B2 | 3/2018 | Swayze et al. |
| 9,924,944 B2 | 3/2018 | Shelton, IV et al. |
| 9,924,947 B2 | 3/2018 | Shelton, IV et al. |
| 9,924,961 B2 | 3/2018 | Shelton, IV et al. |
| 9,931,118 B2 | 4/2018 | Shelton, IV et al. |
| 9,943,309 B2 | 4/2018 | Shelton, IV et al. |
| 9,943,310 B2 | 4/2018 | Harris et al. |
| 9,962,158 B2 | 5/2018 | Hall et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,980,630 B2 | 5/2018 | Larkin et al. |
| 9,980,713 B2 | 5/2018 | Aronhalt et al. |
| 9,980,729 B2 | 5/2018 | Moore et al. |
| 9,987,000 B2 | 6/2018 | Shelton, IV et al. |
| 9,987,006 B2 | 6/2018 | Morgan et al. |
| 9,987,011 B2 | 6/2018 | Williams et al. |
| 9,987,012 B2 | 6/2018 | Shah |
| 9,987,095 B2 | 6/2018 | Chowaniec et al. |
| 9,987,099 B2 | 6/2018 | Chen et al. |

(56) References Cited

U.S. PATENT DOCUMENTS

| | | |
|---|---|---|
| 9,993,248 B2 | 6/2018 | Shelton, IV et al. |
| 9,993,258 B2 | 6/2018 | Shelton, IV et al. |
| 9,999,408 B2 | 6/2018 | Boudreaux et al. |
| 9,999,426 B2 | 6/2018 | Moore et al. |
| 9,999,431 B2 | 6/2018 | Shelton, IV et al. |
| 10,004,497 B2 | 6/2018 | Overmyer et al. |
| 10,004,498 B2 | 6/2018 | Morgan et al. |
| 10,004,501 B2 | 6/2018 | Shelton, IV et al. |
| 10,004,505 B2 | 6/2018 | Moore et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| D826,405 S | 8/2018 | Shelton, IV et al. |
| 10,039,529 B2 | 8/2018 | Kerr et al. |
| 10,045,769 B2 | 8/2018 | Aronhalt et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,058,317 B2 | 8/2018 | Fan et al. |
| 10,058,327 B2 | 8/2018 | Weisenburgh, II et al. |
| 10,058,963 B2 | 8/2018 | Shelton, IV et al. |
| 10,064,618 B2 | 9/2018 | Allen |
| 10,064,621 B2 | 9/2018 | Kerr et al. |
| 10,064,624 B2 | 9/2018 | Shelton, IV et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,080,552 B2 | 9/2018 | Nicholas et al. |
| D831,209 S | 10/2018 | Huitema et al. |
| 10,085,748 B2 | 10/2018 | Morgan et al. |
| 10,085,749 B2 | 10/2018 | Cappola et al. |
| 10,085,806 B2 | 10/2018 | Hagn et al. |
| 10,092,292 B2 | 10/2018 | Boudreaux et al. |
| 10,098,642 B2 | 10/2018 | Baxter, III et al. |
| 10,111,679 B2 | 10/2018 | Baber et al. |
| 10,117,649 B2 | 11/2018 | Baxter, III et al. |
| 10,117,652 B2 | 11/2018 | Schmid et al. |
| 10,123,798 B2 | 11/2018 | Baxter, III et al. |
| 10,123,799 B2 | 11/2018 | Zergiebel et al. |
| 10,130,352 B2 | 11/2018 | Widenhouse et al. |
| 10,130,359 B2 | 11/2018 | Hess et al. |
| 10,130,363 B2 | 11/2018 | Huitema et al. |
| 10,130,366 B2 | 11/2018 | Shelton, IV et al. |
| 10,135,242 B2 | 11/2018 | Baber et al. |
| 10,136,887 B2 | 11/2018 | Shelton, IV et al. |
| 10,136,888 B2 | 11/2018 | Chen et al. |
| 10,136,890 B2 | 11/2018 | Shelton, IV et al. |
| D836,198 S | 12/2018 | Harris et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,159,482 B2 | 12/2018 | Swayze et al. |
| 10,159,483 B2 | 12/2018 | Beckman et al. |
| 10,166,025 B2 | 1/2019 | Leimbach et al. |
| 10,166,026 B2 | 1/2019 | Shelton, IV et al. |
| 10,172,616 B2 | 1/2019 | Murray et al. |
| 10,172,619 B2 | 1/2019 | Harris et al. |
| 10,178,992 B2 | 1/2019 | Wise et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,188,385 B2 | 1/2019 | Kerr et al. |
| 10,188,393 B2 | 1/2019 | Smith et al. |
| 10,188,394 B2 | 1/2019 | Shelton, IV et al. |
| 10,194,910 B2 | 2/2019 | Shelton, IV et al. |
| 10,194,913 B2 | 2/2019 | Nalagatla et al. |
| 10,215,318 B2 | 2/2019 | Gaspar et al. |
| 10,226,251 B2 | 3/2019 | Scheib et al. |
| 10,245,029 B2 | 4/2019 | Hunter et al. |
| 10,245,030 B2 | 4/2019 | Hunter et al. |
| 10,245,038 B2 | 4/2019 | Hopkins et al. |
| 10,258,331 B2 | 4/2019 | Shelton, IV et al. |
| 10,265,068 B2 | 4/2019 | Harris et al. |
| 10,271,851 B2 | 4/2019 | Shelton, IV et al. |
| 10,285,700 B2 | 5/2019 | Scheib |
| 10,285,705 B2 | 5/2019 | Shelton, IV et al. |
| 10,292,702 B2 | 5/2019 | Cardinale et al. |
| 10,292,704 B2 | 5/2019 | Harris et al. |
| 10,307,159 B2 | 6/2019 | Harris et al. |
| 10,314,582 B2 | 6/2019 | Shelton, IV et al. |
| 10,335,149 B2 | 7/2019 | Baxter, III et al. |
| 10,342,535 B2 | 7/2019 | Scheib et al. |
| 10,342,543 B2 | 7/2019 | Shelton, IV et al. |
| 10,349,941 B2 | 7/2019 | Marczyk et al. |
| 10,363,032 B2 | 7/2019 | Scheib et al. |
| 10,456,132 B2 | 10/2019 | Gettinger et al. |
| D869,655 S | 12/2019 | Shelton, IV et al. |
| 10,548,599 B2 | 2/2020 | Marczyk et al. |
| 10,610,219 B2 | 4/2020 | Adams et al. |
| 10,624,636 B2 | 4/2020 | Beardsley et al. |
| 10,631,857 B2 | 4/2020 | Kostrzewski |
| D894,389 S | 8/2020 | Shelton, IV et al. |
| D896,379 S | 9/2020 | Shelton, IV et al. |
| D896,380 S | 9/2020 | Shelton, IV et al. |
| 2001/0025183 A1 | 9/2001 | Shahidi |
| 2002/0022836 A1 | 2/2002 | Goble et al. |
| 2002/0029036 A1 | 3/2002 | Goble et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0134811 A1 | 9/2002 | Napier et al. |
| 2002/0143340 A1 | 10/2002 | Kaneko |
| 2003/0009193 A1 | 1/2003 | Corsaro |
| 2003/0039689 A1 | 2/2003 | Chen et al. |
| 2003/0078647 A1 | 4/2003 | Vallana et al. |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0139741 A1 | 7/2003 | Goble et al. |
| 2003/0153908 A1 | 8/2003 | Goble et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0028502 A1 | 2/2004 | Cummins |
| 2004/0030333 A1 | 2/2004 | Goble |
| 2004/0034357 A1 | 2/2004 | Beane et al. |
| 2004/0044364 A1 | 3/2004 | DeVries et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |

(56) References Cited

U.S. PATENT DOCUMENTS

| | | |
|---|---|---|
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0254566 A1 | 12/2004 | Plicchi et al. |
| 2004/0254590 A1 | 12/2004 | Hoffman et al. |
| 2004/0260315 A1 | 12/2004 | Dell et al. |
| 2004/0267310 A1 | 12/2004 | Racenet et al. |
| 2005/0010213 A1 | 1/2005 | Stad et al. |
| 2005/0032511 A1 | 2/2005 | Malone et al. |
| 2005/0033352 A1 | 2/2005 | Zepf et al. |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096605 A1 | 5/2005 | Green et al. |
| 2005/0096683 A1 | 5/2005 | Ellins et al. |
| 2005/0124855 A1 | 6/2005 | Jaffe et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0154258 A1 | 7/2005 | Tartaglia et al. |
| 2005/0154406 A1 | 7/2005 | Bombard et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0245965 A1 | 11/2005 | Orban, III et al. |
| 2005/0246881 A1 | 11/2005 | Kelly et al. |
| 2005/0256452 A1 | 11/2005 | DeMarchi et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0283188 A1 | 12/2005 | Loshakove et al. |
| 2006/0008787 A1 | 1/2006 | Hayman et al. |
| 2006/0015009 A1 | 1/2006 | Jaffe et al. |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100649 A1* | 5/2006 | Hart ............... A61B 17/08 606/157 |
| 2006/0173470 A1 | 8/2006 | Oray et al. |
| 2006/0180634 A1 | 8/2006 | Shelton et al. |
| 2006/0185682 A1 | 8/2006 | Marczyk |
| 2006/0201989 A1 | 9/2006 | Ojeda |
| 2006/0212071 A1 | 9/2006 | Ginn et al. |
| 2006/0235368 A1 | 10/2006 | Oz |
| 2006/0252993 A1 | 11/2006 | Freed et al. |
| 2006/0271102 A1 | 11/2006 | Bosshard et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010838 A1 | 1/2007 | Shelton et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0073341 A1 | 3/2007 | Smith et al. |
| 2007/0078484 A1 | 4/2007 | Talarico et al. |
| 2007/0084897 A1 | 4/2007 | Shelton et al. |
| 2007/0093869 A1 | 4/2007 | Bloom et al. |
| 2007/0102472 A1 | 5/2007 | Shelton |
| 2007/0106113 A1 | 5/2007 | Ravo |
| 2007/0106317 A1 | 5/2007 | Shelton et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0208359 A1 | 9/2007 | Hoffman |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2008/0003196 A1 | 1/2008 | Jonn et al. |
| 2008/0015598 A1 | 1/2008 | Prommersberger |
| 2008/0021278 A1 | 1/2008 | Leonard et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0051833 A1 | 2/2008 | Gramuglia et al. |
| 2008/0065153 A1 | 3/2008 | Allard et al. |
| 2008/0078802 A1 | 4/2008 | Hess et al. |
| 2008/0078803 A1* | 4/2008 | Shelton ............ A61B 17/07207 227/176.1 |
| 2008/0078807 A1* | 4/2008 | Hess ............... A61B 17/072 227/181.1 |
| 2008/0078808 A1* | 4/2008 | Hess ............... A61B 17/064 227/181.1 |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0128469 A1 | 6/2008 | Dalessandro et al. |

(56) References Cited

U.S. PATENT DOCUMENTS

| | | |
|---|---|---|
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0154299 A1 | 6/2008 | Livneh |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0183193 A1 | 7/2008 | Omori et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0210738 A1* | 9/2008 | Shelton .............. A61B 17/0644 227/176.1 |
| 2008/0249536 A1 | 10/2008 | Stahler et al. |
| 2008/0255413 A1 | 10/2008 | Zemlok et al. |
| 2008/0262654 A1 | 10/2008 | Omori et al. |
| 2008/0287944 A1 | 11/2008 | Pearson et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0020958 A1 | 1/2009 | Soul |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0090763 A1 | 4/2009 | Zemlok et al. |
| 2009/0092651 A1 | 4/2009 | Shah et al. |
| 2009/0099579 A1 | 4/2009 | Nentwick et al. |
| 2009/0099876 A1 | 4/2009 | Whitman |
| 2009/0119011 A1 | 5/2009 | Kondo et al. |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177201 A1 | 7/2009 | Soltz et al. |
| 2009/0177226 A1 | 7/2009 | Reinprecht et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0242610 A1 | 10/2009 | Shelton, IV et al. |
| 2009/0247901 A1 | 10/2009 | Zimmer |
| 2009/0255974 A1 | 10/2009 | Viola |
| 2009/0270895 A1 | 10/2009 | Churchill et al. |
| 2009/0275957 A1 | 11/2009 | Harris et al. |
| 2009/0292283 A1 | 11/2009 | Odom |
| 2009/0308907 A1 | 12/2009 | Nalagatla et al. |
| 2009/0318957 A1 | 12/2009 | Viola et al. |
| 2010/0016888 A1 | 1/2010 | Calabrese et al. |
| 2010/0023024 A1 | 1/2010 | Zeiner et al. |
| 2010/0023052 A1 | 1/2010 | Heinrich et al. |
| 2010/0036370 A1 | 2/2010 | Mirel et al. |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0100124 A1 | 4/2010 | Calabrese et al. |
| 2010/0133316 A1 | 6/2010 | Lizee et al. |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0179022 A1 | 7/2010 | Shirokoshi |
| 2010/0191262 A1 | 7/2010 | Harris et al. |
| 2010/0193566 A1 | 8/2010 | Scheib et al. |
| 2010/0204717 A1 | 8/2010 | Knodel |
| 2010/0222901 A1 | 9/2010 | Swayze et al. |
| 2010/0249497 A1 | 9/2010 | Peine et al. |
| 2010/0267662 A1 | 10/2010 | Fielder et al. |
| 2010/0274160 A1 | 10/2010 | Yachi et al. |
| 2010/0292540 A1 | 11/2010 | Hess et al. |
| 2010/0298636 A1 | 11/2010 | Castro et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0011916 A1 | 1/2011 | Levine |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0034910 A1 | 2/2011 | Ross et al. |
| 2011/0036891 A1 | 2/2011 | Zemlok et al. |
| 2011/0046667 A1 | 2/2011 | Culligan et al. |
| 2011/0060363 A1 | 3/2011 | Hess et al. |
| 2011/0082485 A1 | 4/2011 | Nohilly et al. |
| 2011/0082538 A1 | 4/2011 | Dahlgren et al. |
| 2011/0087276 A1 | 4/2011 | Bedi et al. |
| 2011/0091515 A1 | 4/2011 | Zilberman et al. |
| 2011/0114697 A1 | 5/2011 | Baxter, III et al. |
| 2011/0121049 A1 | 5/2011 | Malinouskas et al. |
| 2011/0125176 A1 | 5/2011 | Yates et al. |
| 2011/0127185 A1* | 6/2011 | Ward ............... A61B 17/07207 206/339 |
| 2011/0137340 A1 | 6/2011 | Cummins |
| 2011/0147433 A1 | 6/2011 | Shelton, IV et al. |
| 2011/0163146 A1 | 7/2011 | Ortiz et al. |
| 2011/0174861 A1 | 7/2011 | Shelton, IV et al. |
| 2011/0192882 A1 | 8/2011 | Hess et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0016413 A1 | 1/2012 | Timm et al. |
| 2012/0029272 A1 | 2/2012 | Shelton, IV et al. |
| 2012/0074198 A1* | 3/2012 | Huitema ........ A61B 17/07207 227/176.1 |
| 2012/0074200 A1 | 3/2012 | Schmid et al. |
| 2012/0080332 A1* | 4/2012 | Shelton, IV ..... A61B 17/07292 206/339 |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080497 A1 | 4/2012 | White et al. |
| 2012/0080498 A1* | 4/2012 | Shelton, IV ........ A61B 17/105 227/178.1 |
| 2012/0109186 A1 | 5/2012 | Parrott et al. |
| 2012/0125792 A1 | 5/2012 | Cassivi |
| 2012/0130421 A1 | 5/2012 | Hafez et al. |
| 2012/0175398 A1 | 7/2012 | Sandborn et al. |
| 2012/0234895 A1 | 9/2012 | O'Connor et al. |
| 2012/0234897 A1 | 9/2012 | Shelton, IV et al. |
| 2012/0241497 A1* | 9/2012 | Mandakolathur Vasudevan ......... A61B 17/0643 227/176.1 |
| 2012/0248169 A1 | 10/2012 | Widenhouse et al. |
| 2012/0283707 A1 | 11/2012 | Giordano et al. |
| 2012/0289979 A1 | 11/2012 | Eskaros et al. |
| 2012/0292367 A1 | 11/2012 | Morgan et al. |
| 2012/0298722 A1 | 11/2012 | Hess et al. |
| 2012/0303002 A1 | 11/2012 | Chowaniec et al. |
| 2013/0006227 A1 | 1/2013 | Takash I No |
| 2013/0012983 A1 | 1/2013 | Kleyman |
| 2013/0020375 A1 | 1/2013 | Shelton, IV et al. |

(56) References Cited

U.S. PATENT DOCUMENTS

| | | |
|---|---|---|
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0030438 A1* | 1/2013 | Fox ................ A61B 17/0682 606/75 |
| 2013/0030462 A1 | 1/2013 | Keating et al. |
| 2013/0041406 A1 | 2/2013 | Bear et al. |
| 2013/0087597 A1 | 4/2013 | Shelton, IV et al. |
| 2013/0098970 A1 | 4/2013 | Racenet et al. |
| 2013/0116669 A1 | 5/2013 | Shelton, IV et al. |
| 2013/0131651 A1 | 5/2013 | Strobl et al. |
| 2013/0153636 A1 | 6/2013 | Shelton, IV et al. |
| 2013/0153641 A1 | 6/2013 | Shelton, IV et al. |
| 2013/0175317 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0214025 A1 | 8/2013 | Zemlok et al. |
| 2013/0214030 A1 | 8/2013 | Aronhalt et al. |
| 2013/0233906 A1 | 9/2013 | Hess et al. |
| 2013/0256373 A1 | 10/2013 | Schmid et al. |
| 2013/0256379 A1 | 10/2013 | Schmid et al. |
| 2013/0256380 A1 | 10/2013 | Schmid et al. |
| 2013/0261661 A1 | 10/2013 | Piraka |
| 2013/0270322 A1 | 10/2013 | Scheib et al. |
| 2013/0317305 A1 | 11/2013 | Stevenson et al. |
| 2013/0324982 A1 | 12/2013 | Smith et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0012299 A1 | 1/2014 | Stoddard et al. |
| 2014/0014705 A1 | 1/2014 | Baxter, III |
| 2014/0018832 A1 | 1/2014 | Shelton, IV |
| 2014/0033674 A1* | 2/2014 | Knodel ................ B21G 7/02 59/77 |
| 2014/0039549 A1 | 2/2014 | Belsky et al. |
| 2014/0041191 A1* | 2/2014 | Knodel ............ A61B 17/07207 29/428 |
| 2014/0048580 A1 | 2/2014 | Merchant et al. |
| 2014/0103098 A1 | 4/2014 | Choi et al. |
| 2014/0107640 A1 | 4/2014 | Yates et al. |
| 2014/0151433 A1 | 6/2014 | Shelton, IV et al. |
| 2014/0158747 A1 | 6/2014 | Measamer et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0188159 A1 | 7/2014 | Steege |
| 2014/0224857 A1* | 8/2014 | Schmid ............ A61B 17/07207 227/180.1 |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0284371 A1 | 9/2014 | Morgan et al. |
| 2014/0291378 A1 | 10/2014 | Shelton, IV et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0309666 A1 | 10/2014 | Shelton, IV et al. |
| 2014/0330161 A1 | 11/2014 | Swayze et al. |
| 2015/0008248 A1 | 1/2015 | Giordano et al. |
| 2015/0053737 A1 | 2/2015 | Leimbach et al. |
| 2015/0053742 A1 | 2/2015 | Shelton, IV et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083781 A1 | 3/2015 | Giordano et al. |
| 2015/0083782 A1 | 3/2015 | Scheib et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0108199 A1 | 4/2015 | Shelton, IV et al. |
| 2015/0122870 A1 | 5/2015 | Zemlok et al. |
| 2015/0144679 A1 | 5/2015 | Scirica et al. |
| 2015/0150620 A1 | 6/2015 | Miyamoto et al. |
| 2015/0173744 A1 | 6/2015 | Shelton, IV et al. |
| 2015/0173748 A1* | 6/2015 | Marczyk ............ A61B 17/068 227/177.1 |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0182220 A1 | 7/2015 | Yates et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0231409 A1 | 8/2015 | Racenet et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0280384 A1 | 10/2015 | Leimbach et al. |
| 2015/0282810 A1 | 10/2015 | Shelton, IV et al. |
| 2015/0289873 A1 | 10/2015 | Shelton, IV et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297229 A1 | 10/2015 | Schellin et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0313594 A1 | 11/2015 | Shelton, IV et al. |
| 2015/0324317 A1 | 11/2015 | Collins et al. |
| 2015/0327864 A1 | 11/2015 | Hodgkinson et al. |
| 2015/0342607 A1 | 12/2015 | Shelton, IV et al. |
| 2015/0374368 A1 | 12/2015 | Swayze et al. |
| 2015/0374369 A1 | 12/2015 | Yates et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374378 A1 | 12/2015 | Giordano et al. |
| 2015/0374379 A1 | 12/2015 | Shelton, IV |
| 2016/0000430 A1 | 1/2016 | Ming et al. |
| 2016/0000431 A1 | 1/2016 | Giordano et al. |
| 2016/0000437 A1 | 1/2016 | Giordano et al. |
| 2016/0000438 A1 | 1/2016 | Swayze et al. |
| 2016/0000442 A1 | 1/2016 | Shelton, IV |
| 2016/0000452 A1 | 1/2016 | Yates et al. |
| 2016/0000453 A1 | 1/2016 | Yates et al. |

(56) References Cited

U.S. PATENT DOCUMENTS

| | | |
|---|---|---|
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015391 A1 | 1/2016 | Shelton, IV et al. |
| 2016/0051257 A1 | 2/2016 | Shelton, IV et al. |
| 2016/0058443 A1 | 3/2016 | Yates et al. |
| 2016/0066913 A1 | 3/2016 | Swayze et al. |
| 2016/0074040 A1 | 3/2016 | Widenhouse et al. |
| 2016/0089137 A1 | 3/2016 | Hess et al. |
| 2016/0089142 A1 | 3/2016 | Harris et al. |
| 2016/0089146 A1 | 3/2016 | Harris et al. |
| 2016/0089147 A1 | 3/2016 | Harris et al. |
| 2016/0089149 A1 | 3/2016 | Harris et al. |
| 2016/0095585 A1 | 4/2016 | Zergiebel et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0166256 A1 | 6/2016 | Baxter, III et al. |
| 2016/0174972 A1 | 6/2016 | Shelton, IV et al. |
| 2016/0174974 A1 | 6/2016 | Schmid et al. |
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192933 A1 | 7/2016 | Shelton, IV |
| 2016/0192936 A1 | 7/2016 | Leimbach et al. |
| 2016/0192996 A1 | 7/2016 | Spivey et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199064 A1 | 7/2016 | Shelton, IV et al. |
| 2016/0199089 A1 | 7/2016 | Hess et al. |
| 2016/0199956 A1 | 7/2016 | Shelton, IV et al. |
| 2016/0206310 A1 | 7/2016 | Shelton, IV |
| 2016/0206314 A1 | 7/2016 | Scheib et al. |
| 2016/0220248 A1 | 8/2016 | Timm et al. |
| 2016/0220249 A1 | 8/2016 | Shelton, IV et al. |
| 2016/0220266 A1 | 8/2016 | Shelton, IV et al. |
| 2016/0220268 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235406 A1 | 8/2016 | Shelton, IV et al. |
| 2016/0235408 A1 | 8/2016 | Shelton, IV et al. |
| 2016/0235409 A1 | 8/2016 | Shelton, IV et al. |
| 2016/0235494 A1 | 8/2016 | Shelton, IV et al. |
| 2016/0242775 A1 | 8/2016 | Shelton, IV et al. |
| 2016/0242776 A1 | 8/2016 | Shelton, IV et al. |
| 2016/0242777 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249909 A1 | 9/2016 | Shelton, IV et al. |
| 2016/0249910 A1 | 9/2016 | Shelton, IV et al. |
| 2016/0249911 A1 | 9/2016 | Timm et al. |
| 2016/0249916 A1 | 9/2016 | Shelton, IV et al. |
| 2016/0249922 A1 | 9/2016 | Morgan et al. |
| 2016/0249927 A1 | 9/2016 | Beckman et al. |
| 2016/0256071 A1 | 9/2016 | Shelton, IV et al. |
| 2016/0256154 A1 | 9/2016 | Shelton, IV et al. |
| 2016/0256156 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256185 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0270780 A1 | 9/2016 | Hall et al. |
| 2016/0270789 A1 | 9/2016 | Gupta et al. |
| 2016/0287249 A1 | 10/2016 | Alexander, III et al. |
| 2016/0287250 A1 | 10/2016 | Shelton, IV et al. |
| 2016/0287251 A1 | 10/2016 | Shelton, IV et al. |
| 2016/0287253 A1 | 10/2016 | Shelton, IV et al. |
| 2016/0338702 A1 | 11/2016 | Ehrenfels et al. |
| 2016/0367246 A1 | 12/2016 | Baxter, III et al. |
| 2016/0367255 A1 | 12/2016 | Wise et al. |
| 2016/0374678 A1 | 12/2016 | Becerra et al. |
| 2016/0374685 A1 | 12/2016 | Abbott et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0055991 A1 | 3/2017 | Kang |
| 2017/0055997 A1 | 3/2017 | Swayze et al. |
| 2017/0055998 A1 | 3/2017 | Baxter, III et al. |
| 2017/0055999 A1 | 3/2017 | Baxter, III et al. |
| 2017/0056000 A1 | 3/2017 | Nalagatla et al. |
| 2017/0056005 A1 | 3/2017 | Shelton, IV et al. |
| 2017/0056006 A1 | 3/2017 | Shelton, IV et al. |
| 2017/0056007 A1 | 3/2017 | Eckert et al. |
| 2017/0056008 A1 | 3/2017 | Shelton, IV et al. |
| 2017/0056011 A1 | 3/2017 | Harris et al. |
| 2017/0056013 A1 | 3/2017 | Harris et al. |
| 2017/0056014 A1 | 3/2017 | Harris et al. |
| 2017/0056015 A1 | 3/2017 | Harris et al. |
| 2017/0095250 A1 | 4/2017 | Kostrzewski et al. |
| 2017/0105727 A1 | 4/2017 | Scheib et al. |
| 2017/0105728 A1 | 4/2017 | Scheib et al. |
| 2017/0105731 A1 | 4/2017 | Scheib et al. |
| 2017/0105733 A1 | 4/2017 | Scheib et al. |
| 2017/0119388 A1 | 5/2017 | Kostrzewski |
| 2017/0189019 A1 | 7/2017 | Harris et al. |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224334 A1 | 8/2017 | Worthington et al. |
| 2017/0224335 A1 | 8/2017 | Weaner et al. |
| 2017/0224342 A1 | 8/2017 | Worthington et al. |
| 2017/0224343 A1 | 8/2017 | Baxter, III et al. |
| 2017/0231626 A1 | 8/2017 | Shelton, IV et al. |
| 2017/0231627 A1 | 8/2017 | Shelton, IV et al. |
| 2017/0231628 A1 | 8/2017 | Shelton, IV et al. |
| 2017/0231633 A1 | 8/2017 | Marczyk et al. |
| 2017/0245856 A1 | 8/2017 | Baxter, III et al. |
| 2017/0245857 A1 | 8/2017 | Shelton, IV et al. |
| 2017/0281155 A1 | 10/2017 | Shelton, IV et al. |
| 2017/0281161 A1 | 10/2017 | Shelton, IV et al. |
| 2017/0281162 A1 | 10/2017 | Shelton, IV et al. |
| 2017/0281164 A1 | 10/2017 | Harris et al. |
| 2017/0281166 A1 | 10/2017 | Morgan et al. |
| 2017/0281168 A1 | 10/2017 | Shelton, IV et al. |
| 2017/0281169 A1 | 10/2017 | Harris et al. |
| 2017/0281171 A1 | 10/2017 | Shelton, IV et al. |
| 2017/0281172 A1 | 10/2017 | Shelton, IV et al. |
| 2017/0281173 A1 | 10/2017 | Shelton, IV et al. |
| 2017/0281174 A1 | 10/2017 | Harris et al. |
| 2017/0281177 A1 | 10/2017 | Harris et al. |
| 2017/0281179 A1 | 10/2017 | Shelton, IV et al. |
| 2017/0281180 A1 | 10/2017 | Morgan et al. |
| 2017/0281183 A1 | 10/2017 | Miller et al. |
| 2017/0281184 A1 | 10/2017 | Shelton, IV et al. |
| 2017/0281185 A1 | 10/2017 | Miller et al. |
| 2017/0281186 A1 | 10/2017 | Shelton, IV et al. |
| 2017/0281187 A1 | 10/2017 | Shelton, IV et al. |
| 2017/0281189 A1 | 10/2017 | Nalagatla et al. |
| 2017/0360423 A1 | 12/2017 | Stevenson et al. |
| 2017/0367695 A1 | 12/2017 | Shelton, IV et al. |
| 2017/0367696 A1 | 12/2017 | Shelton, IV et al. |
| 2017/0367697 A1 | 12/2017 | Shelton, IV et al. |
| 2017/0367698 A1 | 12/2017 | Shelton, IV et al. |
| 2017/0367699 A1 | 12/2017 | Shelton, IV et al. |
| 2018/0103948 A1 | 4/2018 | Baxter, III et al. |
| 2018/0110513 A1 | 4/2018 | Baxter, III et al. |
| 2018/0110517 A1 | 4/2018 | Baxter, III et al. |
| 2018/0168575 A1 | 6/2018 | Simms et al. |
| 2018/0168576 A1 | 6/2018 | Hunter et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |

(56) References Cited

U.S. PATENT DOCUMENTS

| | | |
|---|---|---|
| 2018/0168581 A1 | 6/2018 | Hunter et al. |
| 2018/0168582 A1 | 6/2018 | Swayze et al. |
| 2018/0168583 A1 | 6/2018 | Hunter et al. |
| 2018/0168584 A1 | 6/2018 | Harris et al. |
| 2018/0168585 A1 | 6/2018 | Shelton, IV et al. |
| 2018/0168586 A1 | 6/2018 | Shelton, IV et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168595 A1 | 6/2018 | Overmyer et al. |
| 2018/0168596 A1 | 6/2018 | Beckman et al. |
| 2018/0168597 A1 | 6/2018 | Fanelli et al. |
| 2018/0168598 A1 | 6/2018 | Shelton, IV et al. |
| 2018/0168599 A1 | 6/2018 | Bakos et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168611 A1 | 6/2018 | Shelton, IV et al. |
| 2018/0168612 A1 | 6/2018 | Shelton, IV et al. |
| 2018/0168613 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168616 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168620 A1 | 6/2018 | Huang et al. |
| 2018/0168621 A1 | 6/2018 | Shelton, IV et al. |
| 2018/0168622 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168634 A1 | 6/2018 | Harris et al. |
| 2018/0168635 A1 | 6/2018 | Shelton, IV et al. |
| 2018/0168636 A1 | 6/2018 | Shelton, IV et al. |
| 2018/0168637 A1 | 6/2018 | Harris et al. |
| 2018/0168638 A1 | 6/2018 | Harris et al. |
| 2018/0168639 A1 | 6/2018 | Shelton, IV et al. |
| 2018/0168640 A1 | 6/2018 | Shelton, IV et al. |
| 2018/0168641 A1 | 6/2018 | Harris et al. |
| 2018/0168642 A1 | 6/2018 | Shelton, IV et al. |
| 2018/0168643 A1 | 6/2018 | Shelton, IV et al. |
| 2018/0168644 A1 | 6/2018 | Shelton, IV et al. |
| 2018/0168645 A1 | 6/2018 | Shelton, IV et al. |
| 2018/0168646 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168651 A1 | 6/2018 | Shelton, IV et al. |
| 2018/0296213 A1 | 10/2018 | Strobl |
| 2019/0059886 A1 | 2/2019 | Shelton, IV et al. |
| 2019/0105047 A1 | 4/2019 | Nalagatla et al. |
| 2019/0125344 A1 | 5/2019 | Dinardo et al. |
| 2019/0150927 A1 | 5/2019 | Aranyi et al. |
| 2019/0183503 A1 | 6/2019 | Shelton, IV et al. |
| 2019/0261992 A1 | 8/2019 | Shelton, IV et al. |
| 2019/0269402 A1 | 9/2019 | Murray et al. |
| 2019/0290279 A1 | 9/2019 | Harris et al. |
| 2019/0328390 A1 | 10/2019 | Harris et al. |
| 2019/0343526 A1 | 11/2019 | Harris et al. |
| 2019/0388093 A1 | 12/2019 | Shelton, IV et al. |
| 2020/0015822 A1 | 1/2020 | Marczyk et al. |
| 2020/0046355 A1 | 2/2020 | Harris et al. |
| 2020/0046356 A1 | 2/2020 | Baxter, III et al. |
| 2020/0069308 A1 | 3/2020 | Baxter, III et al. |
| 2020/0085425 A1 | 3/2020 | Baxter, III et al. |
| 2020/0222043 A1 | 7/2020 | Baxter, III et al. |
| 2020/0222044 A1 | 7/2020 | Baxter, III et al. |
| 2020/0222045 A1 | 7/2020 | Shelton, IV et al. |
| 2020/0345352 A1 | 11/2020 | Shelton, IV et al. |
| 2020/0390442 A1 | 12/2020 | Shelton, IV et al. |

FOREIGN PATENT DOCUMENTS

| | | |
|---|---|---|
| AU | 2011218702 B2 | 6/2013 |
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CA | 2813230 A1 | 4/2012 |
| CA | 2795323 A1 | 5/2014 |
| CN | 1163558 A | 10/1997 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101111196 A | 1/2008 |
| CN | 101137402 A | 3/2008 |
| CN | 101507620 A | 8/2009 |
| CN | 101507622 A | 8/2009 |
| CN | 101507623 A | 8/2009 |
| CN | 101507625 A | 8/2009 |
| CN | 101507628 A | 8/2009 |
| CN | 101675898 A | 3/2010 |
| CN | 101683280 A | 3/2010 |
| CN | 201617885 U | 11/2010 |
| CN | 101028205 B | 1/2011 |
| CN | 101934098 A | 1/2011 |
| CN | 201949071 U | 8/2011 |
| CN | 101336835 B | 9/2011 |
| CN | 102188270 A | 9/2011 |
| CN | 101779977 B | 12/2011 |
| CN | 101534723 B | 1/2012 |
| CN | 101310680 B | 4/2012 |
| CN | 202397539 U | 8/2012 |
| CN | 101317782 B | 10/2012 |
| CN | 101541251 A | 11/2012 |
| CN | 202526242 U | 11/2012 |
| CN | 101507633 B | 2/2013 |
| CN | 101023879 B | 3/2013 |
| CN | 101327137 B | 6/2013 |
| CN | 101401736 B | 6/2013 |
| CN | 202982106 U | 6/2013 |
| CN | 101332110 B | 7/2013 |
| CN | 101683281 B | 1/2014 |
| CN | 103648408 A | 3/2014 |
| CN | 203777011 U | 8/2014 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |

(56) References Cited

FOREIGN PATENT DOCUMENTS

| | | |
|---|---|---|
| DE | 4228909 A1 | 3/1994 |
| DE | 9412228 U1 | 9/1994 |
| DE | 19509116 A1 | 9/1996 |
| DE | 19707373 C1 | 2/1998 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 202004012389 U1 | 9/2004 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0070230 B1 | 4/1985 |
| EP | 0156774 A2 | 10/1985 |
| EP | 0050554 B1 | 1/1986 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0379721 B1 | 9/1993 |
| EP | 0277959 B1 | 10/1993 |
| EP | 0233940 B1 | 11/1993 |
| EP | 0261230 B1 | 11/1993 |
| EP | 0324636 B1 | 3/1994 |
| EP | 0591946 A1 | 4/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0630614 A1 | 12/1994 |
| EP | 0634144 A1 | 1/1995 |
| EP | 0639349 A2 | 2/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0676173 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0541987 B1 | 7/1996 |
| EP | 0667119 B1 | 7/1996 |
| EP | 0737446 A1 | 10/1996 |
| EP | 0741996 B1 | 11/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0623312 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 B1 | 9/1999 |
| EP | 0843906 B1 | 3/2000 |
| EP | 0552050 B1 | 5/2000 |
| EP | 0833592 B1 | 5/2000 |
| EP | 0795298 B1 | 6/2000 |
| EP | 0832605 B1 | 6/2000 |
| EP | 0484677 B2 | 7/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1411626 A2 | 4/2004 |
| EP | 1086713 B1 | 5/2004 |

(56) References Cited

FOREIGN PATENT DOCUMENTS

| | | |
|---|---|---|
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1453432 A2 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1496805 A2 | 1/2005 |
| EP | 1256318 B1 | 2/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621143 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1563792 B1 | 4/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |
| EP | 1800610 A1 | 6/2007 |
| EP | 1300117 B1 | 8/2007 |
| EP | 1813199 A1 | 8/2007 |
| EP | 1813200 A2 | 8/2007 |
| EP | 1813201 A1 | 8/2007 |
| EP | 1813202 A1 | 8/2007 |
| EP | 1813203 A2 | 8/2007 |
| EP | 1813207 A1 | 8/2007 |
| EP | 1813209 A1 | 8/2007 |
| EP | 1815950 A1 | 8/2007 |
| EP | 1330991 B1 | 9/2007 |
| EP | 1837041 A1 | 9/2007 |
| EP | 0922435 B1 | 10/2007 |
| EP | 1487359 B1 | 10/2007 |
| EP | 1599146 B1 | 10/2007 |
| EP | 1839596 A1 | 10/2007 |
| EP | 1679096 B1 | 11/2007 |
| EP | 1857057 A2 | 11/2007 |
| EP | 1402821 B1 | 12/2007 |
| EP | 1872727 A1 | 1/2008 |
| EP | 1550410 B1 | 2/2008 |
| EP | 1671593 B1 | 2/2008 |
| EP | 1897502 A1 | 3/2008 |
| EP | 1611856 B1 | 4/2008 |
| EP | 1908417 A2 | 4/2008 |
| EP | 1917929 A1 | 5/2008 |
| EP | 1330201 B1 | 6/2008 |
| EP | 1702568 B1 | 7/2008 |
| EP | 1943955 A2 | 7/2008 |
| EP | 1943957 A2 | 7/2008 |
| EP | 1943959 A1 | 7/2008 |
| EP | 1943962 A2 | 7/2008 |
| EP | 1943964 A1 | 7/2008 |
| EP | 1943976 A2 | 7/2008 |
| EP | 1593337 B1 | 8/2008 |
| EP | 1970014 A1 | 9/2008 |
| EP | 1974678 A2 | 10/2008 |
| EP | 1980213 A2 | 10/2008 |
| EP | 1980214 A2 | 10/2008 |
| EP | 1759645 B1 | 11/2008 |
| EP | 1987780 A2 | 11/2008 |
| EP | 1990014 A2 | 11/2008 |
| EP | 1552795 B1 | 12/2008 |
| EP | 1693008 B1 | 12/2008 |
| EP | 1759640 B1 | 12/2008 |
| EP | 1997439 A2 | 12/2008 |
| EP | 2000101 A2 | 12/2008 |
| EP | 2000102 A2 | 12/2008 |
| EP | 2005894 A2 | 12/2008 |
| EP | 2005897 A2 | 12/2008 |
| EP | 2005901 A1 | 12/2008 |
| EP | 2008595 A2 | 12/2008 |
| EP | 1736104 B1 | 3/2009 |
| EP | 1749486 B1 | 3/2009 |
| EP | 1782743 B1 | 3/2009 |
| EP | 2039302 A2 | 3/2009 |
| EP | 2039308 A2 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 2055243 A2 | 5/2009 |
| EP | 1550409 B1 | 6/2009 |
| EP | 1550413 B1 | 6/2009 |
| EP | 1719461 B1 | 6/2009 |
| EP | 1834594 B1 | 6/2009 |
| EP | 1709911 B1 | 7/2009 |
| EP | 2077093 A2 | 7/2009 |
| EP | 1745748 B1 | 8/2009 |
| EP | 2090231 A1 | 8/2009 |
| EP | 2090237 A1 | 8/2009 |

(56) References Cited

FOREIGN PATENT DOCUMENTS

| | | |
|---|---|---|
| EP | 2090241 A1 | 8/2009 |
| EP | 2090245 A1 | 8/2009 |
| EP | 2090254 A1 | 8/2009 |
| EP | 2090256 A2 | 8/2009 |
| EP | 2095777 A2 | 9/2009 |
| EP | 2098170 A2 | 9/2009 |
| EP | 2110082 A1 | 10/2009 |
| EP | 2110083 A2 | 10/2009 |
| EP | 2110084 A2 | 10/2009 |
| EP | 2111803 A2 | 10/2009 |
| EP | 1813208 B1 | 11/2009 |
| EP | 1908426 B1 | 11/2009 |
| EP | 2116195 A1 | 11/2009 |
| EP | 2116197 A2 | 11/2009 |
| EP | 1607050 B1 | 12/2009 |
| EP | 1762190 B8 | 12/2009 |
| EP | 1815804 B1 | 12/2009 |
| EP | 1875870 B1 | 12/2009 |
| EP | 1878395 B1 | 1/2010 |
| EP | 2151204 A1 | 2/2010 |
| EP | 1813211 B1 | 3/2010 |
| EP | 2165656 A2 | 3/2010 |
| EP | 2165660 A2 | 3/2010 |
| EP | 2165664 A2 | 3/2010 |
| EP | 1566150 B1 | 4/2010 |
| EP | 1813206 B1 | 4/2010 |
| EP | 2184014 A2 | 5/2010 |
| EP | 1769754 B1 | 6/2010 |
| EP | 1854416 B1 | 6/2010 |
| EP | 1911408 B1 | 6/2010 |
| EP | 2198787 A1 | 6/2010 |
| EP | 1647286 B1 | 9/2010 |
| EP | 1825821 B1 | 9/2010 |
| EP | 1535565 B1 | 10/2010 |
| EP | 1702570 B1 | 10/2010 |
| EP | 1785098 B1 | 10/2010 |
| EP | 2005896 B1 | 10/2010 |
| EP | 2030578 B1 | 11/2010 |
| EP | 2036505 B1 | 11/2010 |
| EP | 2245993 A2 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1690502 B1 | 3/2011 |
| EP | 1884201 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 1728475 B1 | 8/2011 |
| EP | 2353545 A1 | 8/2011 |
| EP | 2361562 A1 | 8/2011 |
| EP | 1936253 B1 | 10/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2397079 A1 | 12/2011 |
| EP | 2399538 A2 | 12/2011 |
| EP | 1785102 B1 | 1/2012 |
| EP | 2415416 A1 | 2/2012 |
| EP | 2090253 B1 | 3/2012 |
| EP | 2430986 A2 | 3/2012 |
| EP | 2444008 A2 | 4/2012 |
| EP | 1347638 B1 | 5/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 B1 | 8/2012 |
| EP | 2481359 A1 | 8/2012 |
| EP | 2486860 A2 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 2526883 A1 | 11/2012 |
| EP | 2191778 B1 | 12/2012 |
| EP | 1884206 B1 | 3/2013 |
| EP | 2090238 B1 | 4/2013 |
| EP | 1806103 B1 | 5/2013 |
| EP | 2586380 A1 | 5/2013 |
| EP | 1982657 B1 | 7/2013 |
| EP | 2614782 A2 | 7/2013 |
| EP | 2090234 B1 | 9/2013 |
| EP | 2633830 A1 | 9/2013 |
| EP | 2090244 B1 | 10/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 2713902 A1 | 4/2014 |
| EP | 1772105 B1 | 5/2014 |
| EP | 2759267 A2 | 7/2014 |
| EP | 2777528 A2 | 9/2014 |
| EP | 2777538 A2 | 9/2014 |
| EP | 2446835 B1 | 1/2015 |
| EP | 2891460 A1 | 7/2015 |
| EP | 2923660 A2 | 9/2015 |
| EP | 2371296 B1 | 8/2016 |
| EP | 2116192 B1 | 3/2017 |
| EP | 3135208 A2 | 3/2017 |
| EP | 2621364 B1 | 6/2017 |
| EP | 3005956 B1 | 9/2017 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |

(56) References Cited

FOREIGN PATENT DOCUMENTS

| | | |
|---|---|---|
| GB | 2425903 A | 11/2006 |
| GB | 2423199 B | 5/2009 |
| GR | 930100110 A | 11/1993 |
| JP | S4711908 Y1 | 5/1972 |
| JP | S5033988 U | 4/1975 |
| JP | S56112235 A | 9/1981 |
| JP | S58500053 A | 1/1983 |
| JP | S58501360 A | 8/1983 |
| JP | S59174920 A | 10/1984 |
| JP | S60100955 A | 6/1985 |
| JP | S60212152 A | 10/1985 |
| JP | S6198249 A | 5/1986 |
| JP | S61502036 A | 9/1986 |
| JP | S62170011 U | 10/1987 |
| JP | S6359764 A | 3/1988 |
| JP | S63147449 A | 6/1988 |
| JP | S63203149 A | 8/1988 |
| JP | H02279149 A | 11/1990 |
| JP | H0312126 A | 1/1991 |
| JP | H04215747 A | 8/1992 |
| JP | H04131860 U | 12/1992 |
| JP | H0584252 A | 4/1993 |
| JP | H05123325 A | 5/1993 |
| JP | H05212039 A | 8/1993 |
| JP | H05237126 A | 9/1993 |
| JP | H067357 A | 1/1994 |
| JP | H0630945 A | 2/1994 |
| JP | H0654857 A | 3/1994 |
| JP | H0663054 A | 3/1994 |
| JP | H0626812 U | 4/1994 |
| JP | H06121798 A | 5/1994 |
| JP | H06125913 A | 5/1994 |
| JP | H06197901 A | 7/1994 |
| JP | H06237937 A | 8/1994 |
| JP | H06327684 A | 11/1994 |
| JP | H079622 U | 2/1995 |
| JP | H0731623 A | 2/1995 |
| JP | H0747070 A | 2/1995 |
| JP | H0751273 A | 2/1995 |
| JP | H07124166 A | 5/1995 |
| JP | H07163574 A | 6/1995 |
| JP | H07171163 A | 7/1995 |
| JP | H07255735 A | 10/1995 |
| JP | H07285089 A | 10/1995 |
| JP | H0833641 A | 2/1996 |
| JP | H0833642 A | 2/1996 |
| JP | H08159124 A | 6/1996 |
| JP | H08164141 A | 6/1996 |
| JP | H08182684 A | 7/1996 |
| JP | H08507708 A | 8/1996 |
| JP | H08229050 A | 9/1996 |
| JP | H08336540 A | 12/1996 |
| JP | H08336544 A | 12/1996 |
| JP | H09501081 A | 2/1997 |
| JP | H09501577 A | 2/1997 |
| JP | H09164144 A | 6/1997 |
| JP | H10113352 A | 5/1998 |
| JP | H10118090 A | 5/1998 |
| JP | H10512469 A | 12/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001046384 A | 2/2001 |
| JP | 2001087272 A | 4/2001 |
| JP | 2001514541 A | 9/2001 |
| JP | 2001276091 A | 10/2001 |
| JP | 2001286477 A | 10/2001 |
| JP | 2001517473 A | 10/2001 |
| JP | 2002051974 A | 2/2002 |
| JP | 2002085415 A | 3/2002 |
| JP | 2002143078 A | 5/2002 |
| JP | 2002204801 A | 7/2002 |
| JP | 2002528161 A | 9/2002 |
| JP | 2002314298 A | 10/2002 |
| JP | 2002369820 A | 12/2002 |
| JP | 2003000603 A | 1/2003 |
| JP | 2003500153 A | 1/2003 |
| JP | 2003504104 A | 2/2003 |
| JP | 2003135473 A | 5/2003 |
| JP | 2003148903 A | 5/2003 |
| JP | 2003164066 A | 6/2003 |
| JP | 2003521301 A | 7/2003 |
| JP | 2003523251 A | 8/2003 |
| JP | 2003523254 A | 8/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2004524076 A | 8/2004 |
| JP | 2004531280 A | 10/2004 |
| JP | 2004532084 A | 10/2004 |
| JP | 2004532676 A | 10/2004 |
| JP | 2004329624 A | 11/2004 |
| JP | 2004337617 A | 12/2004 |
| JP | 2004344662 A | 12/2004 |
| JP | 2004344663 A | 12/2004 |
| JP | 2005013573 A | 1/2005 |
| JP | 2005028147 A | 2/2005 |
| JP | 2005028148 A | 2/2005 |
| JP | 2005028149 A | 2/2005 |
| JP | 2005505309 A | 2/2005 |
| JP | 2005505322 A | 2/2005 |
| JP | 2005505334 A | 2/2005 |
| JP | 2005080702 A | 3/2005 |
| JP | 2005103280 A | 4/2005 |
| JP | 2005103281 A | 4/2005 |
| JP | 2005103293 A | 4/2005 |
| JP | 2005511131 A | 4/2005 |
| JP | 2005511137 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005137919 A | 6/2005 |
| JP | 2005144183 A | 6/2005 |
| JP | 2005152416 A | 6/2005 |
| JP | 2005516714 A | 6/2005 |
| JP | 2005521109 A | 7/2005 |
| JP | 2005523105 A | 8/2005 |
| JP | 2005524474 A | 8/2005 |
| JP | 2005296412 A | 10/2005 |
| JP | 2005328882 A | 12/2005 |
| JP | 2005335432 A | 12/2005 |
| JP | 2005342267 A | 12/2005 |
| JP | 2006034975 A | 2/2006 |
| JP | 2006034977 A | 2/2006 |
| JP | 2006034978 A | 2/2006 |
| JP | 2006034980 A | 2/2006 |
| JP | 2006506106 A | 2/2006 |
| JP | 2006510879 A | 3/2006 |
| JP | 2006187649 A | 7/2006 |
| JP | 2006218297 A | 8/2006 |
| JP | 2006223872 A | 8/2006 |
| JP | 2006281405 A | 10/2006 |
| JP | 2006289064 A | 10/2006 |
| JP | 2006334412 A | 12/2006 |
| JP | 2006334417 A | 12/2006 |
| JP | 2006346445 A | 12/2006 |
| JP | 2007000634 A | 1/2007 |
| JP | 2007050253 A | 3/2007 |
| JP | 2007061628 A | 3/2007 |
| JP | 3906843 B2 | 4/2007 |
| JP | 2007083051 A | 4/2007 |
| JP | 2007098130 A | 4/2007 |
| JP | 2007105481 A | 4/2007 |
| JP | 2007117725 A | 5/2007 |
| JP | 2007130471 A | 5/2007 |
| JP | 2007130479 A | 5/2007 |

(56) References Cited

FOREIGN PATENT DOCUMENTS

| | | |
|---|---|---|
| JP | 3934161 B2 | 6/2007 |
| JP | 2007203049 A | 8/2007 |
| JP | 2007203051 A | 8/2007 |
| JP | 2007203055 A | 8/2007 |
| JP | 2007203057 A | 8/2007 |
| JP | 2007524435 A | 8/2007 |
| JP | 2007222615 A | 9/2007 |
| JP | 2007229448 A | 9/2007 |
| JP | 4001860 B2 | 10/2007 |
| JP | 2007252916 A | 10/2007 |
| JP | 2007307373 A | 11/2007 |
| JP | 2007325922 A | 12/2007 |
| JP | 2008068073 A | 3/2008 |
| JP | 2008206967 A | 9/2008 |
| JP | 2008212637 A | 9/2008 |
| JP | 2008212638 A | 9/2008 |
| JP | 2008220956 A | 9/2008 |
| JP | 2008237881 A | 10/2008 |
| JP | 2008259860 A | 10/2008 |
| JP | 2008264535 A | 11/2008 |
| JP | 2008283459 A | 11/2008 |
| JP | 2009006137 A | 1/2009 |
| JP | 2009502351 A | 1/2009 |
| JP | 2009502352 A | 1/2009 |
| JP | 2009022742 A | 2/2009 |
| JP | 2009506799 A | 2/2009 |
| JP | 2009507526 A | 2/2009 |
| JP | 2009072599 A | 4/2009 |
| JP | 2009090113 A | 4/2009 |
| JP | 2009106752 A | 5/2009 |
| JP | 2009189836 A | 8/2009 |
| JP | 2009189837 A | 8/2009 |
| JP | 2009189838 A | 8/2009 |
| JP | 2009201998 A | 9/2009 |
| JP | 2009536082 A | 10/2009 |
| JP | 2009261944 A | 11/2009 |
| JP | 2009268908 A | 11/2009 |
| JP | 2009539420 A | 11/2009 |
| JP | 2009291604 A | 12/2009 |
| JP | 2010504808 A | 2/2010 |
| JP | 2010504809 A | 2/2010 |
| JP | 2010504846 A | 2/2010 |
| JP | 2010505524 A | 2/2010 |
| JP | 2010069310 A | 4/2010 |
| JP | 2010075695 A | 4/2010 |
| JP | 2010088876 A | 4/2010 |
| JP | 2010098844 A | 4/2010 |
| JP | 4461008 B2 | 5/2010 |
| JP | 4549018 B2 | 9/2010 |
| JP | 2010214166 A | 9/2010 |
| JP | 2010540192 A | 12/2010 |
| JP | 4783373 B2 | 9/2011 |
| JP | 2011524199 A | 9/2011 |
| JP | 5140421 B2 | 2/2013 |
| JP | 5162595 B2 | 3/2013 |
| JP | 2013128791 A | 7/2013 |
| JP | 5333899 B2 | 11/2013 |
| JP | 2013541982 A | 11/2013 |
| JP | 2013541993 A | 11/2013 |
| JP | 2013542000 A | 11/2013 |
| KR | 20110003229 A | 1/2011 |
| RU | 1814161 A1 | 5/1993 |
| RU | 2008830 C1 | 3/1994 |
| RU | 2052979 C1 | 1/1996 |
| RU | 94026118 A | 7/1996 |
| RU | 94014586 A | 11/1996 |
| RU | 2098025 C1 | 12/1997 |
| RU | 2141279 C1 | 11/1999 |
| RU | 2144791 C1 | 1/2000 |
| RU | 2152756 C1 | 7/2000 |
| RU | 2161450 C1 | 1/2001 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 2242183 C2 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO-8202824 A1 | 9/1982 |
| WO | WO-8602254 A1 | 4/1986 |
| WO | WO-9115157 A1 | 10/1991 |
| WO | WO-9220295 A1 | 11/1992 |
| WO | WO-9221300 A1 | 12/1992 |
| WO | WO-9308755 A1 | 5/1993 |
| WO | WO-9313718 A1 | 7/1993 |
| WO | WO-9314690 A1 | 8/1993 |
| WO | WO-9315648 A1 | 8/1993 |
| WO | WO-9315850 A1 | 8/1993 |
| WO | WO-9319681 A1 | 10/1993 |
| WO | WO-9400060 A1 | 1/1994 |
| WO | WO-9411057 A1 | 5/1994 |
| WO | WO-9412108 A1 | 6/1994 |
| WO | WO-9417737 A1 | 8/1994 |
| WO | WO-9418893 A1 | 9/1994 |
| WO | WO-9420030 A1 | 9/1994 |
| WO | WO-9422378 A1 | 10/1994 |
| WO | WO-9423659 A1 | 10/1994 |
| WO | WO-9424943 A1 | 11/1994 |
| WO | WO-9424947 A1 | 11/1994 |
| WO | WO-9502369 A1 | 1/1995 |
| WO | WO-9503743 A1 | 2/1995 |
| WO | WO-9506817 A1 | 3/1995 |
| WO | WO-9509576 A1 | 4/1995 |
| WO | WO-9509577 A1 | 4/1995 |
| WO | WO-9514436 A1 | 6/1995 |
| WO | WO-9517855 A1 | 7/1995 |
| WO | WO-9518383 A1 | 7/1995 |
| WO | WO-9518572 A1 | 7/1995 |
| WO | WO-9519739 A1 | 7/1995 |
| WO | WO-9520360 A1 | 8/1995 |
| WO | WO-9523557 A1 | 9/1995 |
| WO | WO-9524865 A1 | 9/1995 |
| WO | WO-9525471 A3 | 9/1995 |
| WO | WO-9526562 A1 | 10/1995 |
| WO | WO-9529639 A1 | 11/1995 |
| WO | WO-9604858 A1 | 2/1996 |
| WO | WO-9618344 A2 | 6/1996 |
| WO | WO-9619151 A1 | 6/1996 |
| WO | WO-9619152 A1 | 6/1996 |
| WO | WO-9620652 A1 | 7/1996 |
| WO | WO-9621119 A1 | 7/1996 |
| WO | WO-9622055 A1 | 7/1996 |
| WO | WO-9623448 A1 | 8/1996 |
| WO | WO-9624301 A1 | 8/1996 |
| WO | WO-9627337 A1 | 9/1996 |
| WO | WO-9631155 A1 | 10/1996 |
| WO | WO-9635464 A1 | 11/1996 |
| WO | WO-9639085 A1 | 12/1996 |
| WO | WO-9639086 A1 | 12/1996 |
| WO | WO-9639087 A1 | 12/1996 |
| WO | WO-9639088 A1 | 12/1996 |
| WO | WO-9639089 A1 | 12/1996 |
| WO | WO-9700646 A1 | 1/1997 |
| WO | WO-9700647 A1 | 1/1997 |
| WO | WO-9701989 A1 | 1/1997 |
| WO | WO-9706582 A1 | 2/1997 |
| WO | WO-9710763 A1 | 3/1997 |
| WO | WO-9710764 A1 | 3/1997 |
| WO | WO-9711648 A2 | 4/1997 |
| WO | WO-9711649 A1 | 4/1997 |

(56) References Cited

FOREIGN PATENT DOCUMENTS

| | | |
|---|---|---|
| WO | WO-9715237 A1 | 5/1997 |
| WO | WO-9724073 A1 | 7/1997 |
| WO | WO-9724993 A1 | 7/1997 |
| WO | WO-9730644 A1 | 8/1997 |
| WO | WO-9734533 A1 | 9/1997 |
| WO | WO-9737598 A1 | 10/1997 |
| WO | WO-9739688 A2 | 10/1997 |
| WO | WO-9801080 A1 | 1/1998 |
| WO | WO-9817180 A1 | 4/1998 |
| WO | WO-9822154 A2 | 5/1998 |
| WO | WO-9827880 A1 | 7/1998 |
| WO | WO-9830153 A1 | 7/1998 |
| WO | WO-9847436 A1 | 10/1998 |
| WO | WO-9858589 A1 | 12/1998 |
| WO | WO-9902090 A1 | 1/1999 |
| WO | WO-9903407 A1 | 1/1999 |
| WO | WO-9903408 A1 | 1/1999 |
| WO | WO-9903409 A1 | 1/1999 |
| WO | WO-9912483 A1 | 3/1999 |
| WO | WO-9912487 A1 | 3/1999 |
| WO | WO-9912488 A1 | 3/1999 |
| WO | WO-9915086 A1 | 4/1999 |
| WO | WO-9915091 A1 | 4/1999 |
| WO | WO-9923933 A2 | 5/1999 |
| WO | WO-9923959 A1 | 5/1999 |
| WO | WO-9925261 A1 | 5/1999 |
| WO | WO-9929244 A1 | 6/1999 |
| WO | WO-9934744 A1 | 7/1999 |
| WO | WO-9945849 A1 | 9/1999 |
| WO | WO-9948430 A1 | 9/1999 |
| WO | WO-9951158 A1 | 10/1999 |
| WO | WO-0024322 A1 | 5/2000 |
| WO | WO-0024330 A1 | 5/2000 |
| WO | WO-0041638 A1 | 7/2000 |
| WO | WO-0048506 A1 | 8/2000 |
| WO | WO-0053112 A2 | 9/2000 |
| WO | WO-0054653 A1 | 9/2000 |
| WO | WO-0057796 A1 | 10/2000 |
| WO | WO-0064365 A1 | 11/2000 |
| WO | WO-0072762 A1 | 12/2000 |
| WO | WO-0072765 A1 | 12/2000 |
| WO | WO-0078222 A1 | 12/2000 |
| WO | WO-0103587 A1 | 1/2001 |
| WO | WO-0105702 A1 | 1/2001 |
| WO | WO-0110482 A1 | 2/2001 |
| WO | WO-0135845 A1 | 5/2001 |
| WO | WO-0154594 A1 | 8/2001 |
| WO | WO-0158371 A1 | 8/2001 |
| WO | WO-0162158 A2 | 8/2001 |
| WO | WO-0162161 A1 | 8/2001 |
| WO | WO-0162162 A1 | 8/2001 |
| WO | WO-0162163 A1 | 8/2001 |
| WO | WO-0162164 A2 | 8/2001 |
| WO | WO-0162169 A2 | 8/2001 |
| WO | WO-0178605 A2 | 10/2001 |
| WO | WO-0180757 A2 | 11/2001 |
| WO | WO-0191646 A1 | 12/2001 |
| WO | WO-0200121 A1 | 1/2002 |
| WO | WO-0207608 A2 | 1/2002 |
| WO | WO-0207618 A1 | 1/2002 |
| WO | WO-0217799 A1 | 3/2002 |
| WO | WO-0219920 A1 | 3/2002 |
| WO | WO-0219932 A1 | 3/2002 |
| WO | WO-0226143 A1 | 4/2002 |
| WO | WO-0230297 A2 | 4/2002 |
| WO | WO-0232322 A2 | 4/2002 |
| WO | WO-0236028 A1 | 5/2002 |
| WO | WO-0243571 A2 | 6/2002 |
| WO | WO-02058568 A1 | 8/2002 |
| WO | WO-02060328 A1 | 8/2002 |
| WO | WO-02065933 A2 | 8/2002 |
| WO | WO-02067785 A2 | 9/2002 |
| WO | WO-02080781 A2 | 10/2002 |
| WO | WO-02085218 A2 | 10/2002 |
| WO | WO-02087586 A1 | 11/2002 |
| WO | WO-02098302 A1 | 12/2002 |
| WO | WO-03000138 A2 | 1/2003 |
| WO | WO-03001329 A2 | 1/2003 |
| WO | WO-03001986 A2 | 1/2003 |
| WO | WO-03013363 A1 | 2/2003 |
| WO | WO-03013372 A2 | 2/2003 |
| WO | WO-03015604 A2 | 2/2003 |
| WO | WO-03020106 A2 | 3/2003 |
| WO | WO-03020139 A2 | 3/2003 |
| WO | WO-03024339 A1 | 3/2003 |
| WO | WO-03030743 A2 | 4/2003 |
| WO | WO-03037193 A1 | 5/2003 |
| WO | WO-03055402 A1 | 7/2003 |
| WO | WO-03057048 A1 | 7/2003 |
| WO | WO-03057058 A1 | 7/2003 |
| WO | WO-03063694 A1 | 8/2003 |
| WO | WO-03077769 A1 | 9/2003 |
| WO | WO-03079911 A1 | 10/2003 |
| WO | WO-03082126 A1 | 10/2003 |
| WO | WO-03086206 A1 | 10/2003 |
| WO | WO-03088845 A2 | 10/2003 |
| WO | WO-03047436 A3 | 11/2003 |
| WO | WO-03090630 A2 | 11/2003 |
| WO | WO-03094743 A1 | 11/2003 |
| WO | WO-03094745 A1 | 11/2003 |
| WO | WO-03094746 A1 | 11/2003 |
| WO | WO-03094747 A1 | 11/2003 |
| WO | WO-03101313 A1 | 12/2003 |
| WO | WO-03105698 A2 | 12/2003 |
| WO | WO-03105702 A2 | 12/2003 |
| WO | WO-2004004578 A1 | 1/2004 |
| WO | WO-2004006980 A2 | 1/2004 |
| WO | WO-2004011037 A2 | 2/2004 |
| WO | WO-2004014238 A2 | 2/2004 |
| WO | WO-03079909 A3 | 3/2004 |
| WO | WO-2004019769 A1 | 3/2004 |
| WO | WO-2004019803 A1 | 3/2004 |
| WO | WO-2004021868 A2 | 3/2004 |
| WO | WO-2004028585 A2 | 4/2004 |
| WO | WO-2004030554 A1 | 4/2004 |
| WO | WO-2004032754 A2 | 4/2004 |
| WO | WO-2004032760 A2 | 4/2004 |
| WO | WO-2004032762 A1 | 4/2004 |
| WO | WO-2004032763 A2 | 4/2004 |
| WO | WO-2004032783 A1 | 4/2004 |
| WO | WO-2004034875 A2 | 4/2004 |
| WO | WO-2004047626 A1 | 6/2004 |
| WO | WO-2004047653 A2 | 6/2004 |
| WO | WO-2004049956 A2 | 6/2004 |
| WO | WO-2004050971 A2 | 6/2004 |
| WO | WO-2004052426 A2 | 6/2004 |
| WO | WO-2004056276 A1 | 7/2004 |
| WO | WO-2004056277 A1 | 7/2004 |
| WO | WO-2004058079 A2 | 7/2004 |
| WO | WO-2004062516 A1 | 7/2004 |
| WO | WO-2004064600 A2 | 8/2004 |
| WO | WO-2004078050 A2 | 9/2004 |
| WO | WO-2004078051 A2 | 9/2004 |
| WO | WO-2004078236 A2 | 9/2004 |
| WO | WO-2004086987 A1 | 10/2004 |
| WO | WO-2004096015 A2 | 11/2004 |
| WO | WO-2004096057 A2 | 11/2004 |
| WO | WO-2004103157 A2 | 12/2004 |
| WO | WO-2004105593 A1 | 12/2004 |
| WO | WO-2004105621 A1 | 12/2004 |
| WO | WO-2004112618 A2 | 12/2004 |
| WO | WO-2004112652 A2 | 12/2004 |
| WO | WO-2005027983 A2 | 3/2005 |
| WO | WO-2005037329 A2 | 4/2005 |
| WO | WO-2005042041 A1 | 5/2005 |
| WO | WO-2005044078 A2 | 5/2005 |
| WO | WO-2005055846 A2 | 6/2005 |
| WO | WO-2005072634 A2 | 8/2005 |
| WO | WO-2005078892 A1 | 8/2005 |
| WO | WO-2005079675 A2 | 9/2005 |
| WO | WO-2005087128 A1 | 9/2005 |
| WO | WO-2005096954 A2 | 10/2005 |
| WO | WO-2005112806 A2 | 12/2005 |
| WO | WO-2005112808 A1 | 12/2005 |

(56) References Cited

FOREIGN PATENT DOCUMENTS

| | | |
|---|---|---|
| WO | WO-2005115251 A1 | 12/2005 |
| WO | WO-2005115253 A2 | 12/2005 |
| WO | WO-2005117735 A1 | 12/2005 |
| WO | WO-2005122936 A1 | 12/2005 |
| WO | WO-2006023486 A1 | 3/2006 |
| WO | WO-2006023578 A2 | 3/2006 |
| WO | WO-2006027014 A1 | 3/2006 |
| WO | WO-2006028314 A1 | 3/2006 |
| WO | WO-2006044490 A2 | 4/2006 |
| WO | WO-2006044581 A2 | 4/2006 |
| WO | WO-2006044810 A2 | 4/2006 |
| WO | WO-2006049852 A2 | 5/2006 |
| WO | WO-2006051252 A1 | 5/2006 |
| WO | WO-2006059067 A1 | 6/2006 |
| WO | WO-2006083748 A1 | 8/2006 |
| WO | WO-2006085389 A1 | 8/2006 |
| WO | WO-2006092563 A1 | 9/2006 |
| WO | WO-2006092565 A1 | 9/2006 |
| WO | WO-2006115958 A1 | 11/2006 |
| WO | WO-2006125940 A1 | 11/2006 |
| WO | WO-2006132992 A2 | 12/2006 |
| WO | WO-2007002180 A2 | 1/2007 |
| WO | WO-2007016290 A2 | 2/2007 |
| WO | WO-2007018898 A2 | 2/2007 |
| WO | WO-2007059233 A2 | 5/2007 |
| WO | WO-2007074430 A1 | 7/2007 |
| WO | WO-2007089603 A2 | 8/2007 |
| WO | WO-2007098220 A2 | 8/2007 |
| WO | WO-2007121579 A1 | 11/2007 |
| WO | WO-2007129121 A1 | 11/2007 |
| WO | WO-2007131110 A2 | 11/2007 |
| WO | WO-2007137304 A2 | 11/2007 |
| WO | WO-2007139734 A2 | 12/2007 |
| WO | WO-2007142625 A2 | 12/2007 |
| WO | WO-2007145825 A2 | 12/2007 |
| WO | WO-2007146987 A2 | 12/2007 |
| WO | WO-2007147439 A1 | 12/2007 |
| WO | WO-2008020964 A2 | 2/2008 |
| WO | WO-2008021969 A2 | 2/2008 |
| WO | WO-2008039237 A1 | 4/2008 |
| WO | WO-2008039249 A1 | 4/2008 |
| WO | WO-2008039270 A1 | 4/2008 |
| WO | WO-2008045383 A2 | 4/2008 |
| WO | WO-2008057281 A2 | 5/2008 |
| WO | WO-2008070763 A1 | 6/2008 |
| WO | WO-2008089404 A2 | 7/2008 |
| WO | WO-2008101080 A1 | 8/2008 |
| WO | WO-2008101228 A2 | 8/2008 |
| WO | WO-2008103797 A2 | 8/2008 |
| WO | WO-2008109125 A1 | 9/2008 |
| WO | WO-2008112912 A2 | 9/2008 |
| WO | WO-2008118728 A1 | 10/2008 |
| WO | WO-2008124748 A1 | 10/2008 |
| WO | WO-2009005969 A2 | 1/2009 |
| WO | WO-2009022614 A1 | 2/2009 |
| WO | WO-2009023851 A1 | 2/2009 |
| WO | WO-2009033057 A2 | 3/2009 |
| WO | WO-2009039506 A1 | 3/2009 |
| WO | WO-2009046394 A1 | 4/2009 |
| WO | WO-2009067649 A2 | 5/2009 |
| WO | WO-2009091497 A2 | 7/2009 |
| WO | WO-2009120944 A2 | 10/2009 |
| WO | WO-2009137761 A2 | 11/2009 |
| WO | WO-2009143092 A1 | 11/2009 |
| WO | WO-2009143331 A1 | 11/2009 |
| WO | WO-2009150650 A2 | 12/2009 |
| WO | WO-2009152307 A1 | 12/2009 |
| WO | WO-2010028332 A2 | 3/2010 |
| WO | WO-2010030434 A1 | 3/2010 |
| WO | WO-2010045425 A1 | 4/2010 |
| WO | WO-2010050771 A2 | 5/2010 |
| WO | WO-2010054404 A1 | 5/2010 |
| WO | WO-2010056714 A1 | 5/2010 |
| WO | WO-2010063795 A1 | 6/2010 |
| WO | WO-2010090940 A1 | 8/2010 |
| WO | WO-2010093333 A1 | 8/2010 |
| WO | WO-2010098871 A2 | 9/2010 |
| WO | WO-2011008672 A2 | 1/2011 |
| WO | WO-2011013103 A1 | 2/2011 |
| WO | WO-2011044343 A2 | 4/2011 |
| WO | WO-2011060311 A2 | 5/2011 |
| WO | WO-2012006306 A2 | 1/2012 |
| WO | WO-2012/013577 A1 | 2/2012 |
| WO | WO-2012021671 A1 | 2/2012 |
| WO | WO-2012040438 A1 | 3/2012 |
| WO | WO-2012044551 A1 | 4/2012 |
| WO | WO-2012044554 A1 | 4/2012 |
| WO | WO-2012044597 A1 | 4/2012 |
| WO | WO-2012044606 A2 | 4/2012 |
| WO | WO-2012044820 A1 | 4/2012 |
| WO | WO-2012044844 A2 | 4/2012 |
| WO | WO-2012044853 A1 | 4/2012 |
| WO | WO-2012058213 A2 | 5/2012 |
| WO | WO-2012068156 A2 | 5/2012 |
| WO | WO-2012127462 A1 | 9/2012 |
| WO | WO-2012135705 A1 | 10/2012 |
| WO | WO-2012143913 A2 | 10/2012 |
| WO | WO-2012148667 A2 | 11/2012 |
| WO | WO-2012148703 A2 | 11/2012 |
| WO | WO-2012160163 A1 | 11/2012 |
| WO | WO-2012166503 A1 | 12/2012 |
| WO | WO-2013009699 A2 | 1/2013 |
| WO | WO-2013016633 A1 | 1/2013 |
| WO | WO-2013036409 A1 | 3/2013 |
| WO | WO-2013043707 A2 | 3/2013 |
| WO | WO-2013043717 A1 | 3/2013 |
| WO | WO-2013043721 A2 | 3/2013 |
| WO | WO-2013062978 A2 | 5/2013 |
| WO | WO-2013148762 A2 | 10/2013 |
| WO | WO-2013151888 A1 | 10/2013 |
| WO | WO-2013167427 A1 | 11/2013 |
| WO | WO-2014004199 A1 | 1/2014 |
| WO | WO-2014004294 A2 | 1/2014 |
| WO | WO-2015153340 A2 | 10/2015 |
| WO | WO-2016/057225 A1 | 4/2016 |

OTHER PUBLICATIONS

"Indian Standard: Automotive Vehicles—Brakes and Braking Systems (IS 11852-1:2001)", Mar. 1, 2001.
Allegro MicroSystems, LLC, Automotive Full Bridge Mosfet Driver, A3941-DS, Rev. 5, 21 pages, http://www.allegromicro.com/~/media/Files/Datasheets/A3941-Datasheetashx?la=en.
Anonymous: "Stamping (metalworking)—Wikipedia," Jun. 6, 2016, Retrieved from the Internet: URL: https://en.wikipedia.org/w/index.php?title=Stamping_(metalworking)&oldid=723906245 [retrieved on May 15, 2018].
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Breedveld et al., "A New, Easily Miniaturized Sterrable Endoscope," IEEE Engineering in Medicine and Biology Magazine (Nov./Dec. 2005).
Byrne et al., "Molecular Imprinting Within Hydrogels," Advanced Drug Delivery Reviews, 54 (2002) pp. 149-161.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.

(56) References Cited

OTHER PUBLICATIONS

Chen et al., "Elastomeric Biomaterials for Tissue Engineering," Progress in Polymer Science 38 (2013), pp. 584-671.
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Curved Tip Reload with Tri-Staple™ Technology," (2012), 2 pages.
Covidien Brochure, "Endo GIA™ Reloads with Tri-Staple™ Technology and Endo GIA™ Ultra Universal Staplers," (2010), 2 pages.
Covidien Brochure, "Endo GIA™ Reloads with Tri-Staple™ Technology," (2010), 1 page.
Covidien Brochure, "Endo GIA™ Reloads with Tri-Staple™ Technology," (2010), 2 pages.
Covidien Brochure, "Endo GIA™ Black Reload with Tri-Staple™ Technology," (2012), 2 pages.
Covidien Brochure, "Endo GIA™ Ultra Universal Stapler," (2010), 2 pages.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Stapler™ Technology," (23 pages).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Disclosed Anonymously, "Motor-Driven Surgical Stapler Improvements," Research Disclosure Database No. 526041, Published: Feb. 2008.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Erdmann et al., "Evaluation of the Soft Tissue Biocompatibility of MgCa0.8 and Surgical Steel 316L In Vivo: A Comparative Study in Rabbits," Biomed. Eng. OnLine 2010 9:63 (17 pages).
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
http://ninpgan.netipublications/51-100/89.pdf; 2004, Ning Pan, On Uniqueness of Fibrous Materials, Design & Nature II. Eds: Colins, M. and Brebbia, C. WIT Press, Boston, 493-504.
Jeong et al., "Thermosensitive Sol-Gel Reversible Hydrogels," Advanced Drug Delivery Reviews, 54 (2002) pp. 37-51.
Li et al. "Mg—Zr—Sr Alloys as Biodegradable Implant Materials," *Acta Biomaterialia* 8 (2012) 3177-3188 (12 pages).
Matsuda, "Thermodynamics of Formation of Porous Polymeric Membrane from Solutions," Polymer Journal, vol. 23, No. 5, pp. 435-444 (1991).
Miyata et al., "Biomolecule-Sensitive Hydrogels," Advanced Drug Delivery Reviews, 54 (2002) pp. 79-98.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Pitt et al., "Attachment of Hyaluronan to Metallic Surfaces," J. Biomed. Mater. Res. 68A: pp. 95-106, 2004.
Qiu et al., "Environment-Sensitive Hydrogels for Drug Delivery," Advanced Drug Delivery Reviews, 53 (2001) pp. 321-339.
Schellhamuner et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Sells et al., Covidien Summary: Clinical Study "UCONN Biodynamics: Final Report on Results," (2 pages).
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Solorio et al., "Gelatin Microspheres Crosslinked with Genipin for Local Delivery of Growth Factors," J. Tissue Eng. Regen. Med. (2010), 4(7): pp. 514-523.
The Sodem Aseptic Battery Transfer Kit, Sodem Systems, 2000, 3 pages.
Van Meer et al., "A Disposable Plastic Compact Wrist for Smart Minimally Invasive Surgical Tools," LAAS/CNRS (Aug. 2005).
Yan et al, Comparison of the effects of Mg—6Zn and Ti—3Al—2.5V alloys on TGF-$\beta$/TNF-$\alpha$/VEGF/b-FGF in the healing of the intestinal track in vivo, Biomed. Mater. 9 (2014), 11 pages.
Yan et al., "Comparison of the effects of Mg—6Zn and titanium on intestinal tract in vivo," J Mater Sci: Mater Med (2013), 11 pages.
Young, "Microcellular foams via phase separation," Journal of Vacuum Science & Technology A 4(3), (May/Jun. 1986).

\* cited by examiner

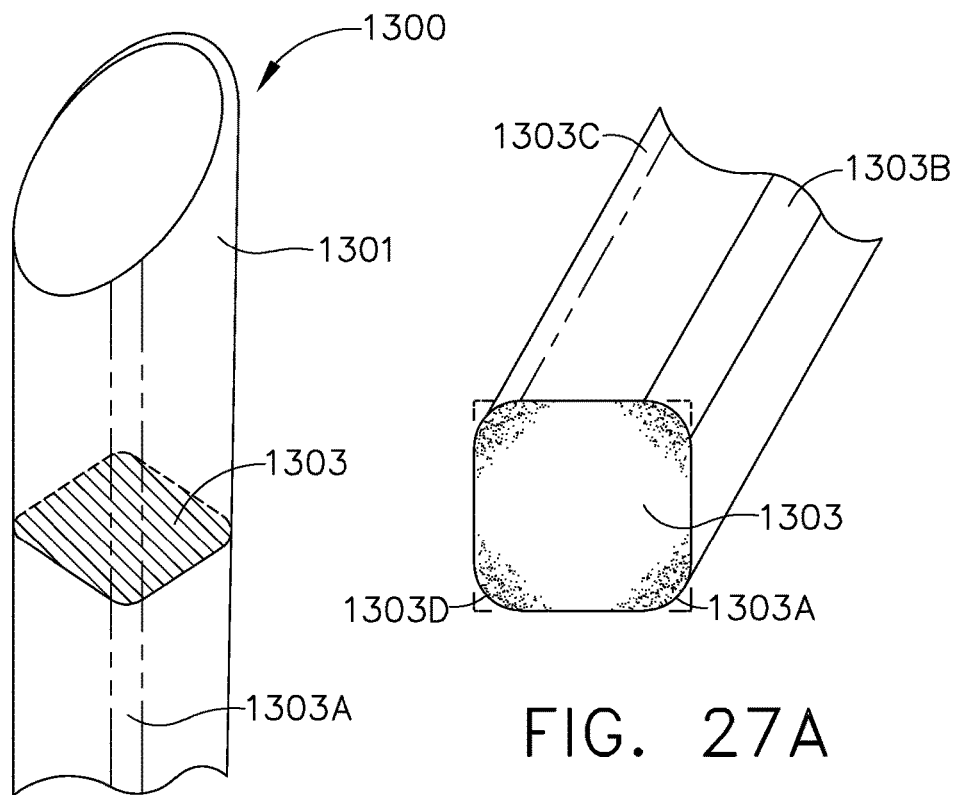
FIG. 27
FIG. 27A
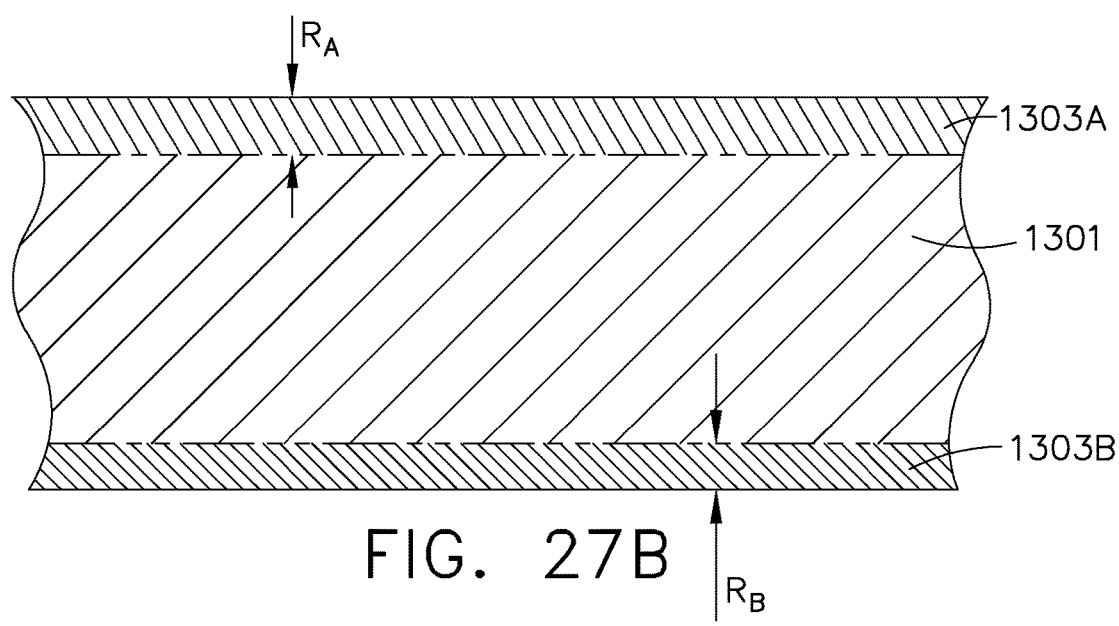
FIG. 27B

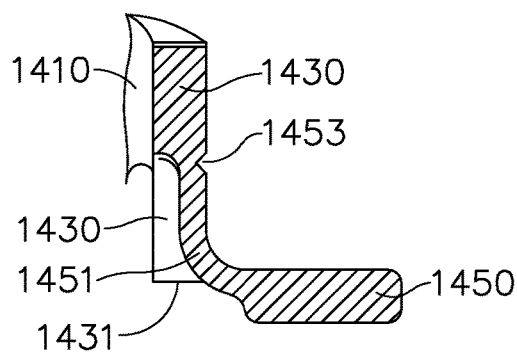
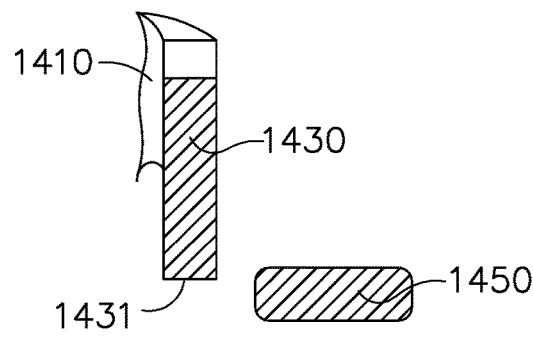
FIG. 28A  FIG. 28B
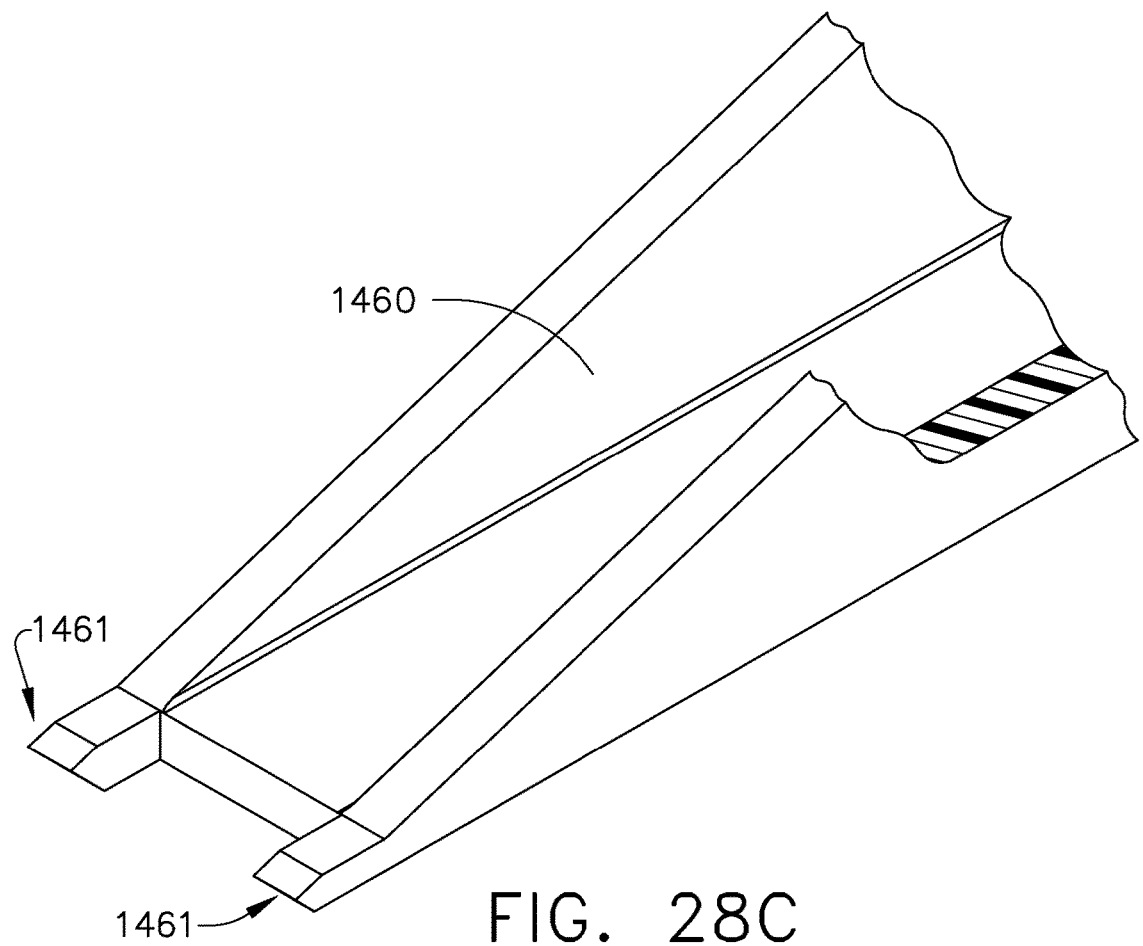
FIG. 28C

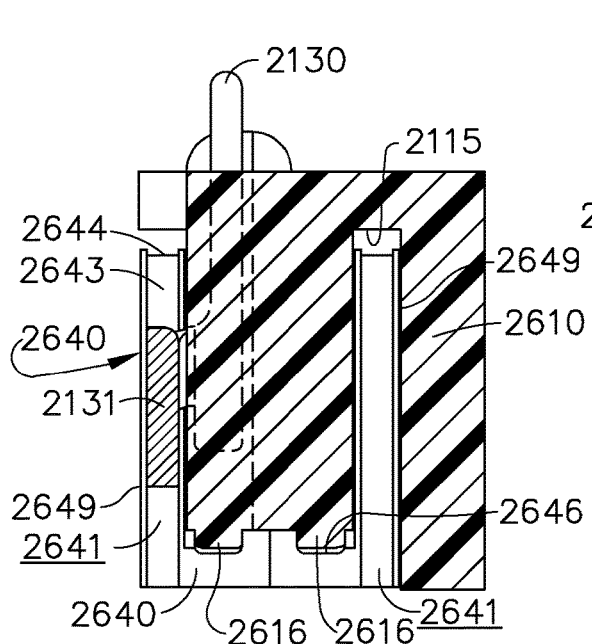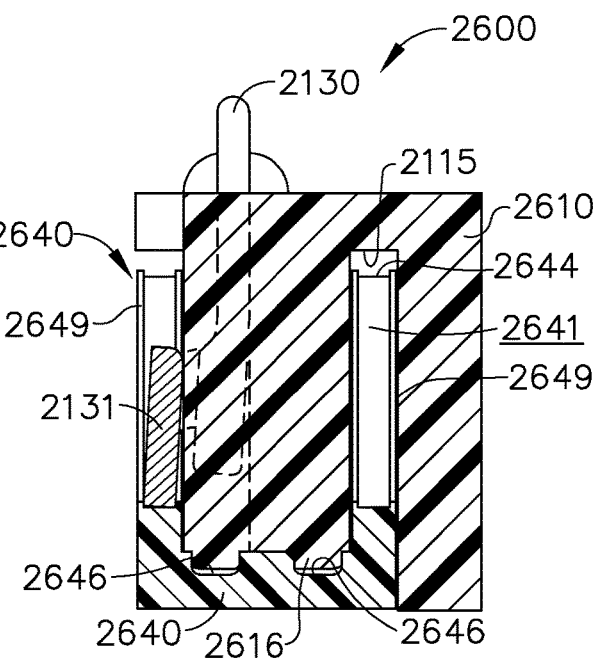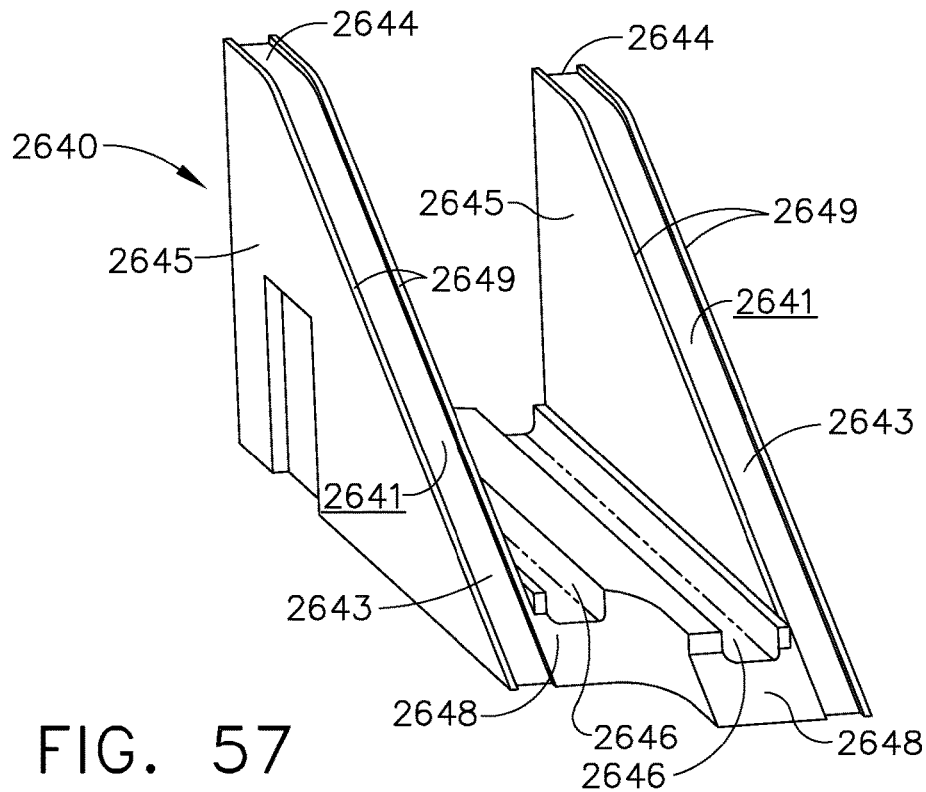

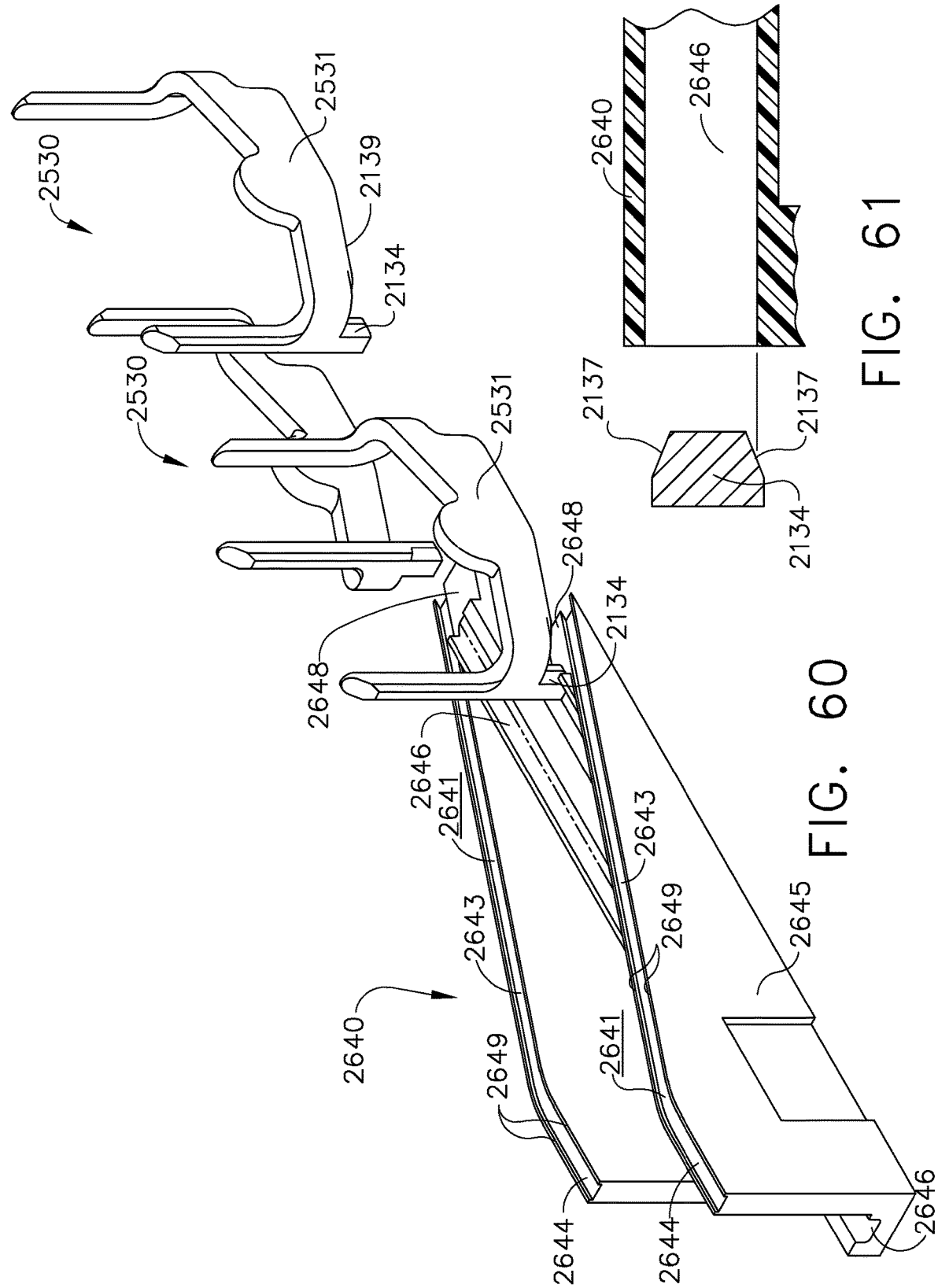

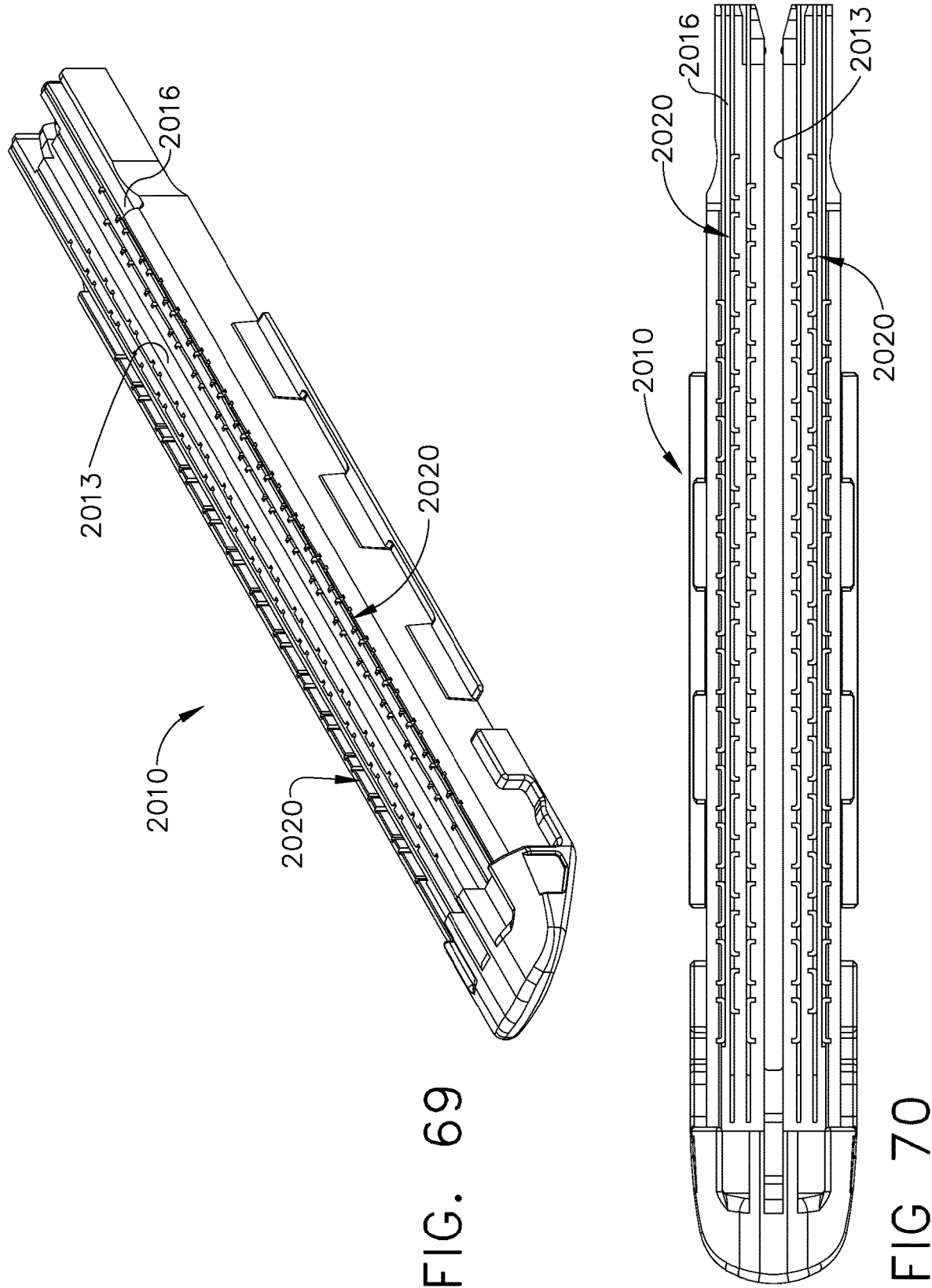

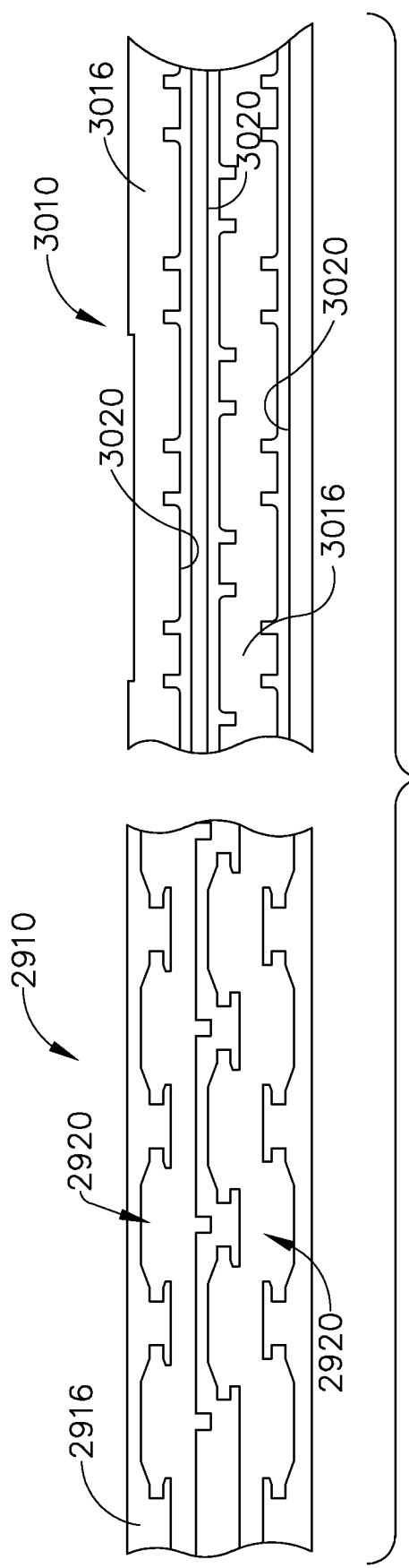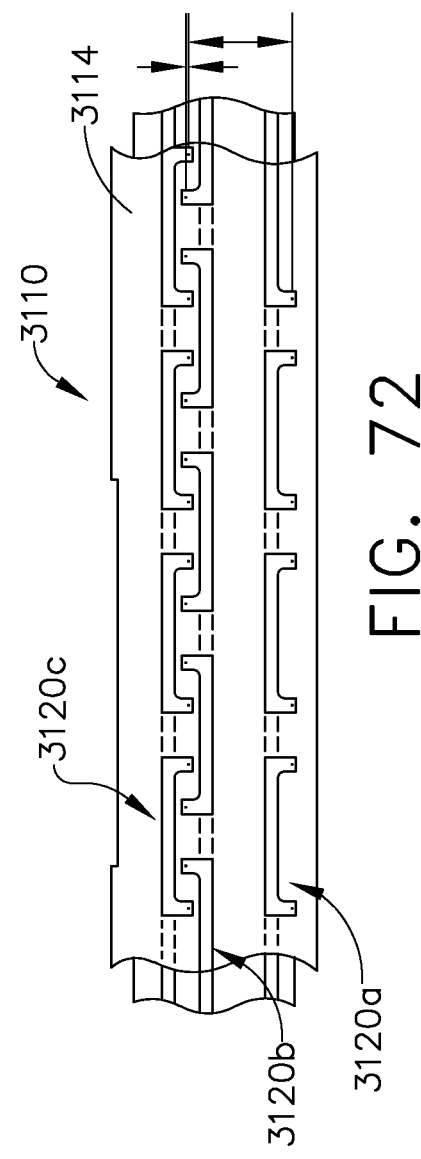
FIG. 71
FIG. 72

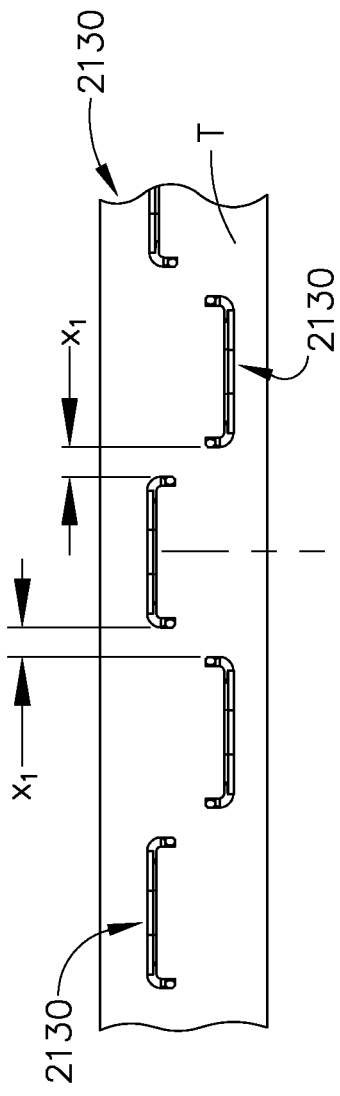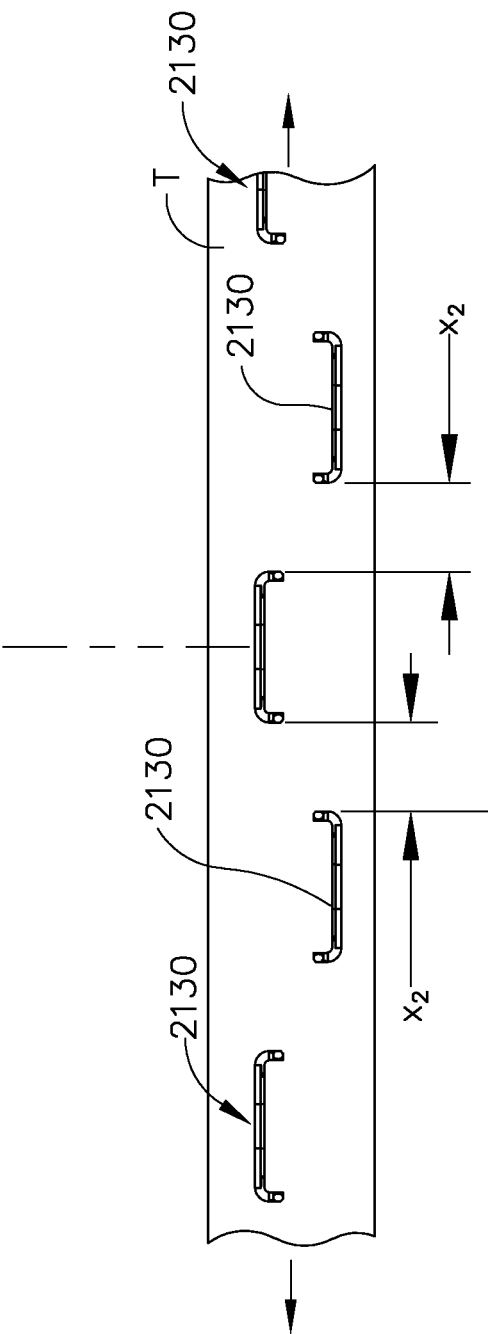

STAPLE CARTRIDGE ASSEMBLY COMPRISING VARIOUS TISSUE COMPRESSION GAPS AND STAPLE FORMING GAPS

BACKGROUND

The present invention relates to surgical instruments and, in various embodiments, to surgical stapling and cutting instruments and staple cartridges for use therewith.

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows.

The foregoing discussion is intended only to illustrate various aspects of the related art in the field of the invention at the time, and should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows:

FIG. 27 is a partial perspective view of a staple leg in accordance with at least one embodiment;

FIG. 27A is a partial cross-sectional end view of the staple leg of FIG. 27;

FIG. 27B is a partial longitudinal cross-section of the staple leg of FIG. 27;

FIG. 28A is a partial cross-sectional view of the portion of the staple strip of FIG. 28 taken along line 28A-28A in FIG. 28;

FIG. 28B is a partial cross-sectional view of the portion of the staple strip of FIG. 28 taken along line 28B-28B in FIG. 28;

FIG. 28C is a partial perspective view of a sled configured to engage the staple strip of FIG. 28;

FIG. 57 is a perspective view of a firing member of a staple cartridge assembly in accordance with at least one embodiment comprising alignment channels;

FIG. 58 is a diagram illustrating the firing member of FIG. 57 and a staple positioned in a staple cavity of a staple cartridge assembly;

FIG. 59 is a diagram illustrating the firing member of FIG. 57 aligning the staple of FIG. 58 within the staple cavity of FIG. 58;

FIG. 60 is a perspective view of the firing member of FIG. 57 and staples arranged in two longitudinal rows;

FIG. 61 is a partial cross-sectional view of an alignment channel of the firing member of FIG. 57 and a portion of the staple of FIG. 58;

FIG. 69 is a bottom perspective view of the cartridge body of the staple cartridge assembly of FIG. 32;

FIG. 70 is a bottom view of the cartridge body of FIG. 32;

FIG. 71 is a diagram illustrating the cartridge body of FIG. 67 to an alternative embodiment of a cartridge body;

FIG. 72 is a partial top plan view of a staple cartridge assembly in accordance with at least one embodiment;

FIG. 88 illustrates the spacing of the staples of FIG. 35 in unstretched tissue;

FIG. 89 illustrates the spacing of the staples of FIG. 35 in stretched tissue;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
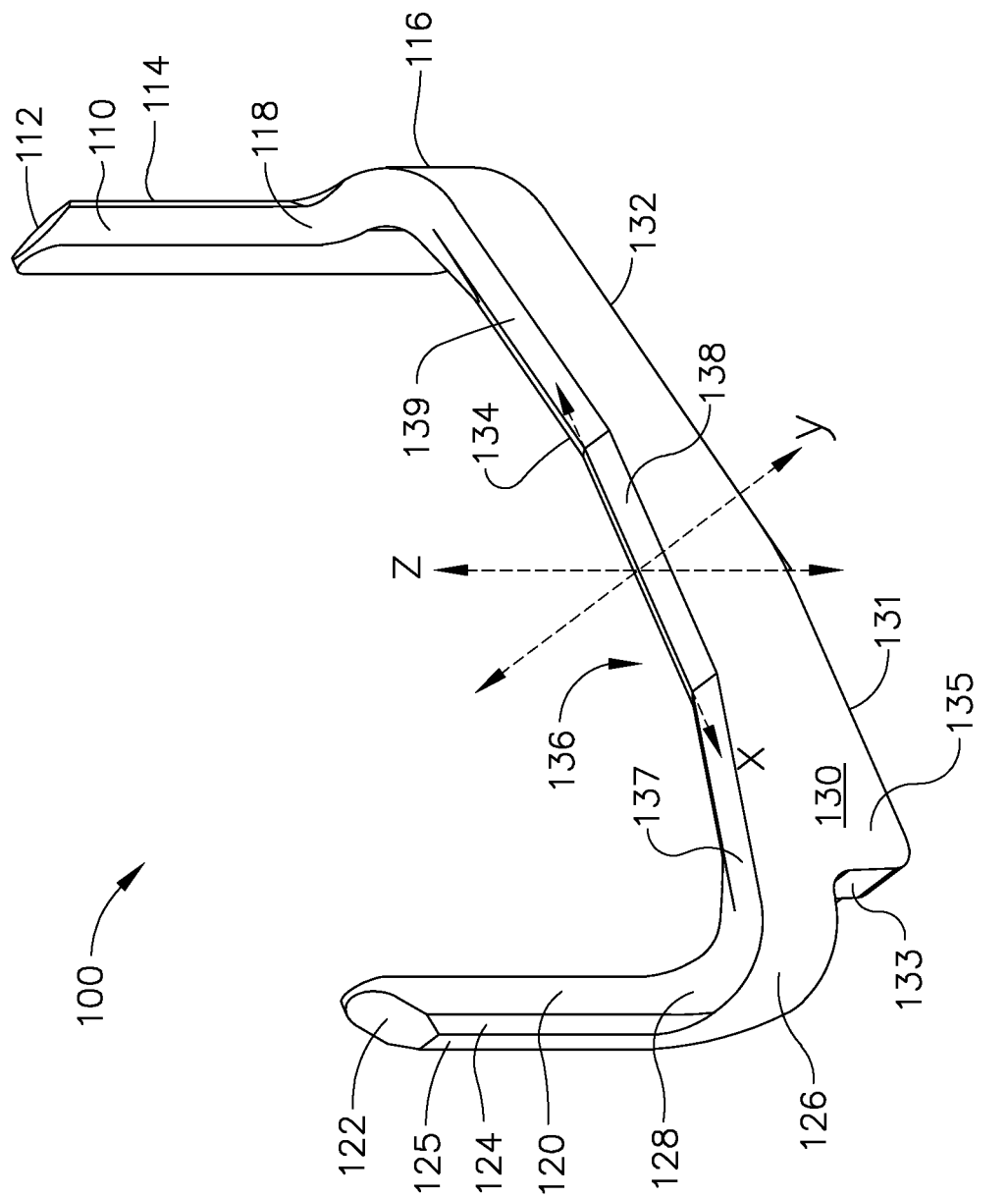
FIG. 1 is a perspective view of a staple for use with a surgical stapling instrument in accordance with at least one embodiment.

The Applicant of the present application owns the following U.S. patent applications that were filed on Aug. 26, 2015 and which are each herein incorporated by reference in their respective entireties:

U.S. patent application Ser. No. 14/836,324, entitled SURGICAL STAPLES FOR MINIMIZING STAPLE ROLL, now U.S. Patent Application Publication No. 2017/0056005;

U.S. patent application Ser. No. 14/836,020, entitled SURGICAL STAPLES COMPRISING FEATURES FOR IMPROVED FASTENING OF TISSUE, now U.S. Pat. No. 10,098,642;

U.S. patent application Ser. No. 14/836,411, entitled SURGICAL STAPLES COMPRISING HARDNESS VARIATIONS FOR IMPROVED FASTENING OF TISSUE, now U.S. Pat. No. 10,357,251;

U.S. patent application Ser. No. 14/836,058, entitled SURGICAL STAPLE STRIPS FOR PERMITTING VARYING STAPLE PROPERTIES AND ENABLING EASY CARTRIDGE LOADING, now U.S. Pat. No. 10,433,845;

U.S. patent application Ser. No. 14/836,110, entitled SURGICAL STAPLING CONFIGURATIONS FOR CURVED AND CIRCULAR STAPLING INSTRUMENTS, now U.S. Patent Application Publication No. 2017/0056000;

U.S. patent application Ser. No. 14/836,036, entitled STAPLE CARTRIDGE ASSEMBLY WITHOUT A BOTTOM COVER, now U.S. Pat. No. 10,213,203;

U.S. patent application Ser. No. 14/836,077, entitled STAPLE CARTRIDGE ASSEMBLY COMPRISING STAPLE CAVITIES FOR PROVIDING BETTER STAPLE GUIDANCE, now U.S. Pat. No. 10,517,599;

U.S. patent application Ser. No. 14/836,225, entitled STAPLE CARTRIDGE ASSEMBLY INCLUDING STAPLE GUIDES, now U.S. Pat. No. 10,028,744;

U.S. patent application Ser. No. 14/836,351, entitled STAPLE CARTRIDGE ASSEMBLY COMPRISING STAPLE ALIGNMENT FEATURES ON A FIRING MEMBER, now U.S. Pat. No. 10,470,769;

U.S. patent application Ser. No. 14/836,294, entitled STAPLES CONFIGURED TO SUPPORT AN IMPLANTABLE ADJUNCT, now U.S. Pat. No. 10,188,394;

U.S. patent application Ser. No. 14/836,375, entitled STAPLES COMPRISING A COVER, now U.S. Pat. No. 10,390,829; and U.S. patent application Ser. No. 14/836,137, entitled STAPLE CARTRIDGE ASSEMBLY INCLUDING FEATURES FOR CONTROLLING THE ROTATION OF STAPLES WHEN BEING EJECTED THEREFROM, now U.S. Pat. No. 10,166,026.

Applicant of the present application also owns the following patent applications that were filed on Dec. 23, 2013 and which are each incorporated by reference herein in their respective entireties:

U.S. patent application Ser. No. 14/138,554, entitled SURGICAL INSTRUMENTS WITH ARTICULATABLE SHAFT ARRANGEMENTS;

U.S. patent application Ser. No. 14/138,465, entitled SURGICAL STAPLES AND STAPLE CARTRIDGES;

U.S. patent application Ser. No. 14/138,474, entitled ARTICULATABLE SURGICAL INSTRUMENTS WITH SEPARATE AND DISTINCT CLOSING AND FIRING SYSTEMS;

U.S. patent application Ser. No. 14/138,485 entitled SURGICAL CUTTING AND STAPLING INSTRUMENTS WITH INDEPENDENT JAW CONTROL FEATURES;

U.S. patent application Ser. No. 14/138,475, entitled SURGICAL STAPLES AND STAPLE CARTRIDGES;

U.S. patent application Ser. No. 14/138,481, entitled SURGICAL STAPLES AND METHODS FOR MAKING THE SAME;

U.S. patent application Ser. No. 14/138,489 entitled SURGICAL STAPLES, STAPLE CARTRIDGES AND SURGICAL END EFFECTORS;

U.S. Design patent application Ser. No. 29/477,488, entitled SURGICAL FASTENER;

U.S. patent application Ser. No. 14/138,505 entitled FASTENER CARTRIDGE COMPRISING AN EXTENDABLE FIRING MEMBER;

U.S. patent application Ser. No. 14/138,518 entitled FASTENER CARTRIDGE COMPRISING A FIRING MEMBER CONFIGURED TO DIRECTLY ENGAGE AND EJECT FASTENERS FROM THE FASTENER CARTRIDGE;

U.S. patent application Ser. No. 14/138,530 entitled FASTENER CARTRIDGE COMPRISING A FIRING MEMBER INCLUDING FASTENER TRANSFER SURFACES;

U.S. patent application Ser. No. 14/138,507, entitled MODULAR SURGICAL INSTRUMENTS;

U.S. patent application Ser. No. 14/138,497, entitled SURGICAL CUTTING AND STAPLING INSTRUMENTS WITH ARTICULATABLE END EFFECTORS; and U.S. patent application Ser. No. 14/138,516, entitled SURGICAL CUTTING AND STAPLING METHODS.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

A staple, or fastener, disclosed herein is configured for use with a surgical stapling instrument. Discussed in greater detail below, the staple is removably stored in a staple cavity of a staple cartridge. The staple cartridge comprises a sled configured to receive a firing actuation from the surgical stapling instrument which imparts a force on the staple to eject the staple from the staple cavity. When the staple is ejected, or driven, out of the staple cavity by the sled, the staple undergoes a deformation process where the staple forms into a fired configuration from an unfired configuration. The staple forms into the fired configuration when the staple contacts corresponding forming pockets of an anvil of the surgical stapling instrument.

Various staples disclosed herein comprise a flat-formed staple which can be cut and/or stamped from a sheet of material, for example. The sheet of material can be metallic and can comprise stainless steel and/or titanium, for example. In at least one instance, outlines can be traced, etched, and/or cut into the sheet of material which are machined and/or laser cut to form the staples into a manufactured shape.

The staples comprise a pair of staple legs and a staple base portion, or crown, from which the staple legs extend. Each staple leg comprises a staple tip, or piercing portion, which is configured to pierce the tissue and contact a corresponding forming pocket of the anvil of the surgical stapling instrument. The staple legs are configured to change shape to achieve a formed configuration to fasten the tissue. The staple base portion defines a first plane and the staple legs define a second plane which is laterally offset from but at least substantially parallel to the first plane. Embodiments are envisioned where the first and second planes are not parallel.

The flat-formed staple 100 depicted in FIGS. 1-4 comprises a proximal staple leg 110, a distal staple leg 120, and a staple base portion 130. The staple 100 further comprises vertical transition portions, or bends, 118, 128 and lateral transition portions, or bends, 116, 126. The vertical transition portions 118, 128 bend, or extend, the legs 110, 120 vertically, or upward, from the staple base portion 130. The lateral transition portions 116, 126 extend the staple legs 110, 120 laterally outward, or at least substantially perpendicularly with respect to the staple base portion 130. The staple legs 110, 120 define a first plane and the staple base portion 130 defines a second plane. Together, the vertical transition portions 118, 128 and the lateral transition portions 116, 126 permit the staple legs 110, 120 to be laterally offset and parallel with respect to the staple base portion 130. Stated another way, the first plane is offset from and at least substantially parallel to the second plane. In FIGS. 1-4, the first plane is offset in the negative Y direction. Other staples may be used in conjunction with a plurality of staples 100 where the other staples comprise a first plane which is offset in the positive Y direction. The use of both types of staples permits staple rows to be nested, or interwoven, where staple legs of neighboring rows may be at least substantially aligned and/or share a common longitudinal axis. In various instances, the staple rows can be nested to provide denser staple rows.

The proximal staple leg 110 and the distal staple leg 120 comprise staple tips 112, 122 and corners 114, 124, respectively. The tips 112, 122 are configured to pierce tissue and contact a forming pocket of an anvil of a surgical stapling instrument. The tips 112, 122 contact the anvil when the staple 100 receives a driving force to eject the staple 100 from a corresponding staple cavity in the staple cartridge. The tips 112, 122 and/or legs 110, 120 of the staple 100 will then begin forming from an unfired configuration to a fired configuration. The proximal staple leg 120 further comprises a leading engagement foot 117 comprising a chamfered surface, or edge, 119. As the sled contacts the staple 100 upon the sled's distal translation, a feature of the sled can engage the leading engagement foot 117 to aid in preventing longitudinal staple roll, or rotation, for example. The engagement foot 117 can comprise a push point that is configured to be pushed on to load the staple 100 into a staple cartridge.

Since the staple 100 is a flat-formed staple, the staple legs 110, 120, tips 112, 122, and/or other portions of the staple 100 can be further developed, or worked, after being stamped from a flat, or at least substantially flat, stock. Further developing the staple 100 can provide specific properties creating and/or altering preferential bending planes, toughness, and/or elasticity, for example. Traditional wire-formed staples comprise desirable properties advantageous for surgical fastening and can be implemented with the staple 100. Methods for constructing the corners 114, 124 and/or tips 112, 122, for example, may include any suitable process including cold working, for example. A specific process may include coining by working the corners 114, 124 into a rounded, angled, oblique, and/or parabolic profile, for example. The staple tips 112, 122 can also be worked using similar methods to provide an adequate tip configured to pierce tissue and form against a corresponding forming pocket of the anvil.

The staple base portion 130 comprises an inclined drive surface 132, a final drive surface 131, and a distal wall 133. In various embodiments, the staple 100 is supported in a staple cartridge by a pan where the final drive surface 131 is configured to rest on the pan. In various other embodiments where a staple cartridge is pan-less, the final drive surface does not rest on a pan, rather, the final drive surface comprises an initial position residing above a bottom surface of the pan-less staple cartridge. This would allow a bottom surface of the sled and the bottom surface of the pan-less staple cartridge to be at least substantially flush as the sled translates through the cartridge. The drive surface 132 of each staple base portion 130 is configured to receive the driving force $F_s$ from the sled of the surgical stapling instrument. When the sled translates distally through the staple cartridge, the sled contacts the drive surface 132 to lift the staple 100 out of the cartridge and, in addition, contact the final drive surface 131 to form the staple 100 into its fired configuration.

The distal wall 133 acts as a distal-most wall of the staple base portion 130 and is positioned proximal of the distal staple leg 120 resulting in a lack of any portion of the staple base portion 130 underneath the distal staple leg 120. Having a greater amount of mass in the base portion 130 of the staple 100 increases the ability of the staple 100 to resist rotational motion caused by the moment $M_S$ applied by the sled. Increasing the moment of inertia of the staple base portion 130 increases the ability to resist rotational motion. As a result, a greater torque, or larger moment, would be required to cause longitudinal staple roll.

The staple base portion 130 further comprises a top surface, or compression surface, 136 comprising a proximal surface 139, an intermediate surface 138, and a distal surface 137. The proximal surface 139 is angled, or slanted, upward toward the proximal leg 110. The distal surface 137 is angled, or slanted, upward toward the distal leg 120. The intermediate surface 138 is at least substantially parallel to the final drive surface 131. This valley-like configuration limits the stress concentration of tissue captured near the transition portions 118, 128, 116, 126 where the legs 110, 120 extend from the staple base portion 130. In various embodiments, these surfaces 137, 138, 139 can be curved to create a concave surface. In traditional staples, when formed, the connections where the legs meet the staple base produce locations responsible for highly localized tissue stress. This is especially true in the event that such a traditional staple buckles, or is crushed, or flattened, rather than formed into a true "B" configuration.

Figure 2:
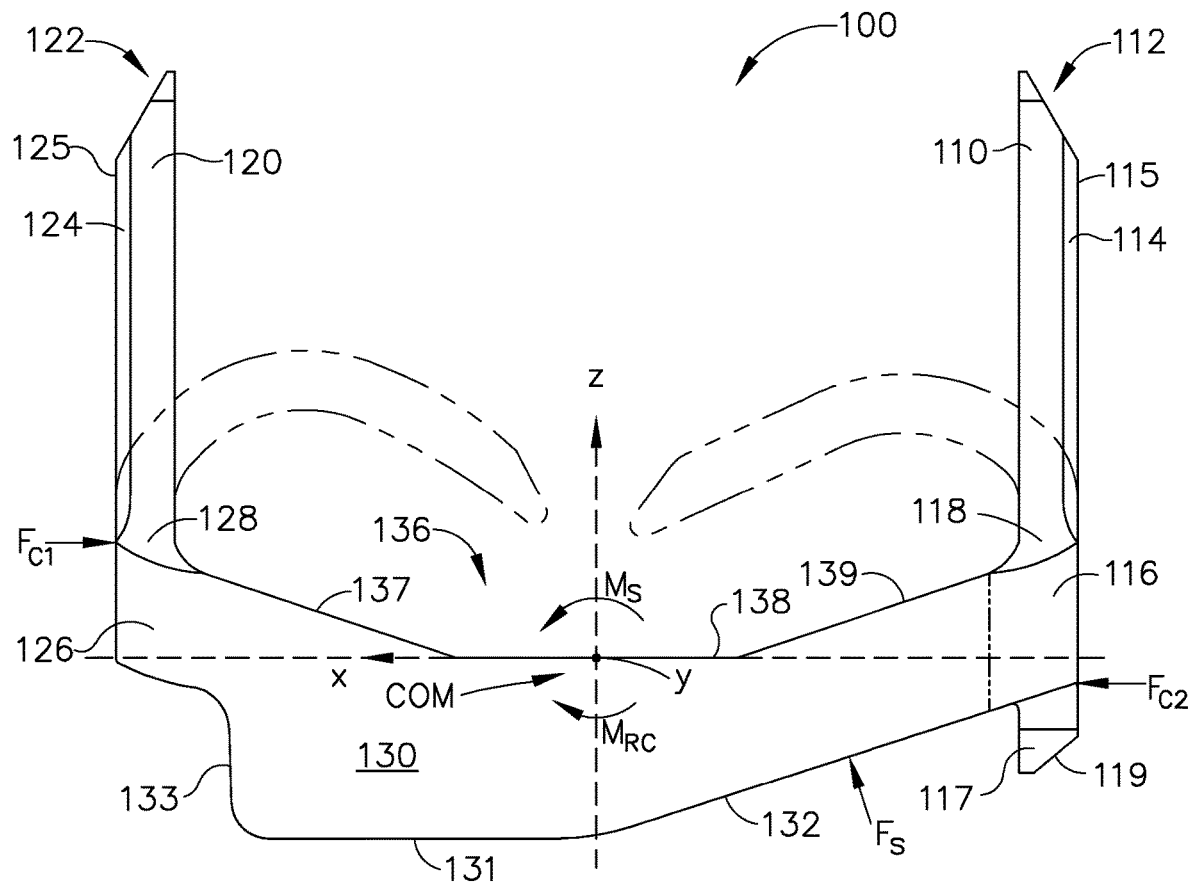
FIG. 2 is a side elevation view of the staple of FIG. 1.
Figure 3:
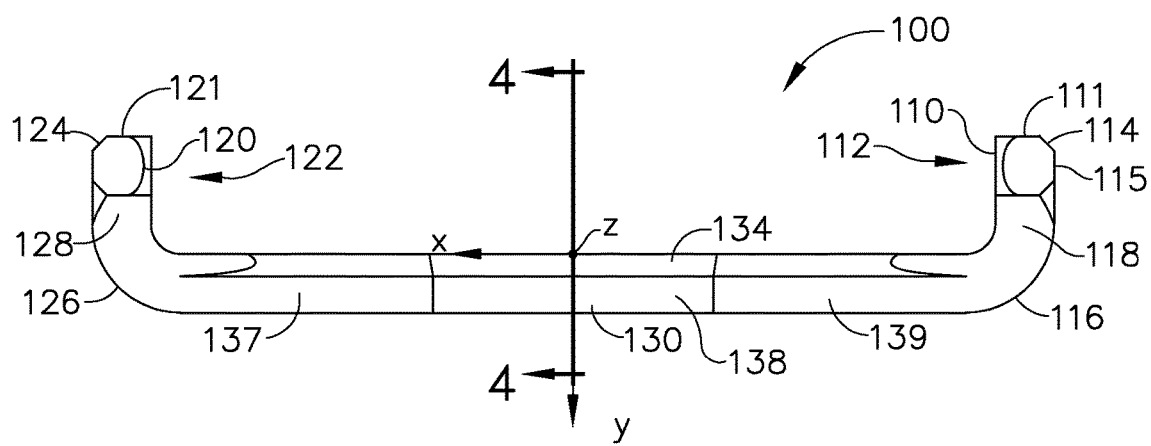
FIG. 3 is a top view of the staple of FIG. 1.

In various embodiments, the dynamics of the staple 100 are predictable when ejected from a staple cartridge. As the staple 100 is ejected from its corresponding staple cavity, a driving force $F_S$ from the sled generates a moment $M_S$. One preventive measure for preventing staple roll includes increasing the moment of inertia of the staple 100, discussed above, which is configured to prevent, as illustrated in FIG. 2, longitudinal roll, or rotation of the staple. In the event that the staple 100 rolls longitudinally in the distal direction, or, in other words, rotates counterclockwise about the Y axis, outer, longitudinal staple leg surfaces 115, 125 of the staple 100 will contact the guide surfaces, or sidewalls, of the staple cartridge. This contact produces corresponding reaction forces $F_{C1}$ and $F_{C2}$. More particularly, as the staple 100 is driven out of the staple cavity and rotated about the Y axis, the wall 115 of the proximal staple leg 110 contacts a proximal sidewall of the staple cartridge producing a reaction force $F_{C2}$ which acts upon the staple leg 110 below the center of mass. The wall 125 of the distal staple leg 120 contacts a distal sidewall of the staple cartridge producing a reaction force $F_{C1}$ which acts upon the staple leg 120 above the center of mass. Both reaction forces, $F_{C1}$ and $F_{C2}$, contribute to a reactional moment $M_{RC}$ to counteract, or balance, the applied moment $M_S$ acting on the staple 100. The reaction forces discussed herein may be distributed loads acting upon a surface area of each of the staple legs 110, 120.

Figure 4:
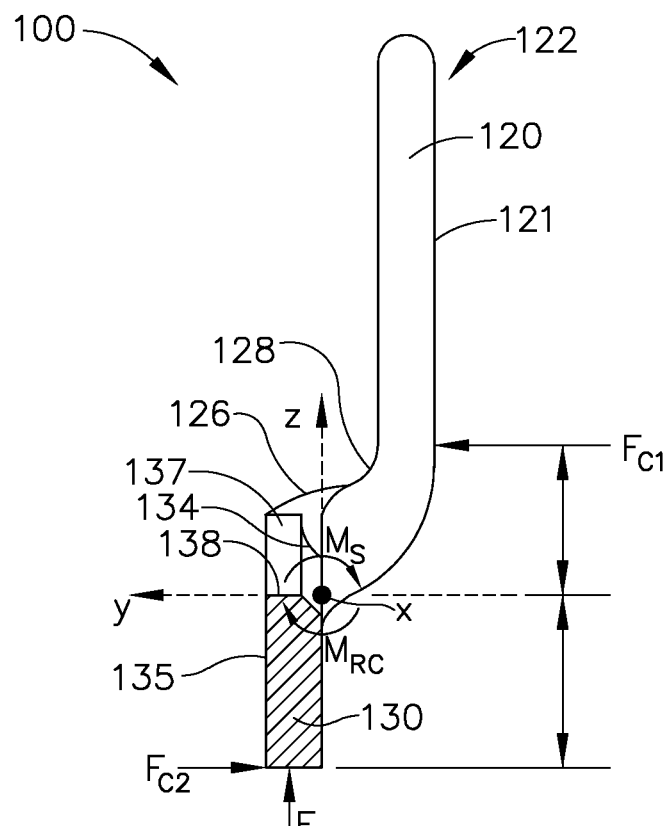
FIG. 4 is a cross-sectional view of the staple of FIG. 1 taken along line 4-4 in FIG. 3.

The moment of inertia of the staple 100 is also configured to prevent, as illustrated in FIG. 4, lateral roll, or rotation of the staple 100. The staple base portion 130 comprises a notch 134 defined in the top surface 136 on a side of the staple base portion 130 closest to the legs 110, 120. The notch 134 contributes to the predictability of the dynamics of the staple 100 before formation and upon formation when ejected from the staple cartridge. For example, referring primarily to FIG. 4, the notch 134 is configured to induce rotation of the staple 100 toward a particular cavity sidewall. In the event that the staple 100 rolls laterally, or, in other words, rotates in the direction of the applied moment $M_S$, outer, lateral staple leg walls 111, 121 of the staple 100 will contact the guide surfaces, or sidewalls, of the staple cartridge producing corresponding reaction forces $F_{C1}$ and $F_{C2}$. For example, as the staple 100 is driven out of the staple cavity and rotated in the direction of the applied moment $M_S$, the walls 111, 121 of the staple legs 110, 120 contact a corresponding sidewall of the staple cartridge producing a reaction force $F_{C1}$ which act upon the staple legs 110, 120 above the center of mass. An outer lateral wall 135 of the staple base portion 130 contacts another corresponding sidewall of the staple cartridge producing a reaction force $F_{C2}$ which acts upon the staple base portion 130 below the center of mass. Reaction forces $F_{C1}$ and $F_{C2}$ produce a reactional moment $M_{RC}$ to counteract, or balance, the applied moment $M_S$ acting on the staple 100 from the sled. The reaction forces discussed herein may be distributed loads acting upon a surface area of each of the staple legs 110, 120 and the staple base portion 130. In various embodiments, the staple 100 is encouraged to roll laterally in the direction of the applied moment $M_S$ to control which walls of the staple cavity are going to be contacted for staple guidance as the staple 100 is ejected from the staple's 100 corresponding staple cavity.

Figure 5:
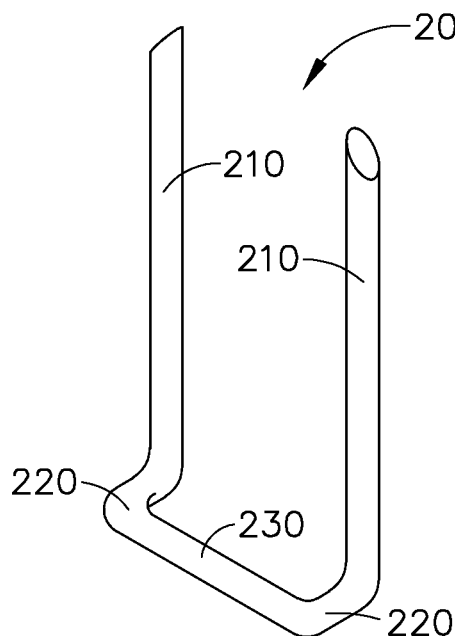
FIG. 5 is a perspective view of a staple for use with a surgical stapling instrument in accordance with at least one embodiment.
Figure 6:
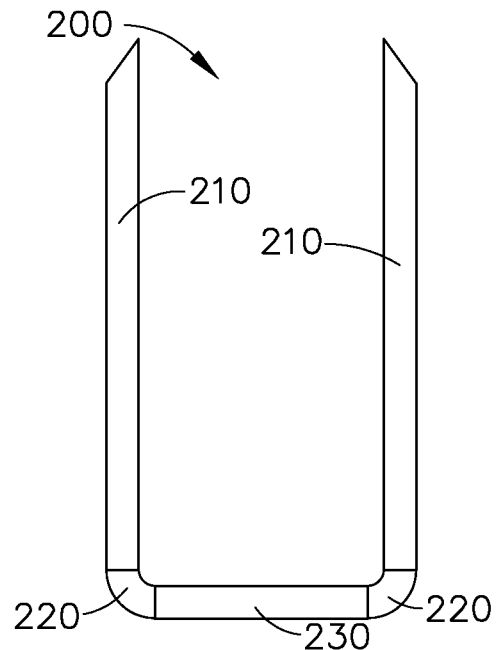
FIG. 6 is a side elevation view of the staple of FIG. 5.
Figure 7:
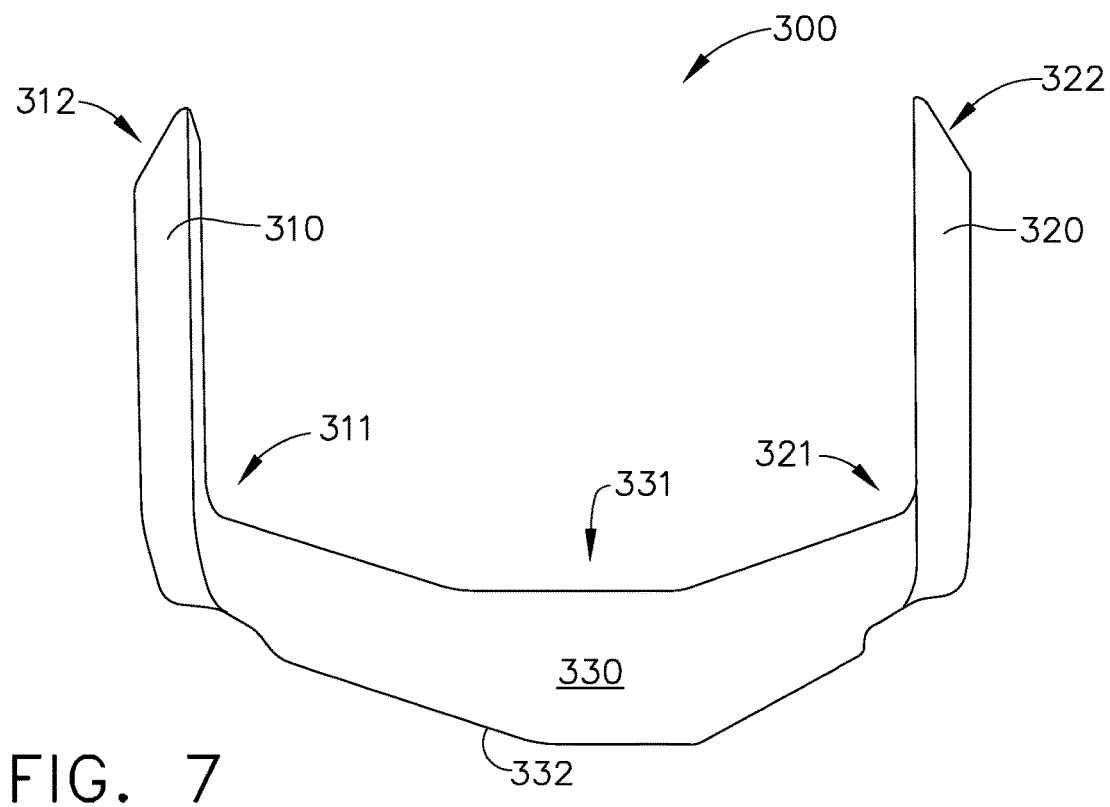
FIG. 7 is a side elevation view of a staple for use with surgical stapling instrument in accordance with at least one embodiment.
Figure 8:
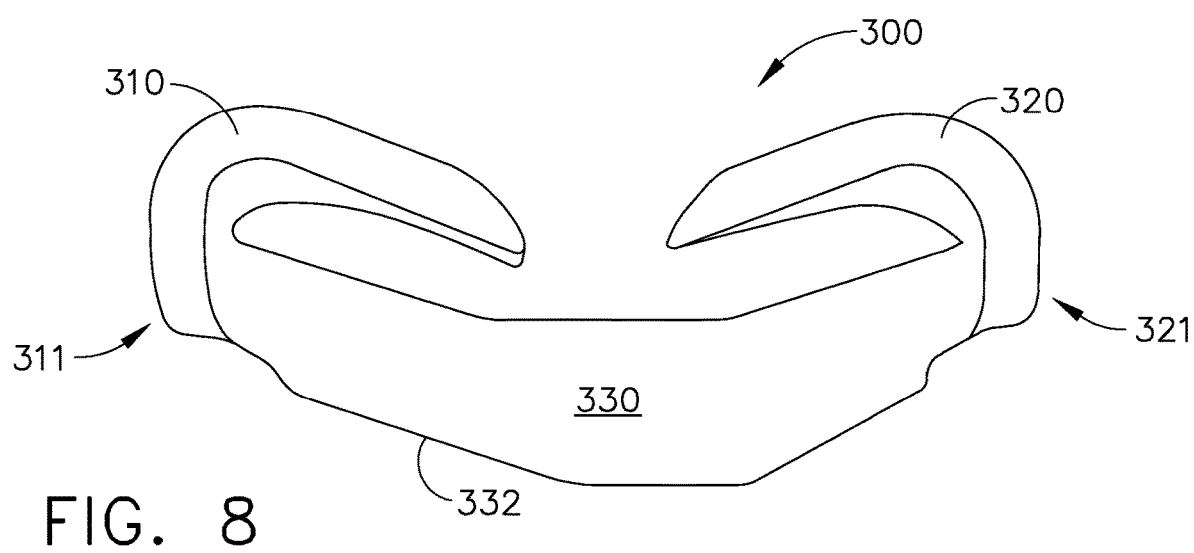
FIG. 8 is a side elevation view of the staple of FIG. 7 in a formed configuration.

FIGS. 5 and 6 illustrate a wire-formed staple 200 comprising staple legs 210 and a staple base portion 230. The staple legs 210 are offset and bent at a substantially ninety degree angle from the staple base portion 230. The staple legs 210 reside in a first plane which is at least substantially perpendicular to a second plane defined by the staple base portion 230 and the bend portions 220 of the staple legs 210.

FIGS. 7-10 illustrate a staple 300 comprising a proximal staple leg 310, a distal staple leg 320, and a staple base portion, or crown, 330 having a drive surface 332. The staple legs 310, 320 extend from the staple base portion 330 and each staple leg 310, 320 comprises a laterally outward bend portion and an upward bend portion. The laterally outward bend portions of the staple legs bend the staple legs laterally outward with respect to the staple base portion. The upward bend portions of the staple legs bend the staple legs vertically with respect to the staple base portion. The staple 300 comprises a first zone 331 comprising a first hardness, second zones 311, 321 comprising a second hardness, and third zones 312, 322 comprising a third hardness. Embodiments are envisioned where the staple 300 comprises more or less zones than depicted. Varying certain properties, such as the hardness, of different portions of the staple 300 can provide greater control and predictability when forming the staple against corresponding forming pockets such as forming pockets 341 of anvil 340, for example. The first hardness of the first zone 331 may be greater than that of the second hardness of the second zones 311, 321. In many instances, it is desirable to have ductile staple legs 310, 320 capable of permanently changing shape without fracture or, in other words, having staple legs 310, 320 with a high plasticity, while having a staple base portion 330 that supports the staple legs 310, 320 and comprises a hardness greater than the staple legs 310, 320, for example. A greater hardness would increase the staple base portion's 330 ability to resist deformation upon the application of an external and/or internal force, such as a force from the staple legs upon being compressed against the anvil, for example.

Metal working different portions of the staples disclosed herein can comprise several advantages. One of these advantages may include being able to prevent crushing, or buckling, of the staple legs during formation and, instead, encourage the staple legs to deform in a desired configuration as a result of the contact with the corresponding forming pockets.

Figure 9:
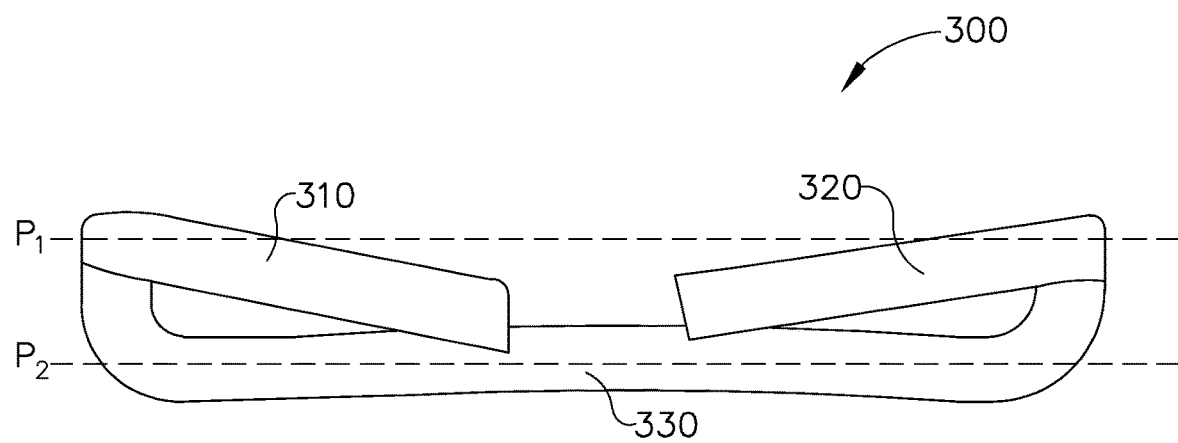
FIG. 9 is a top view of the staple of FIG. 7 in the formed configuration of FIG. 8.
Figure 10:
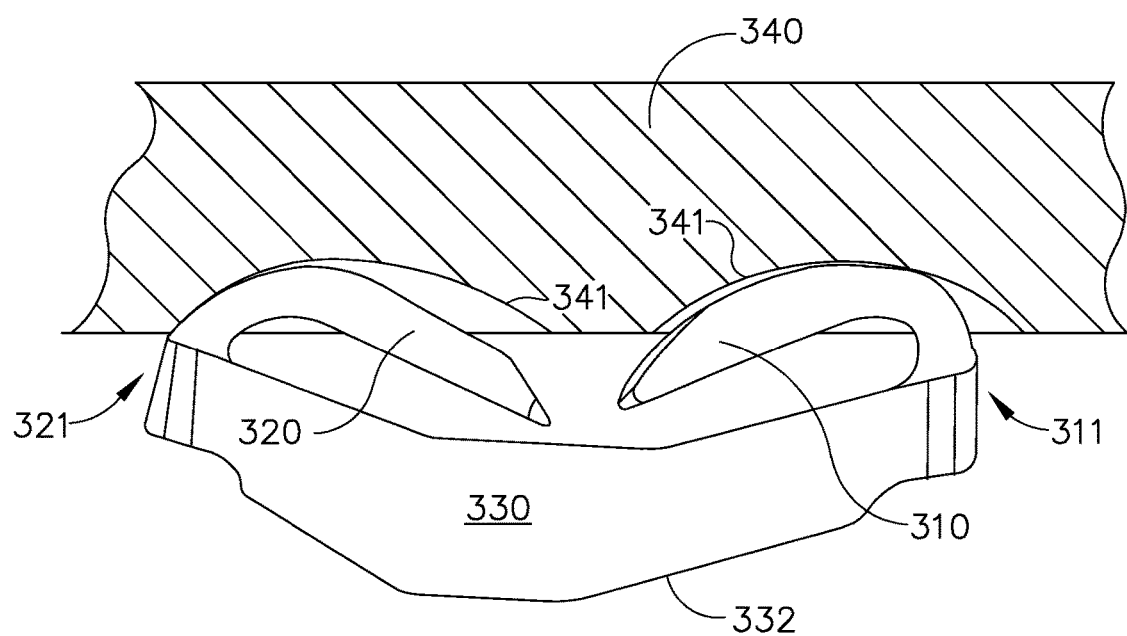
FIG. 10 is a side elevation view of the staple of FIG. 7 in a formed configuration and a partial cross-sectional view of an anvil of a surgical stapling instrument.

The staple 300 may be formed into any desired formation. In an unformed configuration, the staple legs 310, 320 define a first plane $P_1$ and the staple base portion 330 defines a second plane $P_2$. Shown in FIGS. 9 and 10 is an example of a formation of the staple 300 in which the staple legs 310, 320 are formed laterally toward the second plane $P_2$. Variations in hardness of certain zones and/or portions of the staple 300 can be responsible for providing directional encouragement when contacting the forming pockets 341.

Embodiments are envisioned where the staple legs 310, 320 are formed in a direction laterally away from the second plane $P_2$.

Figure 11:
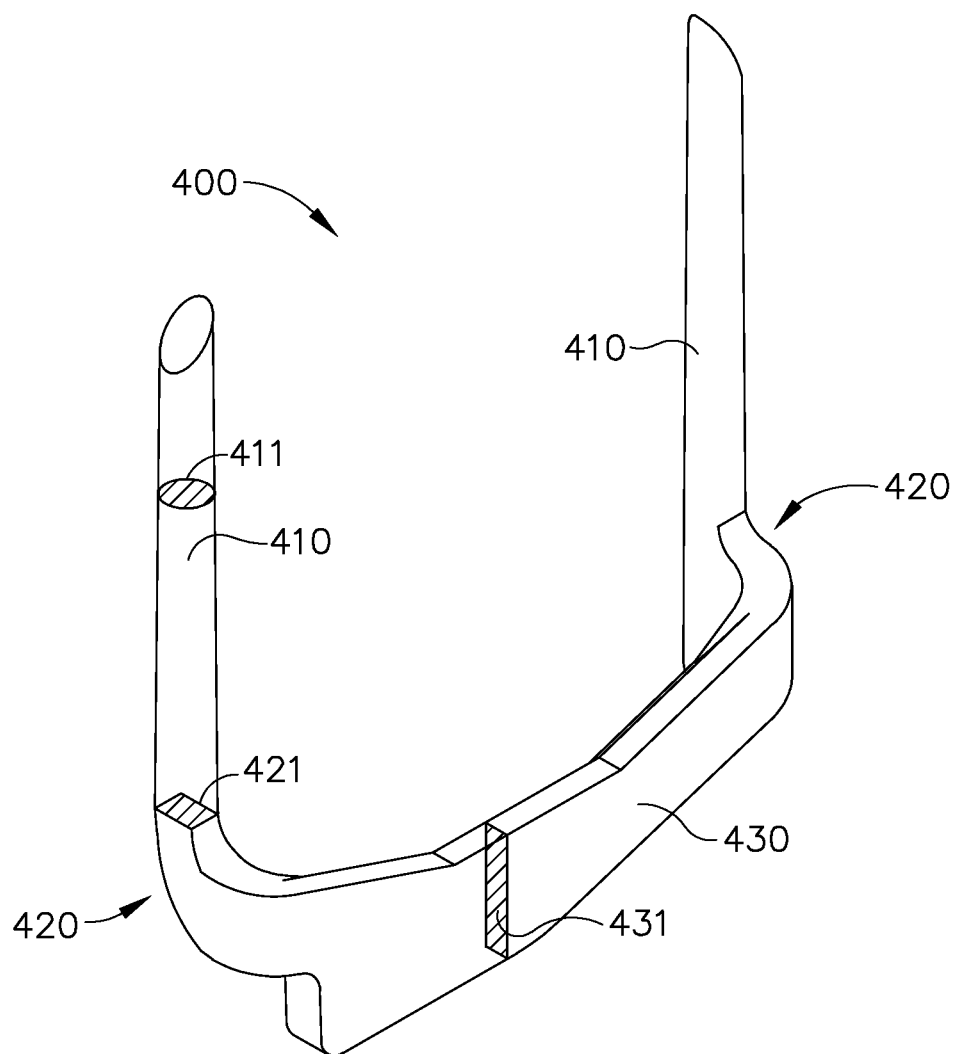
FIG. 11 is a perspective view of a staple for use with a surgical stapling instrument in accordance with at least one embodiment.
Figure 11A:
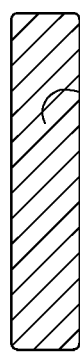
FIGS. 11A-11C are cross-sections of portions of the staple of FIG. 11.
Figure 11B:
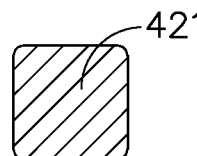
Figure 11C:
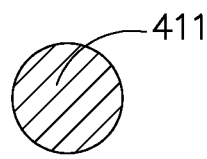

FIGS. 11-11C depict a staple 400 comprising staple legs 410 and a staple base portion 430 formed from a flat sheet of material. The staple base portion 430 comprises a rectangular cross-sectional profile 431 and the staple legs comprise a round cross-sectional profile 411. Having round staple legs 410 that extend from a staple base portion 430 having the rectangular cross-sectional profile 431 can provide a staple base portion and staple legs with no preferential bending planes. The staple 400 comprises bend portions 420 where the staple legs 410 extend from the staple base portion 430. The bend portions 420 comprise a substantially square cross-sectional profile 421. The square profile 421 and the rectangular profile 431 of the bend portions 420 and the staple base portion 430, respectively, provide a stiff connection and backbone to the round staple legs 410. The round staple legs 410 eliminate preferential bending planes that staple legs with a square, rectangular, or any shape with vertices or a non-uniform shape, cross-sections could have.

Figure 12:
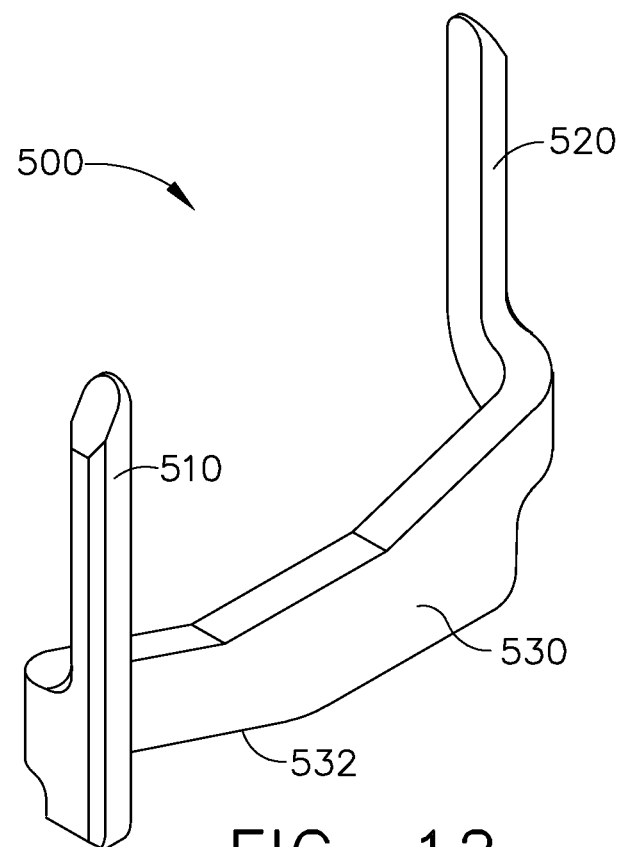
FIG. 12 is a perspective view of a staple for use with a surgical stapling instrument in accordance with at least one embodiment.

FIG. 12 depicts a staple 500 in accordance with at least one embodiment comprising a proximal staple leg 510, a distal staple leg 520, and a staple base portion 530 from which the staple legs 510, 520 extend. The proximal staple leg 510 is bent laterally outward from the staple base portion 530 in a first direction. The distal staple leg 520 is bent laterally outward from the staple base portion in a second direction. The first direction is opposite the second direction. The staple base portion 530 defines a first plane and the staple legs 510, 520 define a second plane which intersects the first plane. One advantage of having the staple legs 510, 520 bent in opposite directions can help prevent lateral roll by counteracting the applied sled moment on each side of the staple base portion 530. This results in an S-shaped configuration and requires complimentary forming pockets.

Figure 13:
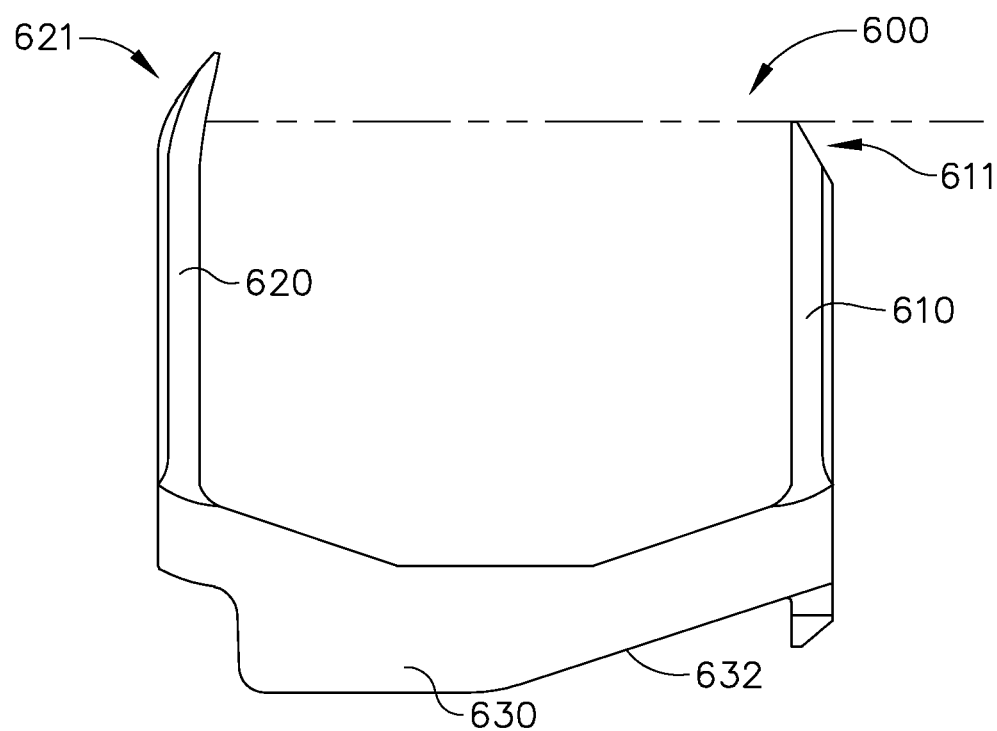
FIG. 13 is a side elevation view of a staple for use with a surgical stapling instrument in accordance with at least one embodiment.

A staple 600 is depicted in FIG. 13 comprising a proximal leg 610, a distal leg 620, and a staple base portion 630 having a drive surface 632. The distal leg 620 is longer than the proximal leg 610 resulting in an offset contact timing of the tips 611, 621 of the staple legs 610, 620 against the forming pockets of the anvil. In various embodiments, the distal leg may comprise a tip that comprises an initial pre-bent configuration to aid in the forming process when initially contacting the anvil. This pre-formed tip 621 would require less compressive force than the staple tip 611 to begin deformation against the anvil. Having the longer staple leg, in this case the distal staple leg 620, contact the anvil before the shorter, or proximal, staple leg, 610 may require the staple tip 621 of the longer leg 620 to have, to a certain degree, a pre-formed tip before the tip 611 is deformed.

Figure 14:
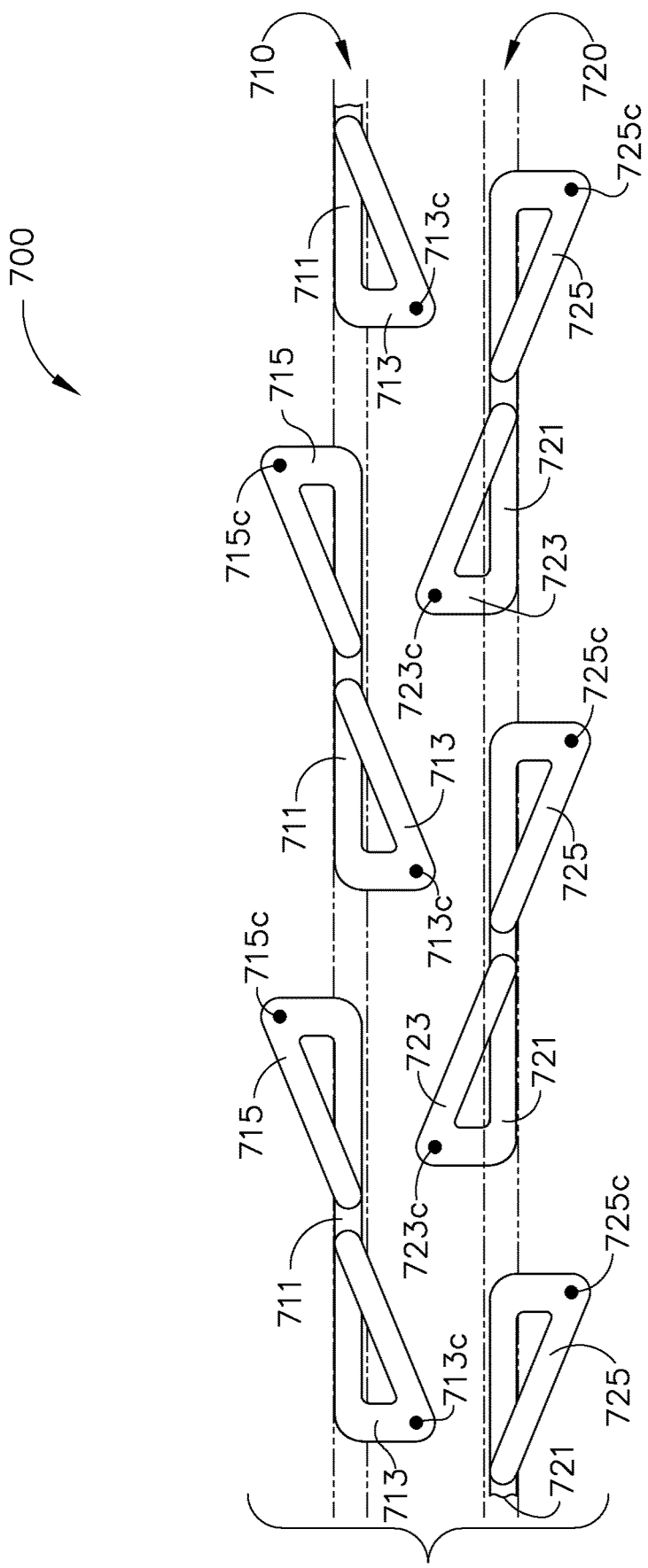
FIG. 14 is a partial top view of a formed staple configuration comprising a plurality of staples in accordance with at least one embodiment.

FIG. 14 illustrates an arrangement 700 of formed staples 711, 721. The staples 711 are arranged in a first row 710 and the staples 721 are arranged in a second row 720 which is adjacent to the first row 710. The staples 711, 712 may be similar to that of the staple 600 illustrated in FIG. 13 discussed above. The staples 711 comprise laterally opposing legs 713, 715. The staples 721 comprise laterally opposing legs 723, 725. The laterally opposing legs 713, 715 each comprise tips configured to contact forming pockets of an anvil at contact points 713c, 715c, respectively. The laterally opposing legs 723, 725 also each comprise tips configured to contact forming pockets of an anvil at contact points 723c, 725c, respectively. The laterally opposing legs 713, 715 each form inwardly toward the staple base portion from which they extend. The laterally opposing legs 723, 725 also each form inwardly toward the staple base portion from which they extend.

The staple rows 710, 720 are interwoven such that the contact points 723c, 713c are in substantial alignment. Such an arrangement allows for a more densely arranged staple row configuration in a staple cartridge and/or a more densely arranged forming pocket configuration on an anvil. Also, intersecting purchase planes may provide for a higher quality purchase and a larger area of purchase coverage in the tissue. The intersecting purchase planes may guarantee that anything captured between the staple rows and the forming pockets is guaranteed to be adequately fastened. This can help when stapling smaller vessels and/or not easily visible vessels that, in conventional staple arrangements, may navigate staple row separations resulting in less than adequate fastening.

Figure 15:
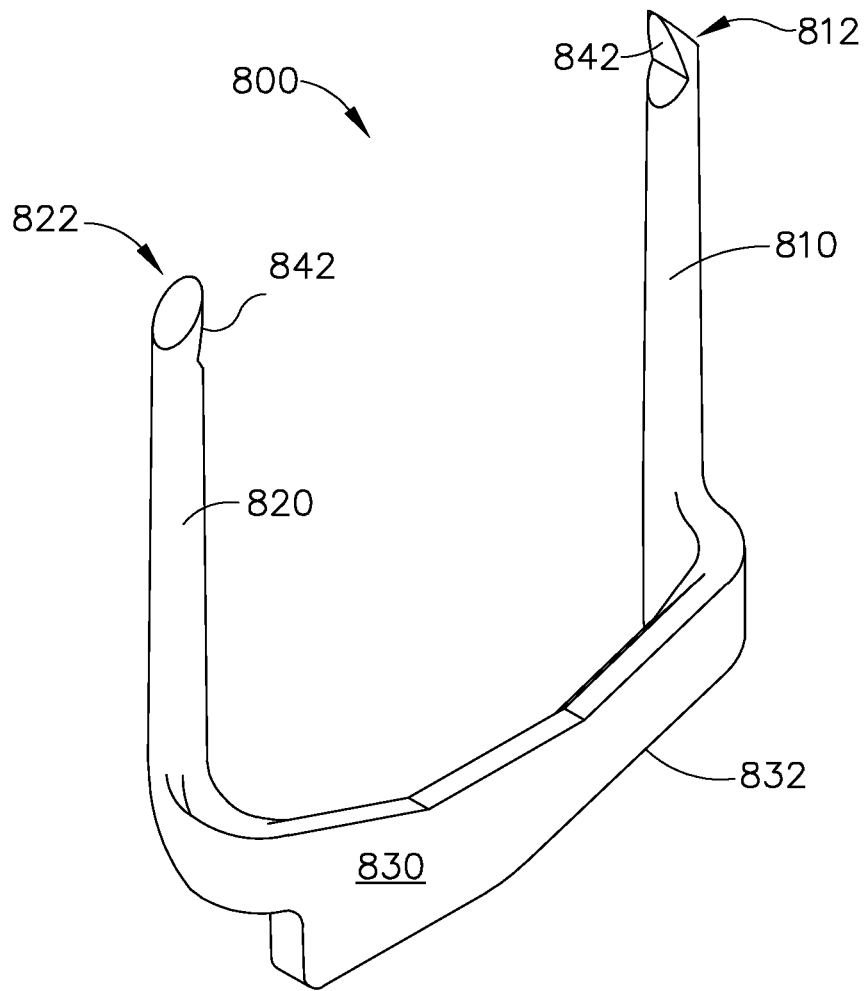
FIG. 15 is a perspective view of a staple for use with a surgical stapling instrument in accordance with at least one embodiment.
Figure 16:
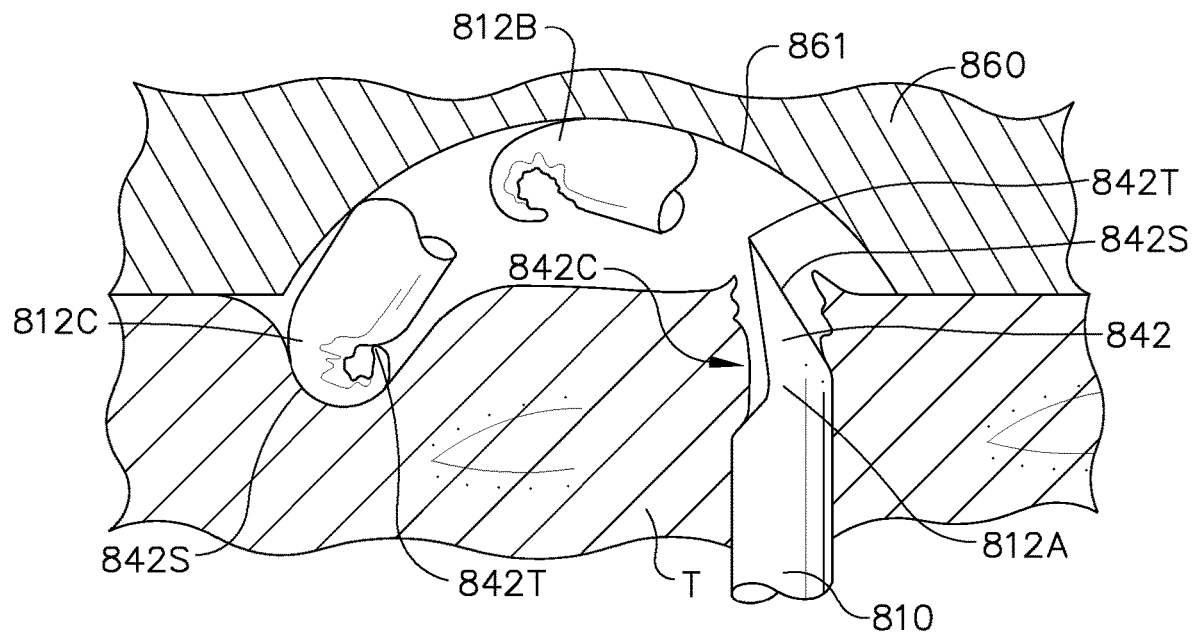
FIG. 16 is a partial cross-sectional view of an anvil illustrating a portion of the staple of FIG. 15 being formed from an unformed configuration to a formed configuration.
Figure 17:
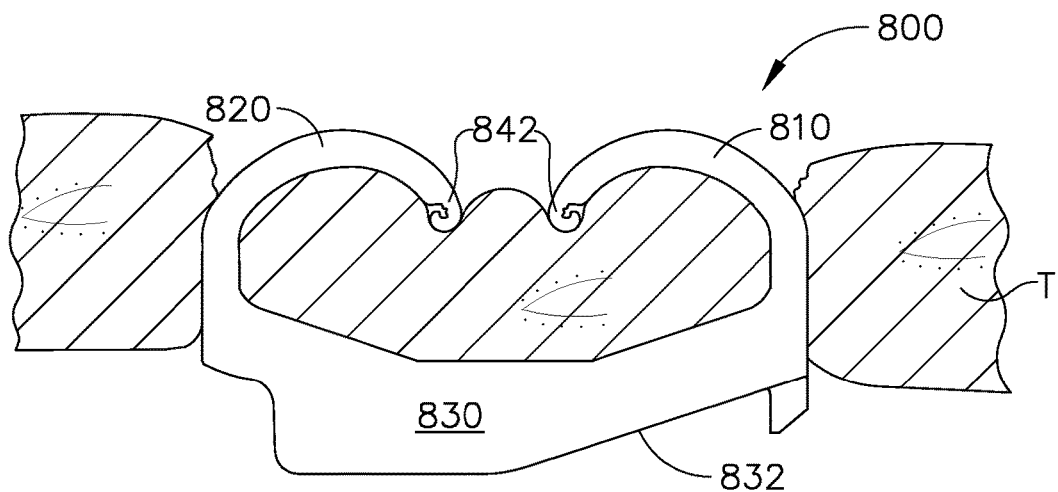
FIG. 17 is an elevation view of the staple of FIG. 15 in a formed configuration.

FIGS. 15-17 depict a staple 800 comprising staple legs 810, 820 and a staple base portion 830 having a drive surface 832. The staple legs 810, 820 comprise tips 842 configured to contact forming pockets of an anvil, such as forming pocket 861 of the anvil 860, for example. The staple tips 842 comprise a piercing tip, or portion, 842T, a curling surface 842S, and a concave cutout portion 842C. The piercing tip 842T is configured to pierce the tissue T upon ejection from the staple cartridge and, once in contact with the forming pocket 861 of the anvil 860, deform within the forming pocket 861. Deformation of the staple tip 842 is encouraged into a certain formation by utilizing the predictable deformability of the concave cutout portion 842C. The curling surface 842S of the staple tip 842 is configured to curl, or deform, from a piercing position 812A, to an intermediate formed position 812B, and to a non-piercing position 812C. Once the staple tip 842 has deformed completely, the piercing tip 842T is shielded, or isolated, from the tissue T by the curling surface 842S. This prevents further piercing of the tissue T after the tip 842 pierces the tissue upon ejection. This arrangement also prevents further injury and/or unwanted irritation that a piercing tip that is exposed after the initial piercing could possibly inflict. Preventing further piercing of the tissue T after the legs are formed also lessens the chance of the staple 800 being pulled through the tissue T. The curling surface 842S acts as a shield configured to shield the piercing tip 842T from the tissue T.

Figure 18:
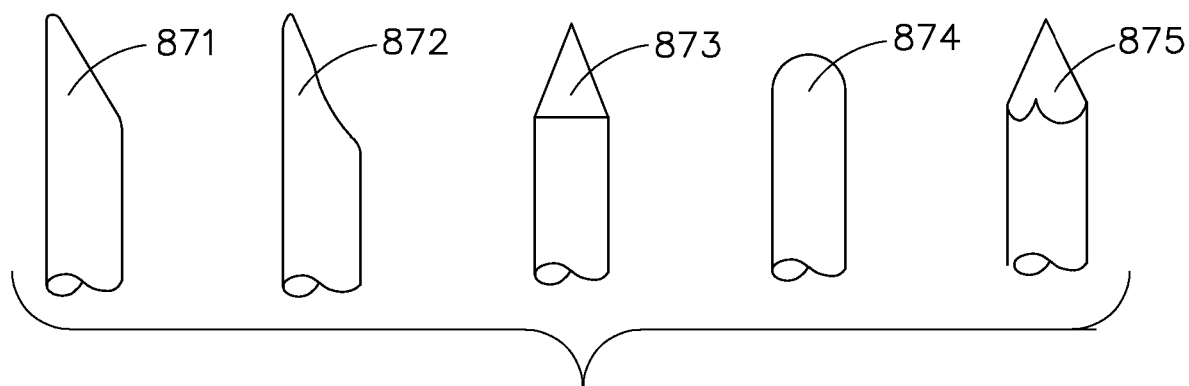
FIG. 18 includes side views of multiple staple tips in accordance with at least one embodiment.

FIG. 18 depicts multiple examples of different types of staple tips 871, 872, 873, 874, and 875 that can be employed with any suitable surgical staple such as the staples disclosed herein. Staple tip 871 comprises a triangular shape with an at least substantially flat face. Staple tip 872 comprises a face with a varying contour. Staple tip 873 comprises a rocket-like shape. Staple tip 874 comprises a nub-like profile. The nub-like profile may be substantially dull, for example. Staple tip 875 comprises a pencil-sharpened profile.

In various embodiments, the staple tips disclosed herein may comprise a material different than that of the staple to which the staple tip is connected in order to make deforming in the fashion desired easier, however, the staple tip material can still be strong enough to prevent unfolding of the staple tip after fastening tissue.

Figure 19:
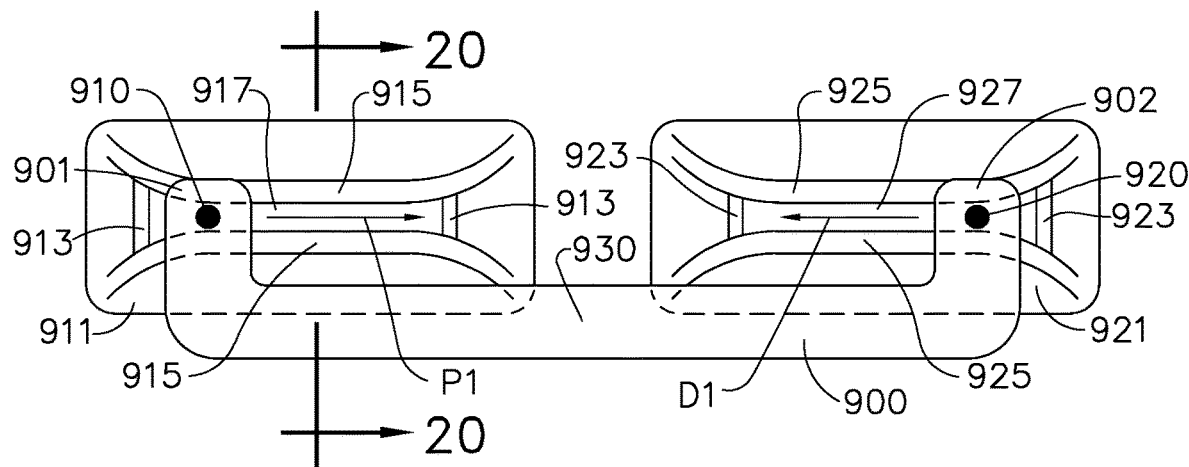
FIG. 19 is a bottom view of a staple in accordance with at least one embodiment and forming pockets of an anvil according to a first arrangement.
Figure 20:
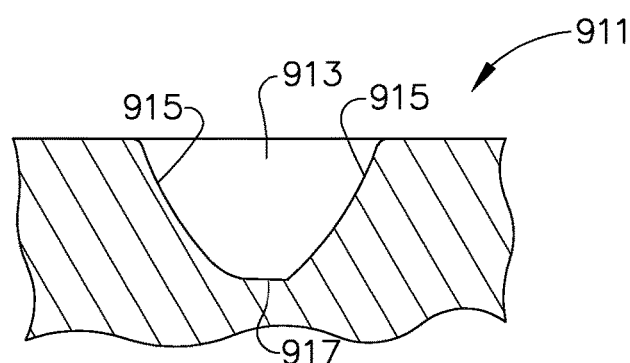
FIG. 20 is partial cross-sectional view of an anvil pocket of FIG. 19 taken along line 20-20 in FIG. 19.

Surgical staples can be encouraged to form into a desired configuration by changing the shape, size, configuration, and/or other aspects of the forming pockets configured to form the staples. FIG. 19 depicts forming pockets 911, 921 configured to form a staple 900. The staple 900 comprises staple legs 901, 902, staple tips 910, 920, and a staple base 930, wherein the staples legs 901, 902 extend from the staple base 930. The staple 900 is configured to contact and form against the corresponding forming pockets 911, 921. The forming pocket 911 comprises a forming channel surface 917 configured to receive a corresponding tip 910 and encourage the tip 910 to form in a direction P1. Shown in FIG. 20, the forming pocket 911 comprises lateral valley-like surfaces 915 and longitudinal valley-like surfaces 913 configured to funnel, or catch, the tip 910 of the staple in the event of minor misalignment upon contact. The staple 900, staple leg 901, and/or staple tip 910 may be driven off target with respect to the forming channel surface 917 upon ejection from the cartridge. The valley-like surfaces permit longitudinal and lateral roll of the staple. Although illustrated as concave surfaces, the valley surfaces may be convex or flat, for example.

The forming pocket 921 comprises a forming channel surface 927 configured to receive a corresponding tip 920 of the staple 900 and encourage the tip 920 to form in a direction D1. The direction D1 is opposite the direction P1 and, as shown in FIG. 19, illustrates an instance in which the staple legs are formed toward each other and at least substantially parallel to the staple base 930. Other embodiments are envisioned where the directions D1, P1 direct the corresponding staple legs in opposite directions but outward with respect to each other. The forming pocket 921 further comprises lateral valley-like surfaces 925 and longitudinal valley like surfaces 923 configured to funnel, or catch, the tip 920 of the staple 900 in the event of minor misalignment upon contact. The staple 900, staple leg 902, and/or staple tip 920 may be driven off target with respect to the forming channel surface 927 upon ejection from the cartridge.

In various embodiments, the longitudinal valley-like surfaces may comprise two separate valley surfaces. The two separate valley surfaces may comprise an initial valley surface nearest the intended point of contact for the corresponding staple tip. The initial valley surface may comprise a larger range of misalignment protection than the other of the separate valley surfaces. The initial valley surface may comprise a larger width and/or height than the other of the separate valley surfaces, for example.

Figure 21:
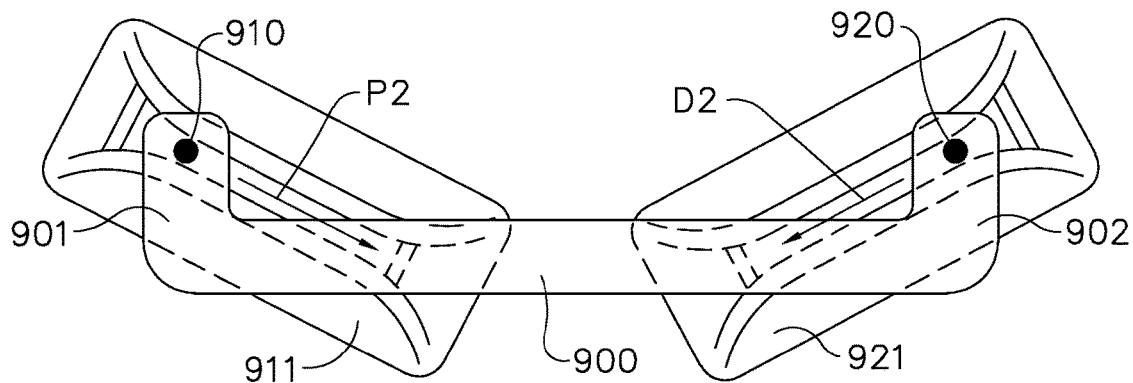
FIG. 21 is a bottom view of the staple and the forming pockets of FIG. 19 according to a second arrangement.

FIG. 21 depicts another arrangement of the staple pockets 911, 921 discussed above. However, the staple pockets 911, 921 in the illustrated arrangement are configured to direct the staple tips inward toward the staple base 130. The leg 901 and tip 910 are configured to be formed in direction P2. The leg 902 and tip 920 are configured to be formed in direction D2. The directions P2, D2 are transverse. Other embodiments are envisioned where the directions P2, D2 direct the corresponding staple legs and tips away from the staple base, or outward.

Figure 22:
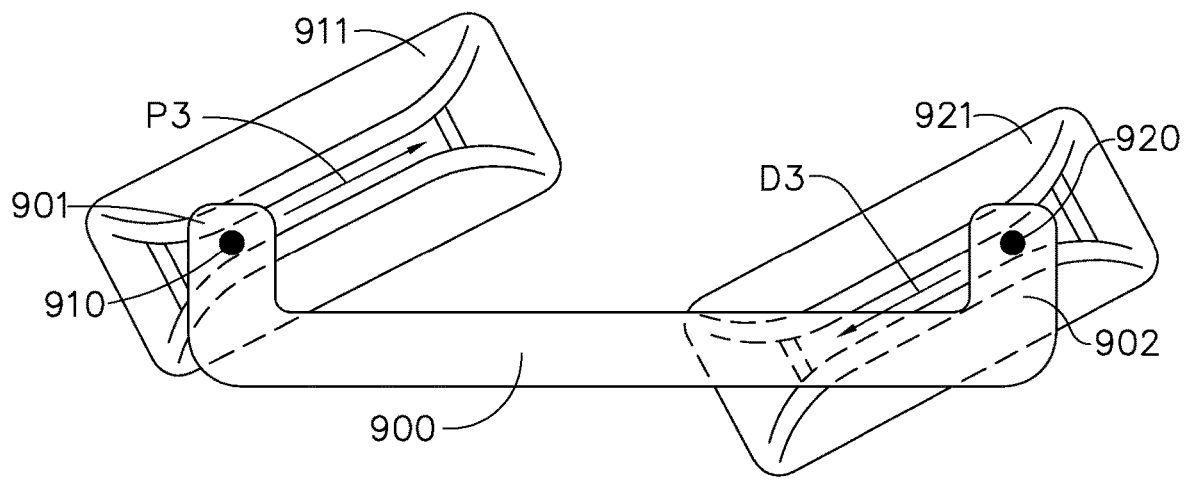
FIG. 22 is a bottom view of the staple and the forming pockets of FIG. 19 according to a third arrangement.

FIG. 22 depicts yet another arrangement of the staple pockets 911, 921 discussed above. The staple pockets 911, 921 in the illustrated arrangement are configured to form the corresponding staple legs 901, 902 and tips 910, 920 in opposite directions where one of the staple legs 902 is directed toward the staple base 930 and one of the staple legs 901 is directed away from the staple base 930. The leg 901 and tip 910 are configured to form in direction P3. The leg 902 and tip 920 are configured to form in direction D3. The directions P3, D3 are at least substantially parallel. Other embodiments are envisioned where the directions P3, D3 are not parallel.

Figure 23:
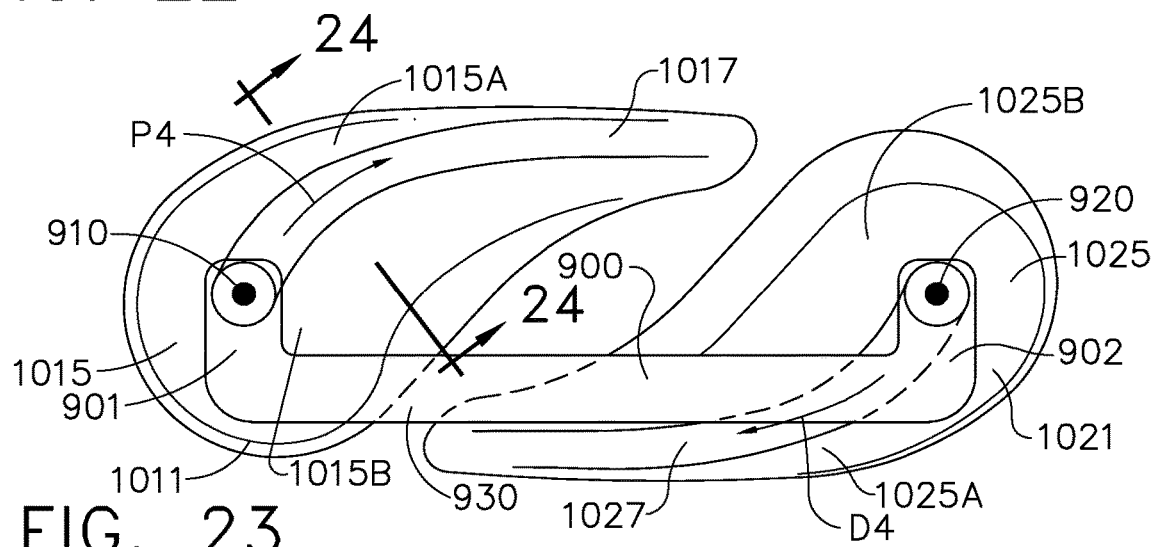
FIG. 23 is a bottom view of the staple of FIG. 19 and forming pockets in accordance with at least one embodiment.
Figure 24:
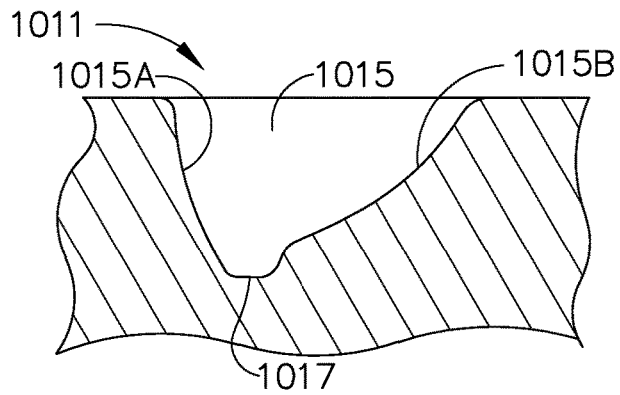
FIG. 24 is a partial cross-sectional view of an anvil pocket of FIG. 23 taken along line 24-24 in FIG. 23.

FIGS. 23 and 24 depict another embodiment of forming pockets 1011, 1021 configured to deform the staple 900. The forming pockets 1011, 1021 comprise an ear-like shape providing nested pockets. This type of arrangement can save space on the staple forming surface of an anvil to allow for more staple pockets and, as a result, more staples in a staple cartridge in a lesser amount of space. The forming pocket 1011 comprises a forming channel surface 1017 configured to receive the corresponding tip 910 and encourage the tip 910 to form in a curved direction P4. Shown in FIG. 24, the forming pocket 1011 comprises a first valley-like, curved surface 1015A and a second valley-like, curved surface 1015B configured to funnel, or catch, the tip 910 of the staple in the event of minor misalignment during contact. The staple 900, staple leg 901, and/or staple tip 910 may be driven off target with respect to the forming channel surface 917 upon ejection from its staple cavity. The valley-like surfaces permit some longitudinal and lateral roll of the staple. Although illustrated as concave surfaces, the valley surfaces may be convex or flat, for example.

The forming pocket 1021 comprises a forming channel surface 1027 configured to receive the corresponding tip 920 of the staple 900 and encourage the tip 920 to form in a direction D4. FIG. 23 illustrates an instance in which the staple legs 901, 902 are formed toward each other with one staple leg 901 formed away from the staple base 930 and one staple leg 902 formed toward the staple base 930. Other embodiments are envisioned where the directions P4, D4 direct the corresponding staple legs 901, 902 in opposite directions but outward with respect to each other. The forming pocket 1021 comprises a first valley-like, curved surface 1025A and a second valley-like, curved surface 1025B configured to funnel, or catch, the tip 920 of the staple 900 in the event of minor misalignment before and/or during contact.

Figure 25:
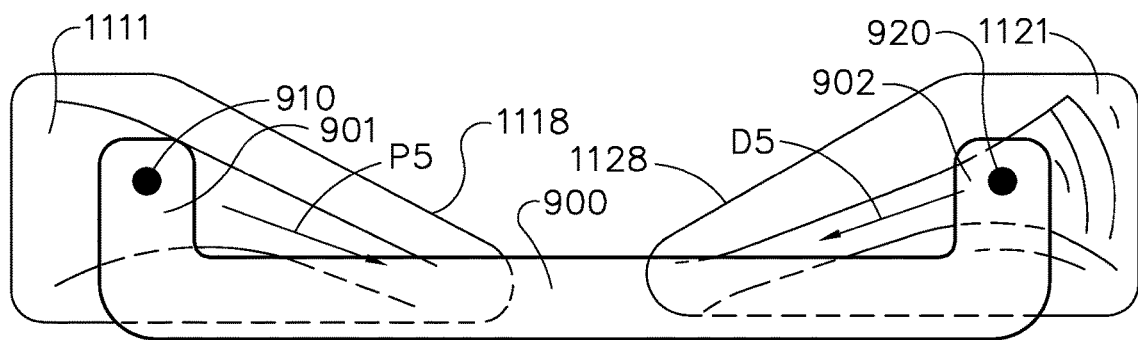
FIG. 25 is a bottom view of the staple of FIG. 19 and forming pockets in accordance with at least one embodiment.

FIG. 25 depicts yet another embodiment of forming pockets comprising anvil forming pockets 1111, 1121 configured to deform corresponding staple legs 901, 902 and tips 910, 920 toward the staple base 930. The forming pockets 1111, 1121 are trapezoidal in shape and can be nested with other similar forming pockets using less space on a forming surface of an anvil. The forming pockets 1111, 1121 are configured to form the staple legs 901, 902 and tips 910, 920 in directions P5, D5, respectively.

Figure 26:
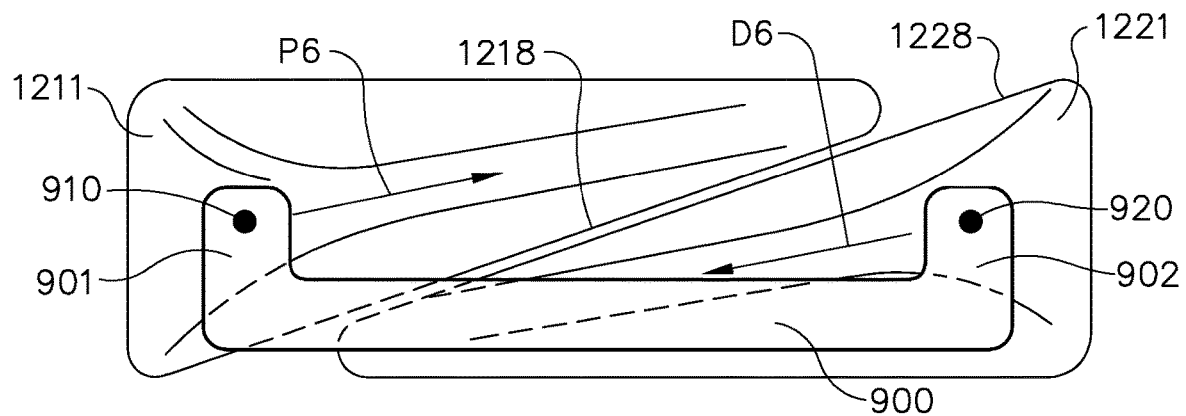
FIG. 26 is a bottom view of the staple of FIG. 19 and forming pockets in accordance with at least one embodiment.

FIG. 26 depicts yet another embodiment of forming pockets comprising anvil forming pockets 1211, 1221 configured to deform corresponding staple legs 901, 902 and tips 910, 920 in directions P6, D6, respectively. The forming pockets 1111, 1121 are triangular in shape and can be nested with each other comprising an even more compact forming pocket arrangement on an anvil of a surgical stapling instrument.

Referring now to FIGS. 27-27B, a staple leg 1300 is depicted. The staple leg 1300 comprises a substantially round staple tip with a substantially square staple leg and a staple leg body portion 1301. The staple leg 1300 comprises hardened corners formed using a coining process, for example, where the corners 1303A, 1303B, 1303C, and 1303D were rounded in order to create preferential bending planes. Stated another way, the staple leg 1300 comprises a cross-sectional profile configured to encourage the staple leg 1300 to bend in a certain direction due to the corner hardening upon contact with an anvil. The corners 1303A, 1303B, 1303C, and 1303D may vary in hardness from one corner to the next, or, may comprise two corners with a first hardness and the other two corners with a second hardness. The corners 1303A, 1303B, 1303C, and 1303D may be coined to provide different radial profiles on the same staple leg. For example, the corner 1303A comprises a radial profile with a radius $R_A$ greater than the radius $R_B$ of the radial profile of corner 1303B shown in FIG. 27B.

Portions of the staples disclosed herein may be hardened at various times of the manufacturing process with any suitable means. For example, hardening process may include bronzing, chemical vapor deposition, physical vapor deposition, laser surface treatment, thermal oxidation, ion nitriding, and/or solid state diffusion, for example. Other portions of the staples may be prevented from being hardened by these processes. Other portions of the staples may be locally annealed, such as the staple tips, for example. Increasing hardness in certain areas can increase the force required to unform the staples after the staples have assumed a fired configuration.

Figure 28:
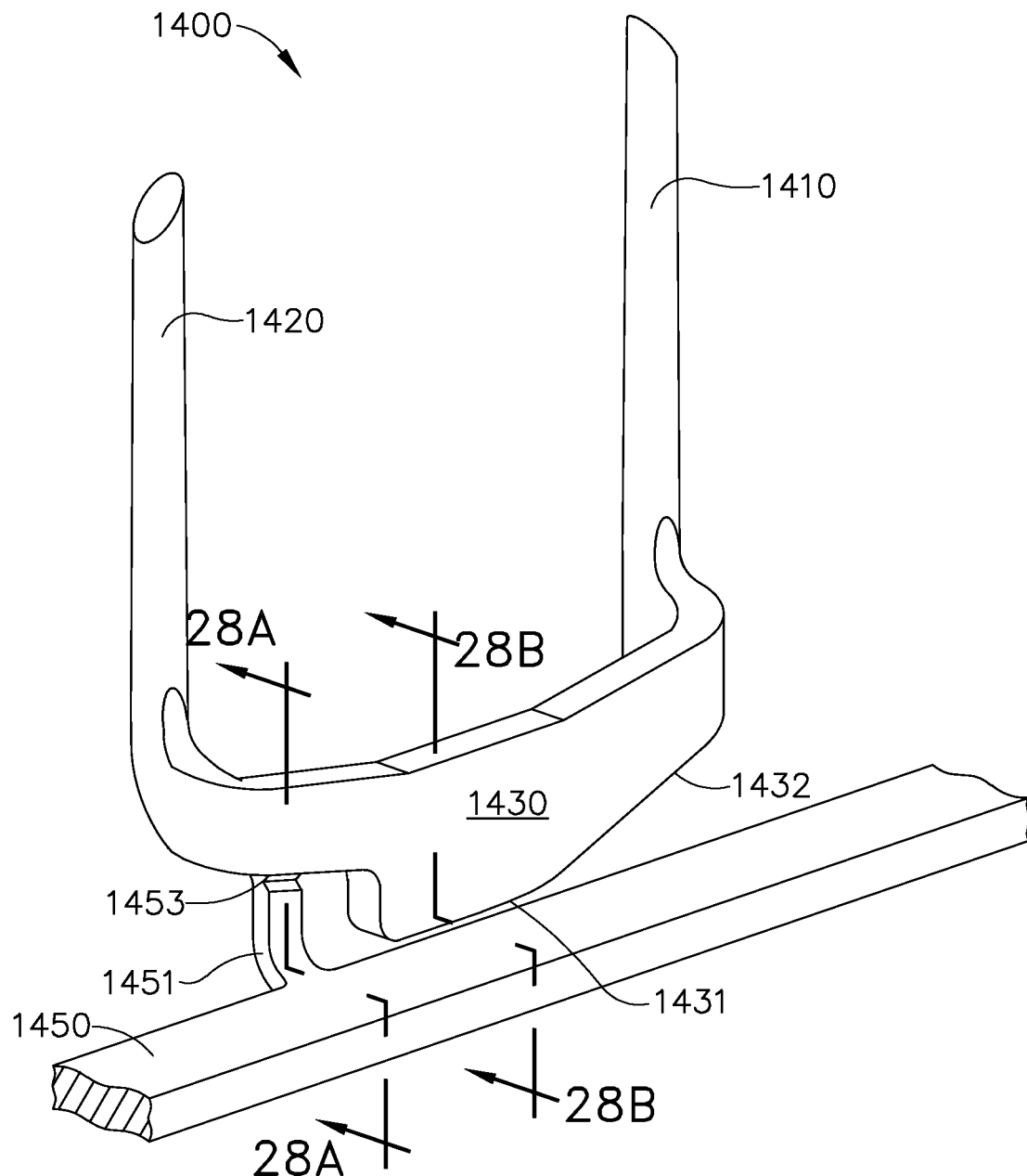
FIG. 28 is a perspective view of a portion of a staple strip manufactured with progressive die stamping.

FIGS. 28-28C depict a staple 1400 and a sled 1460 in accordance with at least one embodiment. The staple 1400 comprises staple legs 1410, 1420, a staple base portion 1430 from which the staple legs 1410, 1420 extend, a drive surface 1432, and a bottom surface 1431. The staple legs 1410, 1420 extend from the staple base portion 1430 in a plane which is a parallel and offset with respect to a plane defined by the staple base portion 1430. The staple 1400 is made with progressive die stamping utilizing a base strip 1450 and a connector portion 1451. Although only a single staple 1400 is shown, a plurality of staples 1400 are attached to the base strip 1450. The connector portion 1451 connects the staple 1400, specifically the staple base portion 1430, to the base strip 1450. The connector portion 1451 comprises a discontinuity, or notch, 1453 configured to permit the staples 1400 to detach from the strip 1450. In at least one instance, the sled 1460 comprises release portions, or striking portions, 1461. The release portions 1461 of the sled 1460 are configured to engage the discontinuities 1453, or connector portions 1451, to separate, break, and/or shear, the staples 1400 from the base strip 1450 and permit the staples to be ejected from their staple cavities by the sled 1460.

Embodiments are envisioned where the base strip 1450 comprises alignment features such as holes, for example, which engage corresponding alignment features on a staple cartridge. Such alignment features may comprise protrusions, for example, that align with the alignment features of the base strip 1450. In various instances, a person loading the staples into the cartridge could align the staples with the staple cavities and/or align the alignment features before pushing the staples into the staple cavities. Certain embodiments are envisioned in which the staple cartridge comprises engagement features configured to engage the discontinuities 1453 when the strip assemblies are loaded into the staple cartridge. The engagement features allow the staples 1400 to be separated from the strip 1450 when the staples 1400 are loaded into a staple cartridge instead of when the staples 1400 are fired. Manufacturing staples using progressive die stamping can permit staples to have different crown sizes, shapes, and/or configurations as well as staple leg sizes, shapes, and/or configurations. Another advantage of using progressive die stamping technology may include the ability to alter the spacing of the rows of staples in which the staples are aligned.

Figure 29:
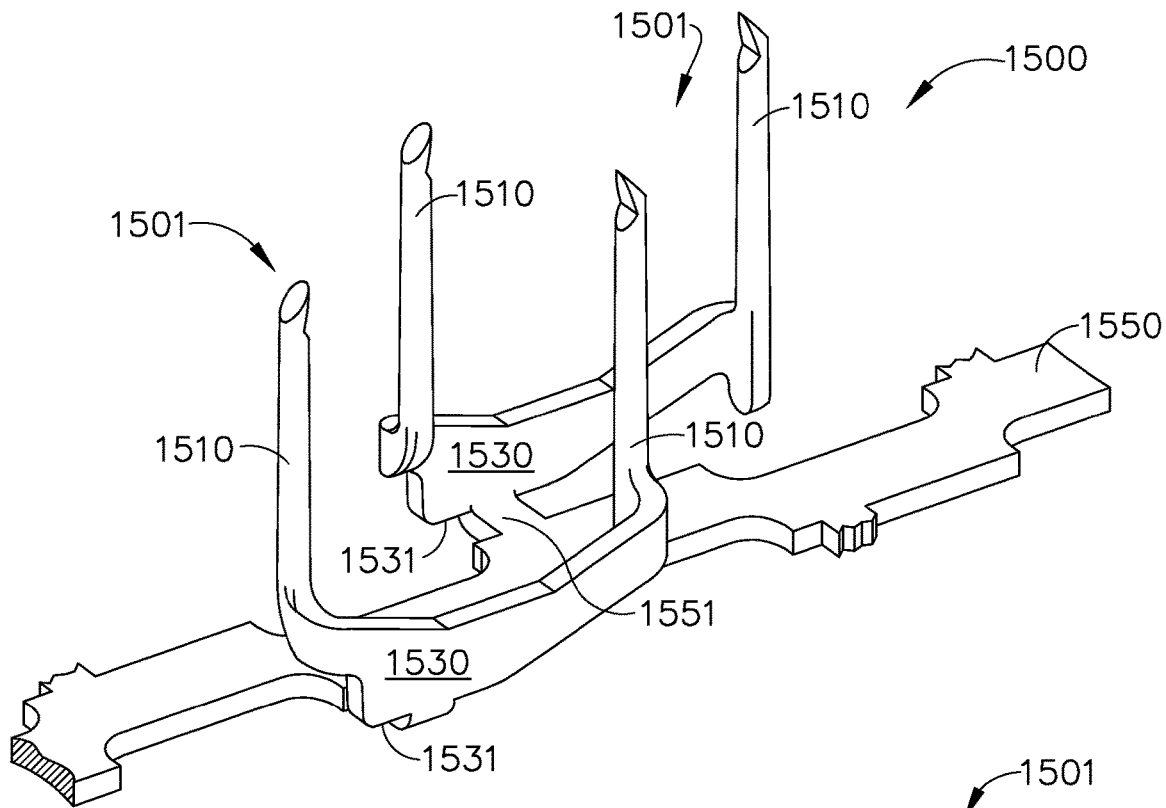
FIG. 29 is a perspective view of a portion of a staple strip manufactured with progressive die stamping in accordance with at least one embodiment.
Figure 30:
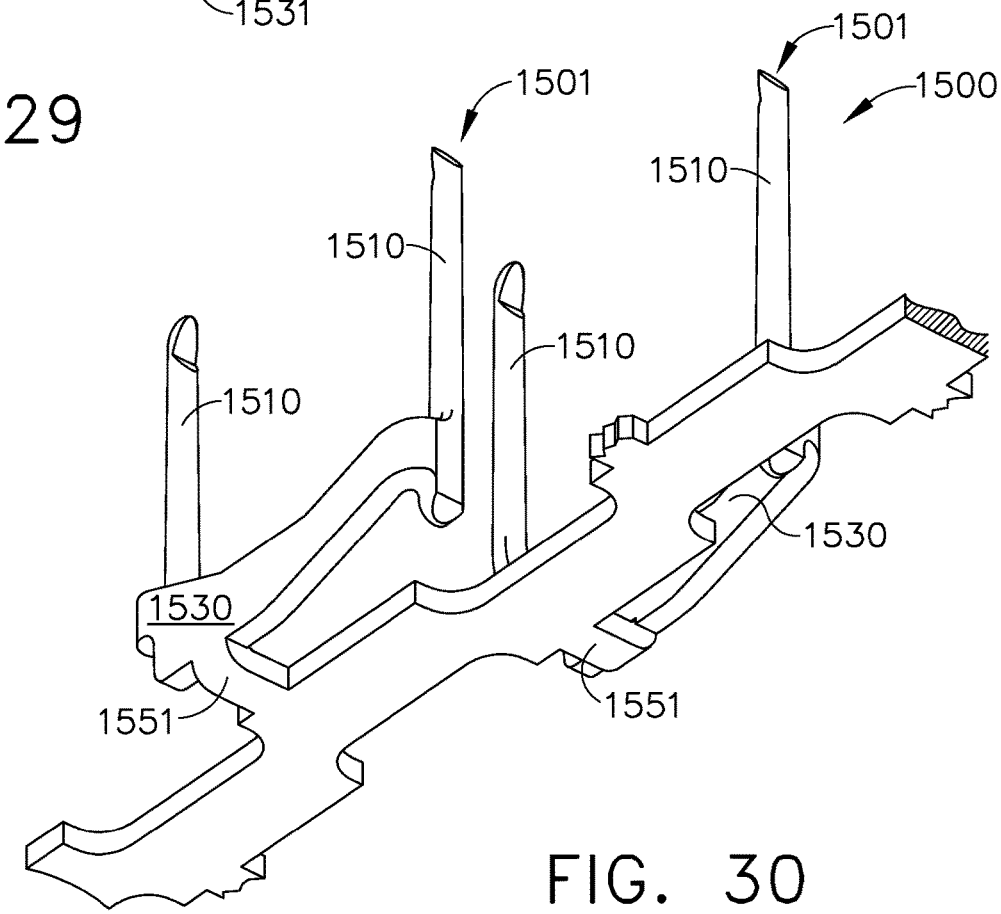
FIG. 30 is a bottom perspective view of the staple strip of FIG. 29.

FIGS. 29 and 30 depict another embodiment of a strip 1500 of staples 1501 made with progressive die stamping. The strip 1500 of staples 1501 comprises a base strip 1550, a connector portion 1551, and staples 1501. Each staple 1501 comprises, one, a staple base portion 1530 comprising a bottom surface 1531 and, two, staple legs 1510 extending from the staple base portion 1530. The connector portion 1551 attaches the bottom surface 1531 of the staple base portion 1530 to the base strip 1550. The staple legs are bent up from the staple base portion 1530 such that the legs 1510 reside in a plane which is offset and at least substantially parallel to a plane defined by the staple base portion 1530. In the illustrated embodiment, the staple legs 1510 are bent in a direction opposite to that of the connector portion 1551. Bending the legs 1510 and the connector portions 1551 in this manner can permit a more dense staple row arrangement. The connector portions 1551 can comprise a discontinuity enabling the staples 1501 to be released from the base strip 1550 upon loading the staples 1501 into a staple cartridge and/or firing the staples 1501 from the staple cartridge as discussed in the previous embodiment.

Figure 31:
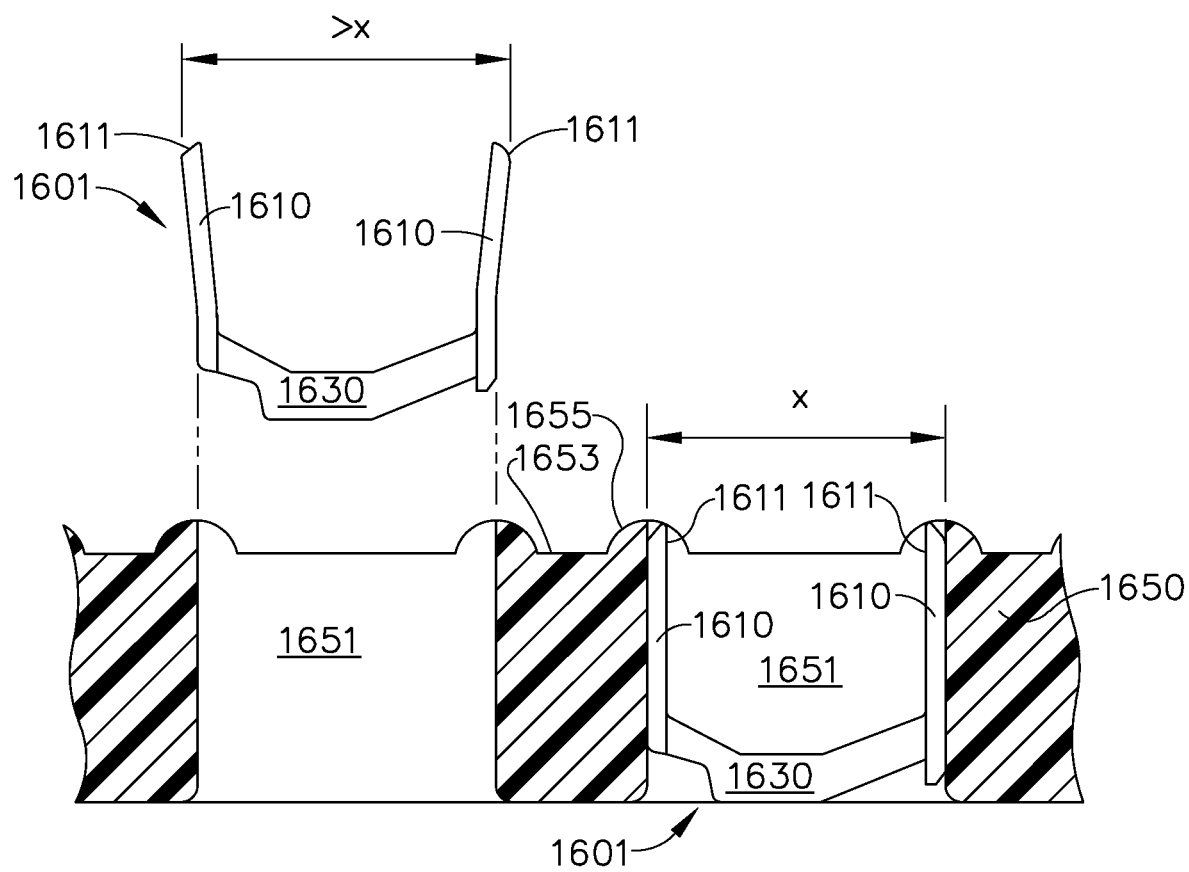
FIG. 31 is a partial cross-sectional view of a staple cartridge and staples in accordance with at least one embodiment.

FIG. 31 depicts a plurality of staples 1601 and a cross-sectional view of a portion of a staple cartridge 1650 in accordance with at least one embodiment. The staples 1601 are removably stored within corresponding staple cavities 1651 of the staple cartridge 1650. The staple cartridge 1650 comprises a deck surface 1653 and staple leg supports 1655. The staples 1601 comprise, one, staple legs 1610 which each comprise a staple tip 1611 and, two, a staple base portion 1630 from which the staple legs 1610 extend. Each staple 1601 comprises a pre-load configuration, a loaded configuration, and a fired configuration where the staple 1601 is ejected from the staple cartridge 1650 and formed against corresponding forming pockets of an anvil. The staple legs 1610 are bent outwardly with respect to the staple base portions 1630 in the pre-load configuration. The staple legs 1610 are biased against sidewalls of the corresponding staple cavity 1651 in the loaded configuration and define a first distance X between the tips 1611 of the staple legs 1610. In the pre-load configuration, the distance between the staple tips 1611 of the staple legs 1610 is greater than X. This biasing force helps support the staples 1601 in the staple cartridge 1650.

Figure 32:
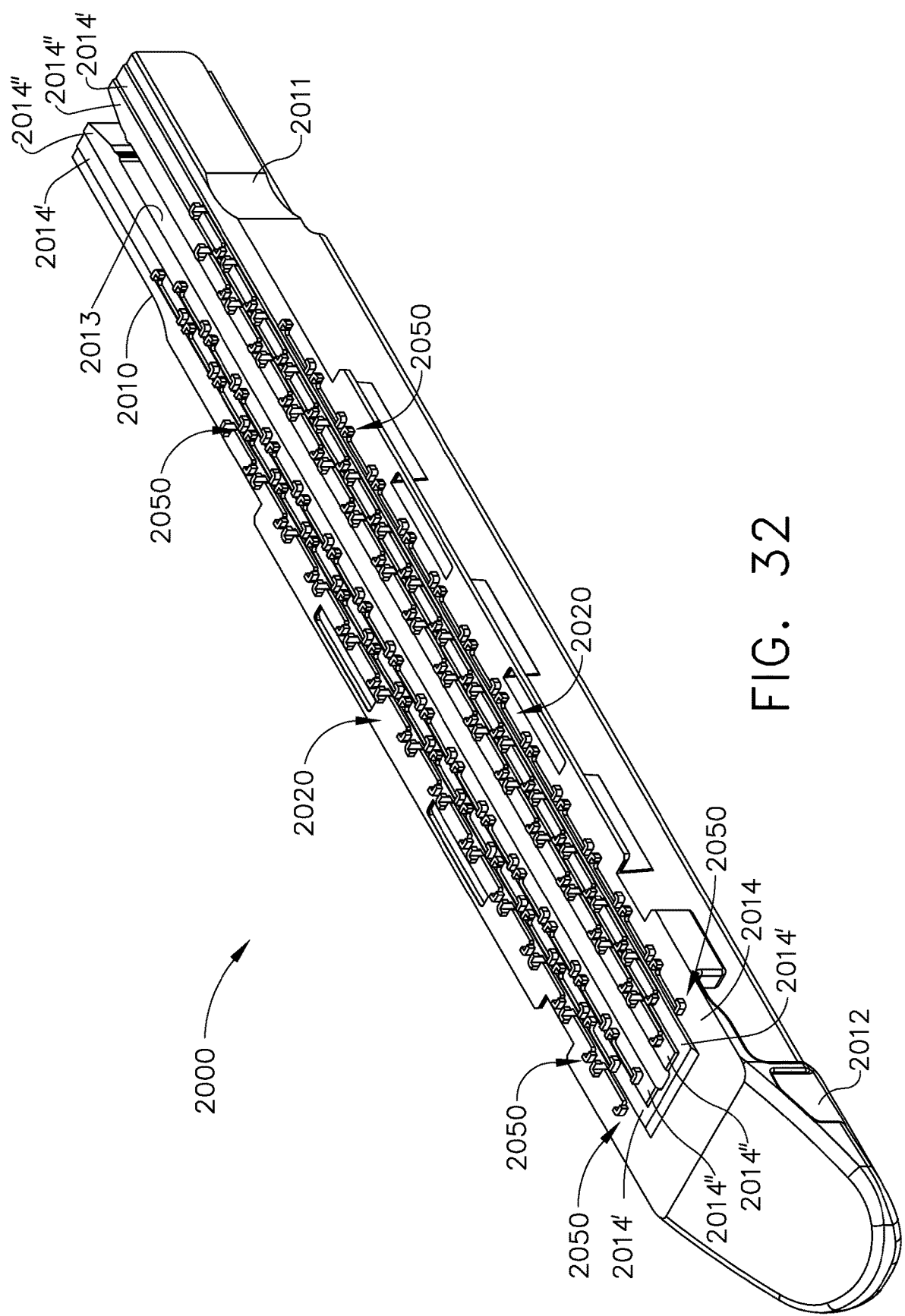
FIG. 32 is a perspective view of a staple cartridge assembly in accordance with at least one embodiment.
Figure 33:
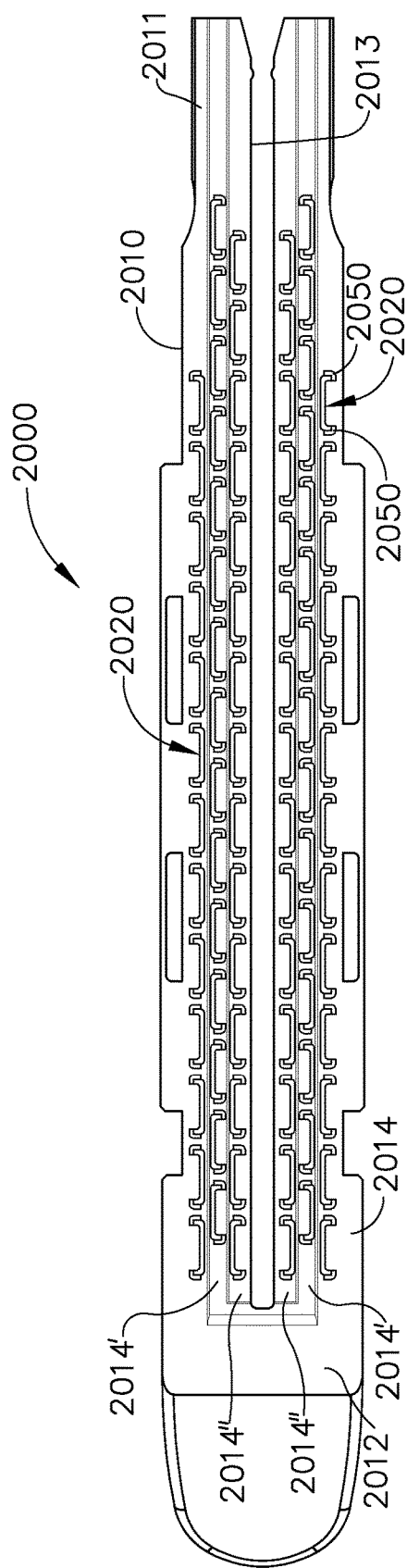
FIG. 33 is a top plan view of the staple cartridge assembly of FIG. 32.
Figure 34:
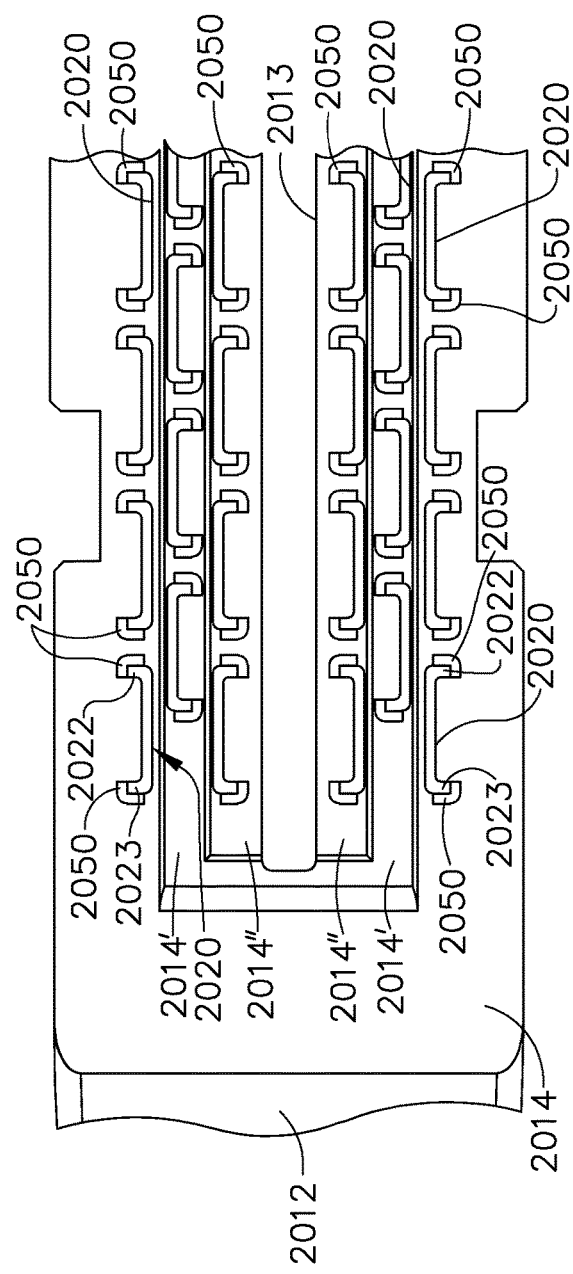
FIG. 34 is a detail view of a distal end of the staple cartridge assembly of FIG. 32.

A staple cartridge 2000 is illustrated in FIGS. 32-34. The staple cartridge assembly 2000 comprises a cartridge body 2010. The cartridge body 2010 is positionable in and removable from a jaw of a surgical stapling instrument. As a result, the staple cartridge 2000 is replaceable; however, other embodiments are envisioned in which the staple cartridge 2000 is not replaceable. The cartridge body 2010 comprises a proximal end 2011, a distal end 2012, and a deck 2014 extending between the proximal end 2011 and the distal end 2012. The deck 2014 is configured to support the tissue of a patient when the tissue is compressed against the deck 2014.

Figure 40:
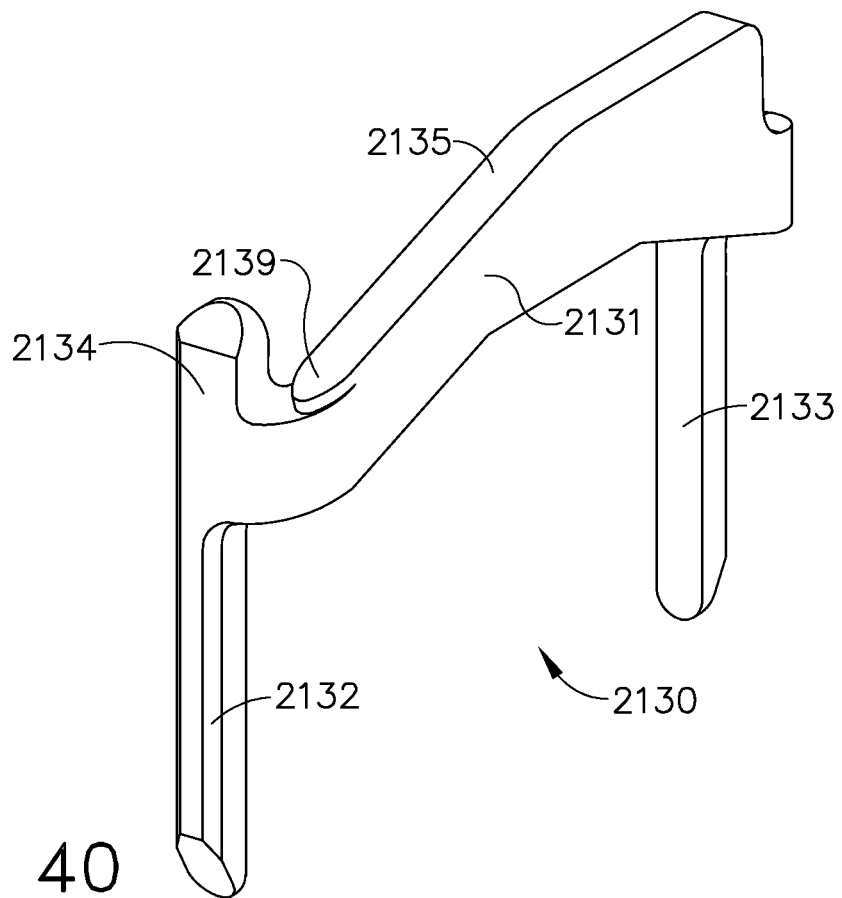
FIG. 40 is a bottom perspective view of the staple of FIG. 39.

The cartridge body 2010 further comprises a plurality of staple cavities 2020 defined therein. The staple cavities 2020 are arranged in six longitudinal rows extending between the proximal end 2011 and the distal end 2012; however, any suitable arrangement of staple cavities 2020 can be utilized. A staple, such as staple 2130 (FIG. 40), for example, is removably stored in each staple cavity 2020. As discussed in greater detail below, the staples are ejected from the staple cavities 2020 by a firing member when the firing member is moved from the proximal end 2011 of the cartridge body 2010 toward the distal end 2012.

Further to the above, the staples are moved from an unfired position to a fired position by the firing member. The firing member lifts the staples toward an anvil, such as anvil 2190 (FIG. 37), for example, to deform the staples between an unfired, undeformed configuration and a fired, deformed configuration. The cartridge body 2010 further comprises a longitudinal slot 2013 defined therein. The slot 2013 is configured to receive the staple firing member and/or a tissue cutting member therein when the staples are ejected from the staple cavities 2020.

In various embodiments, further to the above, the staples do not protrude above the deck 2014 until they are moved toward the anvil by the firing member. Such embodiments may frequently utilize small staples. In other embodiments, the legs of the staples protrude above the deck 2014 when the staples are in their unfired positions. In at least one such embodiment, the cartridge body 2010 further comprises projections 2050 extending from the deck 2014. The projections 2050 extend the staple cavities 2020 above the deck 2014 and guide the staples toward the anvil when the staples are being ejected from the staple cartridge 2000. In such embodiments, the staples may not extend above the projections 2050 until they are moved toward the anvil by the firing member.

Referring primarily to FIG. 34, the projections 2050 do not extend around the entirety of the staple cavities 2020. A first projection 2050 is positioned adjacent a first end of each cavity 2020 and a second projection 2050 is positioned adjacent a second end of each cavity 2020. Each first projection 2050 extends around a first staple leg guide 2022 of a staple cavity 2020 and each second projection 2050 extends around a second staple leg guide 2023 of the staple cavity 2020. Each first projection 2050 provides a proximal bracket which can control and guide the proximal leg of a staple and each second projection 2050 provides a distal bracket which can control and guide the distal leg of the staple. The first projection 2050 of each staple cavity 2020 is not symmetrical with respect to the first end of the staple cavity 2020 and does not extend around the entirety of the first end of the cavity 2020. Similarly, the second projection 2050 of each staple cavity 2020 is not symmetrical with respect to the second end of the staple cavity 2020 and does not extend around the entirety of the second end of the cavity 2020. The first projection 2050 and the second projection 2050 comprise mirror images of one another and are symmetrically arranged with respect to the center of each staple cavity 2020; however, any suitable arrangement of projections could be utilized.

As illustrated in FIGS. 32-34, the cartridge body 2010 comprises steps 2014' and steps 2014" which extend upwardly from the deck 2014. More specifically, the steps 2014' extend upwardly from the deck 2014 and the steps 2014" extend upwardly from the steps 2014'. As a result, the steps 2014" may apply a larger compressive pressure to the tissue than the steps 2014' and, similarly, the steps 2014' may apply a larger compressive pressure to the tissue than the deck 2014. The steps 2014' and 2014" comprise staggered longitudinal plateaus; however, the steps 2014' and 2014" may comprise any suitable configuration. Moreover, further to the above, the projections 2050 extending from the steps 2014" extend above the projections 2050 extending from the steps 2014' and, similarly, the projections 2050 extending from the steps 2014' extend above the projections 2050 extending from the deck 2014. Stated another way, the projections 2050 extending from the deck 2014, the steps 2014', and the steps 2014" are staggered.

A staple cartridge 2100 is illustrated in FIGS. 35-38. The staple cartridge assembly 2100 comprises a cartridge body 2110 and is similar to the staple cartridge assembly 2000 and/or the other staple cartridges disclosed herein in many respects. The cartridge body 2110 comprises a deck 2114, a plurality of staple cavities 2120*a*, and a plurality of staple cavities 2120*b*. The staple cavities 2120*a* are similar to the staple cavities 2120*b* in many respects. For instance, the staple cavities 2120*a* and 2120*b* both comprise a central slot 2121 having a proximal end and a distal end, a proximal staple leg guide 2122 extending laterally from the proximal end of the central slot 2121, and a distal staple leg guide 2123 extending laterally from the distal end of the central slot 2121. That said, the staple cavities 2120*a* and the staple cavities 2120*b* are oriented in different directions. More particularly, the staple leg guides 2122, 2123 of the staple cavities 2120*a* extend toward the staple cavities 2120*b* and, similarly, the staple leg guides 2122, 2123 of the staple cavities 2120*b* extend toward the staple cavities 2120*a*; however, any suitable arrangement can be utilized.

A staple 2130*a* is positioned in each staple cavity 2120*a* and a staple 2130*b* is positioned in each staple cavity 2120*b*. The staples 2130*a* and the staples 2130*b* are similar in many respects. For instance, each staple 2130*a* comprises a base, or crown, 2131, a proximal leg 2132 extending from a proximal end of the base 2131, and a distal leg 2133 extending from a distal end of the base 2131. That said, the staples 2130*a*, 2130*b* are adapted in a manner to fit within the staple cavities 2120*a*, 2120*b*, respectively. For example, when the staples 2130*a* are positioned in the staple cavities 2120*a* and the staples 2130*b* are positioned in the staple cavities 2120*b*, the legs 2132, 2133 of the staples 2130*a* extend toward the staples 2130*b* and the legs 2132, 2133 of the staples 2130*b* extend toward the staples 2130*a*; however, other arrangements are possible.

Figure 35:
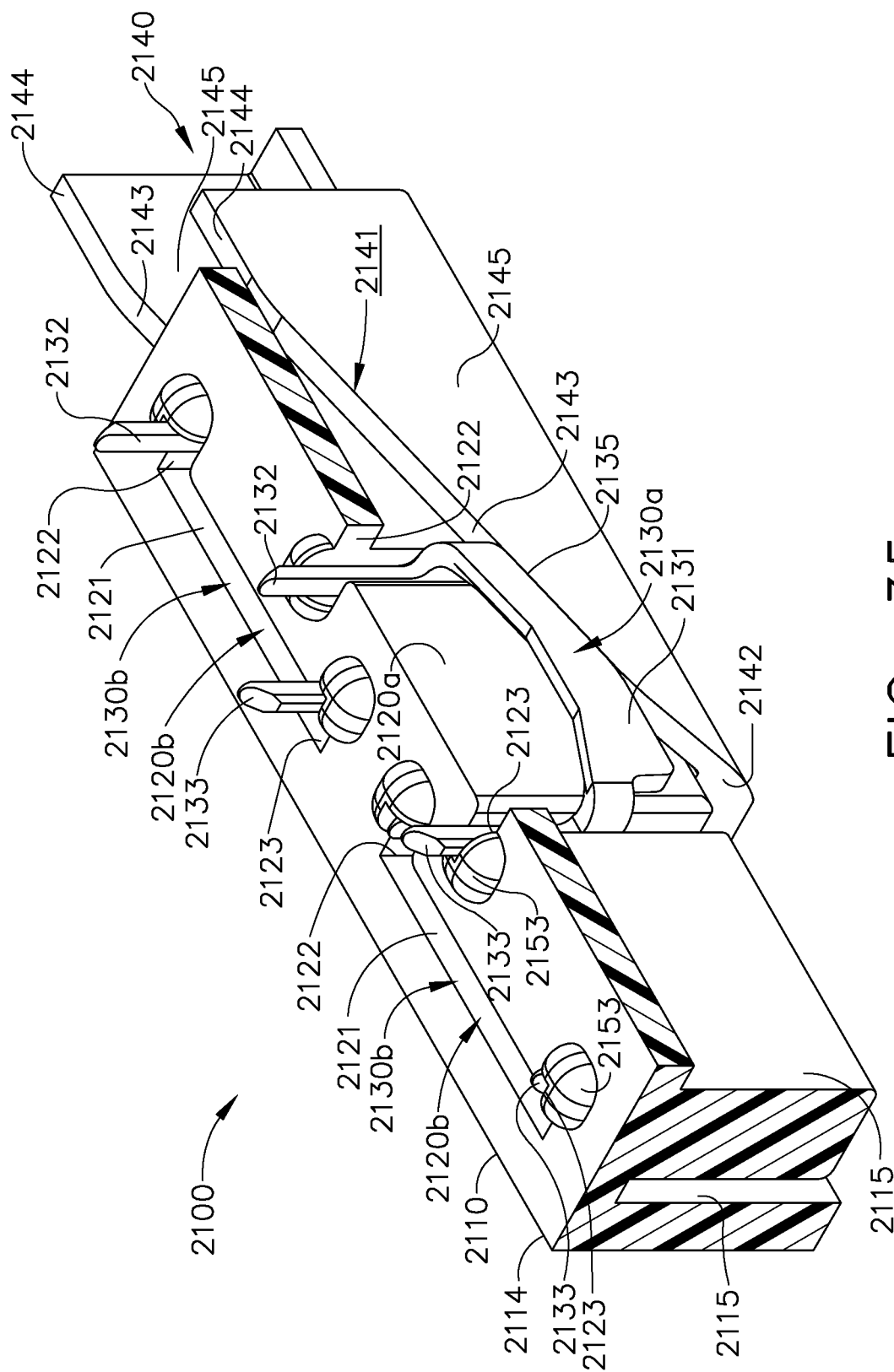
FIG. 35 is a partial cross-sectional perspective view of a staple cartridge assembly in accordance with at least one embodiment illustrating staples being ejected from the staple cartridge assembly by a firing member.
Figure 36:
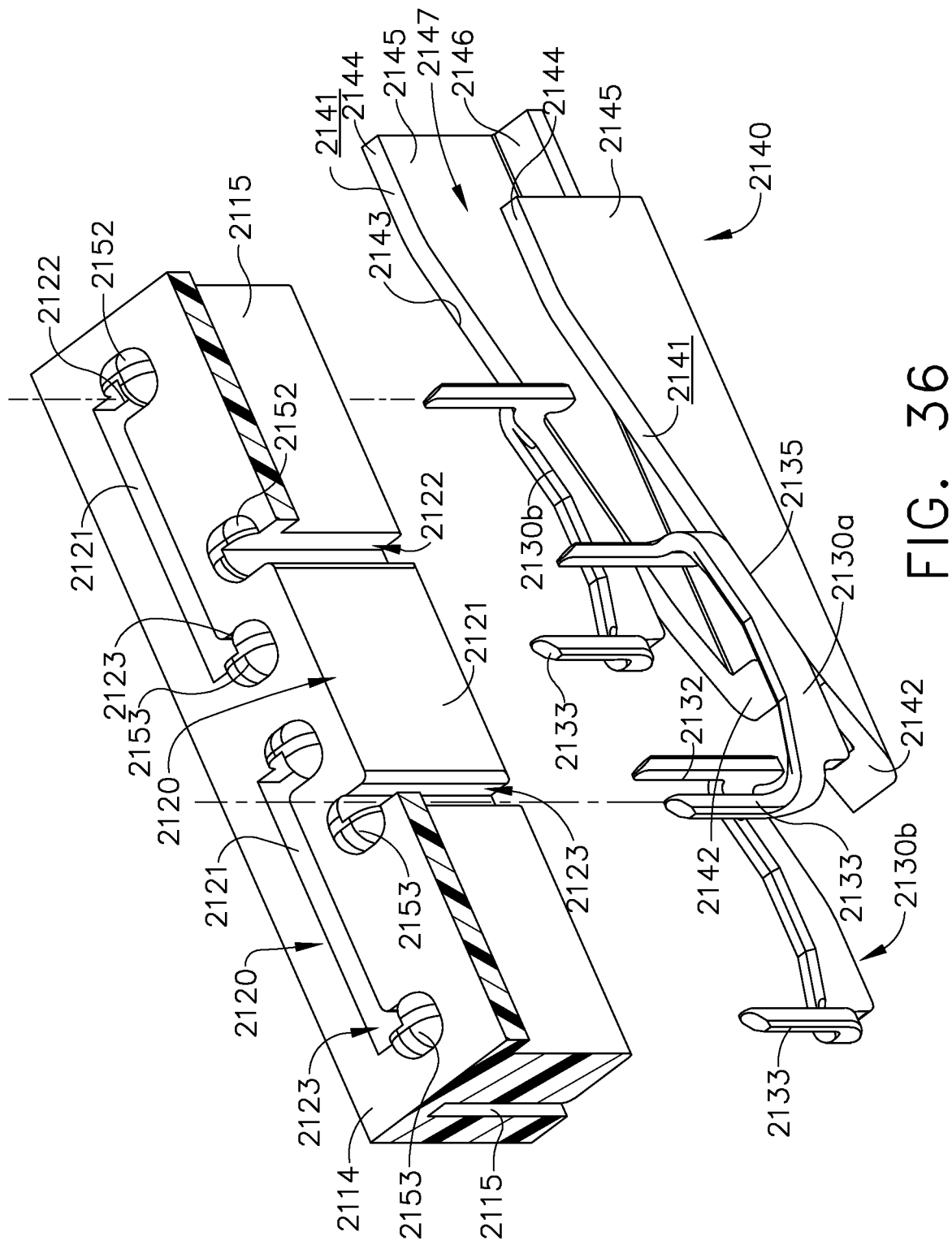
FIG. 36 is a partial exploded view of the staple cartridge assembly of FIG. 35.

Further to the above, the proximal legs 2132 of the staples 2130*a*, 2130*b* are positioned within the staple leg guides 2122 when the staples 2130*a*, 2130*b* are stored in the staple cavities 2120*a*, 2120*b*, respectively. Similarly, the distal legs 2133 of the staples 2130*a*, 2130*b* are positioned within the staple leg guides 2123 when the staples 2130*a*, 2130*b* are stored in the staple cavities 2120*a*, 2120*b*, respectively. Moreover, the bases 2131 of the staples 2130*a*, 2130*b* are positioned in the central slots 2121 of the staple cavities 2120 when he staples 2130*a*, 2130*b* are stored in the staple cavities 2120*a*, 2120*b*, respectively. Referring primarily to FIG. 35, the tips of the staple legs 2132, 2133 extend above the deck 2114 of the cartridge body 2110 when the staples 2130*a*, 2130*b* are in their unfired positions. That said, the tips of the staple legs 2132 are at least partially surrounded by proximal projections 2152 extending from the deck 2114 and the tips of the staple legs 2133 are at least partially surrounded by distal projections 2153 extending from the deck 2114. The proximal projections 2152 extend around the proximal staple leg guides 2122, but they do not extend around the proximal ends of the central slots 2121. Similarly, the distal projections 2153 extend around the distal staple leg guides 2123, but they do not extend around the distal ends of the central slots 2121.

Figure 38:
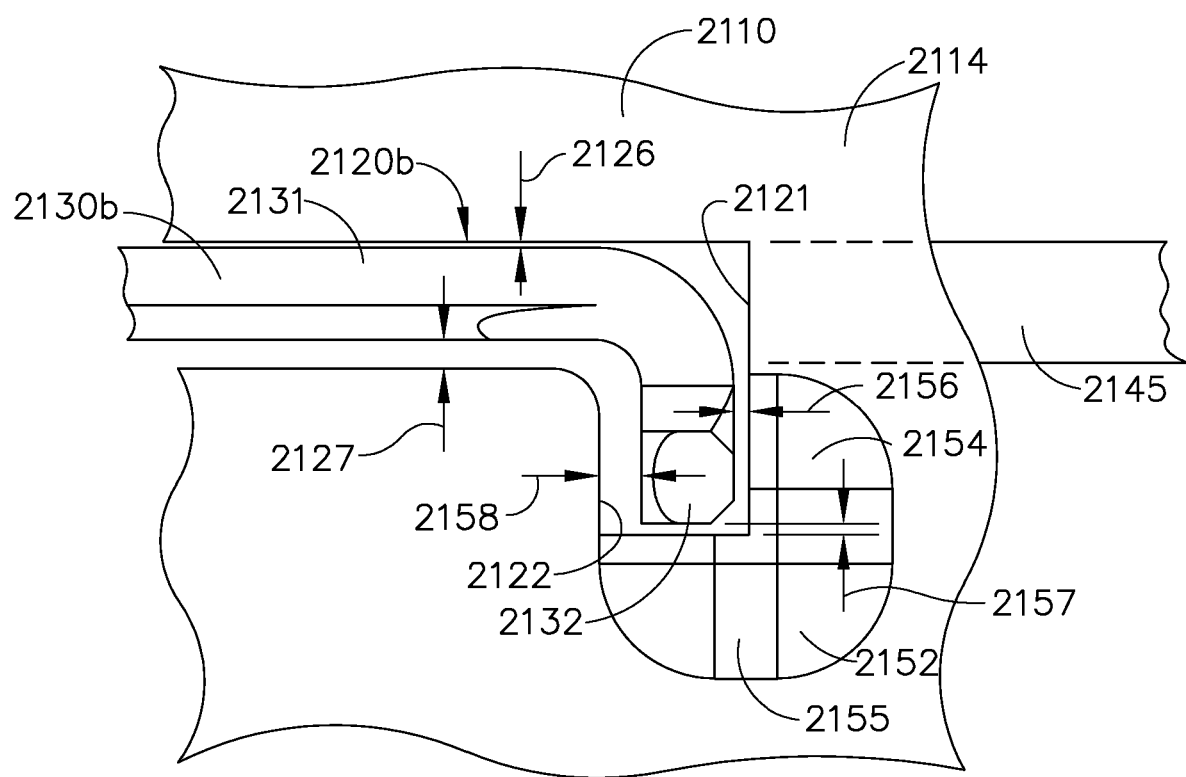
FIG. 38 is a partial plan view of a staple positioned in a staple cavity of the staple cartridge assembly of FIG. 35.

Turning now to FIG. 38, each proximal projection 2152 comprises a first portion 2154 which extends around a proximal side of the proximal guide slot 2122 and a second portion 2155 which extends around a lateral side of the proximal guide slot 2122. The proximal projection 2152 does not extend around a distal side of the proximal guide slot 2122; however, it is envisioned that the proximal projection 2152 can extend around the distal side of the proximal guide slot in alternative embodiments. Similarly, each distal projection 2153 comprises a first portion which extends around a distal side of the distal guide slot 2123 and a second portion which extends around a lateral side of the distal guide slot 2123. The distal projection 2153 does not extend around a proximal side of the distal guide slot 2123; however, it is envisioned that the distal projection 2153 can extend around the proximal side of the distal guide slot in alternative embodiments. In any event, the arrangement depicted in FIG. 38 protects the staple legs 2132, 2133 when the staples 2130*a*, 2130*b* are in their unfired positions and, in addition, guide the staples 2130*a*, 2130*b* as the staples are being fired. Such an arrangement also appropriately controls the flow of tissue relative to the deck 2114 of the cartridge body 2110.

Referring again to FIG. 38, the staple cavities 2120*a* and the staples 2130*a* are sized and configured such that clearance gaps are provided between the staples 2130*a* and the staple cavities 2120*a*. For example, a clearance gap 2156 is present between the proximal leg 2132 of a staple 2130*b* and the proximal sidewall of the proximal guide slot 2122 and, similarly, a clearance gap 2158 is present between the proximal leg 2132 of the staple 2130*b* and the distal sidewall of the proximal guide slot 2122. In addition, a clearance gap 2157 is present between the lateral side of the proximal leg 2132 and the lateral sidewall of the proximal guide slot 2122. Similar gaps can be found between the distal leg 2133 and the distal guide slot 2123. Lateral clearance gaps 2126, 2127 can also be provided between the base 2131 of the staple 2130*b* and the lateral sides of the central slot 2121. Such clearance gaps may be transient and the staple may contact one or more of the sidewalls nonetheless.

Figure 43:
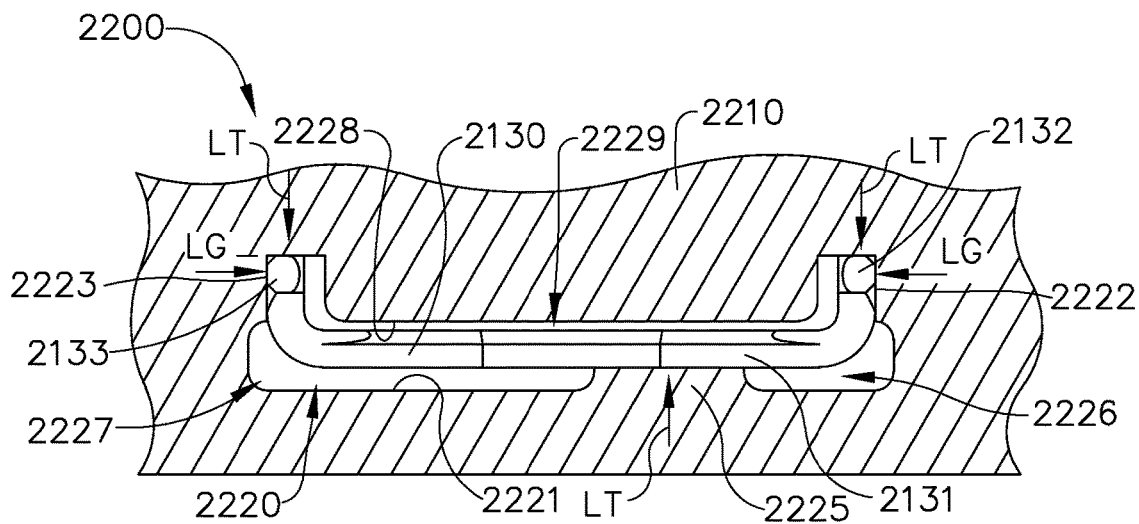
FIG. 43 is a cross-sectional plan view of a staple cavity configured to guide a staple in accordance with at least one embodiment.
Figure 44:
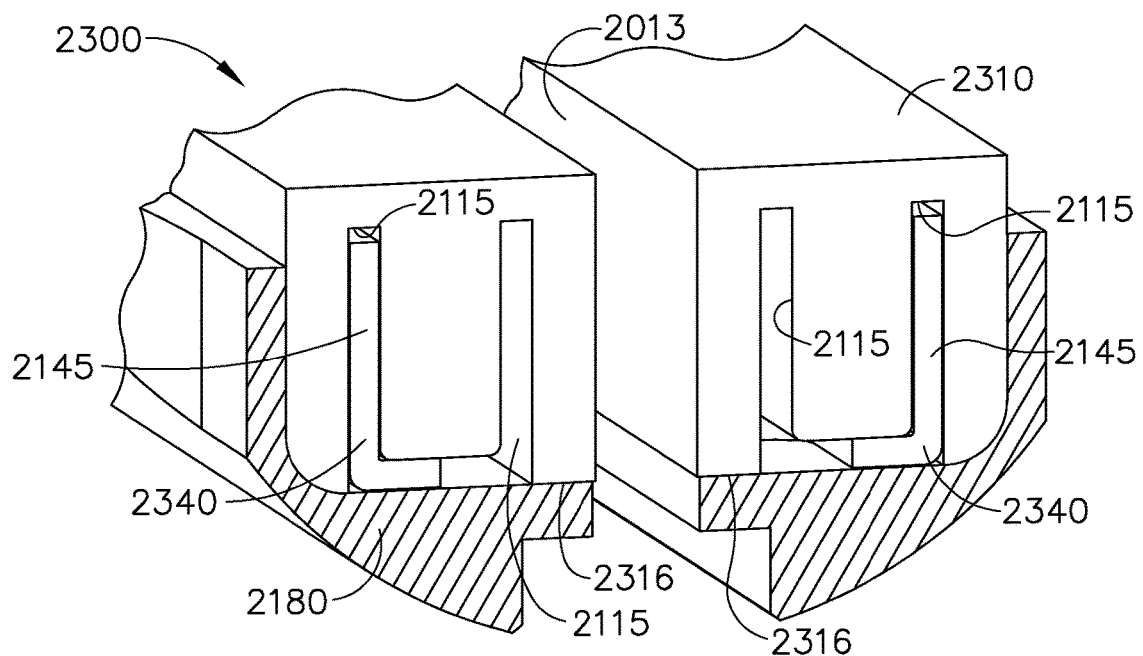
FIG. 44 is a cross-sectional perspective view of a staple cartridge assembly positioned in a jaw of a surgical stapling instrument in accordance with at least one embodiment illustrating a firing member positioned in a cartridge body of the staple cartridge assembly.

A staple cartridge 2200 is illustrated in FIG. 43. The staple cartridge 2200 is similar to the staple cartridges 2000, 2100 and the other staple cartridges disclosed herein in many respects. The staple cartridge 2200 comprises a cartridge body 2210 including staple cavities 2220 defined therein. Each of the staple cavities 2220 has a staple, such as staple 2130, for example, removably stored therein. Each staple cavity 2220 comprises a first guide slot 2222 configured to guide the leg 2132 of the staple 2130, a second guide slot 2223 configured to guide the leg 2133 of the staple 2130, and a central slot 2221. The guide slots 2222 and 2223 extend laterally from the central slot 2221 and the central slot 2221 includes an intermediate guide 2225 configured to guide the base 2131 of the staple 2130. The first guide slot 2222 is sized and configured such that the staple leg 2132 is closely received in a corner of the first guide slot 2222. Similarly, the second guide slot 2223 is sized and configured such that the staple leg 2133 is closely received in a corner of the second guide slot 2223. The intermediate guide 2225 is sized and configured to limit the lateral movement of the staple 2130 within the staple cavity 2220. Moreover, the intermediate guide 2225 is sized and configured to hold the staple legs 2132 and 2133 in the staple leg guide slots 2222 and 2223, respectively.

As discussed above, the intermediate guide 2225 is sized and configured to hold the staple legs 2132 and 2133 against the sidewalls of the guide slots 2222 and 2223, respectively. Such an arrangement creates lateral reaction forces, indicated as force vectors LT in FIG. 43, between the lateral sidewalls of the cavity 2220 and the staple 2130. Such lateral reaction forces generate friction forces between the sidewalls of the cavity 2220 and the staple 2130 when the staple 2130 is ejected from the cavity 2220. It should be understood that friction forces are a function of the surface area in which they are applied and, as such, the intermediate guide 2225 does not extend along the entire length of the central slot 2221. That said, the intermediate guide 2225 has a longitudinal length which is sufficient to control the orientation of the staple 2130 within the cavity 2220. Moreover, the intermediate guide 2225 has a sufficient vertical length sufficient to control the orientation of the staple 2130 during the firing stroke of the staple 2130. In at least one instance, the guide 2225 extends along the entire vertical depth of the cavity 2220.

The intermediate guide 2225 is flat and is configured to interface with a flat surface defined on the lateral side of the base 2131 of the staple 2130; however, any suitable arrangement could be utilized. In certain alternative embodiments, the intermediate guide 2225 comprises a resilient biasing member configured to apply a lateral biasing force to the base 2131 of the staple 2130, for example. In at least one instance, the resilient biasing member could comprise a cantilever spring, for example.

The staple cavity 2220 does not include a lateral guide positioned opposite the lateral intermediate guide 2225. In fact, a clearance gap 2229 is present between a lateral sidewall 2228 and the staple 2130.

Further to the above, referring again to FIG. 43, the staple 2130 is not positioned in the ends of the central slot 2221. More particularly, the central slot 2221 of the cavity 2220 comprises a proximal end 2226 and a distal end 2227 and the staple 2130 does not extend into either the proximal end 2226 or the distal end 2227. Rather, clearance gaps are present between the ends 2226, 2227 and the staple 2130. Such clearance gaps extend between the ends 2226, 2227 and the intermediate guide 2225. As a result, the ends 2226, 2227 of the staple cavity 2220 do not control the longitudinal position of the staple 2130. Instead, the staple leg guides 2222, 2223 control the longitudinal position of the staple 2130. In fact, the legs 2132 and 2133 of the staple 2130 can be biased inwardly by the staple leg guides 2222 and 2223, respectively. Such an arrangement creates longitudinal reaction forces, indicated as force vectors LG in FIG. 43.

As a result of the above, the staple cavity 2220 comprises three control points, or positions, in which the staple cavity 2220 controls the orientation of the staple 2130. These control points comprise discrete control positions with clearance gaps defined therebetween. Stated another way, the guides 2222, 2223, and 2225 triangulate the control of the staple 2130. Alternative embodiments are envisioned which comprise more than three control points. In any event, the control points provided by the staple leg guides 2222 and 2223 are defined in a first control plane. An intermediate control point provided by the intermediate guide 2225 is defined in a second control plane. The first control plane and the second control plane are parallel; however, alternative embodiments are envisioned in which the first control plane and the second control plane are not parallel. Moreover, the first control plane is aligned with, or adjacent to, the staple legs 2132 and 2133 of the staple 2130 and the second control plane is aligned with, or adjacent to, the base 2131 of the staple 2130.

Figure 65:
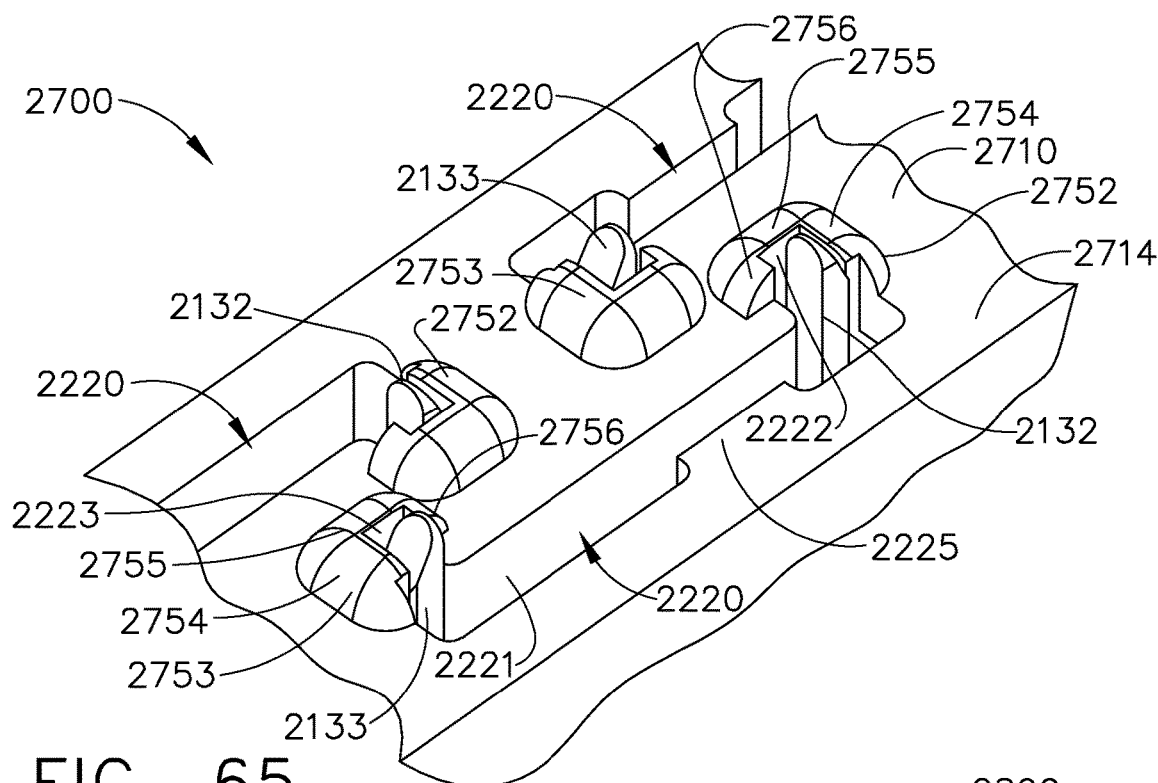
FIG. 65 is a partial perspective view of projections extending from a deck surface of a staple cartridge assembly in accordance with at least one alternative embodiment.

A staple cartridge 2700 is illustrated in FIG. 65. The staple cartridge 2700 comprises a cartridge body 2710 which includes a deck 2714 and a plurality of staple cavities 2220 defined in the deck 2714. Similar to the cartridge body 2110, the cartridge body 2710 includes projections 2752 and 2753 which extend above the deck 2714. The projections 2752 at least partially surround the staple leg guides 2222 of the staple cavities 2220 and the projections 2753 at least partially surround the staple leg guides 2223 of the staple cavities 2220. Similar to projections 2152, 2153, the projections 2752, 2753 each include an outside portion 2754 and a lateral portion 2755. The outside portions 2754 are positioned longitudinally with respect to the staple leg guides 2222 and 2223 while the lateral portions 2755 are positioned laterally with respect to the staple leg guides 2222 and 2223. Unlike the projections 2152, 2153, the projections 2752, 2753 each include an inner portion 2756 which are positioned longitudinally with respect to the staple leg guides 2222 and 2223. The inner portions 2756 are connected to the lateral portions 2755 and the lateral portions 2755 are connected to the outside portions 2754. Similar to the above, the projections 2752, 2753 extend the staple cavities 2220 above the deck 2714.

Figure 66:
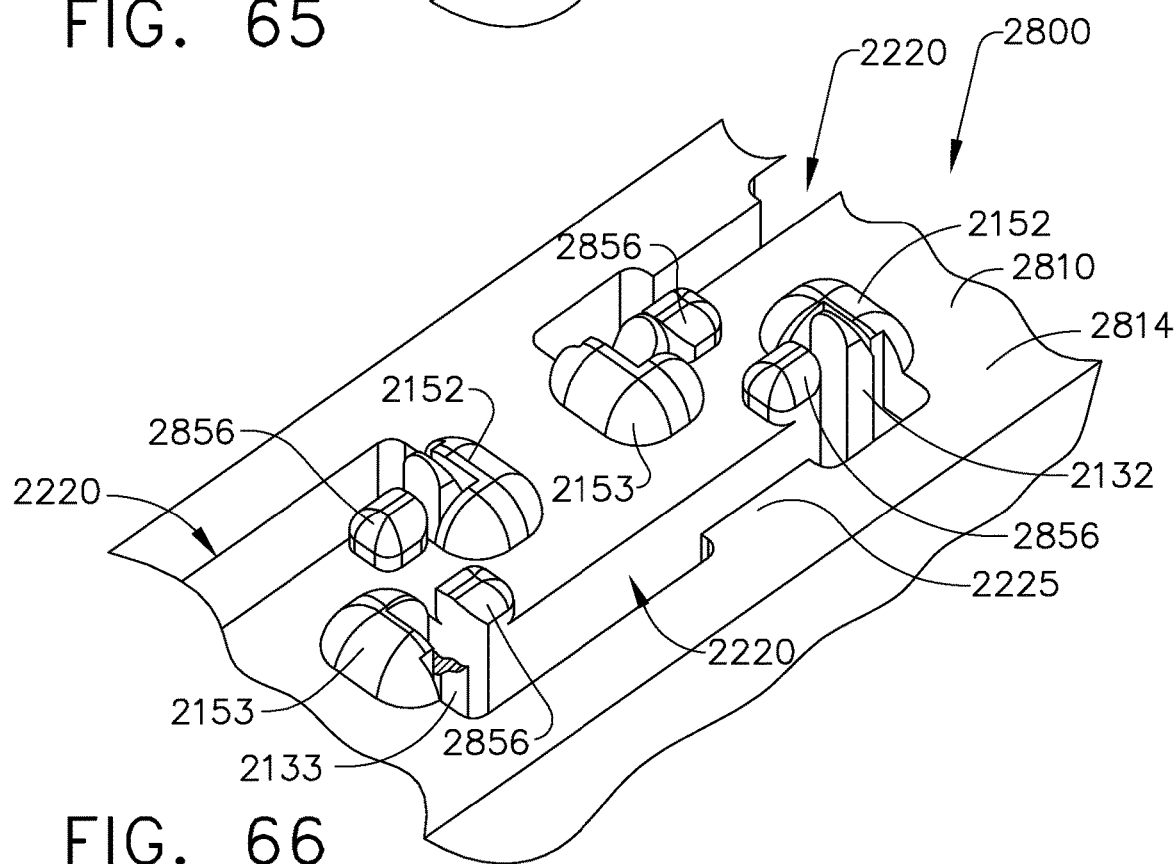
FIG. 66 is a partial perspective view of projections extending from a deck surface of a staple cartridge assembly in accordance with at least one alternative embodiment.

A staple cartridge 2800 is illustrated in FIG. 66. The staple cartridge 2800 comprises a cartridge body 2810 which includes a deck 2814 and a plurality of staple cavities 2220 defined in the deck 2814. Similar to the cartridge body 2110, the cartridge body 2810 includes projections 2152, 2153 which extend above the deck 2114. As outlined above, the projections 2152 at least partially surround the staple leg guides 2222 of the staple cavities 2220 and the projections 2753 at least partially surround the staple leg guides 2223 of the staple cavities 2220. Moreover, the cartridge body 2810 includes inner projections 2856 which are positioned longitudinally with respect to the staple leg guides 2222 and 2223. The inner projections 2856 are not connected to the projections 2152, 2153.

Figure 37:
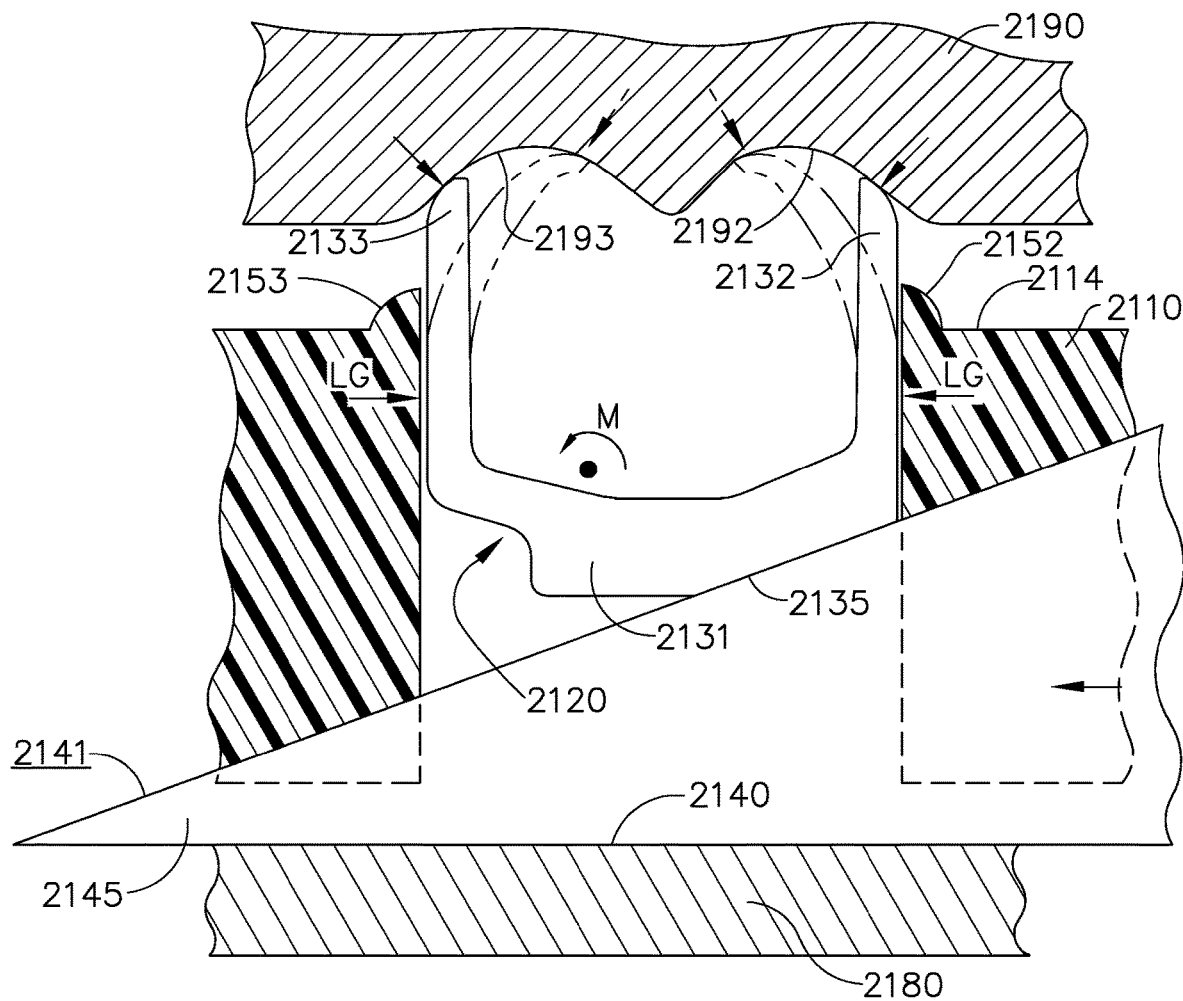
FIG. 37 is a partial cross-sectional view of the staple cartridge assembly of FIG. 35 illustrating a staple being deformed against an anvil by the firing member.

Referring again to FIG. 35, the staples 2130 are driven between unfired positions and fired positions by a firing member, such as sled 2140, for example. The sled 2140 comprises wedges 2145 which are configured to directly engage the staples 2130 and lift the staples 2130 toward an anvil, such as anvil 2190, for example, as illustrated in FIG. 37. The sled 2140 comprises a wedge 2145 for each longitudinal row of staples 2130; however, the sled 2140 may have any suitable number of wedges 2145. Each wedge 2145 comprises an angled drive surface 2141 which slides under the staples 2130 as the sled 2140 is advanced from the proximal end of the staple cartridge 2100 toward the distal end of the staple cartridge 2100. The base 2131 of each staple 2130 comprises an angled drive surface 2135 which is directly contacted by a drive surface 2141. Stated another way, each staple 2130 comprises its own integrally-formed driver having a drive surface 2135. The staples 2130 are comprised of metal and, as a result, the integrally-formed driver is also comprised of metal. That said, the staples disclosed herein can be comprised of any suitable material.

Further to the above, each drive surface 2141 comprises an initial, or distal, portion 2142, a second, or intermediate, portion 2143, and a third, or apex, portion 2144. The initial portion 2142 extends at a first angle and provides an initial contact point for the sled 2140 against a staple 2130 as the sled 2140 is moved distally. As the initial portion 2142 slides under the staple 2130, the staple 2130 is lifted upwardly within the staple cavity 2120. As the sled 2140 continues to move distally, the intermediate portion 2143 comes into contact with the staple 2130. The intermediate portion 2143 extends at a second angle which is different than the first angle. The first angle can be steeper than the second angle when it is desirable for there to be a quick initial upward displacement of the staple 2130 whereas the first angle can be shallower than the second angle when it is desirable to a provide a gradual initial upward displacement of the staple 2130. In either event, the staple 2130 contacts the anvil 2190 while the staple 2130 is being lifted upwardly by the intermediate portion 2143, as illustrated in FIG. 37; however, alternative embodiments are envisioned in which the staple 2130 contacts the anvil 2190 when the staple 2130 is being lifted upwardly by the initial portion 2142. In either event, the proximal leg 2132 of the staple 2130 contacts a proximal forming pocket 2192 defined in the anvil 2190 and the distal leg 2133 contacts a distal forming pocket 2193 defined in the anvil 2190. The forming pockets 2192 and 2193 are configured to bend the legs 2132 and 2133 inwardly to deform the staple 2130 and capture the tissue of a patient within the staple 2130. The apex 2144 of the drive surface 2141 slides under the staple 2130 to finish the forming process. The apex 2144 can comprise a peak of the drive surface 2141, a flat surface, and/or a surface which extends at a third angle which is different than the first angle and/or the second angle.

In various instances, each drive surface 2141 can comprise a portion which trails, or is positioned proximal to, the apex 2144 of the drive surface 2141. Such a trailing portion can be lower than the apex 2144, for example. Moreover, such a trailing portion can provide for a gradual decrease in forming pressure in the staples 2130, for example.

Figure 39:
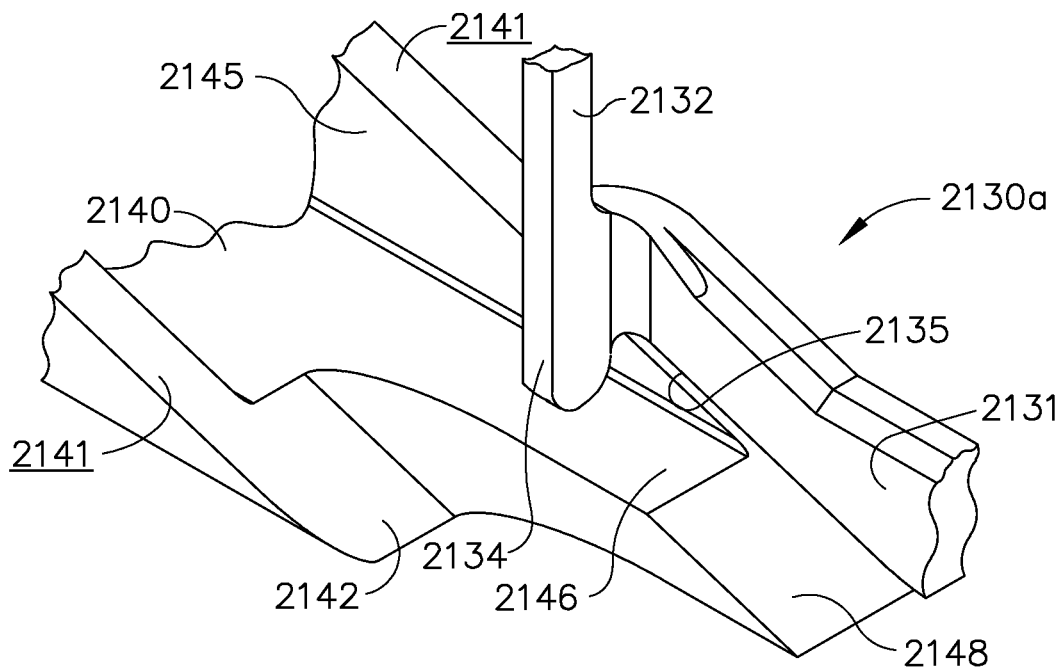
FIG. 39 is a partial perspective view of a staple being lifted by the firing member of the staple cartridge of FIG. 35.
Figure 41:
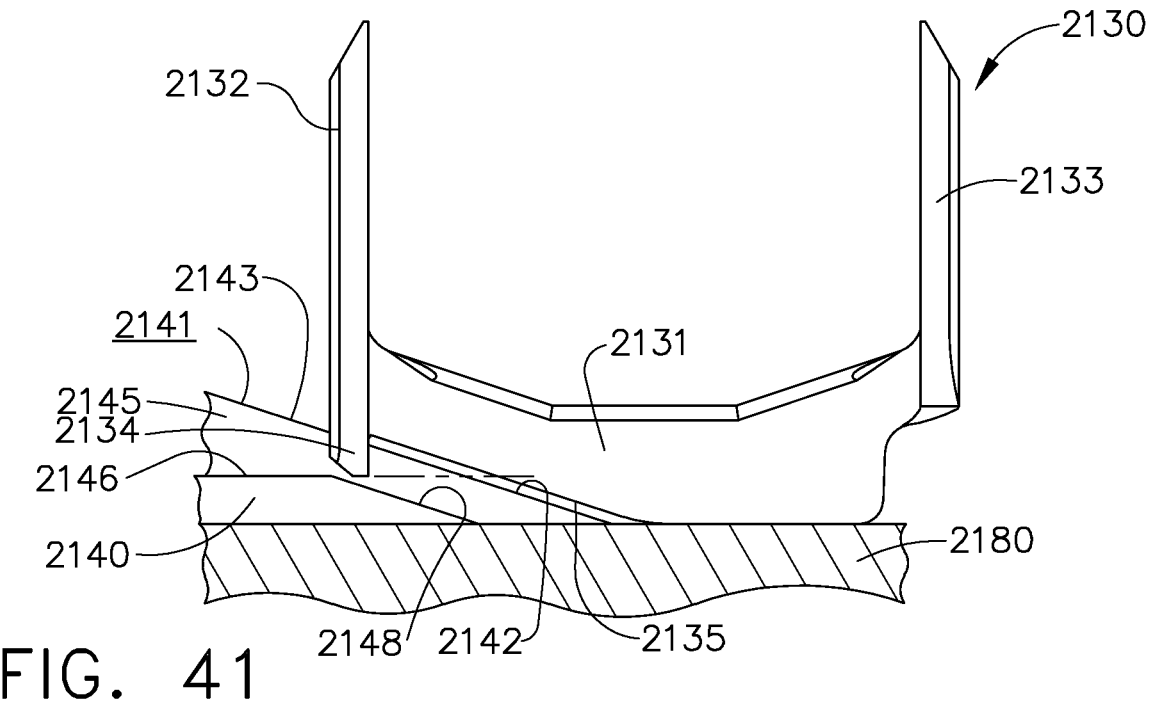
FIG. 41 is a diagram illustrating the staple of FIG. 39 in a level position.
Figure 42:
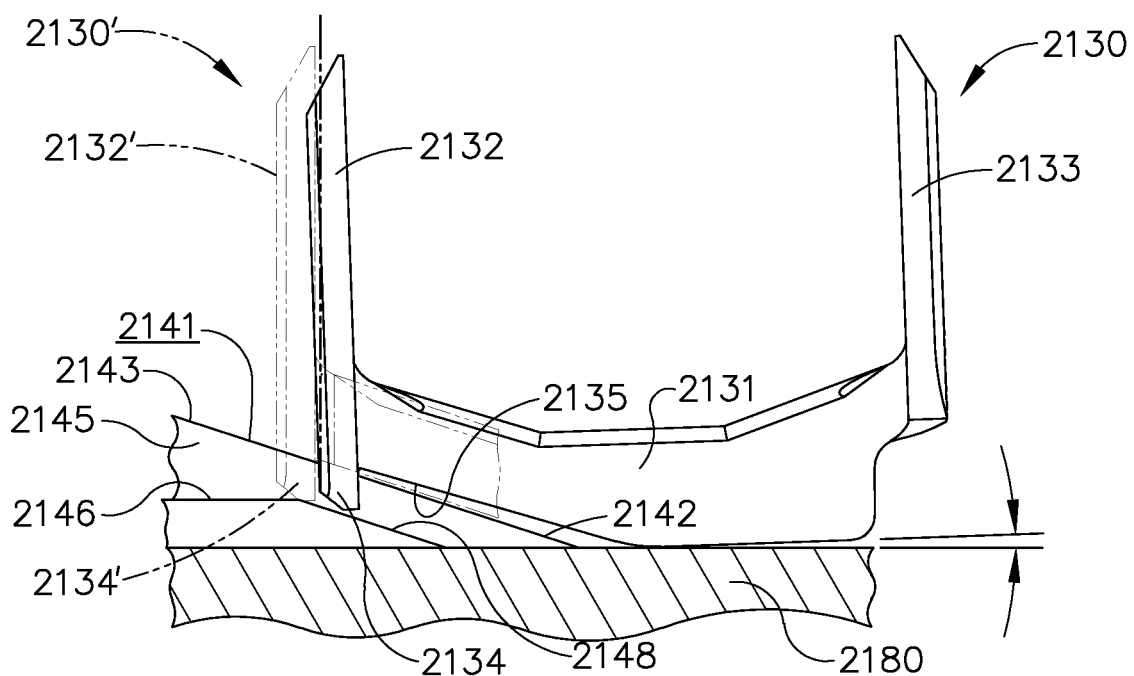
FIG. 42 is a diagram illustrating the staple of FIG. 39 in a crooked position.

Turning now to FIG. 39, the staple 2130 further includes a foot 2134 which extends downwardly from the proximal leg 2132. When the staple 2130 is in its proper orientation in its staple cavity 2120, as illustrated in FIG. 41, the foot 2134 is not contacted by the sled 2140. In such instances, an alignment plateau 2146 of the sled 2140 passes under the foot 2134. When the staple 2130 is not in its proper orientation in its staple cavity 2120, as illustrated in FIG. 42, the sled 2140 can contact the staple 2130 and re-orient the staple 2130. For the purpose of comparison, an improperly oriented staple 2130 and a properly oriented staple 2130' are both illustrated in FIG. 42. The sled 2140 comprises an angled alignment ramp 2148 which is configured to contact the foot 2134 and rotate the staple 2130 into is proper orientation. After the alignment ramp 2148 has properly oriented the staple 2130, the alignment plateau 2146 can slide underneath the foot 2134. As can be appreciated from FIG. 39, the alignment ramp 2148, the alignment plateau 2146, and the foot 2134 are arranged in an alignment plane which is aligned with the forming plane of the legs 2132 and 2133 of the staple 2130. The alignment plane is adjacent to a lifting plane which includes the forming surface 2141 of the sled 2140 and the base 2131 of the staple 2130.

A staple cartridge assembly 2300 is illustrated in FIGS. 44-48. The staple cartridge assembly 2300 is similar to the staple cartridge 2000, 2100, 2200, and the other staple cartridges disclosed herein in many respects. The staple cartridge 2300 comprises a cartridge body 2310 and sleds 2340 which are configured to eject staples removably stored in the cartridge body 2310. Similar to sled 2140, sleds 2340 comprise staple forming ramps 2145. The ramps 2145 are slidably positioned in longitudinal slots 2115 defined in the cartridge body 2110 which are aligned with the lifting portions, or planes, of the staples. Notably, as discussed in greater detail below, the slots 2115 have an open end defined in the bottom 2316 of the cartridge body 2310.

Figure 48:
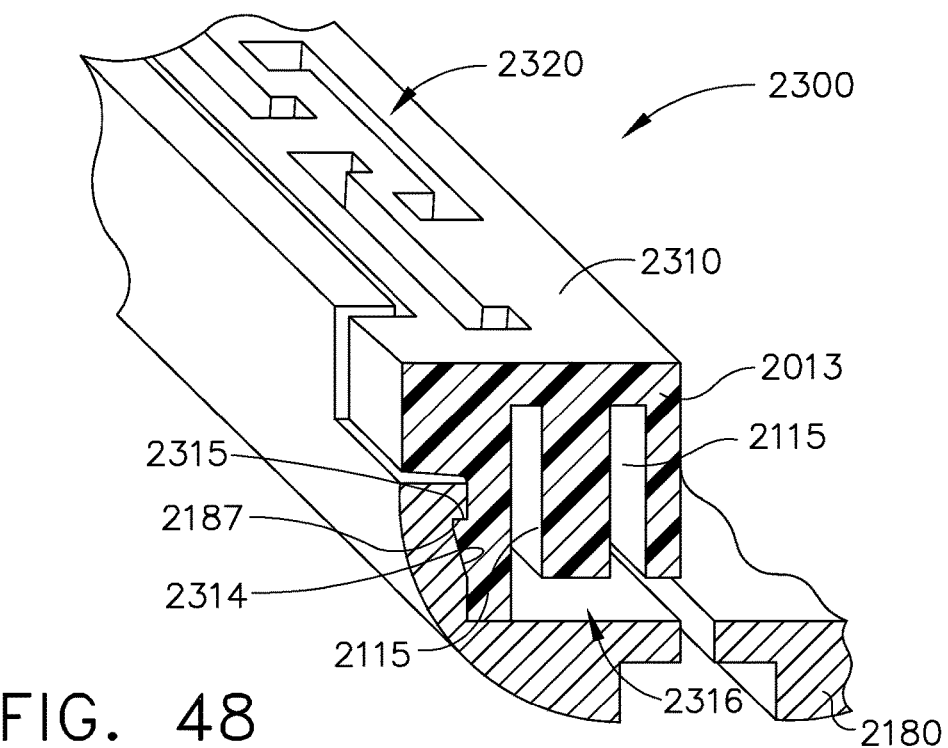
FIG. 48 is a partial cross-sectional perspective view of the staple cartridge assembly of FIG. 44 illustrating a retention feature configured to releasably hold the staple cartridge assembly in the jaw of the surgical stapling instrument.

Further to the above, the staple cartridge assembly 2300 does not include a cover extending around the bottom 2316 of the cartridge body 2310. Referring primarily to FIG. 48, the cartridge body 2310 is directly positioned against the jaw 2180 of the stapling instrument. In embodiments where a staple cartridge is not readily removable from the jaw of a stapling instrument and not readily replaceable with another staple cartridge, the absence of a bottom cover is not necessarily problematic as the jaw 2180 can prevent the staples from falling out of the bottom of the staple cavities 2120 and/or the sleds 2340 from falling out of the bottom of the longitudinal slots 2115. The staple cartridge assembly 2300 is, however, replaceable and, even though it does not include a bottom cover, the staple cartridge assembly 2300 includes features which keep the staples and the sleds 2340 from falling out of the bottom 2316 of the cartridge body 2310, which are described in greater detail further below. Such features could be adapted to any of the staple cartridges disclosed herein.

Figure 45:
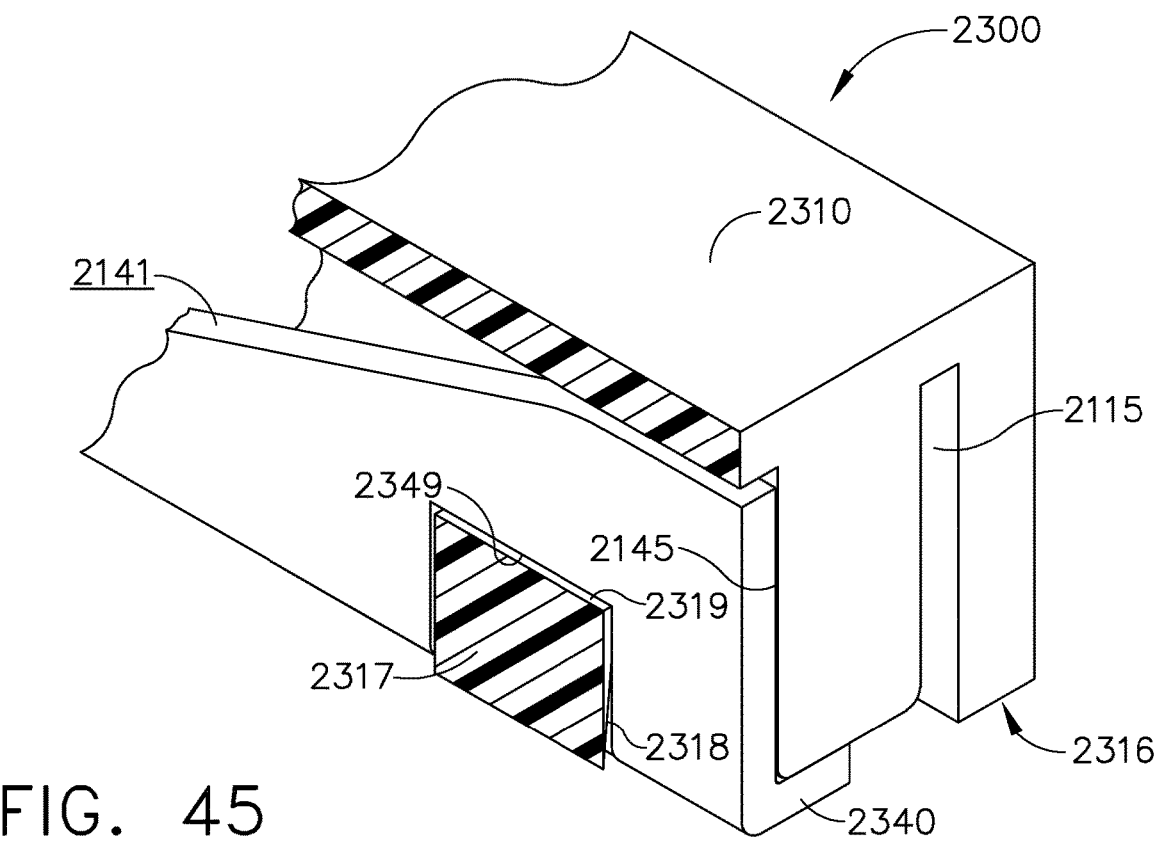
FIG. 45 is a partial cross-sectional perspective view of the staple cartridge assembly of FIG. 44 illustrating a retention feature configured to hold the firing member in the cartridge body when the staple cartridge assembly is not positioned in the jaw of the surgical stapling instrument.
Figure 46:
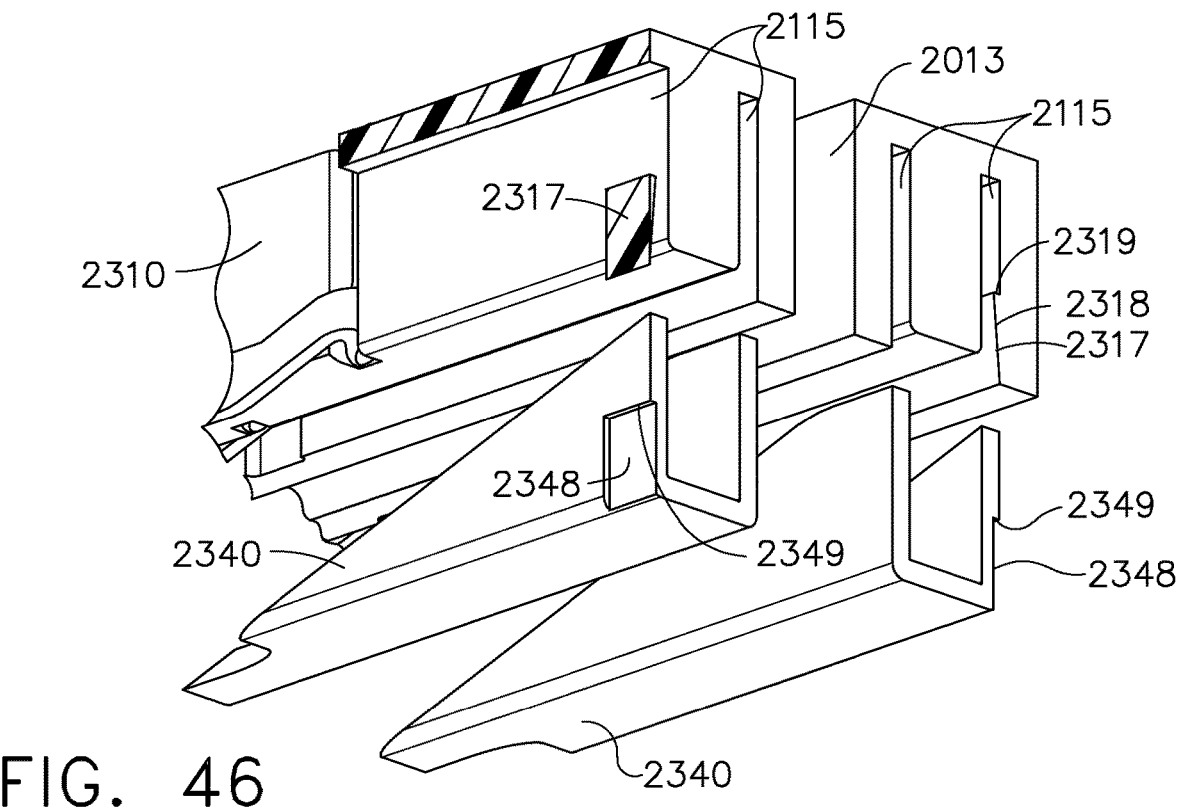
FIG. 46 is a partial cross-sectional exploded view of the staple cartridge assembly of FIG. 44.
Figure 47:
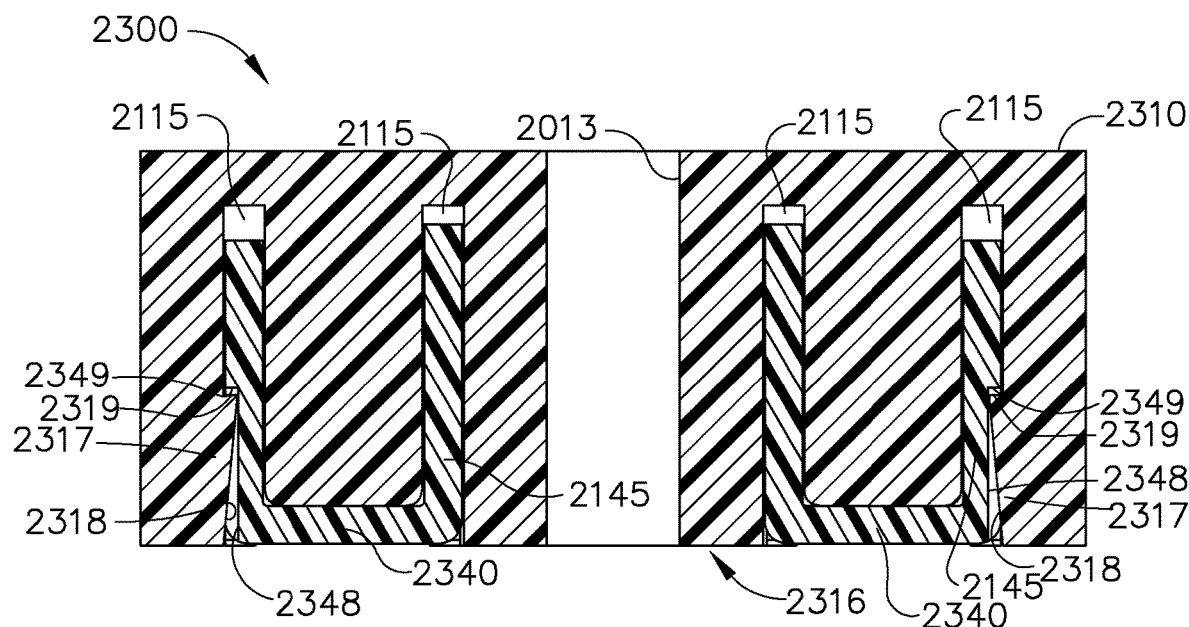
FIG. 47 is a partial cross-sectional end view of the staple cartridge assembly of FIG. 44.

Referring primarily to FIGS. 45-47, the cartridge body 2310 includes retention features configured to hold the sleds 2340 therein. For example, the cartridge body 2310 includes proximal retention features 2317 which are configured to hold the sleds 2340 in the longitudinal slots 2115 when the sleds 2340 are in their proximal, or unfired, positions. The sleds 2340 are in their unfired positions when the staple cartridge assembly 2300 is inserted, or loaded, into the jaw 2180 and, as a result, the proximal retention features 2317 retain the sleds 2340 in the cartridge body 2310 when the cartridge assembly 2300 is being handled by a clinician. Each retention feature 2317 includes an angled surface 2318 and a shoulder 2319. Each sled 2340 includes a corresponding recess 2348 configured to receive an angled surface 2318 and, in addition, a corresponding shoulder 2349 which can be aligned with and/or contact a shoulder 2319 of the retention feature 2317. When the sleds 2340 are inserted into the slots 2115, referring to FIG. 46, the ramps 2145 and/or the sidewalls of the cartridge 2310 can flex to permit the sleds 2340 to slide relative to the angled surfaces and then resiliently snap back to their original positions once the shoulders 2349 of the sleds 2340 have become aligned with the shoulders 2319 of the cartridge body 2310, as illustrated in FIG. 45. The retention features 2317 are also configured to prevent the sleds 2340 from sliding proximally out of the longitudinal slots 2115.

As a result of the above, the proximal retention features 2317 prevent the sleds 2340 from falling out of the cartridge body 2310 when a clinician is handling the staple cartridge assembly 2300. When the sleds 2340 are advanced distally to fire the staples, the sleds 2340 are no longer aligned with the proximal retention features 2317. At such point, however, the staple cartridge assembly 2300 is already in the jaw 2180 and sled retention features are no longer needed. That said, the cartridge body 2310 can include additional retention features which can hold the sleds 2340 in the cartridge body 2310 regardless of the position of the sleds 2340. Such retention features could be configured to hold the sleds 2340 in the cartridge body 2310 when the sleds 2340 are in their distal, or fully fired, positions, for example.

Figure 49:
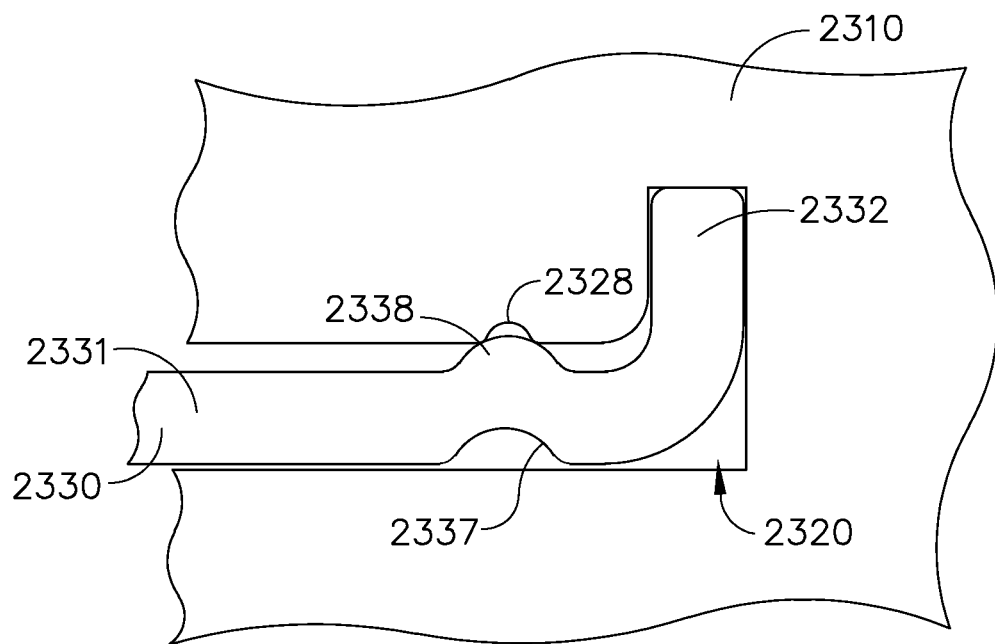
FIG. 49 is a partial plan view of a staple positioned in a staple cavity of a staple cartridge assembly in accordance with at least one embodiment.
Figure 50:
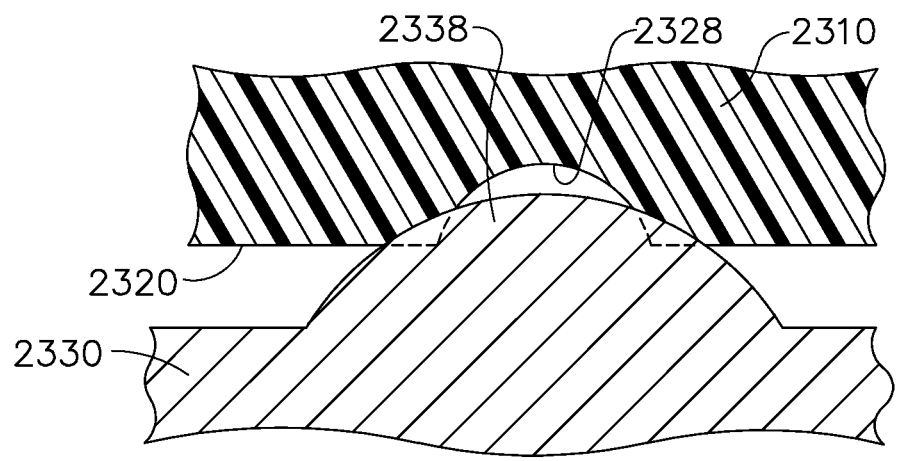
FIG. 50 is a detail view of a retention feature configured to releasably hold the staple in the staple cartridge assembly of FIG. 49.

Further to the above, the staples of the staple cartridges disclosed herein can include one or more features configured to hold the staples in the staple cavities of the staple cartridge. Turning now to FIGS. 49 and 50, a staple 2330 includes a base 2331 and one or more staple legs 2332 extending from the base 2331. The staple 2330 is removably stored in a staple cavity 2320 in the cartridge body 2310, for example. The base 2331 comprises a protrusion 2338 extending therefrom which is engaged with a sidewall of the staple cavity 2320. The interaction between the protrusion 2338 and the staple cavity sidewall keeps the staple 2330 from falling out of the bottom 2316 of the cartridge body 2310. The interaction between the protrusion 2338 and the staple cavity sidewall comprises an interference fit; however, such an interference fit does not prevent the sleds 2340 from ejecting the staples 2330 from the staple cavities 2320. The protrusion 2338 can be formed in the base 2331 during a stamping process, for example. The stamping process can form the protrusion 2338 by creating a dent 2337 in the opposite side of the base 2331. The staple cavity 2320 includes a vertical groove 2328 which is aligned with the protrusion 2338. The groove 2328 increases the contact area between the sidewall of the staple cavity 2320 and the protrusion 2338. In addition, the groove 2328 can control the orientation of the staple 2330 within the staple cavity 2320. Alternative embodiments are envisioned which do not comprise the groove 2328.

Figure 51:
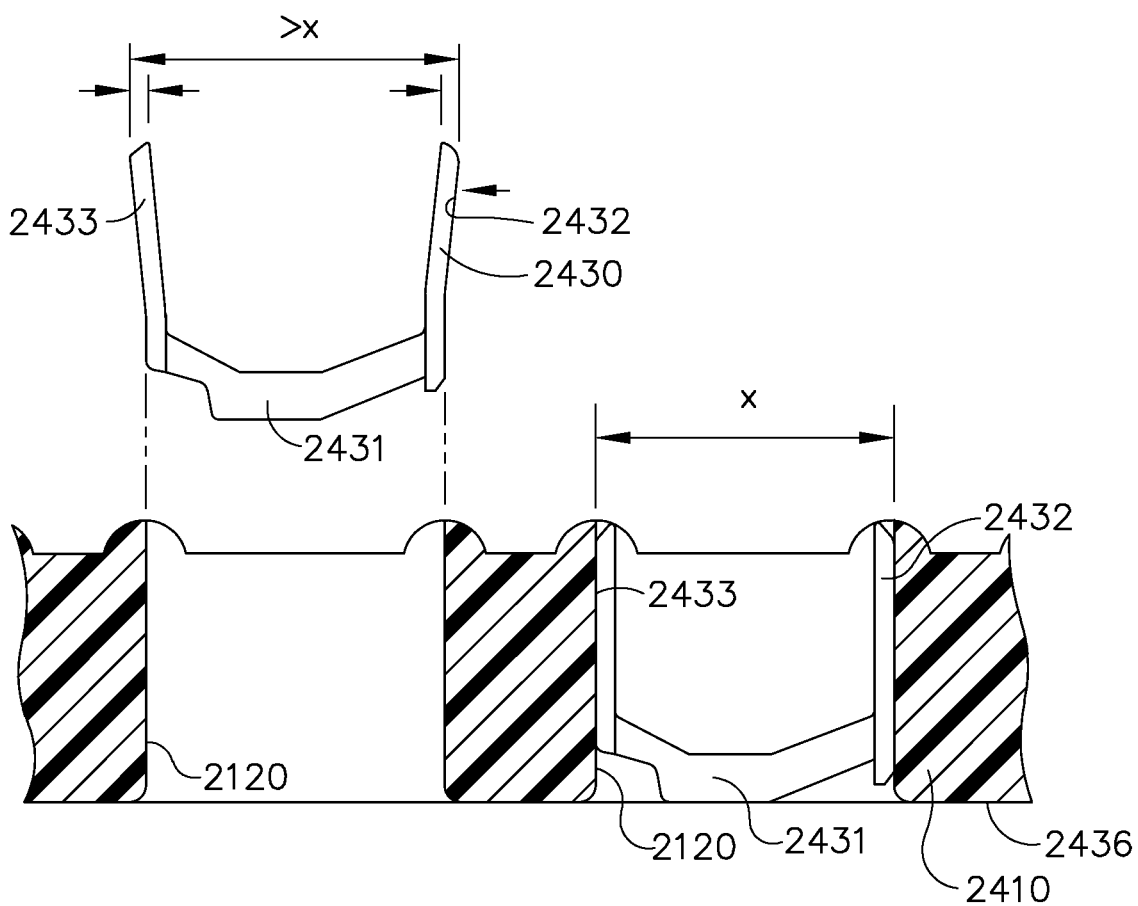
FIG. 51 is a partial cross-sectional elevational view of a staple cartridge assembly in accordance with at least one embodiment.
Figure 52:
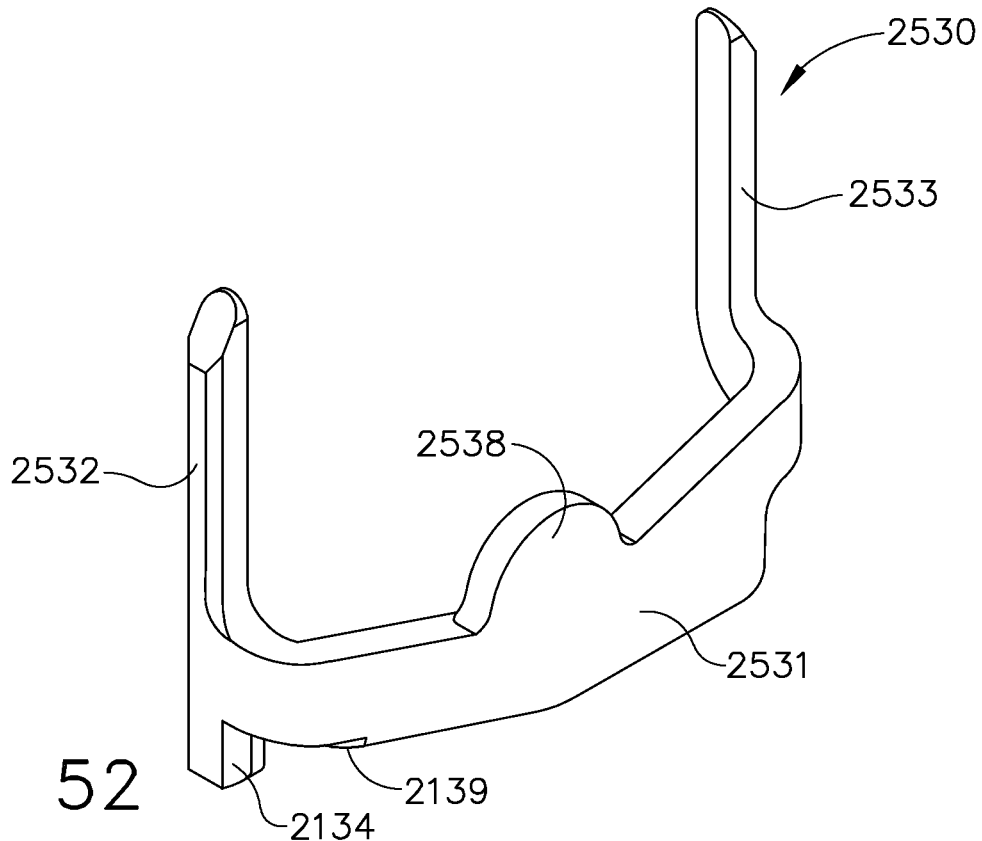
FIG. 52 is a perspective view of a staple in accordance with at least one embodiment.
Figure 53:
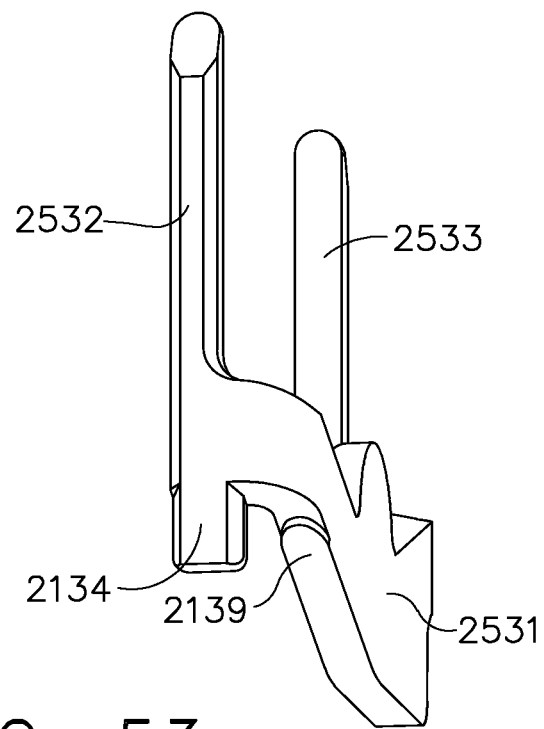
FIG. 53 is a bottom perspective view of the staple of FIG. 52.
Figures 54, 55:
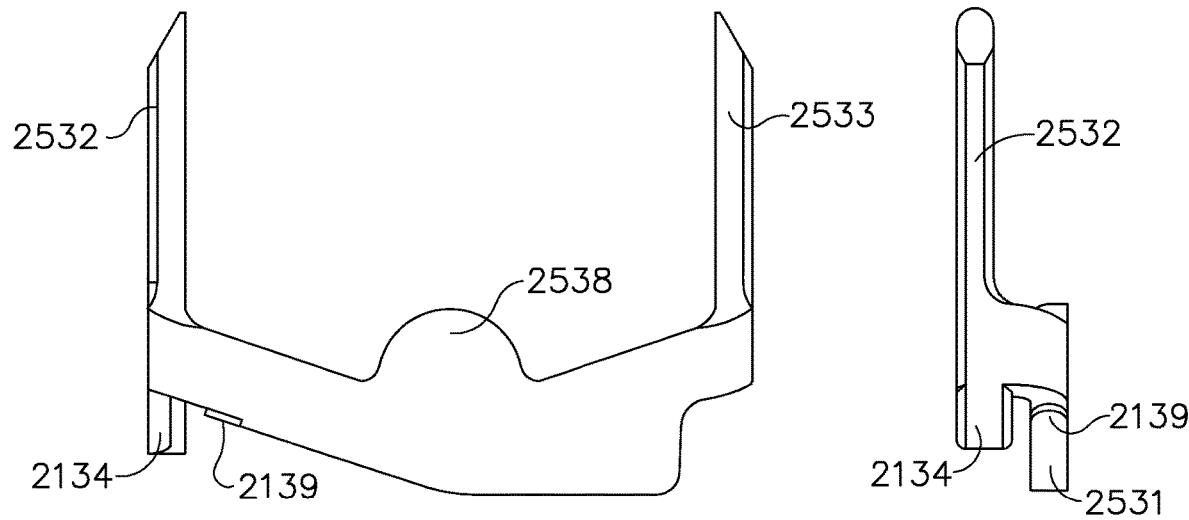
FIG. 54 is a front elevational view of the staple of FIG. 52.
FIG. 55 is a side elevational view of the staple of FIG. 52.
Figure 56:
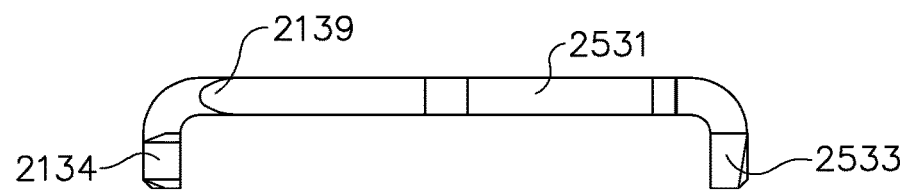
FIG. 56 is a bottom view of the staple of FIG. 52.
Figure 62:
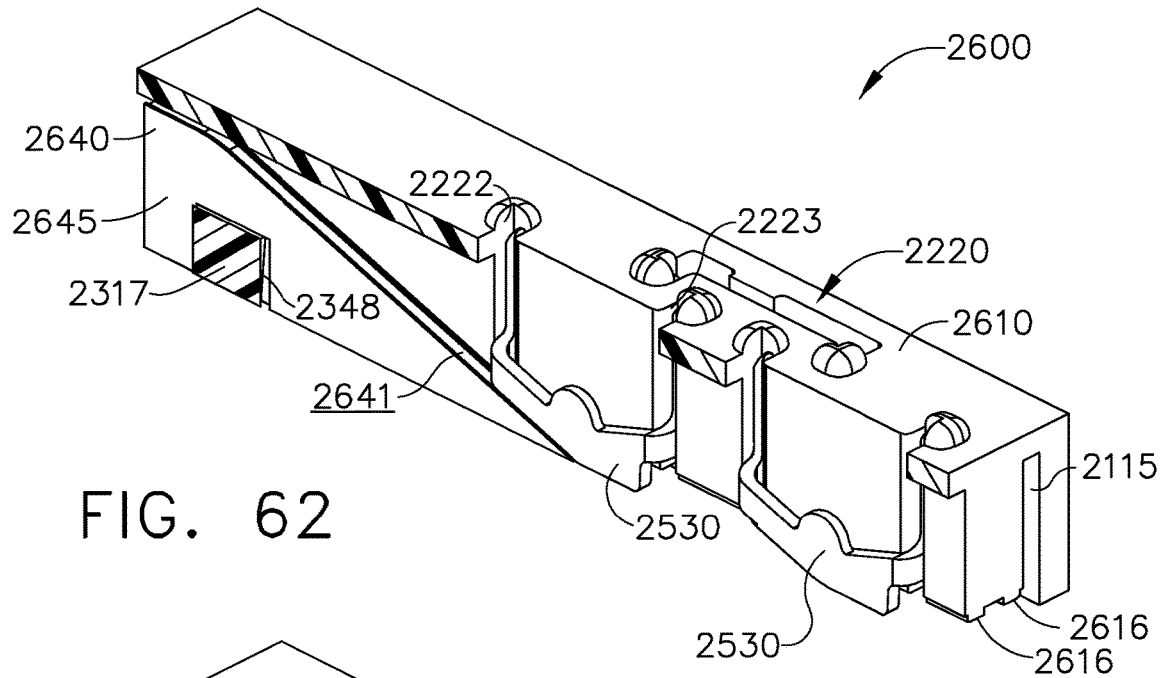
FIG. 62 is a partial cross-sectional perspective view of the staple cartridge assembly of FIG. 58.
Figure 63:
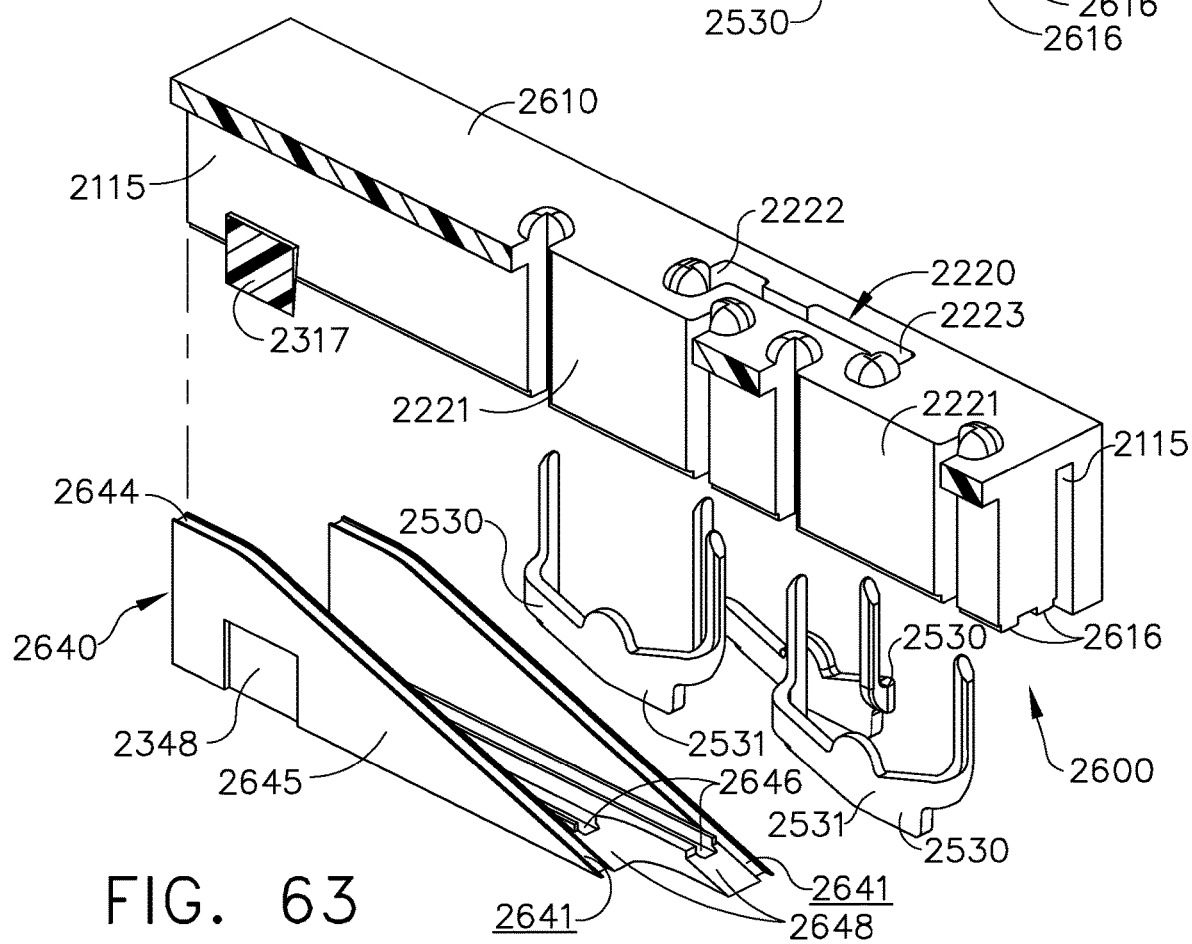
FIG. 63 is a partial exploded view of the staple cartridge assembly of FIG. 58.

In addition to or in lieu of the above, the staples stored in the staple cartridges disclosed herein can include staple legs which are resiliently engaged with the sidewalls of their staple cavities. Turning now to FIG. 51, a staple 2430 can include a base 2431 and staple legs 2432 and 2433 extending from the base 2431. The staples 2430 are similar to the staples 2130, 2330, and/or the other staples disclosed herein in many respects. A staple cartridge body 2410, for example, can include a plurality of staple cavities 2120 defined therein and a staple 2430 positioned in each staple cavity 2120. FIG. 51 depicts a staple 2430 positioned inside a cavity 2120 and a staple 2430 positioned outside a staple cavity 2120 of the cartridge body 2430. When the staples 2430 are not positioned in the staple cavities 2120, the staple legs 2432, 2433 do not extend in parallel directions; rather, they extend outwardly away from each other. When the staples 2430 are positioned in the staple cavities 2120, they are flexed inwardly by the sidewalls of the staple cavities 2120. Stated another way, the staple legs 2432, 2433 are resiliently biased against the sidewalls of the staple cavities and, owing to this biased engagement, the staples 2430 are inhibited from falling out of the bottom 2436 of the cartridge body 2410. As illustrated in FIG. 51, the distance between the staple legs 2432, 2433 when the staples 2130 are positioned in the staple cavities 2120 is X while the distance between the staple legs 2432, 2433 when the staples 2130 are not positioned in the staple cavities is larger than X.

In various embodiments, a cartridge body can include one or more shoulders which are configured to keep the staples stored therein from falling out of the bottom of the cartridge body. The shoulders can at least partially extend underneath the staples.

In certain embodiments, the cartridge body of a staple cartridge assembly can be comprised of plastic and can be formed during an injection molding process, for example. The injection mold can include two halves which are movable toward and away from each other. The interface between the injection mold halves is often called a parting line and it is frequent that flashing, or seepage of the plastic between the mold halves, can occur at the parting line. In at least one embodiment, the parting line of an injection mold can be defined at the interfaces between the deck of the staple cartridge and the staple cavities defined in the deck. As a result of the above, plastic flashing can occur around the perimeter of the staple cavities. Such flashing can releasably hold the staples in the staple cartridge.

Referring again to FIG. 48, the cartridge body 2310 is configured to directly engage the jaw 2180. The jaw 2180 comprises one or more retention shoulders 2315 defined therein. The cartridge body 2310 comprises corresponding retention shoulders 2187 which co-operate with the retention shoulders 2315 to releasably retain the cartridge body 2310 in the jaw 2180. The cartridge body 2310 and/or the jaw 2180 further comprise ramp surfaces 2314 which are configured to facilitate the insertion of the cartridge body 2310 into the jaw 2180. As a result of the above, the cartridge body 2310 can have a snap-fit relationship with the jaw 2180. The snap-fit relationship can be overcome by prying the cartridge body 2310 out of the jaw 2180 such that the staple cartridge assembly 2300 can be replaced.

A staple 2530 is illustrated in FIGS. 52-56. The staple 2530 is similar to the staples 2130, 2330, 2340, and/or the other staples disclosed herein in many respects. The staple 2530 comprises a base 2531 and legs 2532 and 2533 extending from the base 2531. The staple 2530 also includes a projection 2538 extending upwardly from the base 2531. The projection 2538 is aligned with the staple driving plane which includes the base 2531 and is not aligned with tissue capture plane including the staple legs 2532 and 2533. The projections 2538 can compress the tissue outside of the staple capture plane.

A staple cartridge assembly 2600 is illustrated in FIGS. 57-64. The staple cartridge 2600 comprises a cartridge body 2610 including a plurality of staple cavities 2220 defined therein. The staple cartridge 2600 further comprises a staple 2530 positioned in each staple cavity 2220 and sleds 2640 configured to eject the staples 2530 from the staple cavities 2220. The sleds 2640 are similar to the sleds 2140 in many respects. Each sled 2640 comprises a plurality of ramps 2645 wherein each ramp 2645 comprises a drive surface 2641 configured to slide under the staples 2530 and lift the staples 2530 within the staple cavities 2220. Each drive surface 2641 includes an inclined surface 2643 bounded by lateral sidewalls 2649 which define a guide channel that aligns the staples 2530 with respect to the drive surfaces 2641 and/or the staple cavities 2220. The guide channel is configured to receive the bases 2531 of the staples 2530 between the sidewalls 2649 and orient the staples 2530 laterally as the sled 2640 is advanced distally. Such lateral re-alignment is apparent upon comparing FIGS. 58 and 59. Referring again to FIGS. 52-56, each staple 2530 comprises a guide feature 2139 defined on the bases 2531 thereof. The guide feature 2139 of each staple 2530 comprises a curved end, for example, which is configured to interact with the lateral sidewalls 2649 of the guide channels and adjust the lateral position of the staples 2530. In various other embodiments, the guide features 2139 can comprise any suitable configuration.

In addition to or in lieu of the above, referring primarily to FIG. 60, the sleds 2640 comprise guide channels 2646 which are configured to receive the downwardly depending feet 2134 of the staples 2530 and orient the staples 2530 with respect to the drive surfaces 2641 and/or the staple cavities 2220. Each guide channel 2646 comprises a ramp portion 2648 and lateral sidewalls. The guide channels 2646 are configured to receive the bases 2531 of the staples 2530 between the sidewalls of the channels 2646 and orient the staples 2530 laterally as the sled 2640 is advanced distally. Referring primarily to FIG. 61, each foot 2134 comprises lead-in, or beveled, surfaces 2137 which are configured to interact with the sidewalls of the channels 2646 to guide the staples 2530 into the channels 2646. That said, the feet 2134 can comprise any suitable geometry which facilitates the entry of the staples 2530 into the channels 2646. The reader should appreciate that, as the staples 2530 are driven upwardly within the staple cavities 2220 by the drive surfaces 2641, the feet 2134 of the staples 2530 lift out of the channels 2646. By the time that the staples 2530 are being formed by the apexes 2644 of the drive surfaces 2641, the feet 2134 are no longer positioned in the channels 2646.

Figure 64:
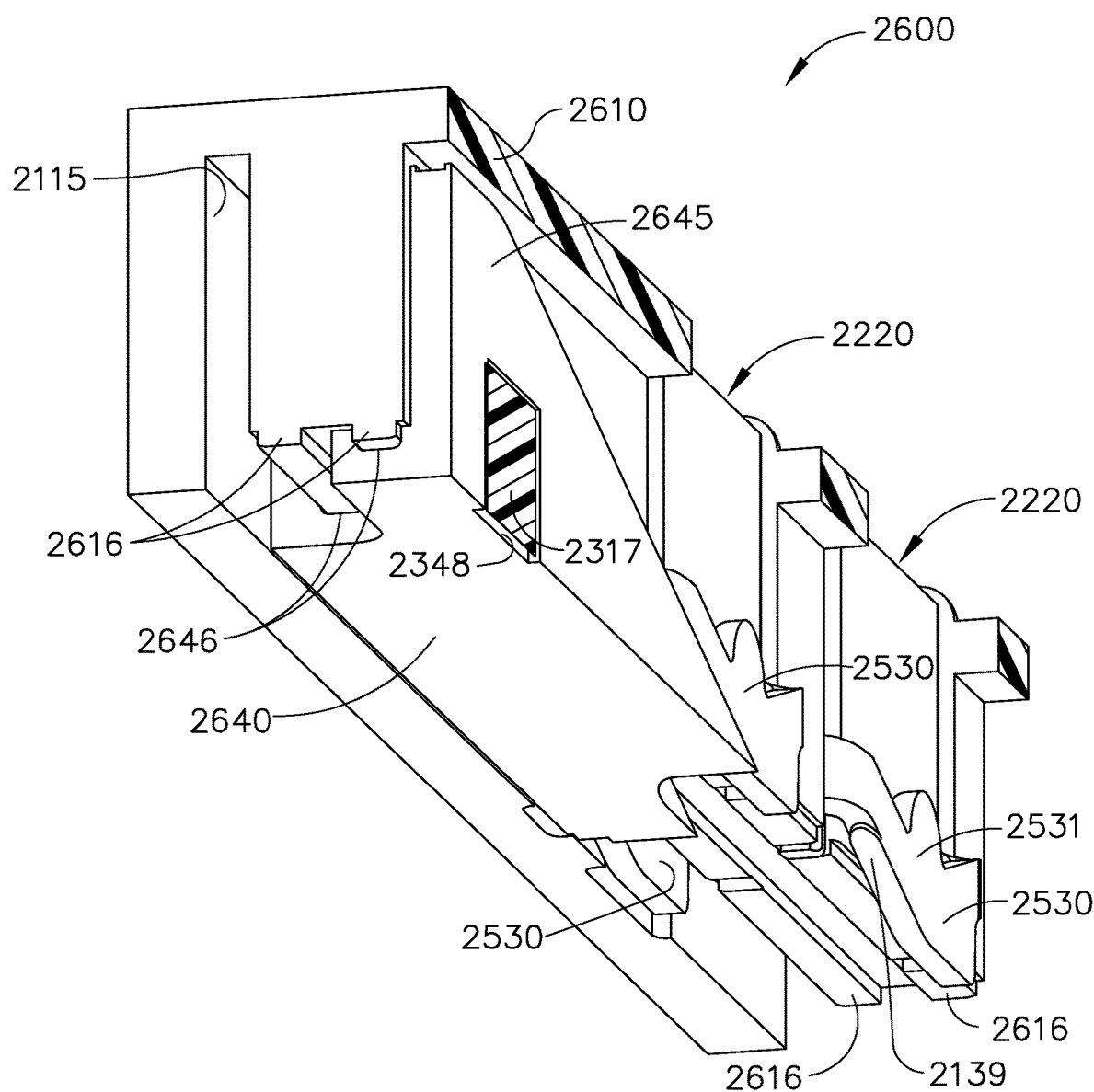
FIG. 64 is a partial bottom cross-sectional perspective view of the staple cartridge assembly of FIG. 58.

Referring primarily to FIGS. 58, 59, and 64, the channels 2646 can also align the sleds 2640 with respect to the cartridge body 2610. More particularly, the cartridge body 2610 further comprises longitudinal rails 2616 extending downwardly into the channels 2646. The rails 2616 are closely received in the channels 2646 to limit or prevent lateral movement between the sleds 2640 and the cartridge body 2610 while permit the longitudinal movement of the sleds 2640 needed to fire the staples 2530 as outlined above. The foot 2134 of each staple 2530 is configured to properly orient the staple 2530 within its staple cavity 2220 in the event that the staple 2530 is misoriented within the staple cavity 2220.

The arrangements disclosed herein allow for a staple cartridge to be more compact than previous staple cartridges.

Figure 67:
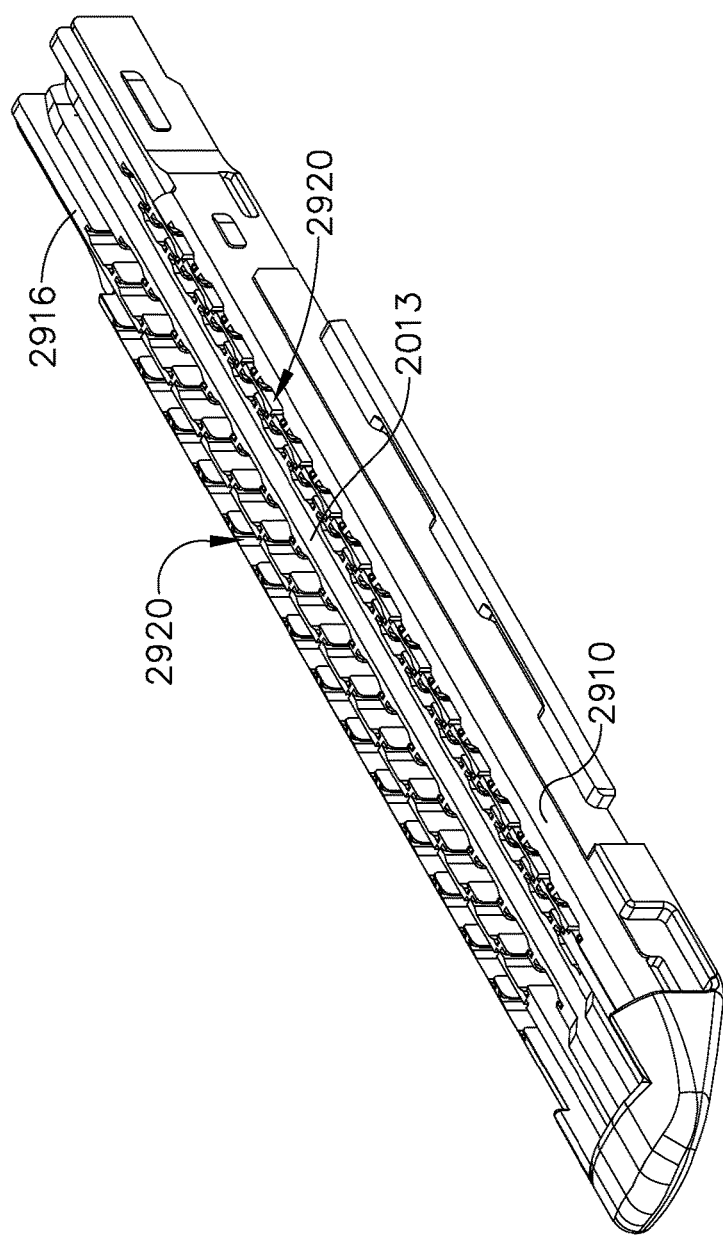
FIG. 67 is a bottom perspective view of a cartridge body of a staple cartridge assembly.
Figure 68:
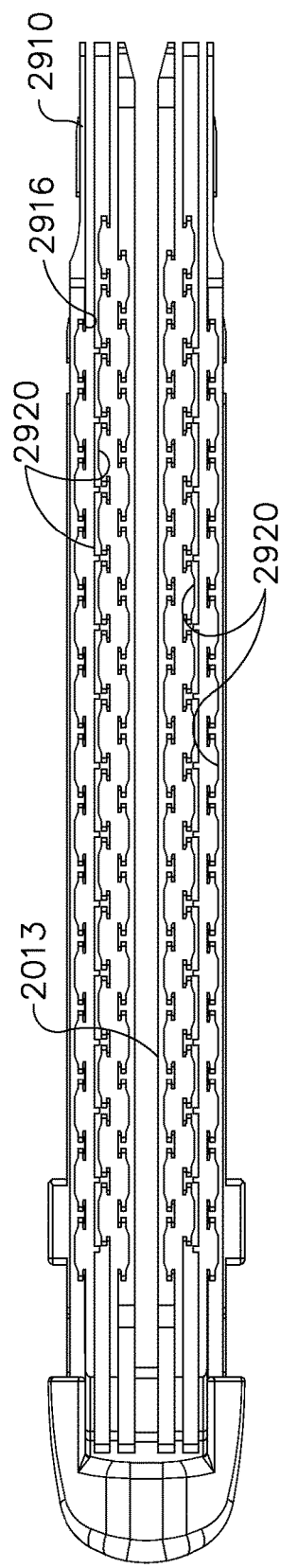
FIG. 68 is a bottom view of the cartridge body of FIG. 67.

Among other things, the staple cartridges disclosed herein that do not utilize staple drivers between the firing member and the staples, i.e., driverless staple cartridges, allow the staple cartridges to have a shorter overall height. Similarly, the staple cartridges that do not include a bottom cover also allow the staple cartridges to have a shorter overall height. Driverless staple cartridges can also allow smaller staple cavities to be utilized. Turning now to FIGS. 67 and 68, a cartridge body 2910 includes staple cavities 2920 and a longitudinal slot 2013 defined therein. FIGS. 67 and 68 show the bottom 2916 of the cartridge body 2910 and the bottom openings of the staple cavities 2920. The reader should appreciate that the staple cavities 2920 are sized and configured to receive staple drivers for driving the staples out of the cartridge body 2910. Turning now to FIGS. 69 and 70 which depicts the bottom 2016 of the cartridge body 2010, the staple cavities 2020 of the cartridge body 2010 are smaller than the staple cavities 2920. As the reader will recall, drivers are not positioned in the staple cavities 2020 and, as a result, the size of the staple cavities 2020 can be reduced. FIG. 71 compares the bottom 2916 of the cartridge body 2910 to the bottom 3016 of an alternative embodiment of a cartridge body 3010. As can be seen in FIG. 71, the cartridge body 3010 includes longitudinal rows of staple cavities 3020 which are much narrower than the longitudinal rows of staple cavities 2920. In various instances, such narrower staple cavities can permit the center lines of the longitudinal rows of staple cavities to be closer to one another. Turning now to FIG. 72, a staple cartridge body 3110 includes longitudinal rows of staple cavities 3120*a*, 3120*b*, and 3120*c* defined in a deck 3114 of the cartridge body 3110 which are positioned closer together than would be permitted in embodiments which use staple drivers to lift the staples within the cartridge body.

Figure 73:
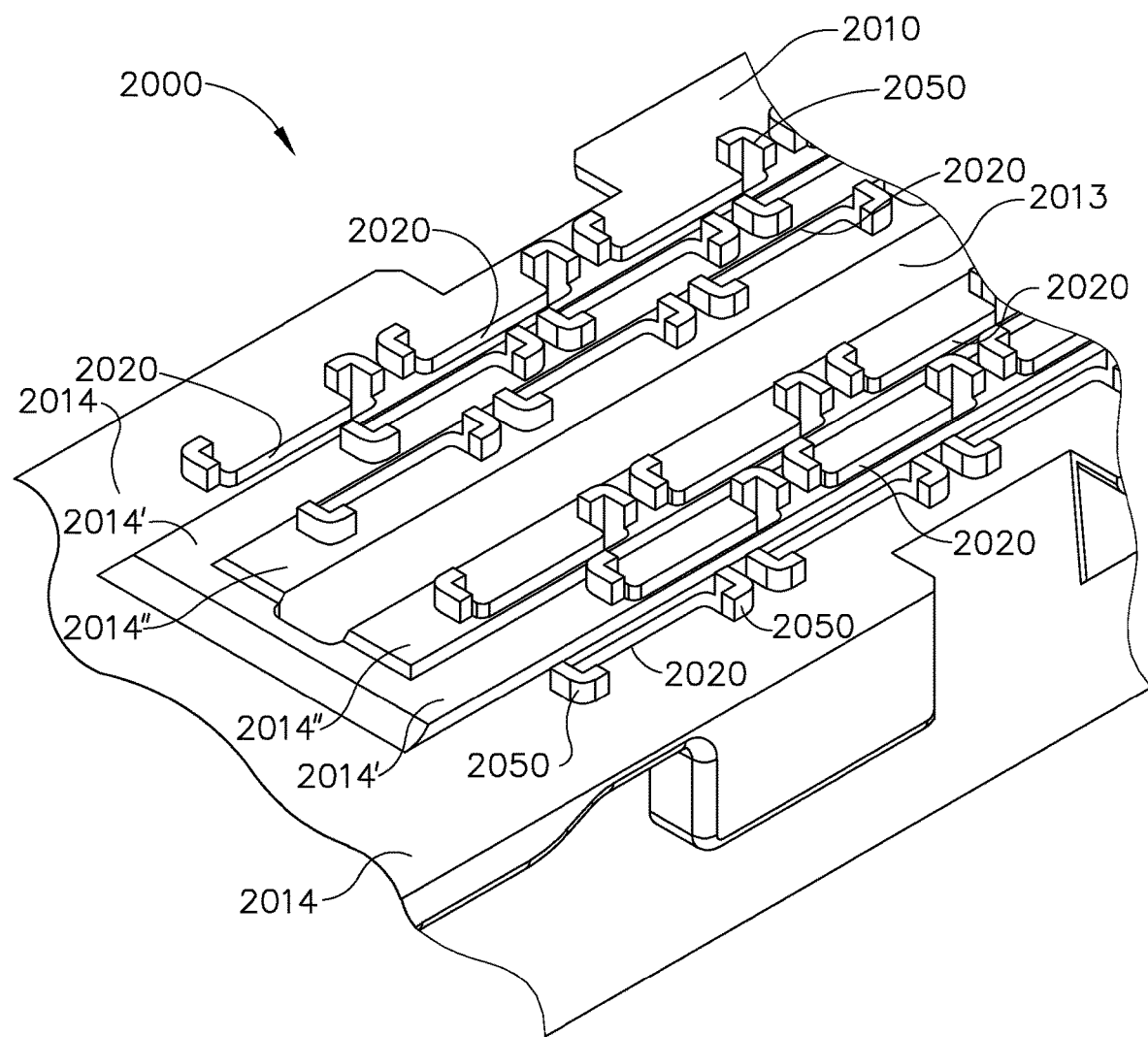
FIG. 73 is a partial perspective view of the staple cartridge of FIG. 32.
Figure 77:
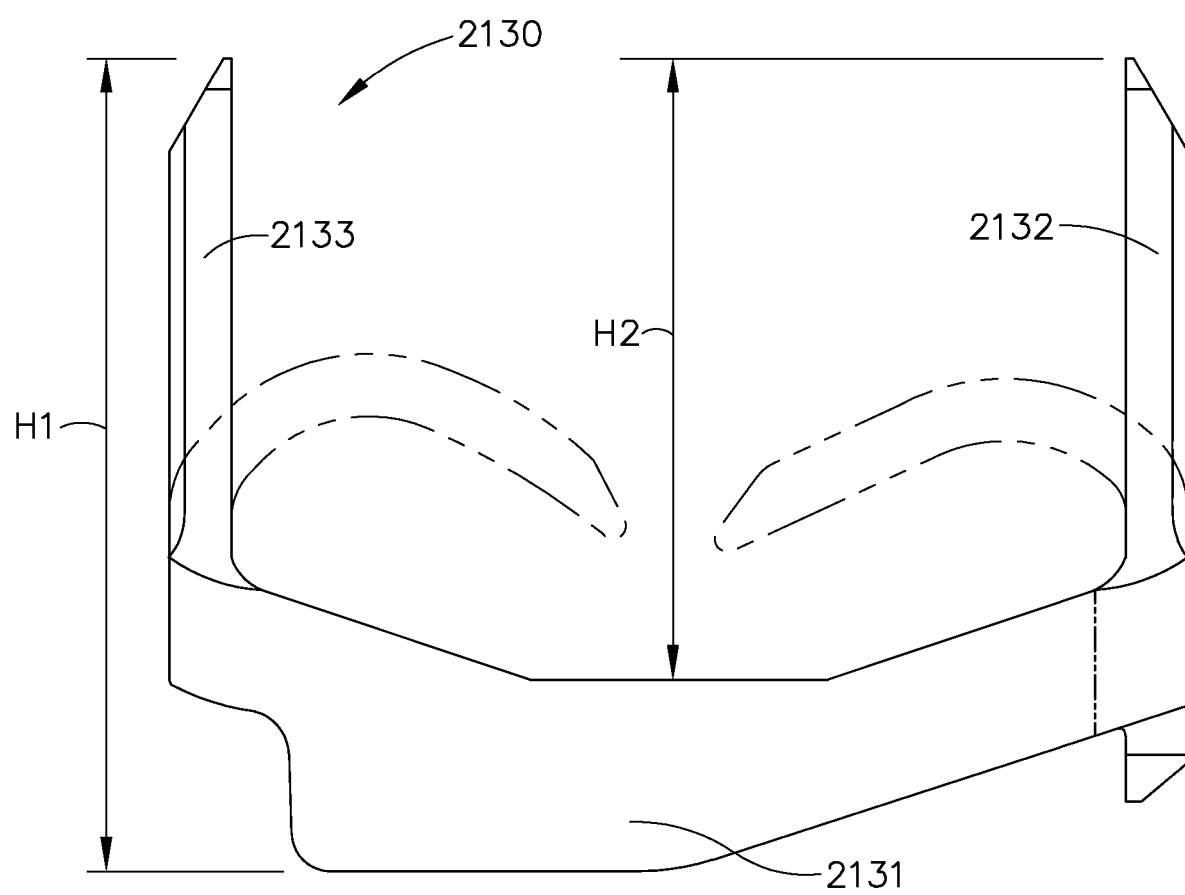
FIG. 77 illustrates a staple of the staple cartridge of FIG. 32 being deformed.

The various embodiments of the staple cartridge assemblies disclosed herein can have any suitable number of staples and/or any suitable size of staples. In certain instances, all of the staples stored in the staple cartridge assembly 2000 (FIG. 73) have the same, or at least substantially the same, size. Referring to FIG. 77, each staple 2130 in the staple cartridge 2000 comprises an unformed, or unfired, overall height H1 defined between the bottom of the base 2131 and the tips of the staple legs 2132, 2133. Similarly, each staple 2130 comprises a tissue capture area defined between the top of the base 2131 and the tips of the staple legs 2132, 2133 which has the same height H2 when the staples 2130 are in their unformed height.

In contrast to the above, a first group of staples stored in the staple cartridge 2000 can have a first unformed height H1 and a second group of staples can have a second unformed height H1 which is different than the first unformed height H1. Also in contrast to the above, a first group of staples stored in the staple cartridge 2000 can have a first tissue capture height H2 and a second group of staples can have a second tissue capture height H2 which is different than the first tissue capture height H2.

The first group of staples can be positioned in a first longitudinal row of staple cavities 2120 while the second group of staples can be positioned in a second longitudinal row of staple cavities 2120. In at least one instance, the first row of staple cavities 2120 can be adjacent the knife slot 2013 in the step 2014" of the cartridge body 2010 while the second row of staple cavities 2120 can be adjacent the first row of staple cavities 2120 in the step 2014' of the cartridge body 2010. In at least one such instance, the first unformed height H1 is shorter than the second unformed height H1, for example.

Further to the above, a third group of staples stored in the staple cartridge 2000 can have a third unformed height H1 which is different than the first unformed height H1 and/or the second unformed height H1. The third group of staples can be positioned in a third longitudinal row of staple cavities 2120. In at least one instance, the third row of staple cavities 2120 can be adjacent the second row of staple cavities 2120 in the deck 2014 of the cartridge body 2010. In at least one such instance, the second unformed height H1 is shorter than the third unformed height H1, for example. In addition to or in lieu of the above, the third group of staples can have a third tissue capture height H2 which is larger than the second tissue capture height H2.

In various embodiments, the first group of staples, the second group of staples, and/or the third group of staples can be deformed to the same overall formed height. Alternatively, the first group of staples can be deformed to a first formed height, the second group of staples can be deformed to a second formed height, and/or the third group of staples can be deformed to a third formed height. In such instances, the first group of staples can apply a larger pressure to the tissue than the second group of staples and, similarly, the second group of staples can apply a larger pressure to the tissue than the third group of staples.

Figure 74:
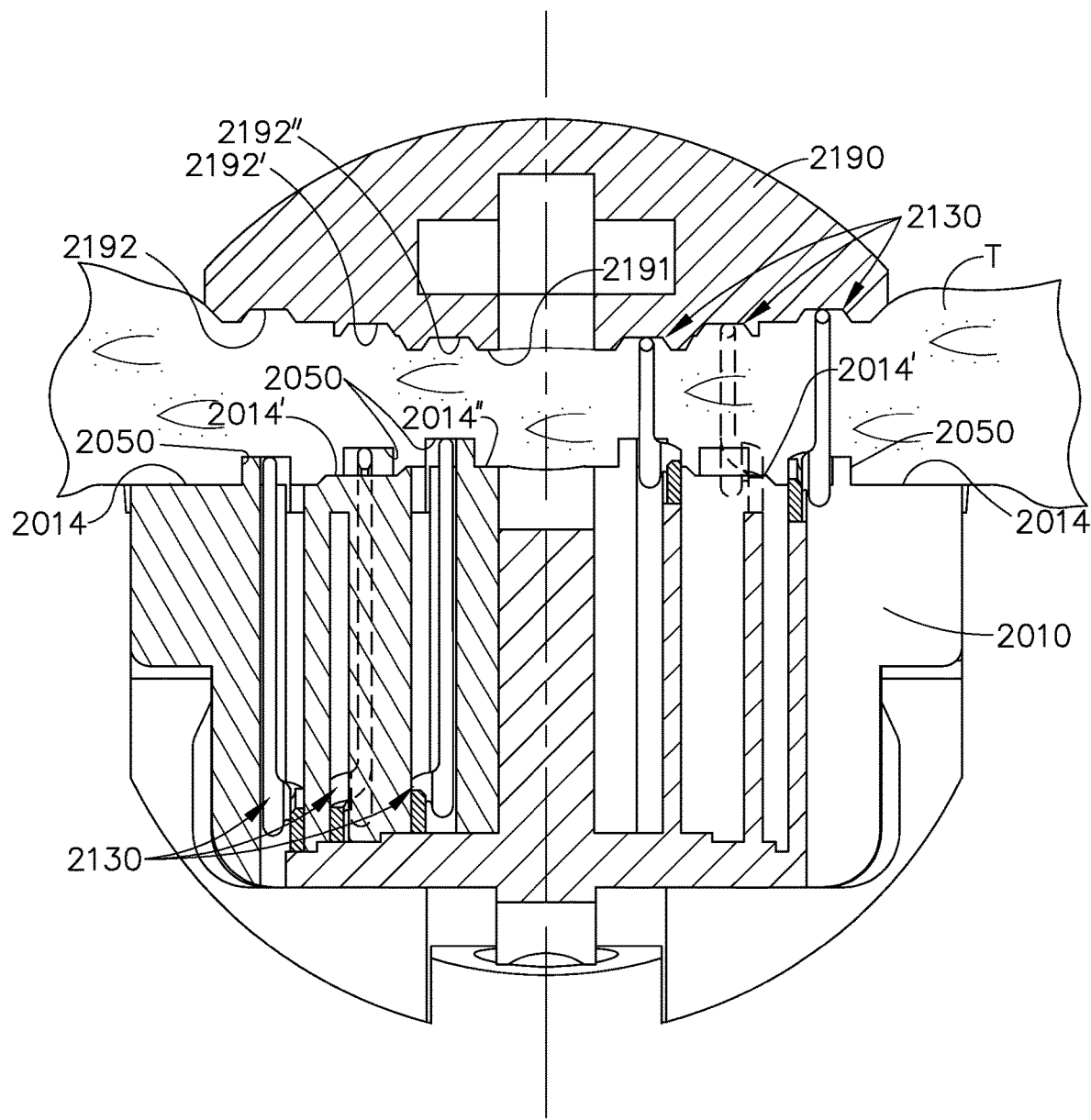
FIG. 74 is a cross-sectional view of the staple cartridge of FIG. 32 and the anvil of FIG. 37 illustrating certain staples in an unfired position and certain staples in a fired position.
Figure 75:
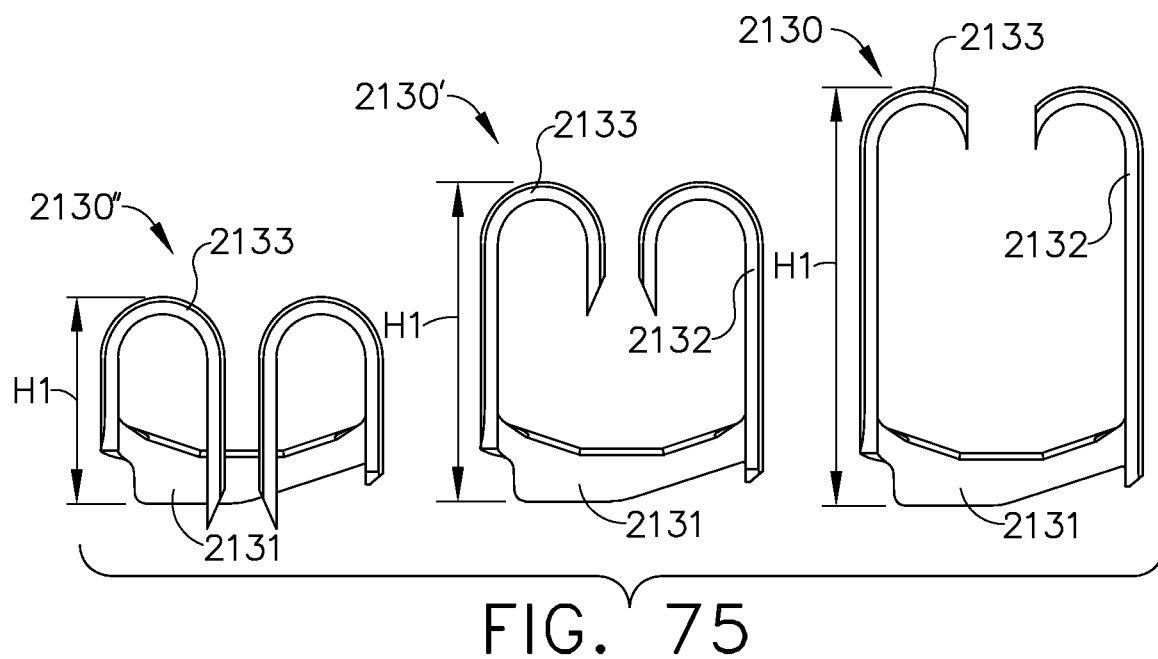
FIG. 75 illustrates the staples of the staple cartridge of FIG. 32 deformed to three different heights.
Figure 76:
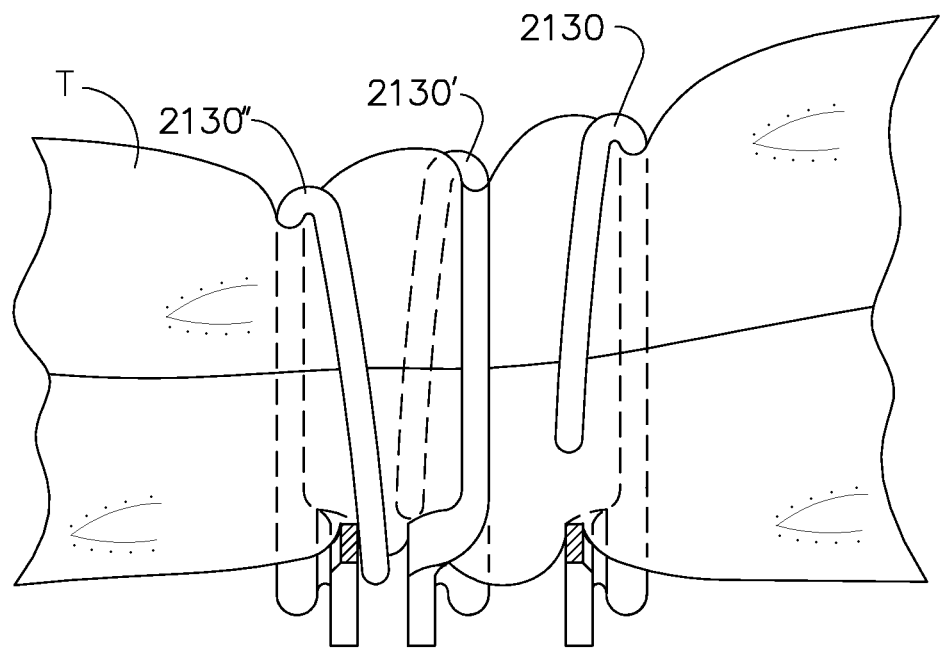
FIG. 76 illustrates the staples of the staple cartridge of FIG. 32 implanted in the tissue of a patient.

Turning now to FIGS. 74-76, staples having the same unformed height can be deformed to different formed heights. For example, a first longitudinal row of staples, represented by staples 2130", can be deformed to a first formed height, a second longitudinal row of staples, represented by staples 2130', can be deformed to a second formed height, and/or a third row of staples, represented by staples 2130, can be deformed to a third formed height. The first formed height is shorter than the second formed height, and the second formed height is shorter than the third formed height, for example. In such instances, the first group of staples can apply a larger pressure to the tissue than the second group of staples and, similarly, the second group of staples can apply a larger pressure to the third group of staples.

Figure 78:
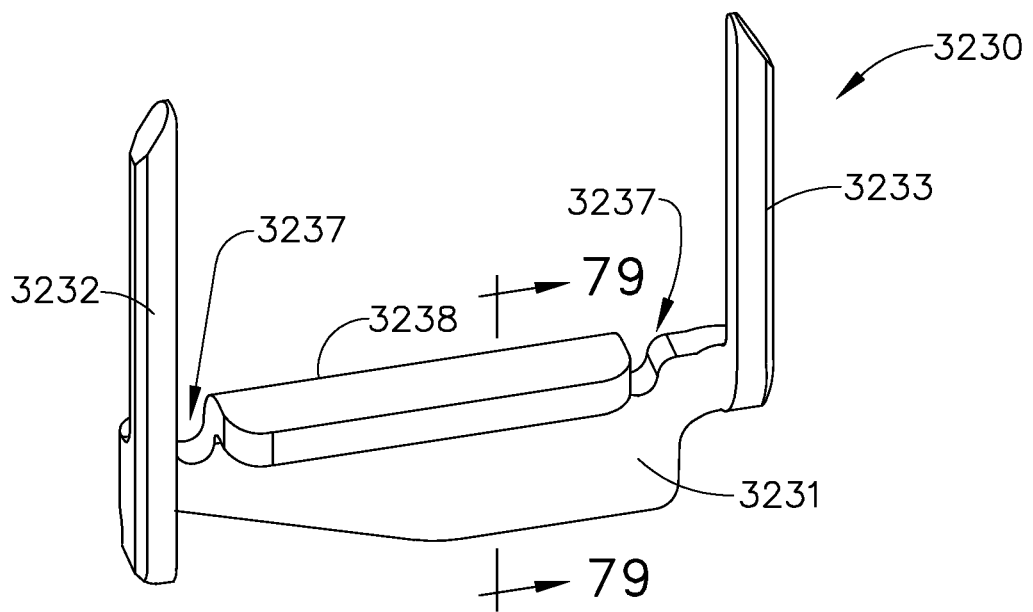
FIG. 78 is a perspective view of a staple in accordance with at least one embodiment.
Figure 79:
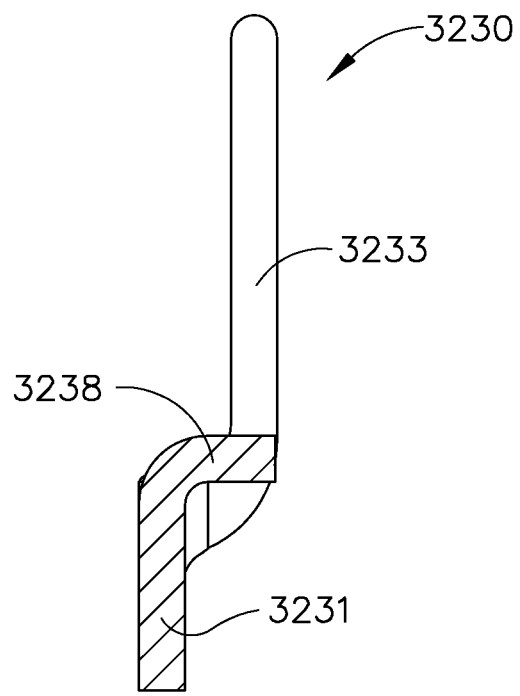
FIG. 79 is a cross-sectional view of the staple of FIG. 78.

A staple 3230 is illustrated in FIGS. 78 and 79. The staple 3230 comprises a base, or crown, 3231, a first leg 3232 extending from the base 3231, and a second leg 3233 extending from the base 3231. Similar to the base 2131 of the staple 2130, the base 3231 of the staple 3230 includes an inclined drive surface defined in a drive plane. Unlike staple 2130, however, the first leg 3232 and the second leg 3233 define a staple forming plane which is transverse to, or non-parallel to, the drive plane.

The staple 3230 further includes a platform 3238 extending from the base 3231. The platform 3238 is integrally formed with the base 3231 and has been folded over such that the platform 3238 extends laterally from the base 3231. The platform 3238 is not directly connected to the legs 3232, 3233. Instead, gaps 3237 are present between the platform 3238 and the legs 3232, 3233. In various other embodiments, the platform 3238 is directly connected to the first leg 3232 and/or the second leg 3233. The platform 3238 extends in a plane, i.e., a support plane, which is transverse to the drive plane and the staple forming plane; however, the platform 3238 can extend in any suitable direction. The platform 3238 is flat, or at least substantially flat; however, the platform 3238 can comprise any suitable shape.

In certain embodiments, the platforms 3238 of the staples 3230 can contact the tissue being stapled when the staples 3230 are implanted into the tissue. The wider platform 3238 can reduce the possibility of the staples 3230 tearing through the tissue.

In various embodiments, a staple cartridge assembly comprises a cartridge body including a deck and staple cavities defined in the deck. The staple cartridge assembly further comprises staples 3230 removably stored in the staple cavities and, in addition, an implantable layer positioned over the deck. The implantable layer can comprise any suitable adjunct such as a tissue thickness compensator and/or a buttress material, for example. A tissue thickness compensator can compensate for variations in the thickness of the tissue being stapled. The implantable layer can be comprised of a woven material and/or a non-woven material, for example.

Further to the above, the platforms 3238 of the staples 3230 can abut the layer when the staples 3230 are implanted into the tissue. In such instances, the platforms 3238 support the layer. Similar to the above, the platforms 3238 can also reduce the possibility of the staples 3230 tearing through the layer. The platforms 3238 of the staples 3230 and the layer can form a co-operative system which distributes the forces, stresses, and/or strains being applied to the tissue over a larger area.

The staple 3230 is formed from a flat sheet of material utilizing a stamping process. During the stamping process, material is removed from the sheet to create the general shape of the staple 3230. The first leg 3232 is bent in a first direction and the second leg 3233 is bent in a second direction; however, both the first leg 3232 and the second leg 3233 can be bent in any suitable direction by a die utilizing a single line of action. The platform 3238 is bent in the same direction as the first leg 3232 during the stamping process, and/or a different stamping process. In certain instances, the platform 3238 can be created utilizing the same single line of action that creates the legs 3232 and 3233. In other instances, the platform 3238 can be created utilizing a second line of action which is transverse or orthogonal to the first line of action.

Figure 86:
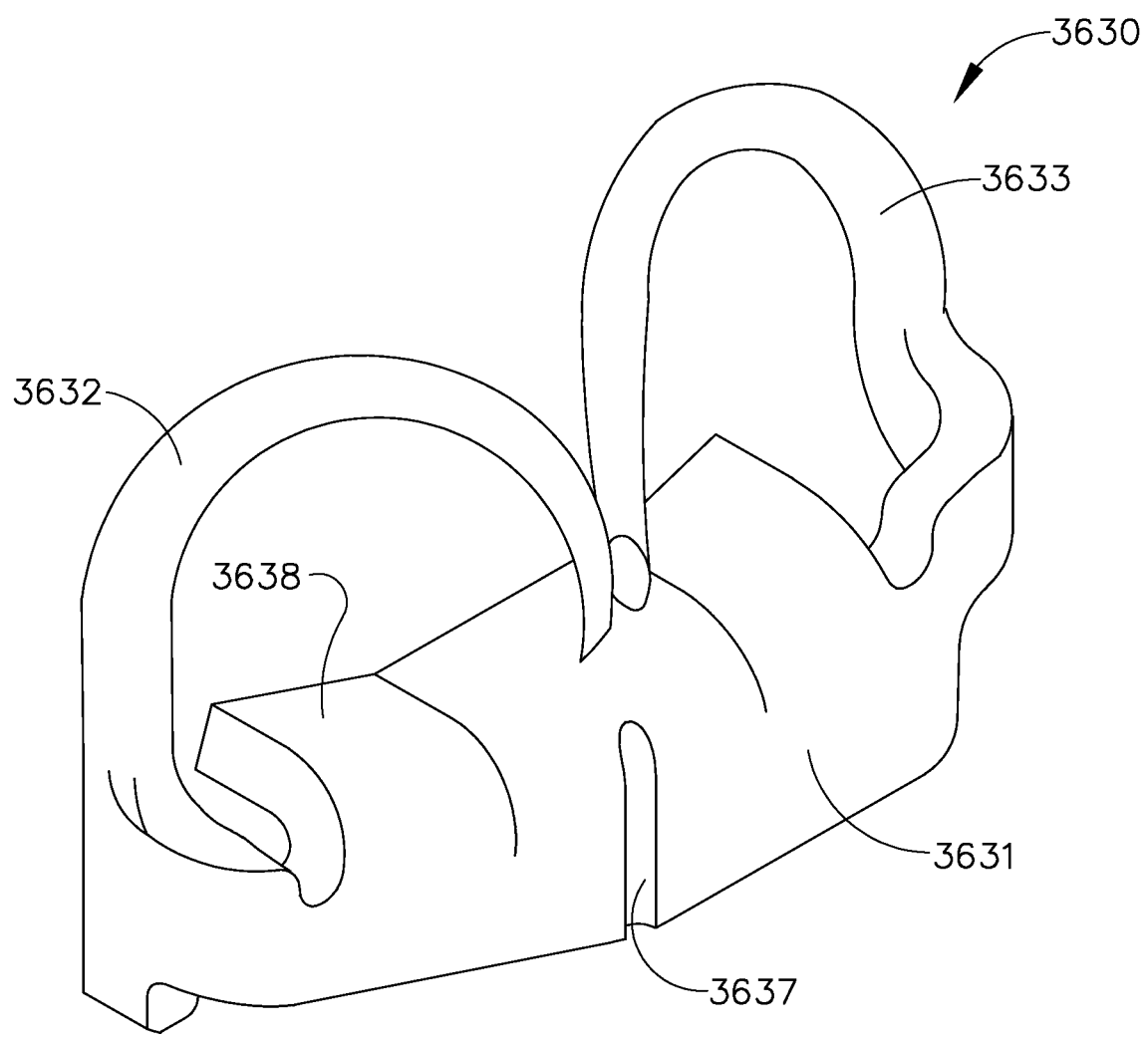
FIG. 86 is a perspective view of a staple in accordance with at least one embodiment illustrated in a deformed configuration.

Turning now to FIG. 86, a staple 3630 comprises a base, or crown, 3631, and legs 3632 and 3633 extending from the base 3631. Similar to the staple 3230, the staple 3630 further comprises a platform 3638 extending from the base 3631. The reader should appreciate that the platform 3238 of the staple 3230 and the platform 3638 of the staple 3630 can increase the moment of inertia, or stiffness, of the staples. The staple 3630 comprises a relief, or flex, slot 3637 in the base 3631 which decreases the stiffness of the staple 3630, for example. Additionally, or alternatively, a relief slot could be provided in the platform 3638. In any event, more than one relief slot could be utilized to provide the desired stiffness of the staple 3630. Moreover, such relief slots could be adapted to any of the staples disclosed herein.

Figure 80:
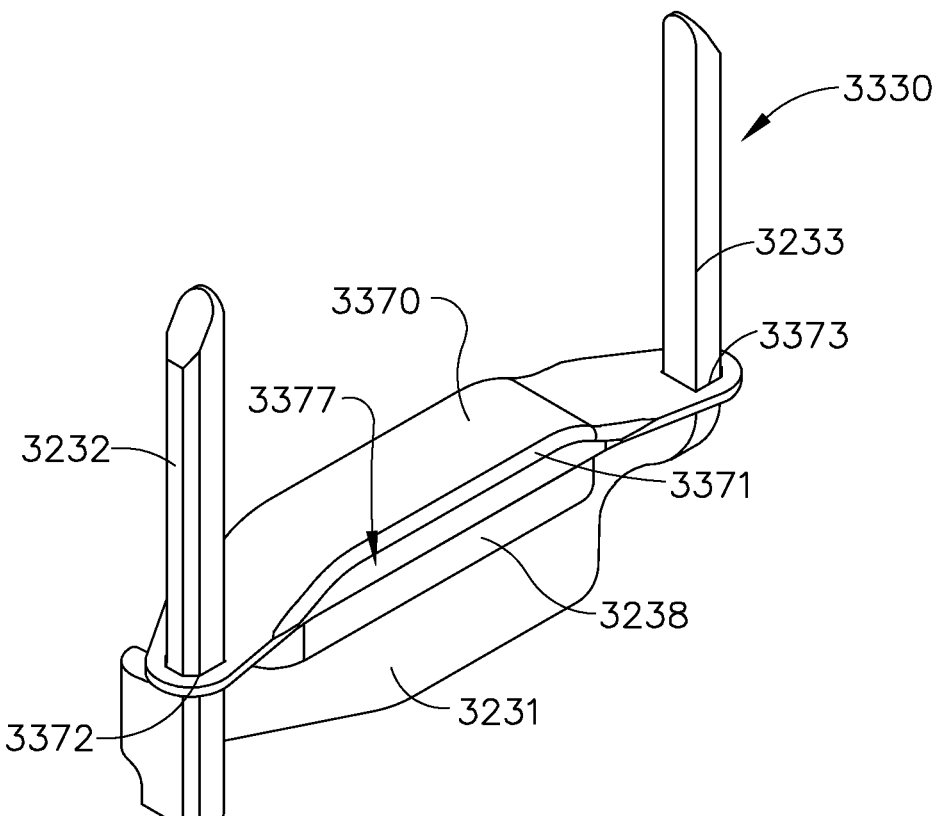
FIG. 80 is a perspective view of a staple assembly in accordance with at least one embodiment.
Figure 81:
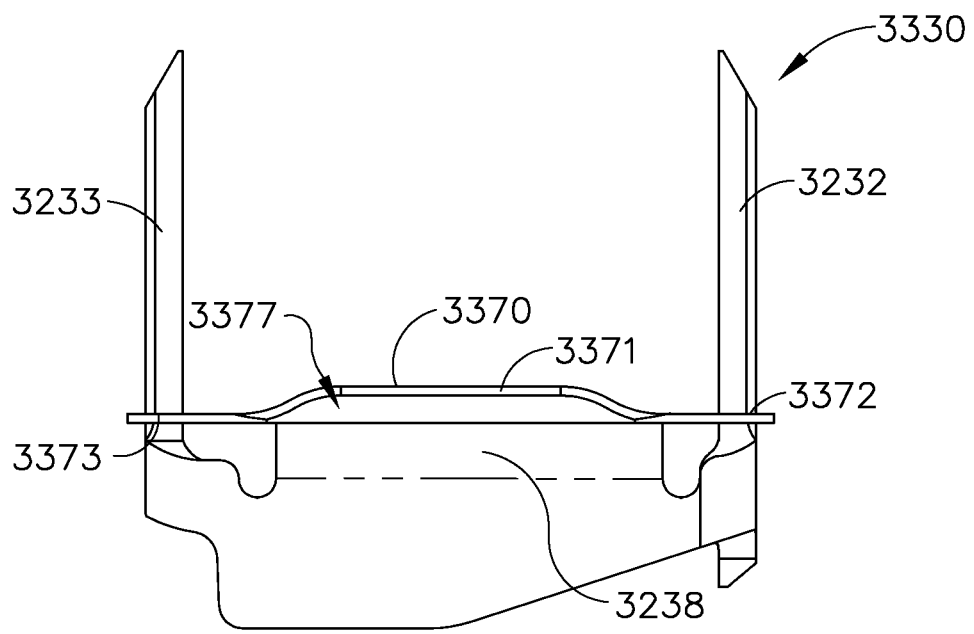
FIG. 81 is an elevational view of the staple assembly of FIG. 80.

In addition to or in lieu of the above, turning now to FIGS. 80 and 81, a staple assembly 3330 comprises a staple 3230 and an implantable adjunct 3370 attached to the staple 3230. The adjunct 3370 comprises a first end including a first aperture 3372 configured to receive the first leg 3232 of the staple 3230 and a second aperture 3373 configured to receive the second leg 3233. As a result, the adjunct 3370 is tethered to the staple legs 3232, 3233 and the movement of the adjunct 3370 relative to the staple 3230 is constrained.

Further to the above, the adjunct 3370 comprises a resilient portion 3371 which extends over the platform 3238 of the staple 3230. A gap 3377 is present between the resilient portion 3371 of the adjunct 3370 and the platform 3238 of the staple 3230 when the staple assembly 3330 is stored in a staple cartridge. When the staple assembly 3330 is ejected from the staple cartridge, the staple legs 3232, 3233 of the staples 3230 penetrate the tissue being stapled and the resilient portion 3371 of the adjunct 3370 comes into contact with the tissue. The resilient portion 3371 is configured to flex, deflect, and/or displace downwardly toward the platform 3238 when the adjunct 3370 comes into contact with the tissue. The resilient portion 3371 can apply a biasing force to the tissue when the tissue is captured within the staple 3230. The movement of the resilient portion 3371 is at least partially constrained by the platform 3238.

Figure 84:
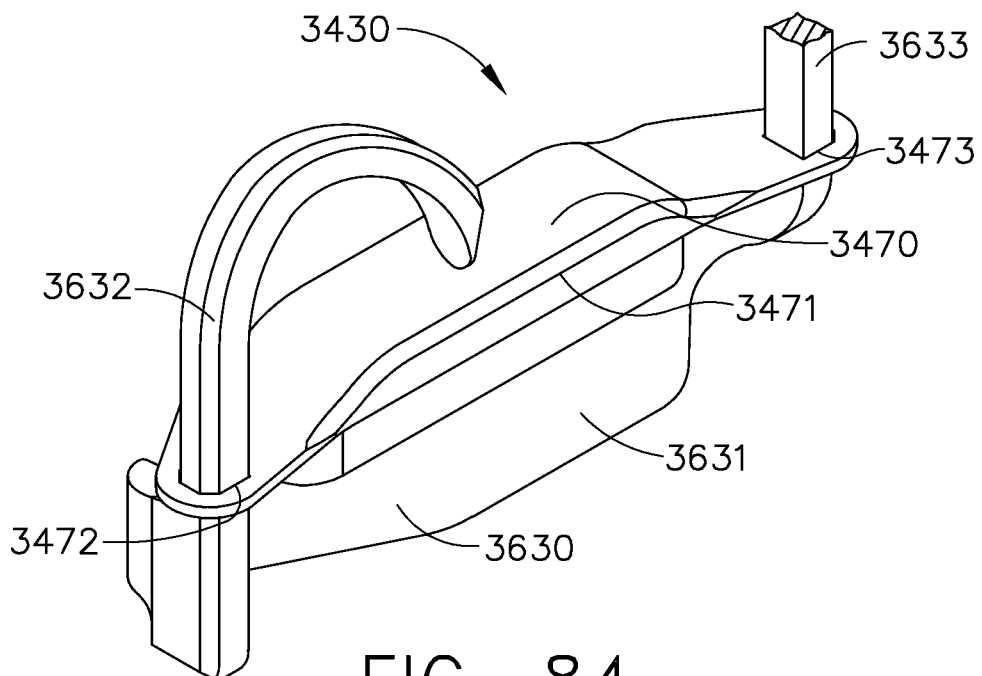
FIG. 84 is a partial perspective view of a staple assembly including the staple adjunct of FIG. 82.

In addition to or in lieu of the above, turning now to FIG. 84, a staple assembly 3430 comprises a staple 3630 and an implantable adjunct 3470 attached to the staple 3230. The adjunct 3470 comprises a first end including a first aperture 3472 configured to receive the first leg 3632 of the staple 3630 and a second aperture 3473 configured to receive the second leg 3633. As a result, the adjunct 3470 is tethered to the staple legs 3632, 3633 and the movement of the adjunct 3470 relative to the staple 3630 is constrained.

Figure 85:
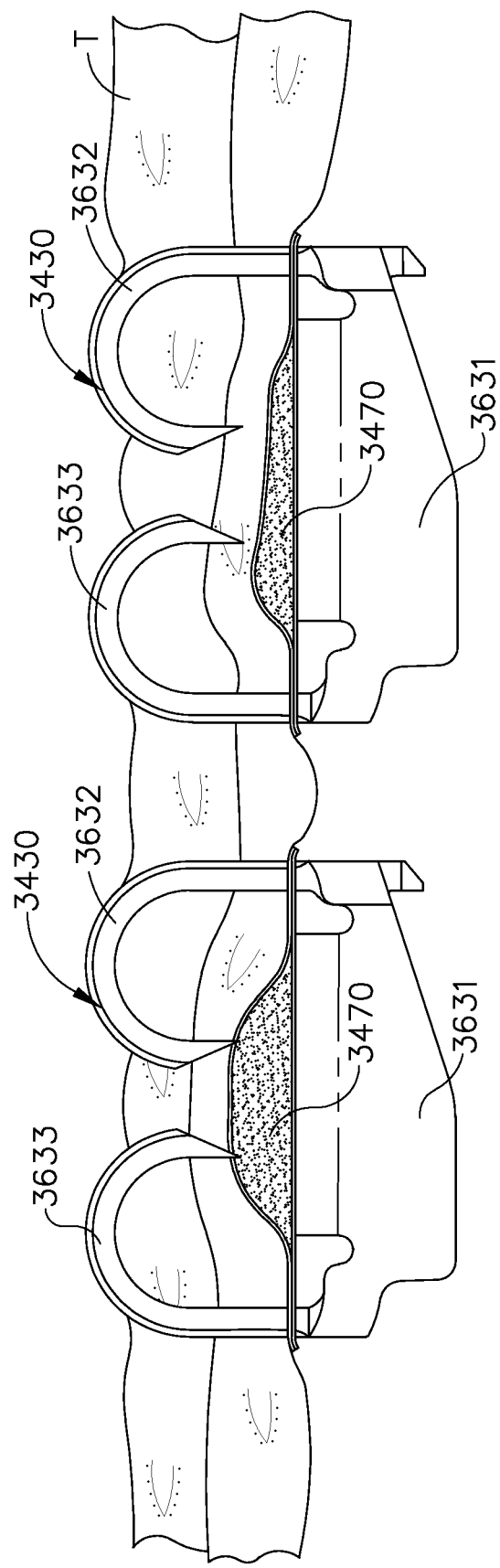
FIG. 85 illustrates the staple assembly of FIG. 84 implanted into tissue.

Further to the above, the adjunct 3470 comprises a resilient portion 3471 which extends over the platform 3638 of the staple 3630. Very little, if any, gap is present between the resilient portion 3471 of the adjunct 3470 and the platform 3638 of the staple 3630 when the staple assembly 3430 is stored in a staple cartridge. When the staple assembly 3430 is ejected from the staple cartridge, the staple legs 3632, 3633 of the staple 3630 penetrate the tissue being stapled and the resilient portion 3471 of the adjunct 3470 comes into contact with the tissue. Referring to FIG. 85, the resilient portion 3471 is configured to flex, deflect, and/or displace downwardly toward the platform 3638 when the adjunct 3470 comes into contact with the tissue. The resilient portion 3471 can apply a biasing force to the tissue when the tissue is captured within the staple 3630. The movement of the resilient portion 3471 is at least partially constrained by the platform 3638.

Figure 82:
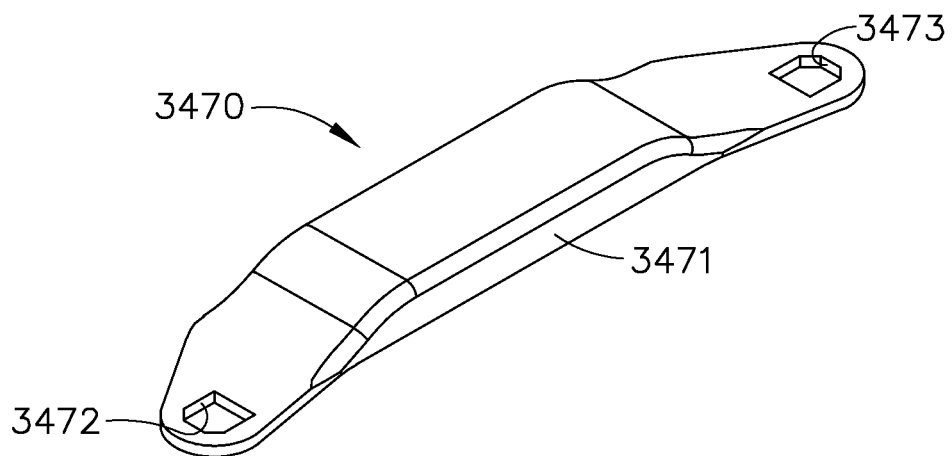
FIG. 82 is a perspective view of an implantable staple adjunct.
Figure 83:
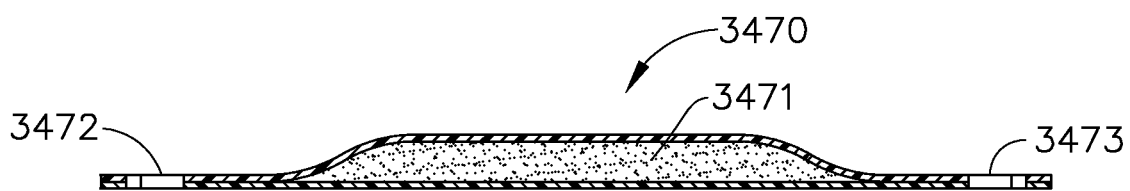
FIG. 83 is a cross-sectional view of the staple adjunct of FIG. 82.

Referring primarily to FIGS. 82 and 83, the resilient portion 3471 of the adjunct 3470 comprises an enclosure. The enclosure is sealed and includes at least one material therein. In various instances, the material comprises a medicament. The medicament is released from the enclosure when the enclosure is ruptured. The enclosure can rupture when the staple assembly 3430 is implanted in the tissue or after a period of time. The adjunct 3470 is comprised of any suitable biocompatible material and, when the biocompatible material comprises a bioabsorbable material, the adjunct 3470 can be absorbed in situ. After a sufficient amount of the adjunct 3470 has been absorbed, the medicament can be released from the adjunct 3470. In various alternative embodiments, an adjunct comprises two separate enclosures. In at least one such embodiment, a first enclosure can contain a first medicament and a second enclosure can contain a second medicament. The first medicament can mix with the second medicament when the enclosures have been ruptured.

Further to the above, the material in the chamber of the resilient portion 3471 can be selected for its mechanical properties such as its elasticity, for example, and can provide the resilient portion 3471 with desirable properties to apply a sufficient biasing force to the tissue. In at least one instance, it may be desirable for the resilient portion 3471 to have mechanical properties which closely resemble that of patient tissue. In other instances, it may be desirable for the resilient portion 3471 to have a stiffness less than the stiffness of patient tissue, for example. Such embodiments may provide a suitable constriction of blood flow within the tissue. In some instances, it may be desirable for the resilient portion 3471 to have a stiffness which is less than the stiffness of the base 3631 but greater than the stiffness of the patient tissue, for example. Such embodiments may provide strain relief to the tissue.

The adjuncts 3370, 3470 can be comprised of a woven material and/or a non-woven material. In at least one instance, the adjuncts 3370, 3470 comprise shells which are comprised of a woven material and/or a non-woven material. The adjuncts 3370, 3470 can be comprised of PGA and/or PLA, for example. In at least one instance, the adjuncts 3370, 3470 comprise shells which are comprised of PGA and/or PLA, for example.

The adjuncts 3370, 3470 are configured to be attached to a single staple. Stated another way, each adjunct 3370, 3470 are only attached to one staple. Such adjuncts can be referred to as pledgets. Alternative embodiments are envisioned in which two or more staples are connected by an adjunct.

Turning now to FIGS. 88 and 89, the various staples disclosed herein, such as staples 2130, for example, can be implanted into the tissue of a patient in longitudinal rows. Two longitudinal rows of staples 2130 are depicted in FIGS. 88 and 89. In various instances, the tissue may stretch in various directions, such as longitudinally, for example. The longitudinal stretch of tissue T is depicted in FIG. 89. As can be seen in FIG. 89, the rows of staples 2130 can stretch along with the tissue T. In such instances, the gaps between the staples 2130 can increase. This gap increase is readily apparent when comparing the unstretched gap distance X1 (FIG. 88) to the stretched gap distance X2 (FIG. 89). The staples 2130 in a third longitudinal row can be positioned and arranged such that they are aligned with or co-extensive with the gaps whether or not the gaps are stretched (X2) or unstretched (X1). Such concepts could be readily adapted to circular and/or curved staple rows, for example.

Figure 87:
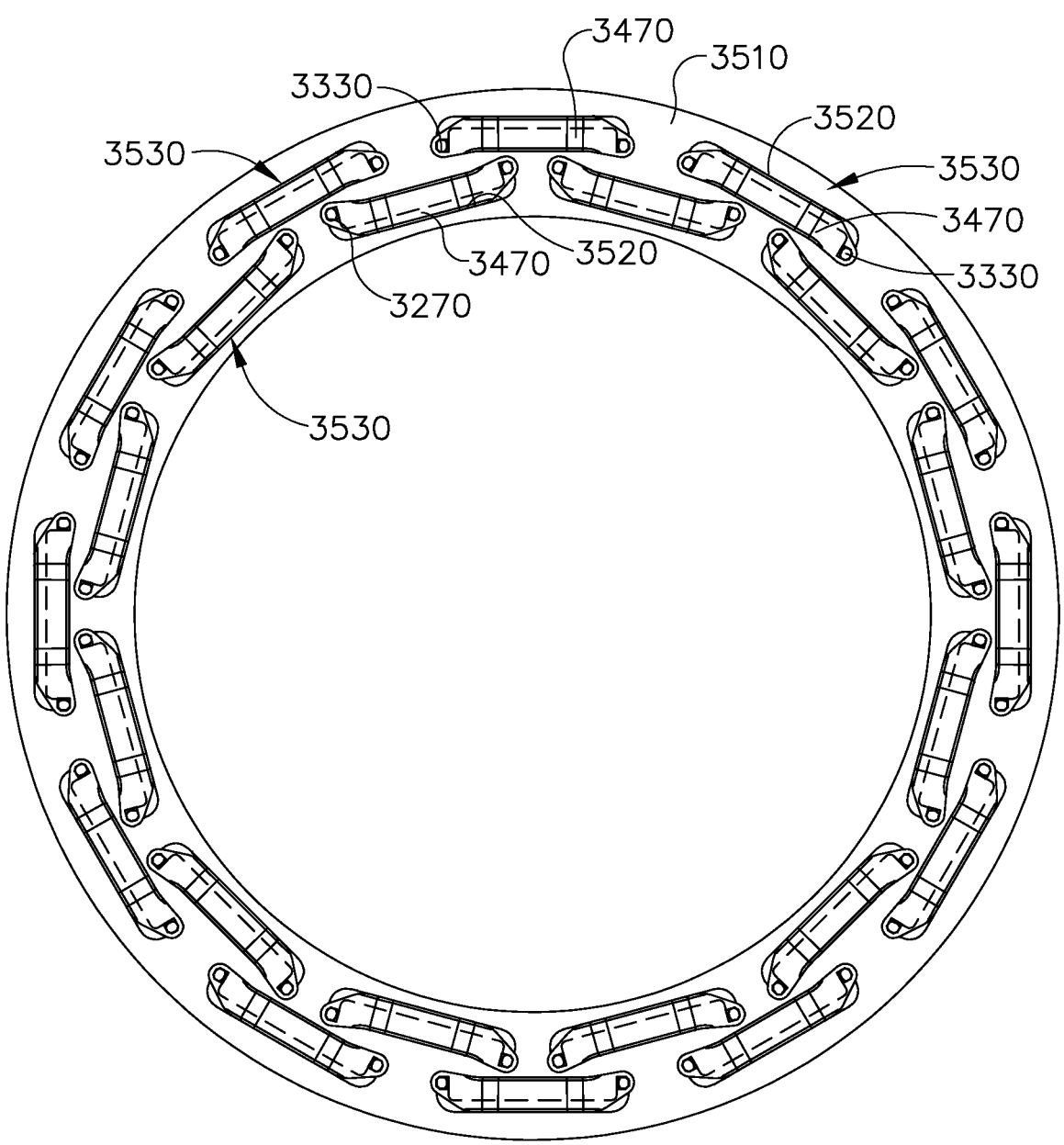
FIG. 87 is a plan view of a circular cartridge body comprising a plurality of the staple assemblies of FIG. 84 in accordance with at least one embodiment.

Turning now to FIG. 87, a circular cartridge body 3510, for example, can utilize the staple assemblies 3430. The cartridge body 3510 comprises a plurality of staple cavities 3520 arranged in circular, concentric rows. As illustrated in FIG. 87, each staple cavity includes a staple assembly 3430 positioned therein; however, any suitable staple could be utilized.

The staples disclosed herein can be comprised of any suitable material. In various instances, the staples are comprised of stainless steel and/or titanium, for example. In certain instances, the staples disclosed herein are comprised of magnesium. The entire disclosures of COMPARISON OF THE EFFECTS OF Mg-6Zn AND Ti-3Al-2.5V ALLOYS ON TGF-β/TNF-α/VEGF/b-FGF IN THE HEALING OF THE INTESTINAL TRACT IN VIVO, *Biomed. Mater.* 9 (2014) 025011, by Yan et al.; COMPARISON OF THE EFFECTS OF Mg-6Zn AND TITANIUM ON INTESTINAL TRACT IN VIVO, *J. Mater. Sci.: Mater. Med.*, by Yan et al. which published online on Mar. 20, 2013; EVALUATION OF THE SOFT TISSUE BIOCOMPATIBILITY OF MgCa0.8 AND SURGICAL STEEL 316L IN VIVO: A COMPARATIVE STUDY IN RABBITS, *Biomed. Eng. OnLine* 2010 9:63, by Erdmann et al.; INVESTIGATION OF THE MECHANICAL AND DEGRADATION PROPERTIES OF Mg—Sr AND Mg—Zn—Sr ALLOYS FOR USE AS POTENTIAL BIODEGRADABLE IMPLANT MATERIALS, *J. Mech. Behavior of Biomed. Mat.* 7 (2012) 87-95, by Brar et al.; Mg—Zr—Sr ALLOYS AS BIODEGRADABLE IMPLANT MATERIALS, *Acta Biomaterialia* 8 (2012) 3177-3188, by Li et al.; ON THE BIODEGRADABILITY, MECHANICAL BEHAVIOR, AND CYTOCOMPATABILITY OF AMORPHOUS $Mg_{72}Zn_{23}Ca_5$ AND CRYSTALLINE $Mg_{70}Zn_{23}Ca_5Pd_2$ ALLOYS AS TEMPORARY IMPLANT MATERIALS, *Soc. Biomat.*, by Pellicer et al., which published online on Aug. 28, 2012, are incorporated by reference herein. In at least one instance, the staples are comprised of a magnesium alloy including zinc and/or silver, for example. Staples including alloys of magnesium and zinc increase the healing performance of tissue. Staples including silver provide anti-microbial benefits. Staples including all three alloys provide a synergistic dynamic.

Staples comprised of magnesium, including those comprised of a magnesium alloy, can be treated to improve the hardness of the staples. In various instances, a magnesium nitride coating is applied to the magnesium staples. The magnesium nitride coating is applied the entirety of the magnesium staples in certain instances while, in other instances, the magnesium nitride coating is applied to only portions of the magnesium staples. For instance, it may be desirable to coat only the staple legs and/or the tips of the staple legs in magnesium nitride as the staple legs need to have a sufficient hardness to penetrate the tissue. In at least one such instance, a mask can be applied to the remainder of the magnesium staple when the magnesium nitride coating is applied to the staple legs. The magnesium nitride coating can be created by introducing the magnesium staples to a nitrogen-rich environment at an elevated temperature and/or pressure, for example.

In addition to or in lieu of the above, one or more surfaces of the magnesium staples can include a coating including carbon.

In addition to or in lieu of the above, other surface hardening techniques could be utilized. For example, the magnesium staples could be hardened using a laser hardening process and/or a plasma discharge hardening process. In at least one instance, a KERONITE ceramic surface treatment, by Keronite International, can be applied to the staples.

As discussed above, certain portions of the magnesium staples may undergo a hardening process while other portions of the magnesium staples may not undergo a hardening process. In some instances, certain portions of the magnesium staples can be hardened to a first hardness while other portions of the magnesium staples can be hardened to a second hardness which is different than the first hardness. The portions of the magnesium staples having a lower hardness will elude magnesium, zinc, and/or silver ions, for example, faster than the portions of the magnesium staples having a higher hardness.

In addition to or in lieu of the above, magnesium staples, including those comprised of a magnesium alloy, can be at least partially covered in a coating including silver. In at least one instance, the silver coating can include ionized silver, for example. In certain instances, an electroplating process can be utilized to apply the silver coating to the magnesium staples. In various instances, the entirety of the magnesium staples are covered in a silver coating. In at least one instance, a portion, or portions, of the magnesium staples are masked during the electroplating process such that the masked portions are not coated, or at least substantially coated, in silver.

In addition to or in lieu of the above, the staples disclosed herein can be coated, or at least partially coated, in an anti-microbial coating. Such a coating can comprise triclosan, for example. In at least one instance, the triclosan is mixed in an absorbable polymer coating. In certain instances, the coating can comprise LAE intermixed with sodium stearate, for example. The entire disclosure of WO 2012013577 A1, entitled COMPOSITION FOR COATING MEDICAL DEVICES CONTAINING LAE AND A POLY- CATIONIC AMPHOTERIC POLYMER, by Gaffar et al., is incorporated by reference herein.

Figure 90:
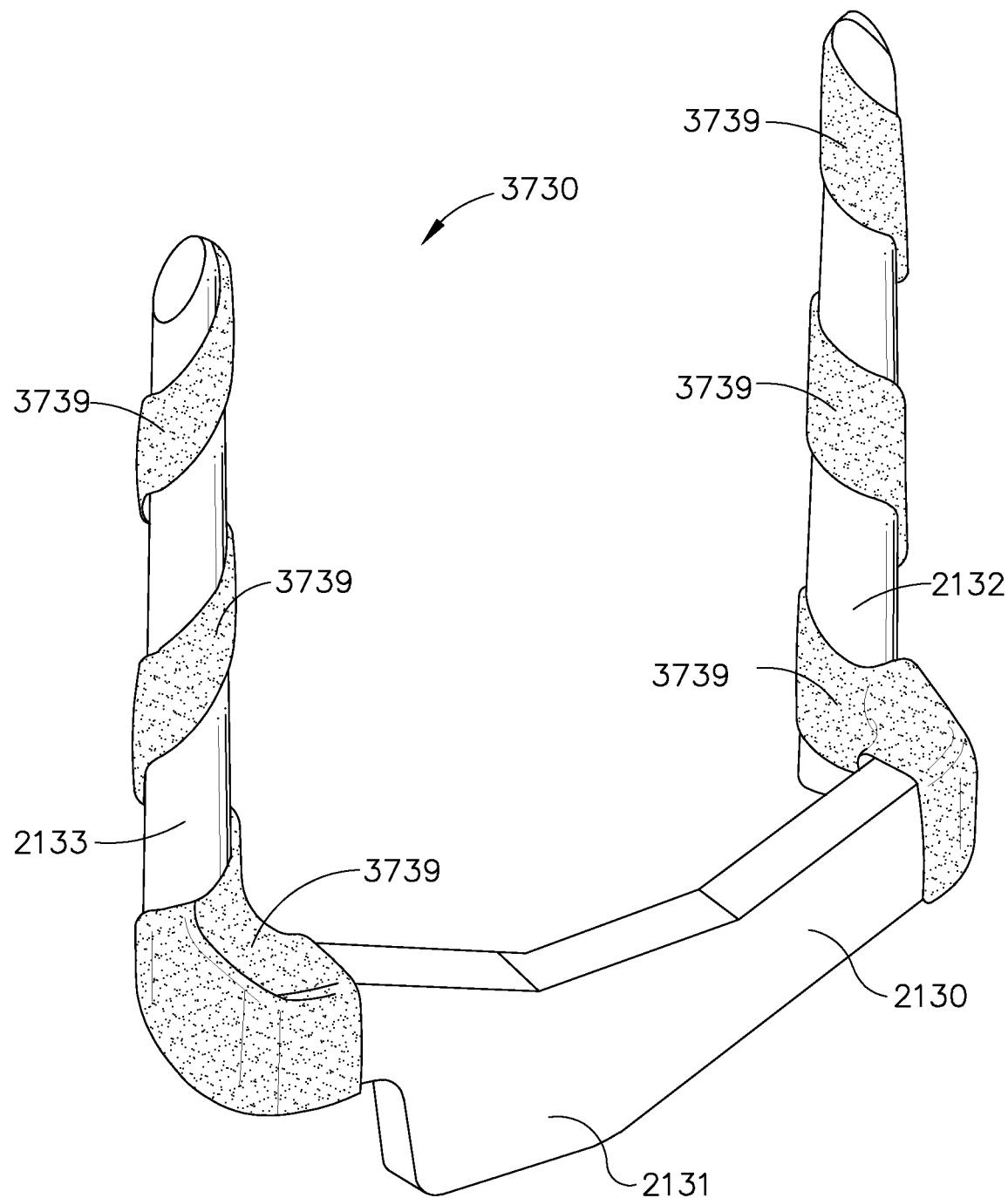
FIG. 90 is a perspective view of a staple in accordance with at least one embodiment.
Figure 91:
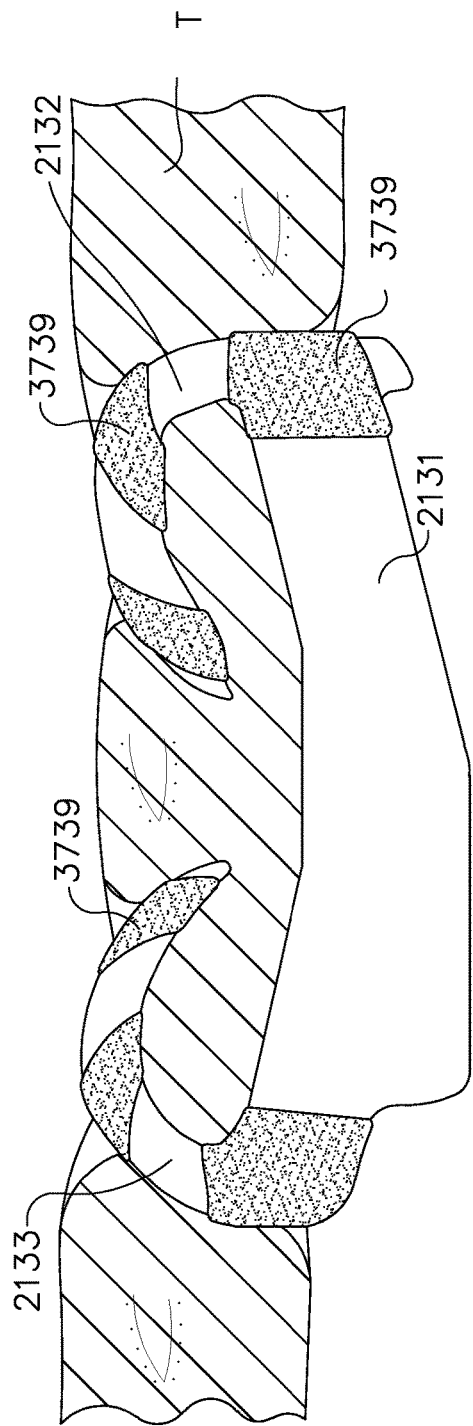
FIG. 91 illustrates the staple of FIG. 90 implanted into tissue.
Figure 92:
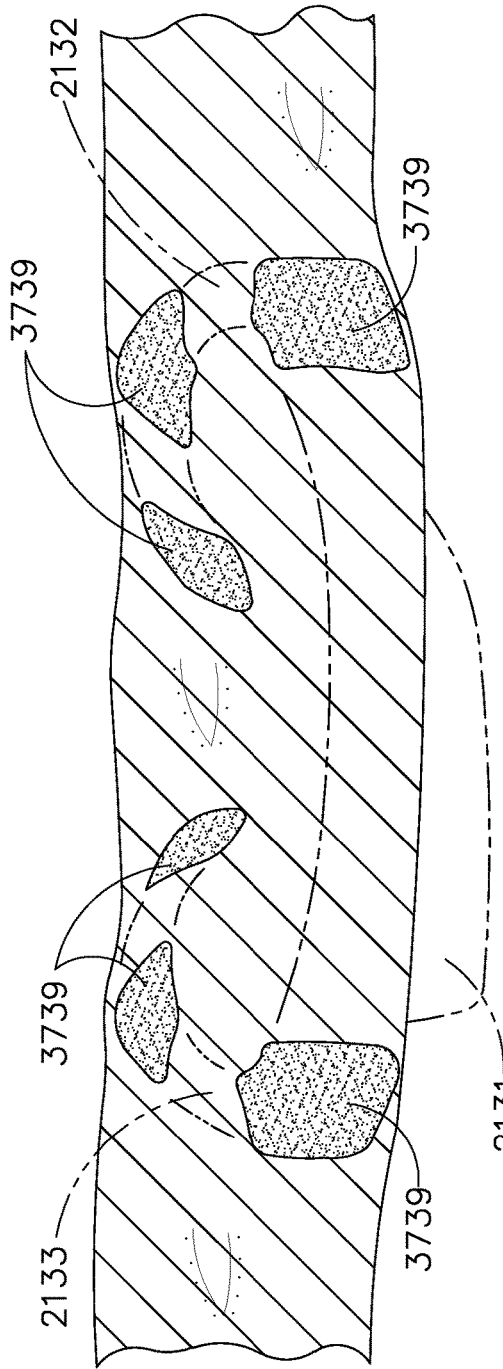
FIG. 92 illustrates the staple of FIG. 90 after being partially dissolved.

Turning now to FIGS. 90-92, a staple 3730 comprises a metal frame and a coating 3739 on less than the entirety of the metal frame. The metal frame includes the staple 2130 and is comprised of magnesium and/or a magnesium alloy, for example. The coating 3739 includes a bioabsorbable polymer; however, the coating 3739 can comprise any suitable material. The coating 3739 extends around the legs 2132, 2133 of the metal frame 2130. More specifically, the coating 3739 spirals around each of the legs 2132, 2133; however, any suitable arrangement of the coating 3739 could be utilized. The coating 3739 also covers the transitions, or corners, between the legs 2132, 2133 and the base, or crown, 2131 of the metal frame 2130. The coating 3739 could also cover a portion of the base 2131. In various instances, the coating 3739 can be strategically applied to areas of the metal frame 2130 that are inherently susceptible to faster bioabsorption, such as the bends, edges, and/or corners of the metal frame 2130, for example. In any event, a portion of the metal frame 2130 is covered by the coating 3739 while a portion of the metal frame 2130 is exposed.

The magnesium, or magnesium alloy, metal frame 2130 is bioabsorbable. Referring primarily to FIG. 91, the portions of the metal frame 2130 that are not covered by the coating 3739 are directly exposed to the body when implanted, and, thus, immediately subjected to the body's natural absorption process. The portions of the metal frame 2130 that are covered by the coating 3739 are not directly exposed to the body, at least not initially, when implanted. The coating 3739 protects, or at least somewhat protects, the portions of the metal frame 2130 that it covers and delays the bioabsorption of such portions. Over time, referring primarily to FIG. 92, the unprotected portions of the metal frame 2130 will bioabsorb, leaving behind the portions of the metal frame 2130 that are protected by the coating 3739. The coating 3739 can substantially encapsulate the portions of the metal frame 2130 that it covers, at least until the coating 3739 itself is bioabsorbed and/or until the metal frame 2130 has sufficiently broken apart. At such point, the portions of the metal frame 2130 that the coating 3739 once protected are exposed and can be bioabsorbed by the body.

The bioabsorbable polymer of the coating 3739 can be comprised of PGA and/or PLA, for example; however, the coating 3739 can be comprised of any suitable material including, but not limited to, bioabsorbable polymers and non-bioabsorbable polymers. In certain instances, the coating 3739 comprises a non cross-linked polymer, for example. Such a polymer can cause the coating 3739 to swell and encapsulate any sharp edges of the metal frame 2130 that are created when the metal frame 2130 deteriorates.

In various embodiments, the coating 3739 can be arranged in a grid, mesh, and/or lattice arrangement on the metal frame 2130 In such an embodiment, the metal frame 2130 can be exposed in the openings in the grid which can allow the metal frame 2130 to be bioabsorbed in such openings. As the metal frame 2130 begins to deteriorate, the latticed coating 3739 can act as a net or cage and hold the fragments of the metal frame 2130 together, for example, at least until the coating 3739 is bioabsorbed.

The coating 3739 can be applied to the metal frame 2130 in any suitable manner. In at least one instance, the coating 3739 can be sprayed onto the metal frame 2130 such that the coating 3739 is applied in a random manner which creates random openings through which the metal frame 2130 can be bioabsorbed. In certain other instances, the coating 3739 can be applied to the metal frame 2130 in a pattern. In at least one such instance, the pattern can include a dot-matrix pattern having islands of coating surrounded by exposed portions of the metal frame 2130.

In certain alternative embodiments, a staple can include two or more coatings. In at least one such instance, a first coating can be bioabsorbed at a first rate and a second coating can be bioabsorbed at a second rate to expose different portions of the metal frame 2130 at different times during the healing process, for example. Such staples can still have uncovered portions; however, it is contemplated that every portion of a staple could be covered by at least one or more coatings.

The therapeutic benefits provided by the materials disclosed herein are a function of the surface area of the staples that is exposed to the patient's body. Staples having a larger surface area may deliver such therapeutic benefits faster than staples having a smaller surface area. That said, staples having a smaller surface area may provide such therapeutic benefits over a longer period of time. Nonetheless, the surface area of the staples disclosed herein can be increased by introducing apertures into the staples. For instance, one or more apertures, or through holes, can be created in the base, or crown, 2131 of the staple 2130, for example. The through holes can permit tissue to grow through the staple 2130 and improve the assimilation of the staple 2130 into the body.

In at least one embodiment, further to the above, the coating 3739 is not positioned in the apertures as the coating 3739 would reduce the available surface absorption area of the staple 2130. However, if delaying the bioabsorption of these staple portions is desired, the apertures in the staple 2130 could be filled, or at least partially filled, with the coating 3739. As discussed above, the coating 3739 can be configured to delay the absorption of the underlying metal frame; however, any suitable coating could be utilized. For example, a coating on the metal frame could encourage tissue ingrowth into the structure of the staple. In at least one such instance, the coating comprises small micropillars that create a porous and/or prickly interaction with the tissue.

In various embodiments, further to the above, a suture, or string, can extend through the apertures defined in the staples. Such a suture can tether the staples together. In various instances, the suture is threaded through the apertures while the staples are positioned in the staple cartridge. In other instances, the suture is threaded through the apertures after the staples have been implanted into the tissue. In at least one embodiment, the suture is positioned in a groove defined in the deck of the staple cartridge and the staples each comprise a slot or hook defined therein which is configured to catch the suture as the staples are being deployed. In any event, the suture can be pulled to gather the stapled tissue together, such as in a purse-string tissue gathering technique, for example.

In various embodiments, the staples disclosed herein can comprise barbs. In at least one instance, barbs are defined on the staple leg such that the barbs engage a layer that is implanted with the tissue. Such barbs can reduce relative movement between the layer and the staples. In certain embodiments, barbs are defined on the base of the staple. Such barbs can grip a layer of tissue positioned adjacent the implanted staples.

Figure 93:
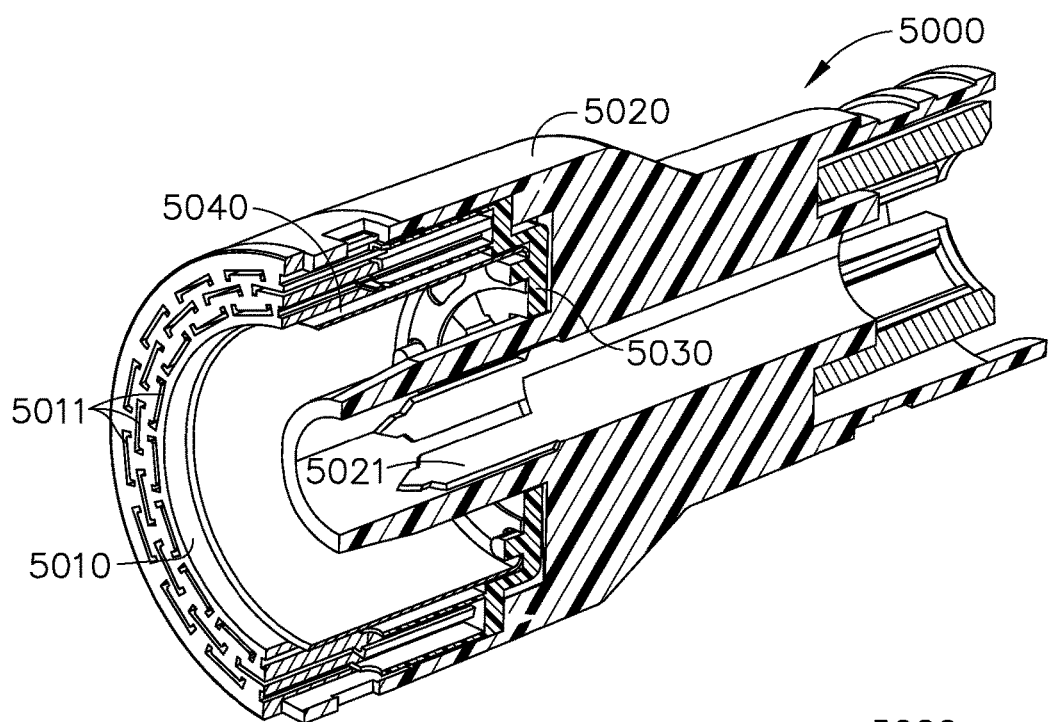
FIG. 93 is a cross-sectional perspective view of a portion of a circular surgical stapler in accordance with at least one embodiment.
Figure 94:
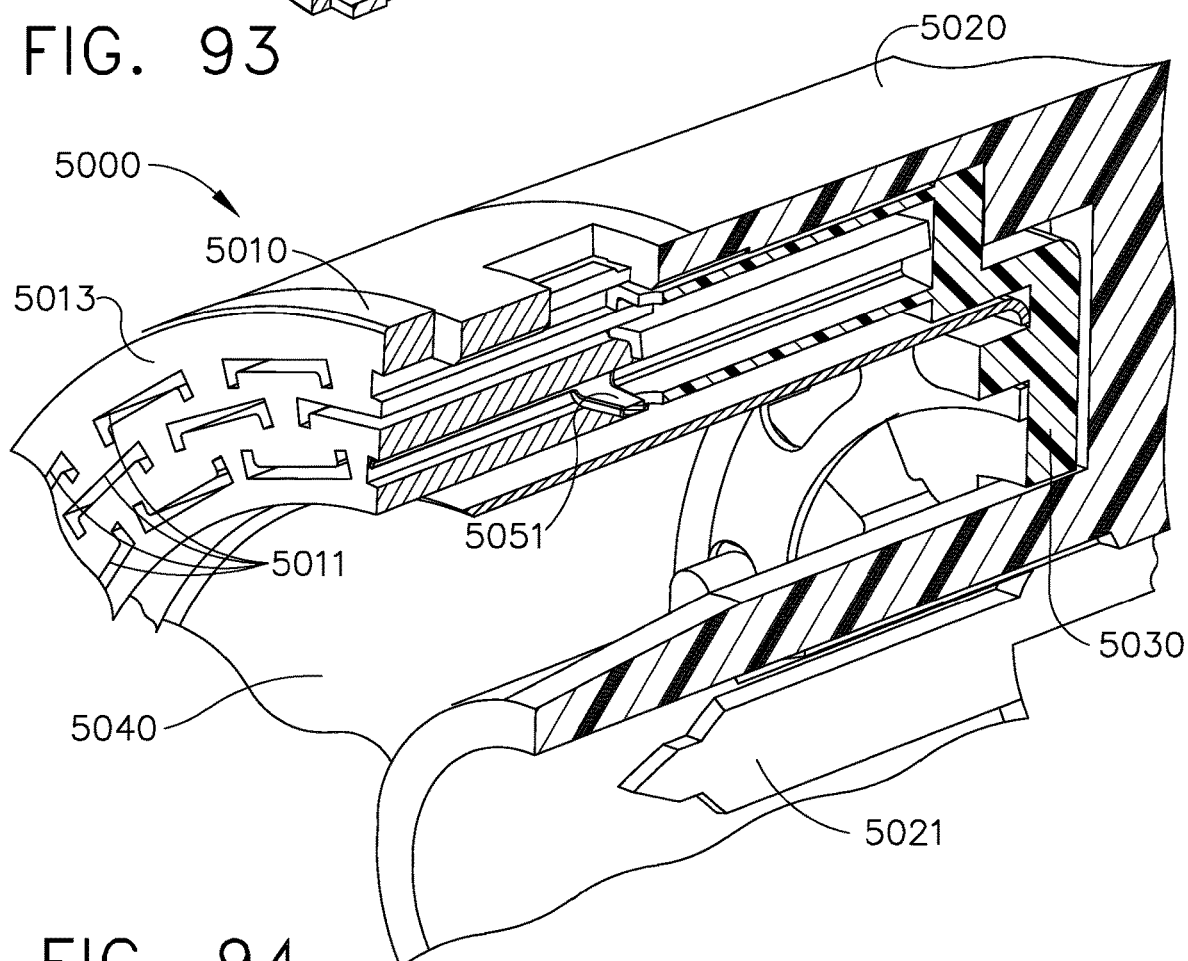
FIG. 94 is a partial cross-sectional perspective view of the circular surgical stapler of FIG. 93.
Figure 95:
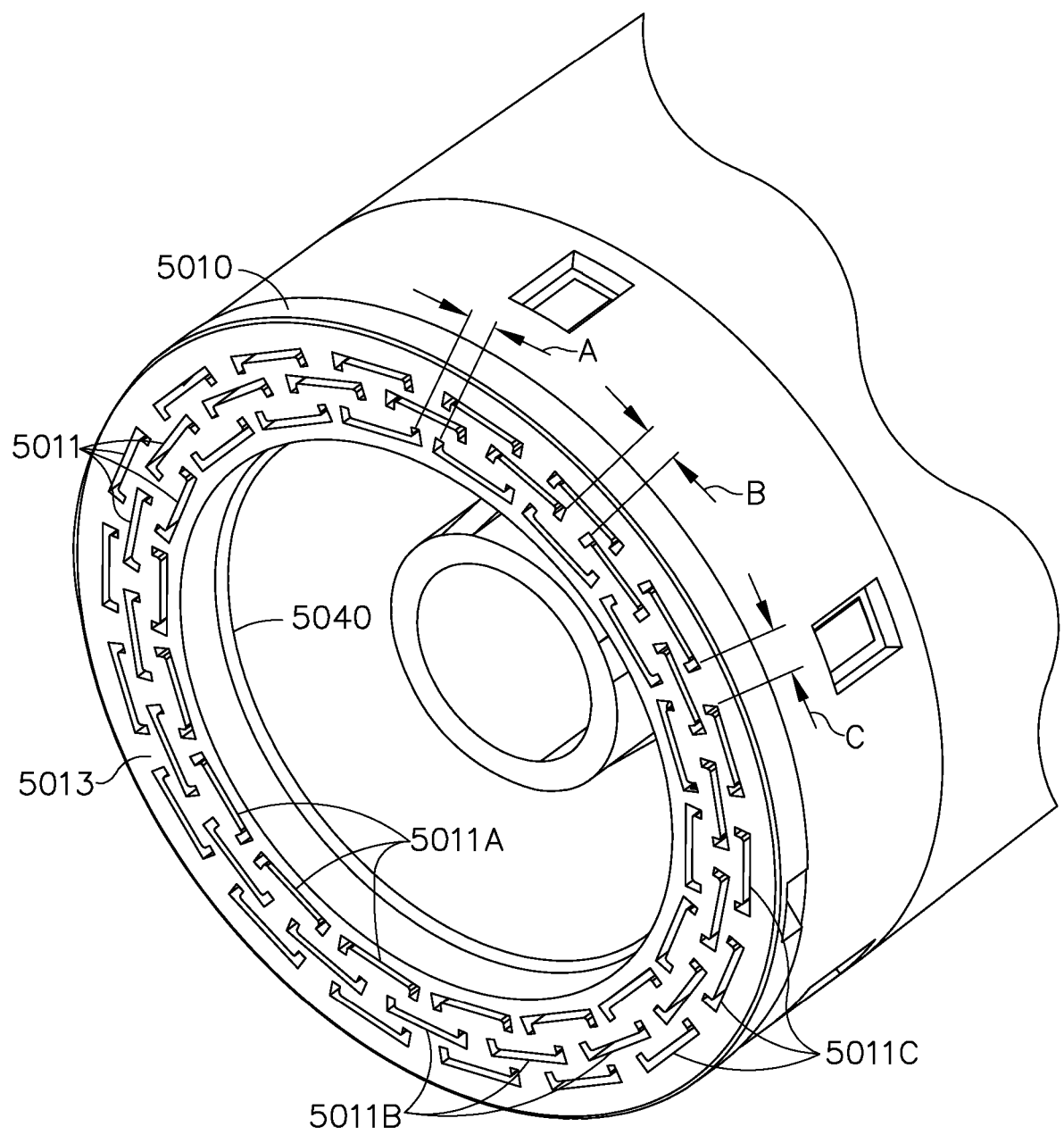
FIG. 95 is a partial perspective view of the circular surgical stapler of FIG. 93.

A circular surgical stapler 5000 is depicted in FIGS. 93-95. The circular surgical stapler 5000 comprises a frame assembly 5020 comprising an attachment portion 5021 configured to operably couple an anvil to the circular surgical stapler 5000. The circular surgical stapler 5000 further comprises a knife member 5040 configured to incise tissue captured by the circular surgical stapler 5000, a surgical staple cartridge 5010 which removably stores a plurality of staples 5051 therein, and a pusher assembly, or driver, 5030 configured to eject the staples 5051 out of the staple cartridge 5010. The surgical staple cartridge 5010 comprises a cartridge deck 5013 and a plurality of staple cavities 5011 defined in the cartridge deck 5013 which removably store the staples 5051. The staples 5051 are similar to the staples discussed in greater detail herein, however, any suitable staple may be used. The staples 5051 comprise staple legs in a plane which is offset from a plane defined by the staple base portion.

Referring primarily to FIG. 95, the staple cavities 5011 of the staple cartridge 5010 comprise an inner row of staple cavities 5011A, an intermediate row of staple cavities 5011B, and an outer row of staple cavities 5011C. Staple row spacing may can include any suitable spacing; however, nested rows may be closer together than non-nested rows. The intermediate row of staple cavities 5011B is positioned radially outward with respect to the inner row of staple cavities 5011A. The outer row of staple cavities 5011C is positioned radially outward with respect to the intermediate row of staple cavities 5011B. The staple cavities 5011A in the inner row comprise an orientation which orients the staple legs of the staples 5051 stored therein such that the staple legs extend radially outward with respect to the staple base. The intermediate row of staple cavities 5011B and the outer row of staple cavities 5011C comprise an orientation which orients the staple legs of the staples 5051 stored therein such that the staple legs extend radially inward with respect to the staple bases.

The staple cavities 5011A in the inner row define a plurality of first gaps therebetween having a distance A. The intermediate row of staple cavities 5011B define a plurality of second gaps with a distance B. The outer row of staple cavities 5011C define a plurality of third gaps with a distance C. The distance A is less than the distances B and C. The distance B is greater than the distance A but less than the distance C. The distance C is greater than the distances A and B. The cavities 5011 are arranged such that the first gaps comprise a distance which is greater than the distances of the second gaps and/or the third gaps. The cavities 5011 are arranged such that the third gaps comprise a distance which is less than the distances of the first gaps and/or the second gaps. Embodiments are envisioned where there are no gaps associated with one or more rows of staple cavities.

The intermediate row of staple cavities 5011B are arranged such that the cavities 5011B overlap the first gaps defined by the inner row of staple cavities 5011A in order to compensate for the lack of tissue ligation in the first gaps. The outer row of staple cavities 5011C are arranged such that the cavities 5011C overlap the second gaps defined by the intermediate row of staple cavities 5011B in order to compensate for the lack of tissue ligation in the second gaps. Overlapping these fastening gaps with such an arrangement increases the ligation ability of the circular surgical stapler 5000. This arrangement also permits the fastened tissue to flex upon fastening. Conventional arrangements utilize greater quantities of staples in the intermediate and/or outer rows in order to increase ligation efficiency; however, such conventional arrangements can limit tissue flexibility after fastening.

Figure 96:
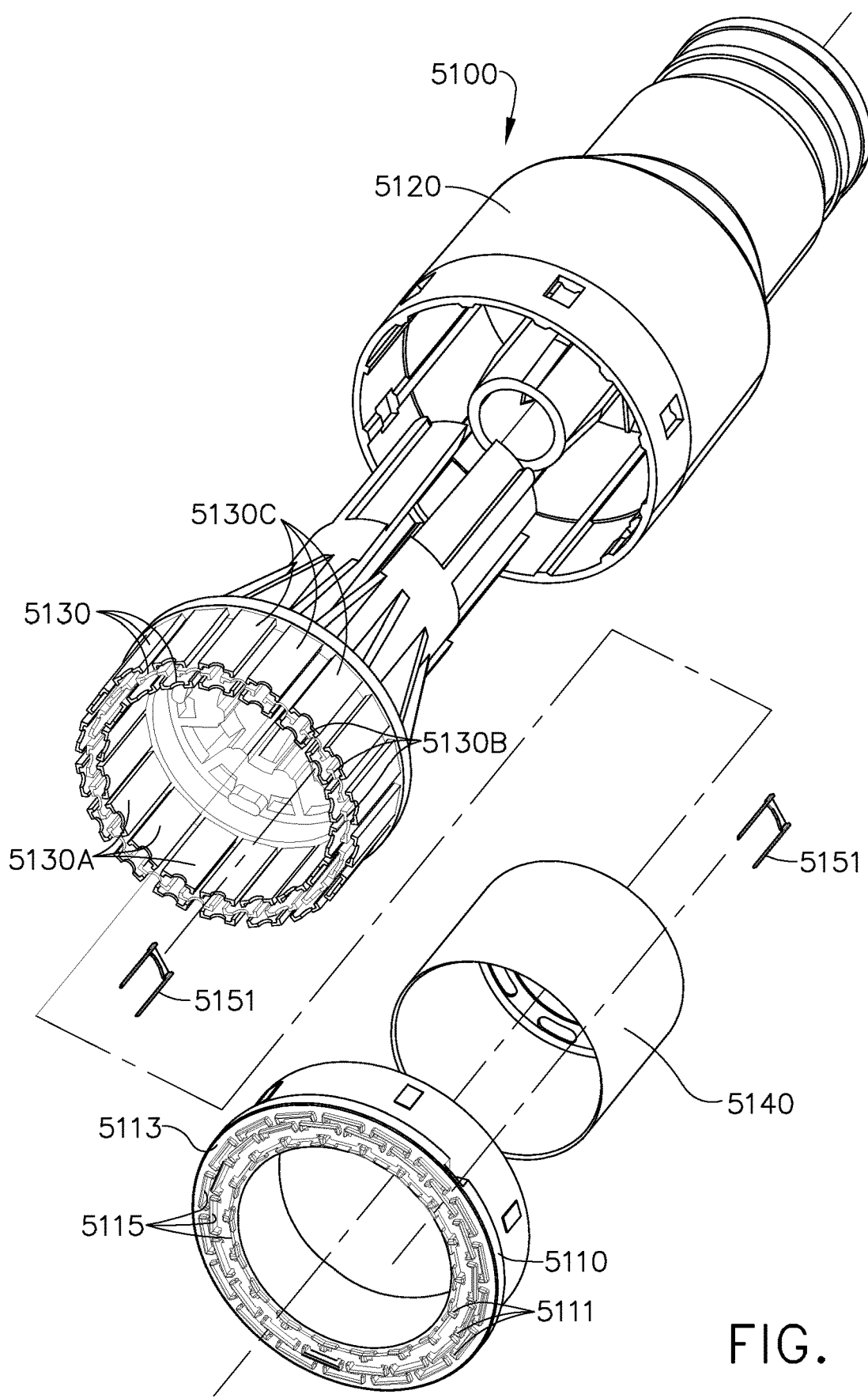
FIG. 96 is a partial exploded perspective view of a circular surgical stapler in accordance with at least one embodiment.
Figure 97:
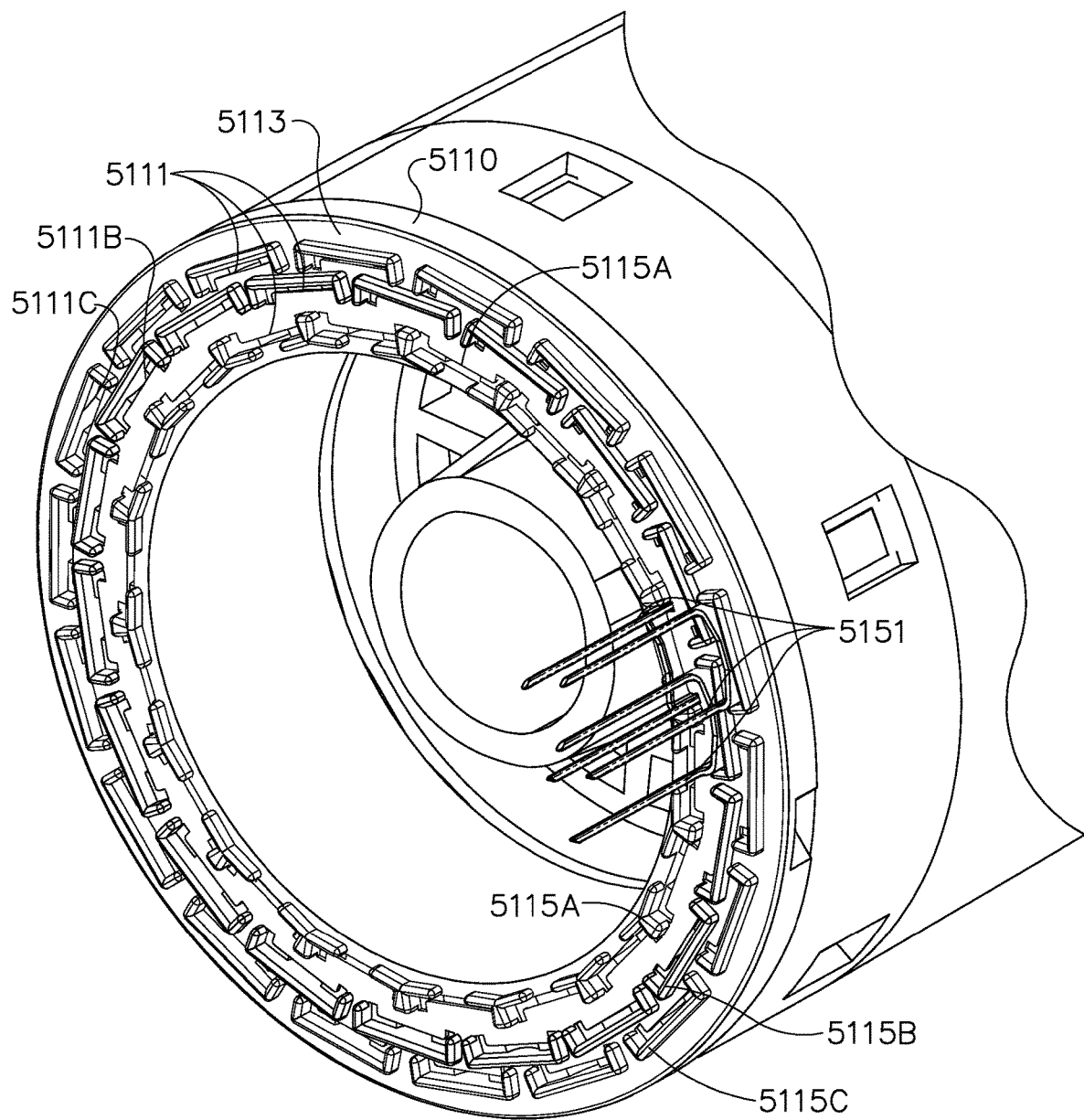
FIG. 97 is a partial perspective view of the circular surgical stapler of FIG. 96 illustrating staples in a preloaded position.
Figure 98:
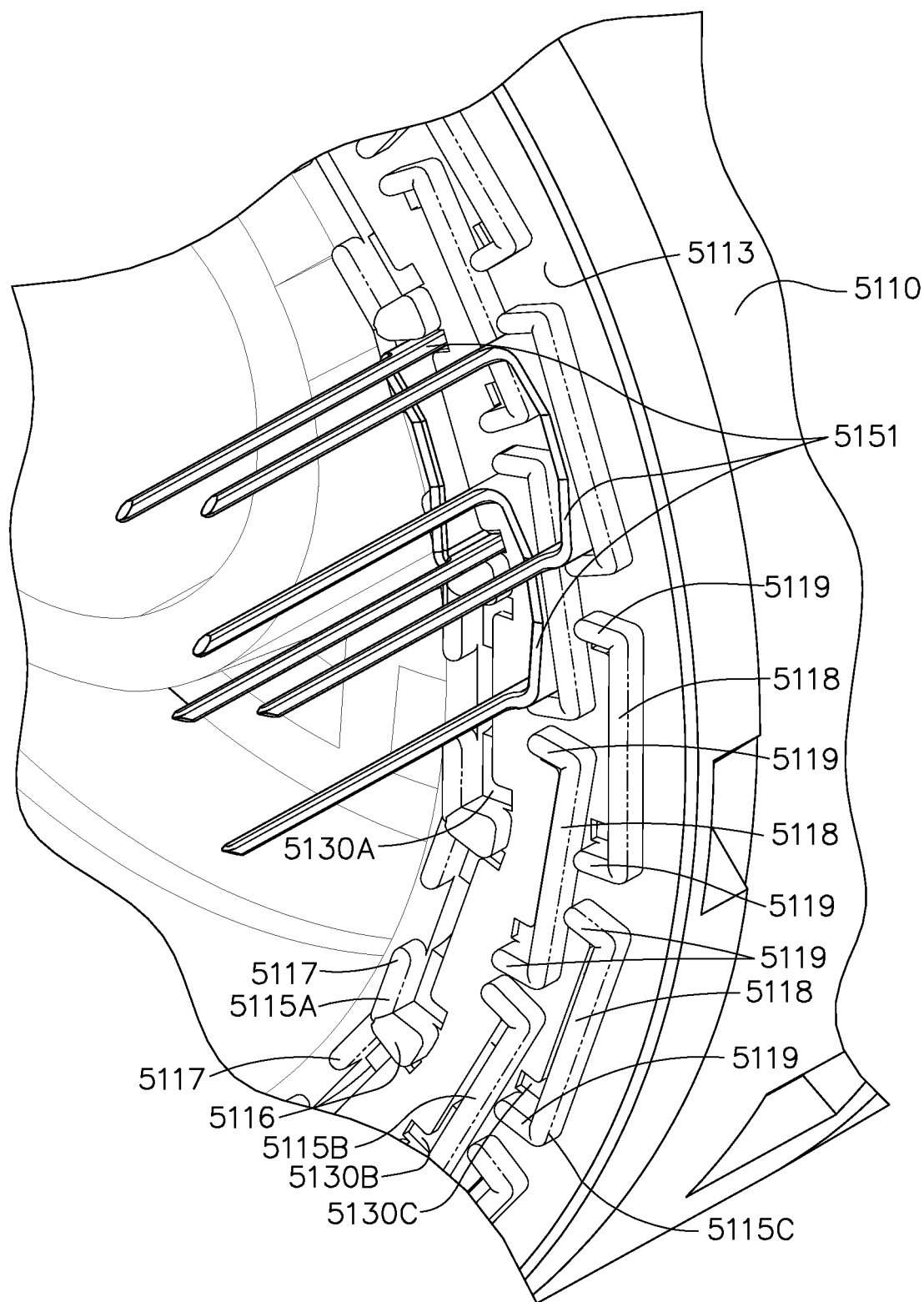
FIG. 98 is a partial perspective view of the circular surgical stapler of FIG. 96.

FIGS. 96-98 illustrate a circular surgical stapler 5100 in accordance with at least one embodiment. The circular surgical stapler 5100 comprises a frame assembly 5120 comprising an attachment portion configured to operably couple an anvil to the circular surgical stapler 5100. The circular surgical stapler 5100 further comprises a knife member 5140 configured to incise tissue captured by the circular surgical stapler 5100, a surgical staple cartridge 5110 which removably stores a plurality of staples 5151 therein, and a pusher assembly, or driver, 5130 configured to eject the staples 5151 out of the staple cartridge 5110. The pusher assembly 5130 comprises an inner row of staple drivers 5130A, an intermediate row of staple drivers 5130B, and an outer row of staple drivers 5130C. The surgical staple cartridge 5110 comprises a cartridge deck 5113 and a plurality of staple cavities 5111 defined in the cartridge deck 5113 which removably store the staples 5151 therein. The surgical staple cartridge 5110 further comprises a plurality of deck features, or staple supports, or guides, 5115 configured to support, guide, and/or control the staples 5151 when the staples 5151 are ejected from the staple cartridge 5110. The deck features, or cavity extenders, 5115 can have a multitude of purposes such as aiding in the gripping of tissue intermediate the anvil and the staple cartridge 5110 and/or storing, releasing, and delivering a medicament to tissue captured with the stapler 5100, for example.

The staple cavities 5111 of the staple cartridge 5110 are similar to the staple cavities 5011 in many respects. The staple cavities 5111 comprise an inner row of staple cavities 5111A, an intermediate row of staple cavities 5111B, and an outer row of staple cavities 5111C. The deck features 5115 comprise a plurality of first deck features 5115A, a plurality of second deck features 5115B, and a plurality of third deck features 5115C. Each first deck feature 5115A comprises an intermediate portion 5116 and two outer portions 5117 to define a T-configuration. The intermediate portion 5116 sits between two staple cavities 5111A and extends from the deck 5113 to guide and/or support neighboring staple legs. The outer portions 5117 branch off of the intermediate portion 5116 in at least substantially opposite directions and extend from the deck 5113 to guide and/or support a portion of a staple base. Combining deck features for more than one cavity in such a manner can save space on the cartridge deck 5113.

Each second deck feature 5115B and each third deck feature 5115C comprise an intermediate portion 5118 and two outer portions 5119 to define a cavity-surrounding configuration. The intermediate portion 5118 extends from the deck 5113 to guide and/or support staple bases of staples removably stored in the intermediate row of staple cavities 5111B and the outer row of staple cavities 5111C. The two outer portions 5119 branch off from the intermediate portion 5118 to support the staple legs that extend from the staple base that the intermediate portion 5118 is guiding and/or supporting.

Figure 99:
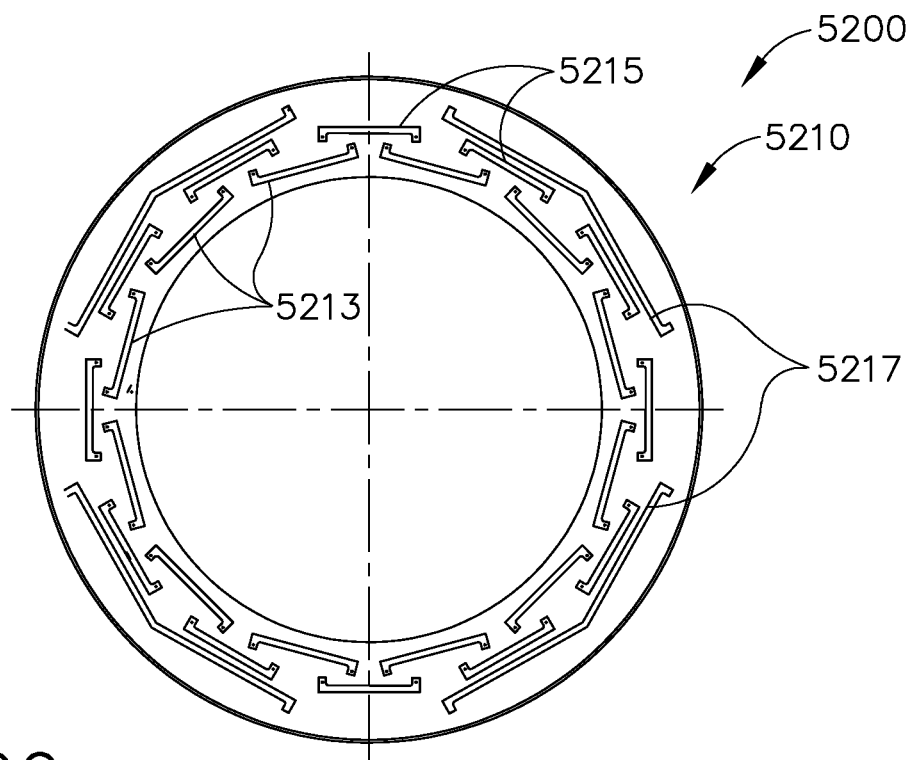
FIG. 99 is an end view of a circular surgical stapling configuration in accordance with at least one embodiment.

FIG. 99 illustrates a circular stapling configuration 5200 for use with a circular surgical stapler in accordance with at least one embodiment. The circular stapling configuration 5200 is an arrangement of staples employable with a circular staple cartridge. A circular staple cartridge employing the circular stapling configuration 5200 comprises corresponding staple cavities to removably store the staples discussed herein. The circular stapling configuration 5200 comprises a plurality of staples 5210 comprising an inner row of staples 5213, an intermediate row of staples 5215, and an outer row of staples 5217. Each staple 5213 is orientated such that its staple legs face outward toward the outer row of staples 5217. Each staple 5215 is orientated such that its staple legs face inward toward the inner row of staples 5113. Each staple 5217 is orientated such that its staple legs face outward away from the inner row of staples 5213 and the intermediate row of staples 5215. Each staple row may reside a certain distance from each other staple row and/or the cutting member to better control blood flow and/or predict tissue behavior at certain points within the stapled tissue.

The outer row of staples 5217 comprise different characteristics than the inner and/or intermediate row of staples 5213, 5215. For example, in various instances, the outer row of staples 5217 are formed into a larger "B" formation resulting in a greater capture volume and/or taller staple forming height to alleviate high tissue compression near the outer row of staples 5217. A larger B formation may also improve blood flow toward the inner rows. In various instances, the outer row of staples 5217 comprise a greater resistance to unfolding by utilizing a larger staple crown, staple leg widths, and/or staple leg thicknesses.

The quantity of staples used in each row of staples can vary in a circular and/or linear surgical staple cartridge. The outer row of staples 5217 comprise a first quantity, the intermediate row of staples 5215 comprise a second quantity, and the inner row of staples 5213 comprise a third quantity. FIG. 99 illustrates a scenario where the first quantity is equal to the second quantity, but, greater than the third quantity. In various embodiments, the first quantity, the second quantity, and the third quantity are different. In various embodiments, the first quantity is greater than the second quantity and the second quantity is greater than the third quantity.

Varying staple crown widths between staple rows can provide an effective and/or efficient stapling arrangement. For example, each outer row staple 5217 comprises a staple crown having a width that is greater than the crown width of each inner row staple 5213 and each intermediate row staple 5215. The staple crown of each outer row staple 5217 is bent laterally in order have a larger crown width staple while maintaining the compact circular stapling arrangement. Some embodiments are envisioned where the crown of each outer row staple 5217 is curved. One advantage of bending or curving the crown of the outer row staples 5217 can include being able to nest the outer row staples 5217 closer to the intermediate row staples 5215 and the inner row staples 5213, for example. Each outer row staple 5217 spans a plurality of gaps defined between the inner row staples 5213 and/or the intermediate row staples 5215. Each intermediate row staple 5215 spans, overlaps, or covers each gap defined between the inner row of staples 5213.

In various embodiments the gaps defined by the inner row staples 5213 can be varied based on the radial position of the row of inner staples. For example, a row of inner staples having a diameter much less than the diameter of the intestine being stapled may comprise much larger gaps between the inner row staples to provide radial flexibility, and/or expansion. A row of inner staples having a diameter less than, but closer to, the diameter of the intestine being stapled may comprise smaller gaps between the inner row staples because, in this instance, vast expansion and/or flexibility may not be necessary.

Figure 100:
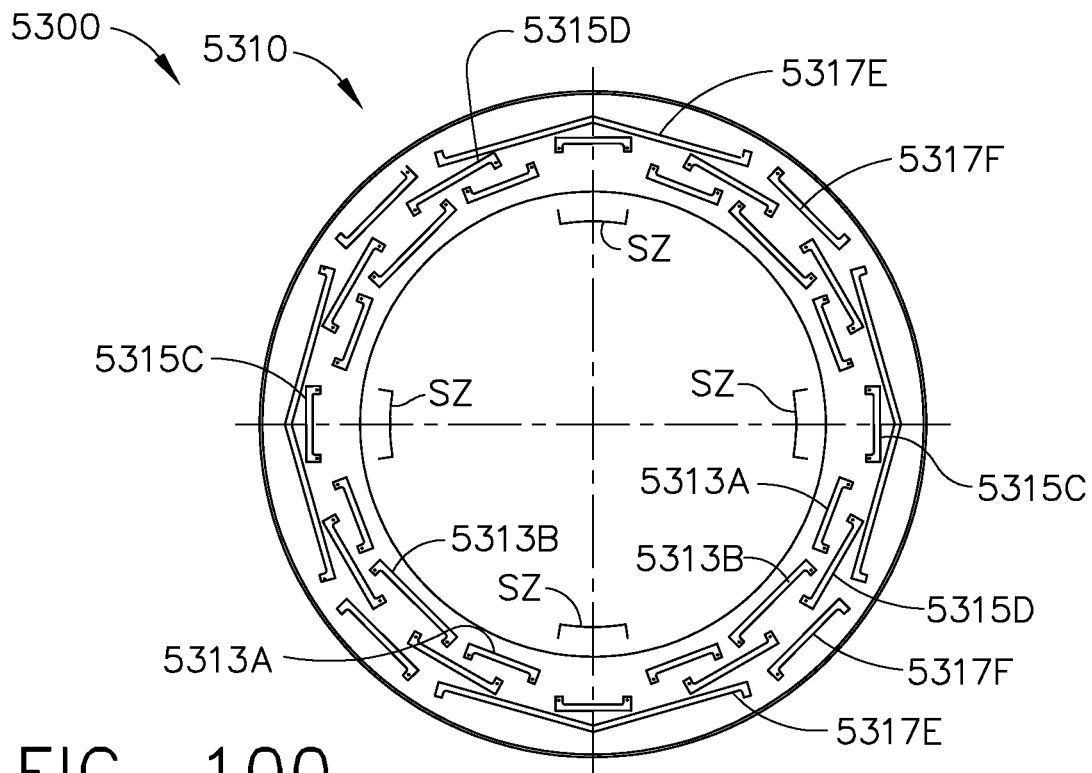
FIG. 100 is an end view of a circular surgical stapling configuration in accordance with at least one embodiment.

FIG. 100 illustrates a circular stapling configuration 5300 for use with a circular surgical stapler in accordance with at least one embodiment. The circular stapling configuration 5300 is an arrangement of staples employable with a circular staple cartridge. A circular staple cartridge employing the circular stapling configuration 5300 comprises corresponding staple cavities to removably store the staples discussed herein. The circular stapling configuration 5300 comprises a plurality of staples 5310 comprising inner row staples 5313A, 5313B, intermediate row staples 5315C, 5315D, and outer row staples 5317E, 5317F. Each staple 5313A, 5313B is orientated such that the staple legs thereof face outward toward the outer row staples 5317E, 5317F. Each staple 5315C, 5315D is orientated such that the staple legs thereof face inward toward the inner row staples 5313A, 5313B. Each staple 5317E, 5317F is orientated such that the staple legs thereof face outward away from the inner row staples 5313A, 5313B and the intermediate row staples 5315C, 5315D. Embodiments are envisioned where various staples within the same row face opposite directions. Embodiments are envisioned where every staple in every row faces the same direction. Embodiments are envisioned where the inner row staples face inward, the intermediate row staples face outward, and the outer row staples face inward, for example.

Varying staple crown widths between and within staple rows can also provide a an effective and/or efficient stapling arrangement. For example, the inner row staples 5313A, 5313B each comprise a different crown width, the intermediate row staples 5315C, 5315D each comprise a different crown width, and the outer row staples 5317E, 5317F each comprise a different crown width. In various embodiments, the crown widths of each staple 5313A, 5313B, 5315C, 5315D, 5317E, and 5317F are all different. Embodiments are envisioned where crown widths of certain staples in one row are equal to crown widths of certain staples in another row. The inner row staples define a stretch zone labeled SZ. The stretch zone SZ can comprise a gap defined between the staples 5313A, for example. The stretch zone SZ permits the stapled tissue to flex.

Figure 101:
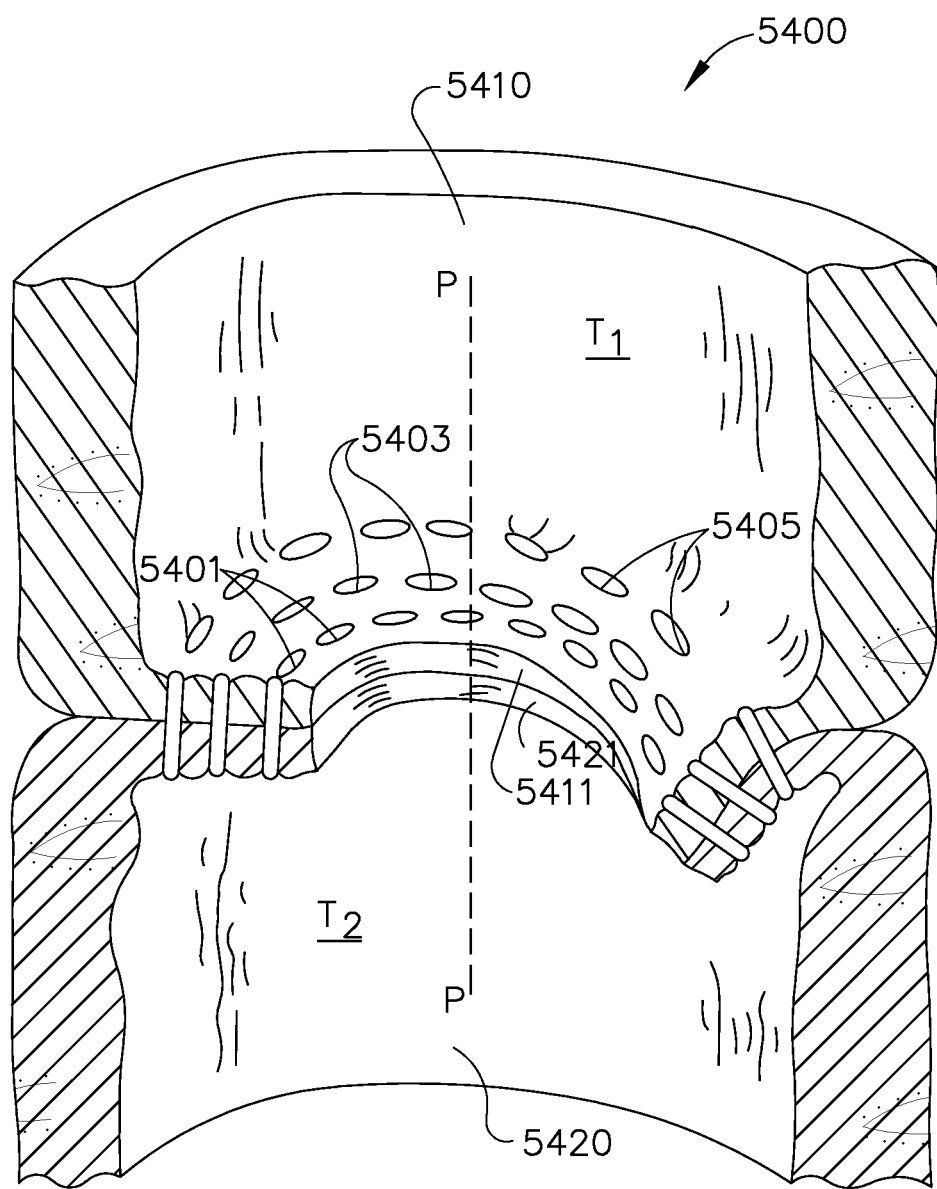
FIG. 101 is partial cross-sectional view of a colon stapled with a circular stapling instrument disclosed herein.

The circular surgical staplers, circular staple cartridges, and/or circular stapling configurations may be employed in a colectomy procedure, for example. FIG. 101 illustrates an example of a part of a colectomy procedure where two portions of intestine are joined providing a new pathway, or passage, 5400 for the digestive system. One portion of intestine $T_1$ comprises an inner wall 5410 and a second portion of intestine $T_2$ comprises an inner wall 5420. The intestine portions $T_1$ and $T_2$ are stapled with inner staples 5401, intermediate staples 5403, and outer staples 5405. The intestine portions $T_1$ and $T_2$ are incised creating a new passage P-P for digestive material to pass. The incision creates cut portions 5411 and 5421 of the intestine portions $T_1$ and $T_2$. The change in diameter between the inner walls 5410, 5420 of the intestine portions $T_1$ and $T_2$ and the cut portions 5411, 5421 can, in some cases, constrict, or narrow, the passage P-P making it difficult for digestive material to pass. It can be desirable to have flexibility of the staple portion starting with the inner staples 5401. One method for providing flexibility utilizes staple gaps defined between staples in the various rows in which the staples are arranged. Another method for providing flexibility utilizes larger sized staples with larger staple crowns. In various instances, gaps between the staples and staple rows permit flexibility of the stapled portion allowing digestive material to pass more easily. In various instances, different size staples permit tissue flexibility.

Figure 102:
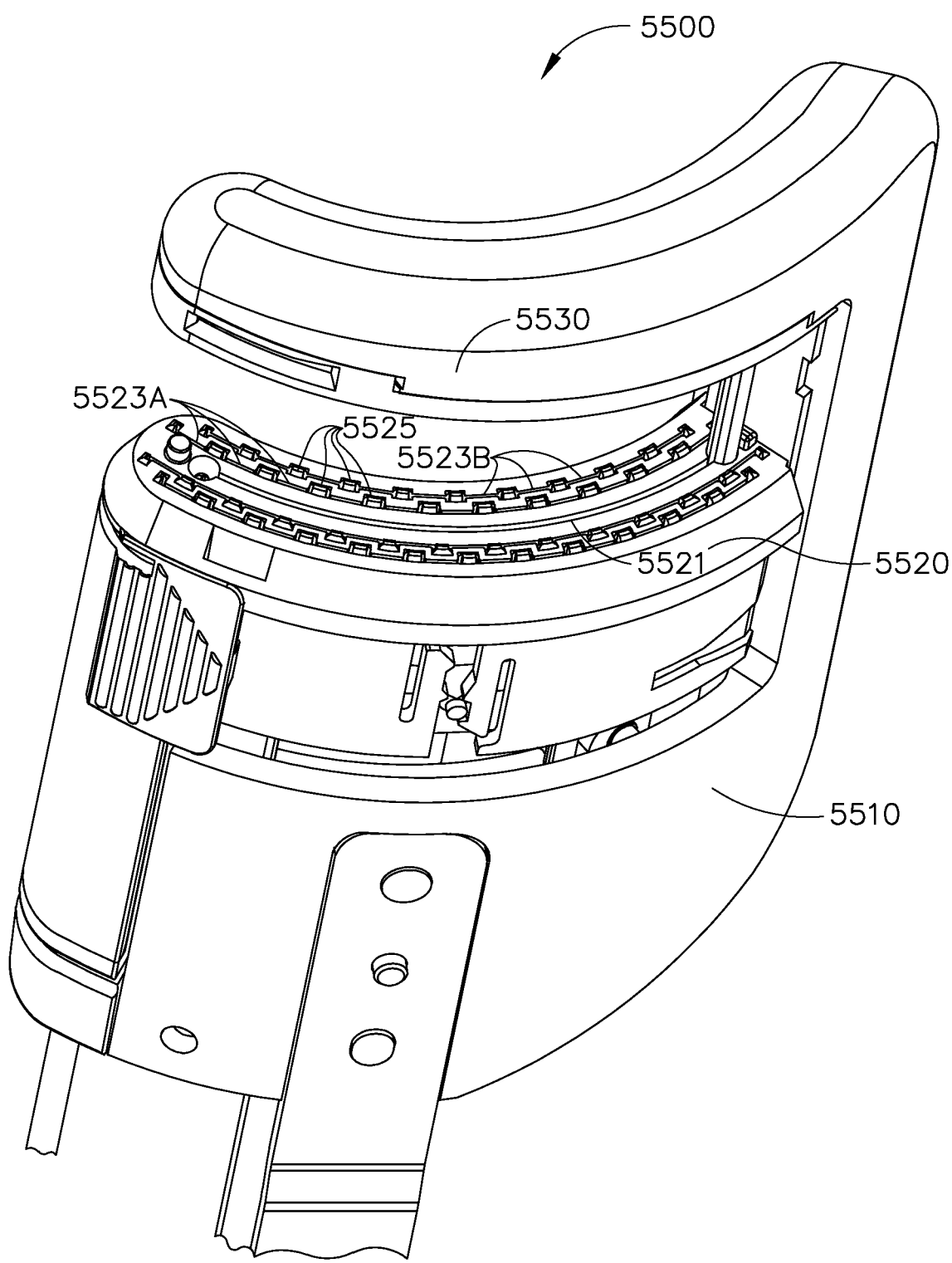
FIG. 102 is a partial perspective view of a curved stapler in accordance with at least one embodiment.
Figure 103:
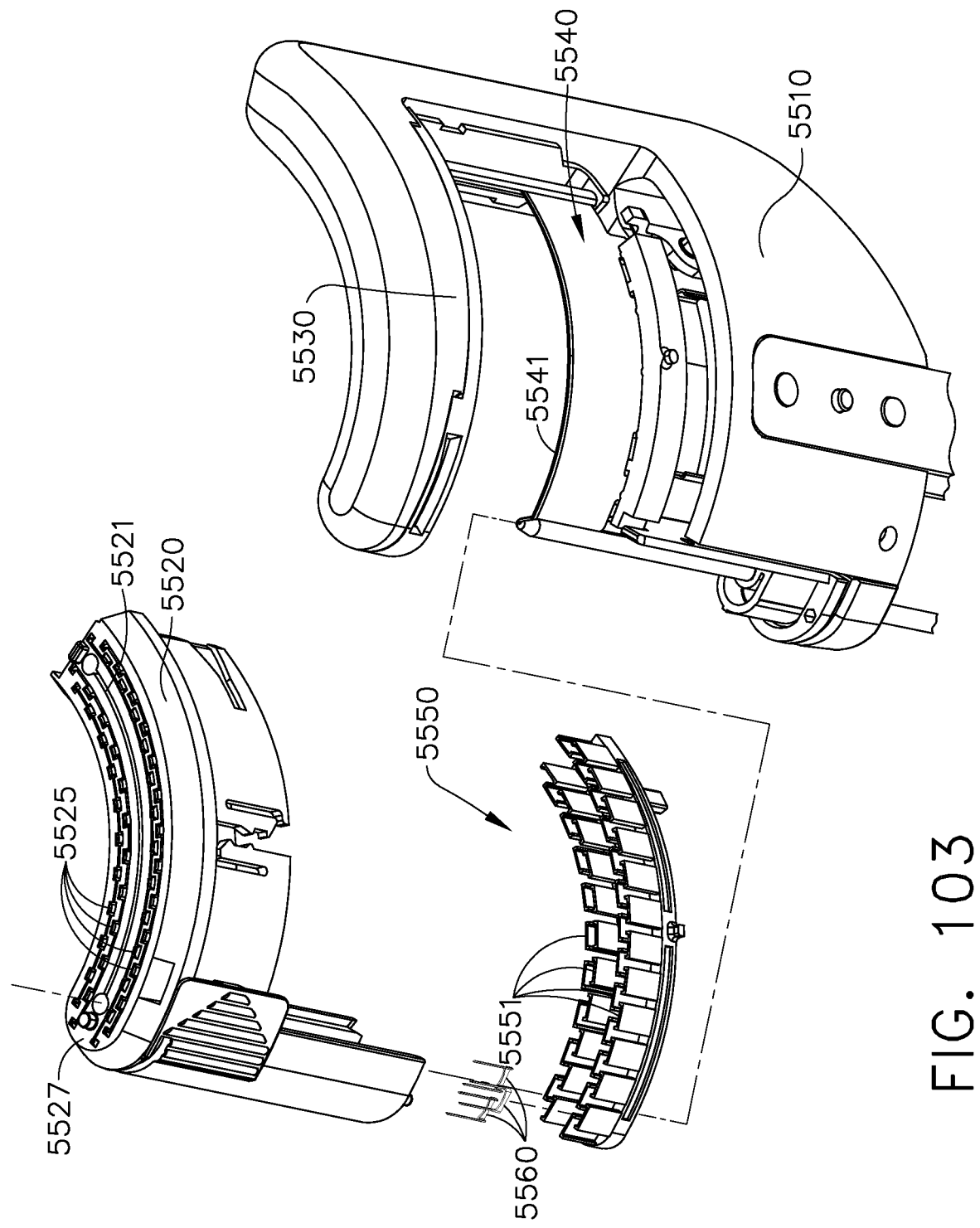
FIG. 103 is a partial exploded view of the curved stapler of FIG. 102.
Figure 104:
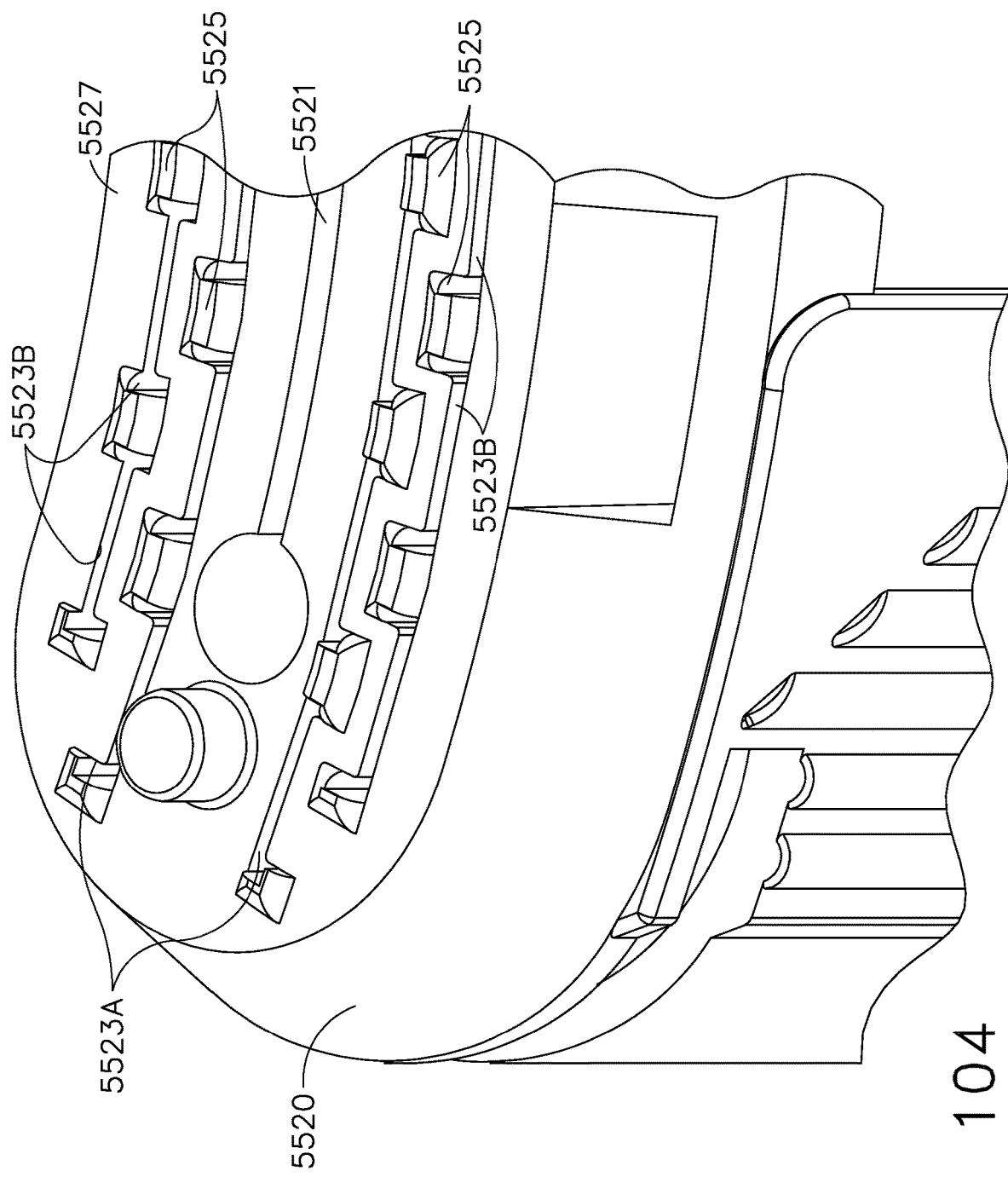
FIG. 104 is a partial perspective view of the curved stapler of FIG. 102.

FIGS. 102-104 depict a curved stapling instrument 5500 in accordance with at least one embodiment configured to capture, incise, and staple tissue. The curved stapling instrument 5500 comprises a frame assembly 5510, a staple cartridge 5520, and an anvil 5530. Upon receiving a first actuation force, the staple cartridge 5520 is driven toward the anvil 5530 to capture tissue therebetween. The curved stapling instrument 5500 further comprises a knife assembly 5540 comprising a cutting member 5541 configured to incise the tissue captured between the staple cartridge 5520 and the anvil 5530. The staple cartridge 5520 comprises a deck 5527 comprising a cutting slot 5521 configured to receive the cutting member 5541, a plurality of staple cavities 5523A and 5523B, and a plurality of staples 5560 removably stored within the staple cavities 5523A, 5523B. The curved stapling instrument 5500 further comprises a driver assembly 5550 comprising a plurality of staple drivers 5551 configured to drive the staples 5560 toward the anvil 5530 upon the application of a second actuation force. The second actuation force is responsible for lifting the driver assembly 5550 and the knife assembly 5540 vertically relative to the curved stapling instrument 5500 in order to incise and staple the tissue.

The staple cartridge 5520 further comprises a plurality of deck features 5525 extending from the deck 5527. Embodiments are envisioned where the deck features 5525 are separate portions configured to be attached to the deck 5527. The deck features 5525 can be extensions of the staple cavities 5523A, 5523B in order to support, guide, and/or control the staples 5560 while loading the staples 5560 into the cartridge 5520, while housing, or supporting, the staples 5560 before ejecting the staples 5560, and/or while ejecting the staples 5560 from the cartridge 5520. A single deck feature 5525 supports two different staple legs of neighboring staples. The deck features 5525 can comprise multiple support walls configured to support one or more sides, faces, and/or edges of each staple leg. Embodiments are envisioned where the deck features 5525 on the outer staple rows, rows furthest from the slot, only correlate with every other staple cavity in each outer row. Staple features may increase in density the closer to the incision the staple features are positioned.

Figure 105:
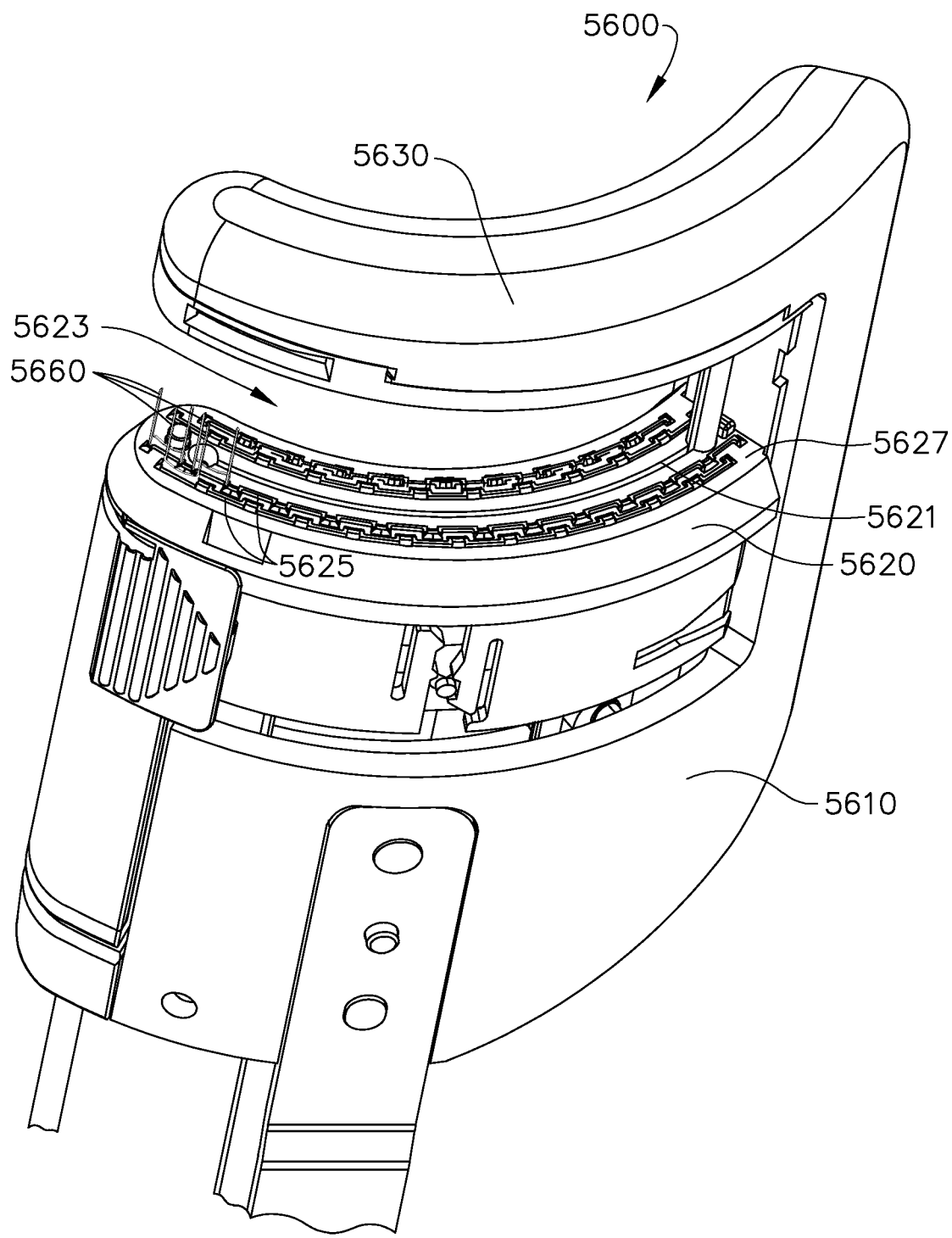
FIG. 105 is a partial perspective view of a curved stapler in accordance with at least one embodiment.
Figure 106:
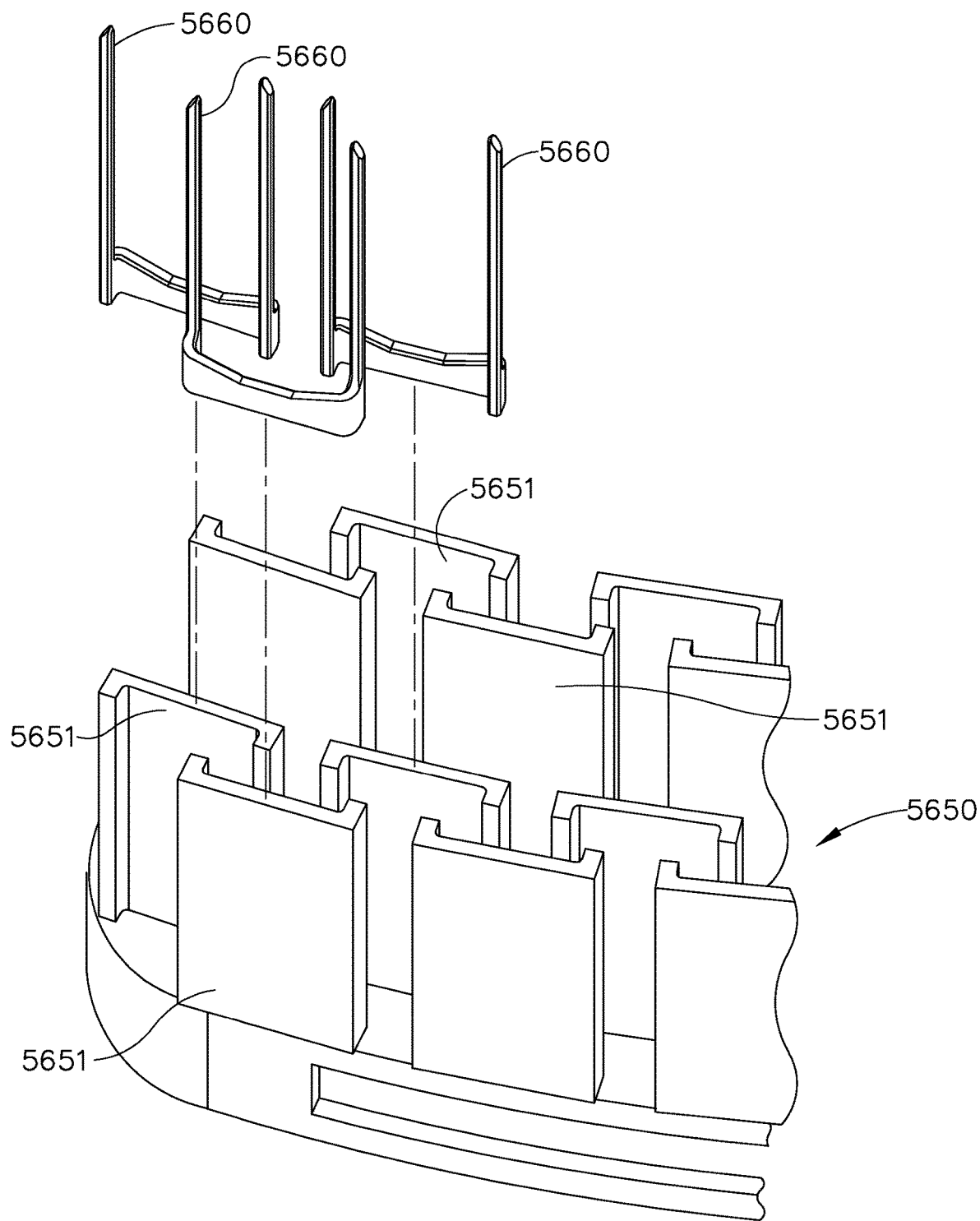
FIG. 106 is a partial perspective view of the curved stapler of FIG. 105.

FIGS. 105 and 106 depict a curved stapling instrument 5600 in accordance with at least one embodiment configured to capture, incise, and staple tissue. The curved stapling instrument 5600 comprises a frame assembly 5610, a staple cartridge 5620, and an anvil 5630. Upon receiving a first actuation force, the staple cartridge 5620 is driven toward the anvil 5630 to capture tissue therebetween. The curved stapling instrument 5600 further comprises a knife assembly comprising a cutting member configured to incise the tissue captured between the staple cartridge 5620 and the anvil 5630. The staple cartridge 5620 comprises a deck 5627 comprising a cutting slot 5621 configured to receive the cutting member, a plurality of staple cavities 5623, and a plurality of staples 5660 removably stored within the staple cavities 5623. The curved stapling instrument 5600 further comprises a driver assembly 5650 comprising a plurality of staple drivers 5651 configured to drive the staples 5660 toward the anvil 5630 upon the application of a second actuation force. The second actuation force is responsible for lifting the driver assembly 5650 and the knife assembly vertically relative to the curved stapling instrument 5600 in order to incise and staple the tissue.

The staple cartridge 5620 further comprises a plurality of deck features 5625 extending from the deck 5627. Embodiments are envisioned where the deck features 5625 are separate portions configured to be attached to the deck 5627. The deck features 5625 can be extensions of the staple cavities 5623 in order to support, guide, and/or control the staples 5660 while loading the staples 5660 into the cartridge 5620, while housing, or supporting, the staples 5660 before ejecting the staples 5660, and/or while ejecting the staples 5660 from the cartridge 5620. The deck features 5625 can comprise multiple support walls configured to support one or more sides, faces, and/or edges of each staple leg. The deck features 5625 extend from at least one of the staple leg walls and at least one of the staple base walls of the staple cavities.

The staple drivers 5651 comprise a flat profile which is at least substantially the same as the bottom profile of the staples 5660. Having similar, or the same, profiles permits an adequate force distribution by the staple drivers 5651 over the staple base portions of the staples 5660. When being formed against the anvil 5630, the similar profiles between the drivers 5651 and the staples 5660 prevents the staples 5660 becoming misaligned.

EXAMPLES

Example 1

A staple cartridge assembly for use with a surgical stapler, wherein the staple cartridge assembly comprises a cartridge body including a proximal end, a distal end, a deck, a longitudinal slot defined in the deck extending from the proximal end toward the distal end and staple cavities, wherein the staple cavities are arranged in longitudinal rows. Each staple cavity comprises a top opening defined in the deck, a bottom opening, a proximal end, a distal end, and a staple cavity sidewall extending between the proximal end and the distal end. The staple cartridge assembly further comprises staples removably stored in the staple cavities, wherein each staple comprises a proximal leg, a distal leg, a base extending between the proximal leg and the distal leg, and a retention projection extending from the base, wherein the retention projections of the staples are engaged with the staple cavity sidewalls to prevent the staples from falling out of the bottom openings of the staple cavities.

Example 2

The staple cartridge assembly of Example 1, further comprising a sled movable from the proximal end toward the distal end to eject the staples through the top openings of the staple cavities.

Example 3

The staple cartridge assembly of Example 2, wherein the cartridge body further comprises a bottom surface defined opposite the deck, a longitudinal channel defined in the bottom surface, wherein at least a portion of the sled is slidably positioned in the longitudinal channel, and a retention portion configured to prevent the sled from falling out of the longitudinal channel through the bottom surface.

Example 4

The staple cartridge assembly of Example 3, wherein the sled is movable between a proximal position and a distal position during a firing stroke, wherein the retention portion is engaged with the sled when the sled is in the proximal position, and wherein the retention portion is not engaged with the sled when the sled is in the distal position.

Example 5

The staple cartridge assembly of Examples 1, 2, 3, or 4, wherein the staple cartridge assembly does not comprise a cover extending around the bottom surface of the cartridge body.

Example 6

The staple cartridge assembly of Examples 1, 2, 3, 4, or 5, wherein the cartridge body comprises at least one snap-fit feature configured to directly engage the surgical stapler.

Example 7

The staple cartridge assembly of Examples 3, 4, or 5, wherein the sled directly engages the staples, and wherein the staple cartridge assembly does not comprise drivers positioned intermediate the sled and the staples.

Example 8

The staple cartridge assembly of Examples 1, 2, 3, 4, 5, 6, or 7, wherein each staple is stamped from a sheet of material, wherein the proximal leg, the distal leg, and the base of each the staple are formed in a staple plane, and wherein the retention projection extends laterally from the staple plane.

Example 9

A staple cartridge assembly for use with a surgical stapler, wherein the staple cartridge assembly comprises a cartridge body including a proximal end, a distal end, a deck, a bottom portion, a longitudinal slot defined in the deck extending from the proximal end toward the distal end, a longitudinal channel defined in the bottom portion, and staple cavities, wherein each staple cavity comprises a top opening defined in the deck and a bottom opening defined in the bottom portion. The staple cartridge assembly further comprises staples removably stored in the staple cavities, a sled slidably positioned in the longitudinal channel, wherein the sled is movable from the proximal end toward the distal end to eject the staples through the top openings of the staple cavities, and a retention portion configured to prevent the sled from falling out of the longitudinal channel through the bottom portion.

Example 10

The staple cartridge assembly of Example 9, wherein the sled is movable between a proximal position and a distal position during a firing stroke, wherein the retention portion is engaged with the sled when the sled is in the proximal position, and wherein the retention portion is not engaged with the sled when the sled is in the distal position.

Example 11

The staple cartridge assembly of Examples 9 or 10, wherein the staple cartridge assembly does not comprise a cover extending around the bottom portion of the cartridge body.

Example 12

The staple cartridge assembly of Examples 9, 10, or 11, wherein the sled directly engages the staples, and wherein the staple cartridge assembly does not comprise drivers positioned intermediate the sled and the staples.

Example 13

A staple cartridge assembly for use with a surgical stapler, wherein the surgical stapler includes a jaw configured to receive the staple cartridge assembly, and wherein the staple cartridge assembly comprises a cartridge body including a proximal end, a distal end, a deck, a bottom portion, wherein the staple cartridge assembly does not comprise an enclosure extending around the bottom portion, a longitudinal slot defined in the deck extending from the proximal end toward the distal end, a longitudinal channel defined in the bottom portion, and staple cavities, wherein each the staple cavity comprises a top opening defined in the deck and a bottom opening defined in the bottom portion. The staple cartridge assembly further comprises staples removably stored in the staple cavities, a sled slidably positioned in the longitudinal channel, wherein the sled is movable from the proximal end toward the distal end to eject the staples through the top openings of the staple cavities during a firing stroke, and means for preventing the sled from falling out of the longitudinal channel through the bottom portion.

Example 14

The staple cartridge assembly of Example 13, wherein the sled directly engages the staples during the firing stroke.

Example 15

The staple cartridge assembly of Examples 13 or 14, further comprising means for preventing the staples from falling out of the staple cavities through the bottom openings.

Example 16

A staple cartridge assembly for use with a surgical stapler, wherein the surgical stapler includes a jaw configured to receive the staple cartridge assembly, and wherein the staple cartridge assembly comprises a cartridge body including a proximal end, a distal end, a deck, a bottom portion, wherein the staple cartridge assembly does not comprise an enclosure extending around the bottom portion, and staple cavities, wherein each the staple cavity comprises a top opening defined in the deck and a bottom opening defined in the bottom portion. The staple cartridge assembly further comprises staples removably stored in the staple cavities, wherein the cartridge body includes shelves integrally formed with the cartridge body that prevent the staples from falling out of the staple cavities through the bottom openings.

Example 17

A staple cartridge assembly for use with a surgical stapler, wherein the staple cartridge assembly comprises a cartridge body including a proximal end, a distal end, a deck, a longitudinal slot defined in the deck extending from the proximal end toward the distal end, and a staple cavity. The staple cavity comprises a top opening defined in the deck, a bottom opening, a proximal guide, a distal guide, a sidewall extending between the proximal guide and the distal guide, and an intermediate guide extending inwardly from the sidewall. The staple cartridge assembly further comprises a staple removably stored in the staple cavity including a proximal leg positioned within the proximal guide, a distal leg positioned within the distal guide, and a base extending between the proximal leg and the distal leg, wherein the intermediate guide is positioned to guide the base and hold the proximal leg in the proximal guide and the distal leg in the distal guide.

Example 18

The staple cartridge assembly of Example 17, wherein the staple cavity further comprises a proximal cavity end proximal to the proximal guide and a distal cavity end distal to the distal guide.

Example 19

The staple cartridge assembly of Example 18, wherein the staple is not positioned in the proximal cavity end and the distal cavity end.

Example 20

The staple cartridge assembly of Examples 18 or 19, wherein a first clearance gap is present between the staple base, the intermediate guide, and the distal cavity end, and wherein a second clearance gap is present between the staple base, the intermediate guide, and the proximal cavity end.

Example 21

The staple cartridge assembly of Examples 17, 18, 19, or 20, wherein the base comprises a flat guide surface interfaced with the intermediate guide.

Example 22

The staple cartridge assembly of Examples 17, 18, 19, 20, or 21, wherein the cartridge body further comprises a plurality of the staple cavities, and wherein the staple cartridge assembly further comprises a plurality of the staples positioned in the staple cavities.

Example 23

The staple cartridge assembly of Examples 17, 18, 19, 20, 21, or 22, wherein the proximal guide, the distal guide, and the intermediate guide triangulate the control of the staple as the staple is ejected from the staple cavity.

Example 24

The staple cartridge assembly of Examples 17, 18, 19, 20, 21, 22 or 23, wherein the proximal guide and the distal guide extend above the deck.

Example 25

The staple cartridge assembly of Examples 17, 18, 19, 20, 21, 22, 23, or 24, wherein the intermediate guide extends above the deck.

Example 26

The staple cartridge assembly of Examples 17, 18, 19, 20, 21, 22, 23, 24, or 25, wherein the proximal leg and the distal leg of the staple define a leg plane, wherein the base comprises a drive surface in a drive plane, and wherein the drive plane is offset from the leg plane.

Example 27

The staple cartridge assembly of Examples 17, 18, 19, 20, 21, 22, 23, 24, 25, or 26, wherein the proximal leg and the distal leg are pinched toward each other by the proximal guide and the distal guide.

Example 28

The staple cartridge assembly of Examples 17, 18, 19, 20, 21, 22, 23, 24, 25, 26, or 27, wherein the intermediate guide comprises a resilient biasing member engaged with the base configured to push the proximal leg into the proximal guide and the distal leg into the distal guide.

Example 29

The staple cartridge assembly of Examples 17, 18, 19, 20, 21, 22, 23, 24, 25, 26, 27, or 28, wherein the intermediate guide is positioned closer to the distal guide than the proximal guide.

Example 30

The staple cartridge assembly of Examples 17, 18, 19, 20, 21, 22, 23, 24, 25, 26, 27, or 28, wherein the intermediate guide is positioned equidistant between the distal guide and the proximal guide.

Example 31

A staple cartridge assembly for use with a surgical stapler, wherein the staple cartridge assembly comprises a cartridge body including a proximal end, a distal end, a deck, a longitudinal slot defined in the deck extending from the proximal end toward the distal end, and a staple cavity. The staple cavity comprises a top opening defined in the deck, a bottom opening, a proximal guide, a distal guide, and a sidewall extending between the proximal guide and the distal guide. The staple cartridge assembly further comprises a staple removably stored in the staple cavity including a proximal leg positioned within the proximal guide, a distal leg positioned within the distal guide, wherein the proximal leg and the distal leg define a leg plane, and wherein the proximal leg and the distal leg are pinched toward each other by the proximal guide and the distal guide, and a base extending between the proximal leg and the distal leg, wherein the base comprises a drive surface in a drive plane, and wherein the drive plane is offset from the leg plane.

Example 32

The staple cartridge assembly of Example 31, wherein the leg plane is parallel to the drive plane

Example 33

The staple cartridge assembly of Examples 31 or 32, wherein the cartridge body further comprises a plurality of the staple cavities, and wherein the staple cartridge assembly further comprises a plurality of the staples positioned in the staple cavities.

Example 34

A staple cartridge assembly for use with a surgical stapler, wherein the staple cartridge assembly comprises a cartridge body including a proximal end, a distal end, a deck, a longitudinal slot defined in the deck extending from the proximal end toward the distal end, and a staple cavity. The staple cavity comprises a top opening defined in the deck, a bottom opening, a proximal guide, a distal guide, a sidewall extending between the proximal guide and the distal end guide, and an intermediate guide extending inwardly from the staple cavity sidewall. The staple cartridge assembly further comprises a staple removably stored in the staple cavity including a proximal leg positioned within the proximal guide, a distal leg positioned within the distal guide, and a base extending between the proximal leg and the distal leg, wherein the proximal guide, the distal guide, and the intermediate guide triangulate the control of the staple as the staple is ejected from the staple cavity.

Example 35

The staple cartridge assembly of Example 34, wherein the cartridge body further comprises a plurality of the staple cavities, and wherein the staple cartridge assembly further comprises a plurality of the staples positioned in the staple cavities.

Example 36

A staple cartridge assembly for use with a surgical stapler, wherein the staple cartridge assembly comprises a cartridge body including a proximal cartridge end, a distal cartridge end, a deck, a longitudinal knife slot defined in the deck extending from the proximal cartridge end toward the distal cartridge end, and a staple cavity. The staple cavity comprises a top opening defined in the deck, a proximal cavity end, a distal cavity end, a proximal guide, a distal guide, wherein the proximal guide and the distal guide extend above the deck, and a cavity slot extending between the proximal cavity end and the distal cavity end, wherein the proximal guide and the distal guide extend laterally with respect to the cavity slot. The staple cartridge assembly further comprises a staple removably stored in the staple cavity including a proximal leg positioned within the proximal guide, a distal leg positioned within the distal guide, and a base extending between the proximal leg and the distal leg, wherein the base is positioned in the cavity slot.

Example 37

The staple cartridge assembly of Example 36, wherein the proximal guide and the distal guide extend toward the knife slot.

Example 38

The staple cartridge assembly of Example 36, wherein the proximal guide and the distal guide extend away from the knife slot.

Example 39

The staple cartridge assembly of Examples 36, 37, or 38, wherein the proximal guide comprises a proximal bracket.

Example 40

The staple cartridge assembly of Example 39, wherein the proximal bracket does not extend around the proximal cavity end.

Example 41

The staple cartridge assembly of Examples 39 or 40, wherein the cavity slot is defined by a longitudinal axis, and wherein the proximal bracket is not aligned with the longitudinal axis.

Example 42

The staple cartridge assembly of Examples 36, 37, 38, 39, 40, or 41, wherein the distal guide comprises a distal bracket.

Example 43

The staple cartridge assembly of Example 42, wherein the distal bracket does not extend around the distal cavity end.

Example 44

The staple cartridge assembly of Examples 42 or 43, wherein the cavity slot is defined by a longitudinal axis, and wherein the distal bracket is not aligned with the longitudinal axis.

Example 45

The staple cartridge assembly of Examples 36, 37, 38, 39, 40, 41, 42, 43, or 44, wherein the proximal leg and the distal leg define a staple leg plane, wherein the base comprises a drive surface in a drive plane offset from the staple leg plane, wherein the proximal guide and the distal guide are aligned with the staple plane, and wherein the proximal guide and the distal guide are not aligned with the drive plane.

Example 46

The staple cartridge assembly of Examples 36, 37, 38, 39, 40, 41, 42, 43, or 44, wherein the proximal leg and the distal leg define a staple leg plane, wherein the base comprises a drive surface in a drive plane offset from the staple leg plane, and wherein the proximal guide and the distal guide define a bracket plane aligned with the staple leg plane.

Example 47

The staple cartridge assembly of Examples 36, 37, 38, 39, 40, 41, 42, 43, 44, 45, or 46, wherein the cartridge body further comprises a plurality of the staple cavities, and wherein the staple cartridge assembly further comprises a plurality of the staples positioned in the staple cavities.

Example 48

The staple cartridge assembly of Examples 36, 37, 38, 39, 40, 41, 42, 43, 44, 45, 46, or 47, wherein a portion of the proximal guide that extends above the deck comprises a staple cavity extender, and wherein a portion of the distal guide that extends above the deck comprises a staple cavity extender Example 49

A staple cartridge assembly for use with a surgical stapler, wherein the staple cartridge assembly comprises a cartridge body including a proximal cartridge end, a distal cartridge end, a deck, and a staple cavity. The staple cavity includes a proximal cavity end, a distal cavity end, a proximal guide extending above and below the deck, a distal guide extending above and below the deck, and a connecting slot extending between the proximal cavity end and the distal cavity end, wherein the proximal guide and the distal guide extend laterally with respect to the connecting slot. The staple cartridge assembly further comprises a staple removably stored in the staple cavity comprising a proximal leg positioned within the proximal guide, a distal leg positioned within the distal guide, and a base extending between the proximal leg and the distal leg, wherein the base is positioned in the cavity slot.

Example 50

The staple cartridge assembly of Example 49, wherein the cartridge body further comprises a plurality of the staple cavities, and wherein the staple cartridge assembly further comprises a plurality of the staples positioned in the staple cavities.

Example 51

The staple cartridge assembly of Examples 49 or 50, wherein the portion of the proximal guide that extends above the deck comprises a staple cavity extender, and wherein the portion of the distal guide that extends above the deck comprises a staple cavity extender Example 52

A fastener cartridge assembly for use with a surgical fastening instrument, wherein the fastener cartridge assembly comprises a cartridge body comprising a proximal cartridge end, a distal cartridge end, a deck, and a fastener pocket. The fastener pocket comprises a proximal pocket end, a distal pocket end, a proximal guide, a distal guide, a proximal pocket extender, wherein the proximal pocket extender extends above the deck, a distal pocket extender, wherein the proximal pocket extender extends above the deck, and a pocket opening extending between the proximal pocket end and the distal pocket end, wherein the proximal guide and the distal guide extend laterally with respect to the pocket opening. The fastener cartridge assembly further comprises a fastener removably stored in the fastener pocket comprising a proximal leg positioned within the proximal guide, a distal leg positioned within the distal guide, and a base extending between the proximal leg and the distal leg, wherein the base is positioned in the pocket opening.

Example 53

The fastener cartridge assembly of Example 52, wherein the cartridge body further comprises a plurality of the fastener pockets, and wherein the fastener cartridge assembly further comprises a plurality of the fasteners positioned in the fastener pockets.

Example 54

A staple cartridge assembly for use with a surgical instrument, the staple cartridge assembly comprising a cartridge body including a proximal end, a distal end, a deck, and staple cavities defined in the deck. The staple cartridge assembly further comprises staples removably positioned in the staple cavities and a firing member comprising a channel aligned with the staples, wherein the channel comprises a first lateral sidewall and a second lateral sidewall, and wherein the channel is configured to receive the staples between the first lateral sidewall and the second lateral sidewall.

Example 55

The staple cartridge assembly of Example 54, wherein the channel is defined on an inclined surface of the firing member.

Example 56

The staple cartridge assembly of Examples 54 or 55, wherein the channel comprises a ramp portion configured to lift the staples within the staple cavities during a firing stroke of the firing member and an apex portion configured to form the staples against an anvil of the surgical instrument to a final formed height.

Example 57

The staple cartridge assembly of Example 56, wherein the channel comprises a trailing portion positioned proximally with respect to the apex portion, and wherein the apex portion is positioned above the trailing portion.

Example 58

The staple cartridge assembly of Examples 54, 55, 56, or 57, wherein the firing member comprises a sled including a plurality of wedges, and wherein the channel is defined on one of the wedges.

Example 59

The staple cartridge assembly of Examples 54, 55, 56, 57, or 58, wherein the firing member further comprises a ramp configured to initially lift the staples within the staple cavities and guide the staples into the channel.

Example 60

The staple cartridge assembly of Examples 54, 55, 56, 57, 58, or 59, wherein the channel comprises a mouth portion and a longitudinal portion, wherein the mouth portion provides a lead-in to the longitudinal portion, and wherein the mouth portion is wider than the longitudinal portion.

Example 61

The staple cartridge assembly of Examples 54, 55, 56, 57, 58, 59, or 60, wherein the staples are received within the channel without a staple driver positioned between the staples and the channel. 57, 58, 59, 60, or 61, wherein the first lateral sidewall is parallel to the second lateral sidewall.

Example 63

The staple cartridge assembly of Examples 54, 55, 56, 57, 58, 59, 60, or 61, wherein the first lateral sidewall is not parallel to the second lateral sidewall.

Example 64

The staple cartridge assembly of Examples 54, 55, 56, 57, 58, 59, 60, or 61, wherein the first lateral sidewall and the second lateral are angled with respect to each other to create a staple entry lead-in.

Example 65

The staple cartridge assembly of Examples 54, 55, 56, 57, 58, 59, 60, 61, 62, 63, or 64, wherein the channel comprises a first channel, and wherein the firing member further comprises a second channel configured to receive the staples.

Example 66

The staple cartridge assembly of Example 65, wherein each staple comprises a drive portion configured to enter the first channel, and a forming portion configured to enter the second channel.

Example 67

The staple cartridge assembly of Examples 65 or 66, wherein the first channel extends at an angle relative to the second channel.

Example 68

The staple cartridge assembly of Examples 65, 66, or 67, wherein the first channel and the second channel are parallel to one another in a first region and non-parallel to one another in a second region.

Example 69

The staple cartridge assembly of Examples 65, 66, 67, or 68, wherein the second channel is configured to receive the staples before the first channel as the firing member is advanced toward the distal end.

Example 70

A staple cartridge assembly for use with a surgical instrument, the staple cartridge assembly comprising a cartridge body comprising a deck and staple cavities defined in the deck, staples removably positioned in the staple cavities, and a firing member comprising a ramp configured to directly engage the staples and a rail extending from the ramp configured to orient the staples relative to the ramp.

Example 71

The staple cartridge assembly of Example 70, wherein the rail comprises a first rail, and wherein the firing member further comprises a second rail extending from the ramp configured to orient the staples relative to the ramp.

Example 72

The staple cartridge assembly of Example 71, wherein the first rail is parallel to the second rail.

Example 73

A staple cartridge assembly for use with a surgical stapling instrument including an anvil, wherein the anvil includes forming pockets, and wherein the staple cartridge assembly comprises a cartridge body comprising a proximal end, a distal end, a deck, and staple cavities defined in the deck. The staple cartridge assembly comprises staples removably positioned in the staple cavities, wherein each staple comprises a staple driving portion and a staple forming portion, and a firing member comprising a first guide channel aligned with the staple driving portions of the staples and a second guide channel aligned with the staple forming portions of the staples, wherein the first guide channel and the second guide channel are configured to co-operatively align the staples with the staple forming pockets of the anvil when the firing member is moved toward the distal end.

Example 74

A staple cartridge assembly comprising a cartridge body including a deck, a first longitudinal row of staple cavities, and a second longitudinal row of staple cavities. The staple cartridge assembly further comprises a plurality of first staples, wherein each first staple is removably stored in the first longitudinal row of staple cavities, and wherein each first staple comprises a unitary structure including a first base including a first drive surface and a first staple leg extending from the first base and including a first tip, wherein a first unformed distance is defined between the first drive surface and the first tip, a plurality of second staples, wherein each second staple is removably stored in the second longitudinal row of staple cavities, and wherein each second staple comprises a unitary structure including a second base including a second drive surface and a second staple leg extending from the second base and including a second tip, wherein a second unformed distance is defined between the second drive surface and the second tip which is different than the first unformed distance, and a firing member configured to directly engage the first staples and the second staples.

Example 75

The staple cartridge assembly of Example 74, wherein the first staples and the second staples are formed from a sheet of metal.

Example 76

The staple cartridge assembly of Examples 74 or 75, wherein each first base includes a first tissue supporting surface, wherein a first tissue capture distance is defined between the first tissue supporting surface and the first tip, wherein each second base includes a second tissue supporting surface, wherein a second tissue capture distance is defined between the second tissue supporting surface and the second tip, and wherein the first tissue capture distance is different than the second tissue capture distance.

Example 77

The staple cartridge assembly of Examples 74, 75, or 76, wherein the deck comprises a first deck height along the first longitudinal row of staple cavities and a second deck height along second the longitudinal row of staple cavities which is different than the first deck height.

Example 78

The staple cartridge assembly of Example 77, wherein the cartridge body further comprises a longitudinal slot configured to receive a cutting member, wherein the first longitudinal row of staple cavities is adjacent the longitudinal slot, wherein the second longitudinal row of staple cavities is adjacent the first longitudinal row of staple cavities, and wherein the second deck height is shorter than the first deck height.

Example 79

The staple cartridge assembly of Examples 74, 75, 76, 77, or 78, wherein the cartridge body further comprises a longitudinal slot configured to receive a cutting member, wherein the first longitudinal row of staple cavities is adjacent the longitudinal slot, and wherein the second longitudinal row of staple cavities is adjacent the first longitudinal row of staple cavities.

Example 80

The staple cartridge assembly of Examples 74, 75, 76, 77, 78, or 79, wherein the first unformed distance is shorter than the second unformed distance.

Example 81

The staple cartridge assembly of Examples 74, 75, 76, 77, 78, 79, or 80, further comprising an anvil configured to deform the staples.

Example 82

The staple cartridge assembly of Example 81, wherein the anvil is configured to deform the first staples to a first deformed height and the second staples to a second deformed height which is different than the first deformed height.

Example 83

The staple cartridge assembly of Examples 81 or 82, wherein the cartridge body is movable toward the anvil to clamp tissue between the anvil and the deck of the cartridge body.

Example 84

The staple cartridge assembly of Examples 81, 82, or 83, wherein the anvil is movable toward the cartridge body to clamp tissue between the anvil and the deck of the cartridge body. 77, 78, 79, 80, 81, 82, 83, or 84, further comprising staple cavity extenders extending from the deck.

Example 86

The staple cartridge assembly of Examples 74, 75, 76, 77, 78, 79, 80, 81, 82, 83, 84, or 85, further comprising an implantable layer positioned over the deck.

Example 87

A staple cartridge assembly comprising a cartridge body comprising a deck, a first longitudinal row of staple cavities, and a second longitudinal row of staple cavities. The staple cartridge assembly further comprises a plurality of first staples, wherein each first staple is removably stored in the first longitudinal row of staple cavities, and wherein each first staple comprises a unitary structure including a first base including a first drive surface and a first tissue supporting surface and a first staple leg extending from the first base including a first tip, wherein a first tissue capture distance is defined between the first tissue supporting surface and the first tip, a plurality of second staples, wherein each second staple is removably stored in the second longitudinal row of staple cavities, and wherein each second staple comprises a unitary structure including a second base including a second drive surface and a second tissue supporting surface and a second staple leg extending from the second base including a second tip, wherein a second tissue capture distance is defined between the second tissue supporting surface and the second tip which is different than the first tissue capture distance, and a firing member configured to directly engage the first staples and the second staples.

Example 88

The staple cartridge assembly of Example 87, wherein the deck comprises a first deck height along the first longitudinal row of staple cavities and a second deck height along second the longitudinal row of staple cavities which is different than the first deck height.

Example 89

The staple cartridge assembly of Example 88, wherein the cartridge body further comprises a longitudinal slot configured to receive a cutting member, wherein the first longitudinal row of staple cavities is adjacent the longitudinal slot, wherein the second longitudinal row of staple cavities is adjacent the first longitudinal row of staple cavities, and wherein the second deck height is shorter than the first deck height.

Example 90

The staple cartridge assembly of Examples 87, 88, or 89, further comprising an anvil configured to deform the staples.

Example 91

The staple cartridge assembly of Example 90, wherein the anvil is configured to deform the first staples to a first deformed height and the second staples to a second deformed height which is different than the first deformed height.

Example 92

The staple cartridge assembly of Examples 90 or 91, wherein the cartridge body is movable toward the anvil to clamp tissue between the anvil and the deck of the cartridge body.

Example 93

A staple cartridge assembly comprising a cartridge body comprising a first longitudinal row of staple cavities and a second longitudinal row of staple cavities, a plurality of first staples removably stored in the first longitudinal row of staple cavities, wherein each first staple is comprised of stamped metal and includes an integrally-formed metal driver, a plurality of second staples removably stored in the second longitudinal row of staple cavities, wherein each second staple is comprised of stamped metal and includes an integrally-formed metal driver, and means for forming the first staples to a first deformed height and the second staples to a second deformed height, wherein the first deformed height is different than the second deformed height.

Example 94

A staple cartridge assembly comprising a staple cartridge body including a deck and staple cavities defined in the deck, staples removable stored in the staple cavities, wherein each staple comprises a base, a leg extending from the base, and a platform extending laterally from the base, and an implantable layer positioned over the deck, wherein the platforms of the staples are configured to abut the layer when the staples are implanted into the tissue of a patient.

Example 95

The staple cartridge assembly of Example 94, wherein each staple is stamped from a sheet of material, wherein the base defines a base plane, and wherein the platform is folded out of the base plane.

Example 96

The staple cartridge assembly of Examples 94 or 95, wherein the implantable layer comprises a woven material.

Example 97

The staple cartridge assembly of Examples 94, 95, or 96, wherein the implantable layer comprises a non-woven material.

Example 98

The staple cartridge assembly of Examples 94, 95, 96, or 97, further comprising a retention member extending from the leg adjacent the base, wherein the retention member is configured to engage the implantable layer when staples are implanted into the tissue of a patient.

Example 99

The staple cartridge assembly of Examples 94, 95, 96, 97, or 98, wherein the platform is flat.

Example 100

The staple cartridge assembly of Examples 94, 95, 96, 97 98, or 99, wherein the platform is not directly attached to the leg.

Example 101

A staple cartridge assembly comprising a staple cartridge body including a deck and staple cavities defined in the deck, staples removable stored in the staple cavities, wherein each staple comprises a crown, a first leg and a second leg extending from the crown, and a platform extending laterally from the crown, and an implantable layer positioned over the deck, wherein the platforms of the staples are configured to support the layer when the staples are implanted into the tissue of a patient.

Example 102

The staple cartridge assembly of Example 101, wherein each staple is stamped from a sheet of material, wherein the crown defines a crown plane, and wherein the platform is folded out of the crown plane.

Example 103

The staple cartridge assembly of Examples 101 or 102, wherein the implantable layer comprises a woven material.

Example 104

The staple cartridge assembly of Examples 101, 102, or 103, wherein the implantable layer comprises a non-woven material.

Example 105

The staple cartridge assembly of Examples 101, 102, 103, or 104, further comprising a retention member extending from the leg adjacent the crown, wherein the retention member is configured to engage the implantable layer when staples are implanted into the tissue of a patient.

Example 106

The staple cartridge assembly of Examples 101, 102, 103, 104, or 105, wherein the platform is flat.

Example 107

The staple cartridge assembly of Examples 101, 102, 103, 104, 105, or 106, wherein each staple comprises a compliant adjunct positioned adjacent the crown.

Example 108

The staple cartridge assembly of Example 107, wherein the compliant adjunct extends between the first leg and the second leg.

Example 109

The staple cartridge assembly of Examples 107 or 108, wherein the compliant adjunct is attached to the first leg and the second leg.

Example 110

The staple cartridge assembly of Examples 107, 108, or 109, wherein the compliant adjunct comprises a first aperture and a second aperture, wherein the first leg extends through the first aperture, and wherein the second leg extends through the second aperture.

Example 111

The staple cartridge assembly of Examples 107, 108, 109, or 110, wherein the compliant adjunct comprises a cavity and at least one medicament positioned in the cavity.

Example 112

The staple cartridge assembly of Examples 107, 108, 109, 110, or 111, wherein the compliant adjunct comprises a compressible enclosure.

Example 113

A staple cartridge assembly comprising a staple cartridge body including a deck and staple cavities defined in the deck, and staples removably stored in the staple cavities, wherein each staple comprises a crown, a first leg and a second leg extending from the crown, a platform extending laterally from the crown, and a compliant adjunct positioned adjacent the crown.

Example 114

The staple cartridge assembly of Example 113, wherein the compliant adjunct extends between the first leg and the second leg.

Example 115

The staple cartridge assembly of Examples 113 or 114, wherein the compliant adjunct is attached to the first leg and the second leg.

Example 116

The staple cartridge assembly of Examples 113, 114, or 115, wherein the compliant adjunct comprises a first aperture and a second aperture, wherein the first leg extends through the first aperture, and wherein the second leg extends through the second aperture.

Example 117

The staple cartridge assembly of Examples 113, 114, 115, or 116, wherein the compliant adjunct comprises a cavity and at least one medicament positioned in the cavity.

Example 118

The staple cartridge assembly of Examples 113, 114, 115, 116, or 117, wherein the compliant adjunct comprises a compressible enclosure.

Example 119

A staple cartridge assembly comprising a cartridge body including a deck and a plurality of staple cavities defined in the deck, and a plurality of staples stored in the staple cavities, wherein each staple comprises a first portion comprised of an alloy including zinc and magnesium and a second portion comprised of an absorbable polymer, wherein the second portion is disposed on the first portion, and wherein the second portion covers less than the entirety of the first portion.

Example 120

The staple cartridge assembly of Example 119, wherein the first portion comprises a base and a staple leg extending from the base, and wherein the second portion extends around the staple leg in a spiral pattern.

Example 121

The staple cartridge assembly of Examples 119 or 120, wherein the second portion is coated on the first portion in a dot-matrix pattern.

Example 122

The staple cartridge assembly of Examples 119, 120, or 121, wherein the first portion comprises a base and a staple leg extending from the base, wherein a corner is defined between the base and the staple leg, and wherein the second portion covers the corner.

Example 123

The staple cartridge assembly of Examples 119, 120, 121, or 122, wherein the absorbable polymer comprises a non-crosslinked polymer.

Example 124

The staple cartridge assembly of Examples 119, 120, 121, 122, or 123, wherein the second portion is coated on the first portion in a mesh pattern.

Example 125

The staple cartridge assembly of Examples 119, 120, 121, 122, 123, or 124, wherein the first portion comprises a base and a staple leg extending from the base, wherein the staple leg comprises a tissue penetrating tip, and wherein the staple further comprises magnesium nitride disposed on the tip.

Example 126

The staple cartridge assembly of Examples 119, 120, 121, 122, 123, 124, or 125, wherein the staple further comprises a coating of ionized silver on at least part of the first portion that is not coated by the second portion.

Example 127

The staple cartridge assembly of Examples 119, 120, 121, 122, 123, 124, 125, or 126, further comprising at least one aperture in the first portion.

Example 128

A staple cartridge assembly comprising a cartridge body including a deck and a plurality of staple cavities defined in the deck and a plurality of staples stored in the staple cavities, wherein each staple comprises a metal frame comprised of a magnesium alloy and an absorbable polymer coated on the metal frame, wherein the absorbable polymer does not cover every portion of the metal frame.

Example 129

A staple cartridge assembly comprising a cartridge body including a deck and a plurality of staple cavities defined in the deck, and a plurality of staples stored in the staple cavities, wherein each staple comprises a metal frame comprised of a magnesium alloy, wherein the metal frame comprises a base and a leg extending from the base, and wherein the leg comprises a tissue penetrating tip, and a magnesium nitride coating on the tip.

Example 130

The staple cartridge assembly of Example 129, wherein each staple further comprises an absorbable polymer coated on the metal frame, and wherein the absorbable polymer does not cover every portion of the metal frame.

Example 131

The staple cartridge assembly of Examples 129 or 130, wherein each staple further comprises a coating comprising silver on at least a portion of the metal frame.

Example 132

A staple cartridge assembly comprising a cartridge body including a deck and a plurality of staple cavities defined in the deck, and a plurality of staples stored in the staple cavities, wherein each staple comprises a metal frame comprised of a magnesium alloy, wherein the metal frame comprises a base and a leg extending from the base, and wherein the leg comprises a tissue penetrating tip, and a coating comprising silver on at least a portion of the metal frame.

Example 133

The staple cartridge assembly of Example 132, wherein each staple further comprises an absorbable polymer coated on the metal frame, and wherein the absorbable polymer does not cover every portion of the metal frame.

Example 134

The staple cartridge assembly of Examples 132 or 133, further comprising a magnesium nitride coating on the tip.

Example 135

A staple cartridge assembly comprising a cartridge body including a deck and a plurality of staple cavities defined in the deck, and a plurality of staples stored in the staple cavities, wherein each staple comprises a metal frame comprised of a magnesium alloy, wherein the metal frame comprises a base and a leg extending from the base, and wherein the leg comprises tissue penetrating tip, and an aperture defined in the metal frame.

Example 136

The staple cartridge assembly of Example 135, wherein each staple further comprises an absorbable polymer coated on the metal frame, and wherein the absorbable polymer does not cover every portion of the metal frame.

Example 137

The staple cartridge assembly of Example 135, wherein each staple further comprises an absorbable polymer coated on the metal frame, and wherein the absorbable polymer is not positioned in the aperture.

Example 138

The staple cartridge assembly of Example 135, wherein each staple further comprises an absorbable polymer coated on the metal frame, and wherein the absorbable polymer is positioned in the aperture.

Example 139

The staple cartridge assembly of Example 135, wherein each staple further comprises an absorbable polymer coated on the metal frame, and wherein the aperture is filled with the absorbable polymer.

Example 140

A staple cartridge assembly for stapling tissue comprising a cartridge body including a proximal end, a distal end, and a plurality of staple cavities, a plurality of staples positioned in the staple cavities, wherein each staple comprises a base, a leg extending from the base, wherein the leg comprises a tip configured to penetrate the tissue, and a foot extending from the base, and a firing member configured to eject the staples from the staple cavities, wherein the firing member is configured to contact the foot of any staple that is misoriented within its staple cavity prior to ejecting the misoriented staple from its staple cavity.

Example 141

The staple cartridge assembly of Example 140, wherein the firing member comprises a firing ramp configured to contact the bases of the staples to drive the staples out of the staple cavities and an alignment ramp configured to contact the feet of the staples if the staples are misoriented.

Example 142

The staple cartridge assembly of Examples 140 or 141, wherein the firing member further comprises a firing channel aligned with the firing ramp, wherein the firing channel is configured to receive the bases of the staples, and an alignment channel aligned with the alignment ramp, wherein the alignment channel is configured to receive the feet of the staples once the staples are properly oriented.

Example 143

The staple cartridge assembly of Examples 141 or 142, wherein the alignment ramp extends distally with respect to the firing ramp such that the alignment ramp can contact the feet of the staples before the firing ramp contacts the bases of the staples.

Example 144

The staple cartridge assembly of Examples 140, 141, 142, or 143, wherein the foot of the staple is positioned proximally with respect to the base of the staple.

Example 145

The staple cartridge assembly of Examples 140, 141, 142, 143, or 144, wherein the firing member is not configured to contact the feet of the staples if the staples are properly oriented within the staple cavities.

Example 146

A staple cartridge assembly for stapling tissue comprising a cartridge body comprising a proximal end and a distal end, and a plurality of staple cavities, wherein each staple cavity comprises a top opening, a proximal wall, and a distal wall. The staple cartridge assembly further comprises a firing member and a plurality of staples positioned in the staple cavities, wherein each staple comprises a base, a proximal leg extending from the base, a distal leg extending from the base, and center of mass defined in the base, wherein the distal wall provides a distal reaction force to the staple above the center of mass and the proximal wall provides a proximal reaction force to the staple below the center of mass wherein the staple is lifted toward the top opening by the firing member. The staple cartridge assembly further comprises a firing member configured to eject the staples from the staple cavities, wherein the firing member is configured to contact the foot of any staple that is misoriented within its staple cavity prior to ejecting the misoriented staple from its staple cavity.

Example 147

The staple cartridge assembly of Example 146, wherein the base defines a drive plane, and wherein the proximal leg and the distal leg are not in the drive plane.

Example 148

The staple cartridge assembly of Examples 146 or 147, wherein the proximal leg and the distal leg are offset laterally from the center of mass of the staple.

Example 149

The staple cartridge assembly of Examples 146, 147, or 148, wherein the distal wall applies the distal reaction force to the distal leg and the proximal wall applies the proximal reaction force to the proximal leg.

Example 150

The staple cartridge assembly of Example 147, wherein the proximal leg extends to a first side of the drive plane and the distal leg extends to a second side of the drive plane.

Example 151

The staple cartridge assembly of Examples 146, 147, 148, 149, or 150, wherein the base comprises a notch defined therein configured to shift the center of mass of the staple toward a side of the staple cavity.

Example 152

A staple cartridge assembly for stapling tissue comprising a cartridge body including a proximal end, a distal end, and a plurality of staple cavities. The staple cartridge assembly further comprises a plurality of staples positioned in the staple cavities, wherein each staple comprises a base defining a drive plane and a leg extending from the base, wherein the leg extends to a side of the drive plane, a firing member configured to eject the staples from the staple cavities, and means for reducing the rotation of the staples within the staple cavities when the firing member is driving the staples out of the staple cavities.

Example 153

A surgical staple cartridge for use with a surgical stapling instrument, the surgical staple cartridge comprising a cartridge body, a plurality of staple cavities, and a plurality of staples removably stored in the staple cavities, wherein each staple comprises a staple base portion which defines a first plane, a center of mass located within the staple base portion, a first staple leg extending from the staple base portion, and a second staple leg extending from the staple base portion, wherein the first staple leg and the second staple leg define a second plane which is offset and at least substantially parallel to the first plane.

Example 154

The surgical staple cartridge of Example 153, wherein the first staple leg and the second staple leg are configured to form toward the staple base portion.

Example 155

The surgical staple cartridge of Examples 153 or 154, wherein the staple base portion comprises a compression surface comprising a contour configured to limit tissue compression.

Example 156

The surgical staple cartridge of Examples 153, 154, or 155, wherein the staple base portion comprises a bottom surface, and wherein the first staple leg further comprises an engagement foot elevated above the bottom surface.

Example 157

The surgical staple cartridge of Examples 153, 154, 155, or 156, wherein the staple base portion comprises an inner wall and a top surface, wherein the inner wall and the top surface comprise a cutout configured to cause the staple base portion to lean toward the staple legs.

Example 158

The surgical staple cartridge of Examples 153, 154, 155, 156, or 157, wherein the first staple leg extends higher than the second staple leg.

Example 159

The surgical staple cartridge of Examples 153, 154, 155, 156, 157, or 158, wherein the staple base portion comprises a rectangular cross-sectional profile.

Example 160

The surgical staple cartridge of Examples 153, 154, 155, 156, 157, 158, or 159, wherein the first staple leg and the second staple leg comprise a substantially round cross-sectional profile.

Example 161

The surgical staple cartridge of Examples 153, 154, 155, 156, 157, 158, 159, or 160, wherein the first staple leg and the second staple leg comprise coined corners.

Example 162

The surgical staple cartridge of Examples 153, 154, 155, 156, 157, 158, 159, 160, or 161, wherein the first staple leg is proximal the second staple leg, wherein the staple base portion comprises a distal wall, and wherein the distal wall is proximal to the second staple leg.

Example 163

The surgical staple cartridge of Examples 153, 154, 155, 156, 157, 158, 159, 160, 161, or 162, wherein the first staple leg comprises a first height and the second staple leg comprises a second height different than the first height.

Example 164

The surgical staple cartridge of Examples 153, 154, 155, 156, 157, 158, 159, 160, 161, 162, or 163, wherein the first staple leg and the second staple leg each comprise a staple tip configured to form against corresponding forming pockets of an anvil, wherein the corresponding forming pockets comprise a valley and a forming surface, and wherein the valley is configured to funnel the staple tips toward the forming surface.

Example 165

The surgical staple cartridge of Examples 153, 154, 155, 156, 157, 158, 159, 160, 161, 162, 163, or 164, wherein the first staple leg and the second staple leg are configured to form against corresponding forming pockets, wherein the corresponding forming pockets are configured to form the first staple leg in a first direction and the second staple leg in a second direction, and wherein the first direction is opposite and at least substantially parallel to the second direction.

Example 166

The surgical staple cartridge of Example 165, wherein the first direction points away from the staple base portion, and wherein the second direction points toward the staple base portion.

Example 167

The surgical staple cartridge of Examples 153, 154, 155, 156, 157, 158, 159, 160, 161, 162, 163, 164, 165, or 166, wherein the first staple leg and the second staple leg are configured to form against corresponding forming pockets, wherein the corresponding forming pockets are configured to form the first staple leg in a first curved direction and the second staple leg in a second curved direction.

Example 168

A surgical staple comprising a staple base portion defining a first plane, a first staple leg extending at least substantially perpendicular from the staple base portion, and a second staple leg extending at least substantially perpendicular from the staple base portion, wherein the first staple leg and the second staple leg define a second plane, wherein the first plane and the second plane intersect.

Example 169

A surgical staple cartridge comprising a plurality of the surgical staple of Examples 152, 153, 154, 155, 156, 157, 158, 159, 160, 161, 162, 163, 164, 165, 166, 167, or 168, wherein the surgical staples are arranged in a plurality of woven rows.

Example 170

The surgical staple of Examples 168 or 169, wherein the staple is configured to form into an S-shape configuration.

Example 171

A surgical staple comprising a staple base portion comprising a bottom surface which defines a bottom plane, a center of mass located within the staple base portion, and a first staple leg and a second staple leg extending from the staple base portion and defining a staple leg plane which is offset and at least substantially parallel to the staple base portion, wherein the first staple leg comprises an engagement foot elevated above the bottom plane.

Example 172

The surgical staple of Example 171, wherein the engagement foot is laterally offset with respect to the staple base portion.

Example 173

A surgical staple cartridge for use with a surgical stapler including an anvil to staple tissue, wherein the anvil comprises a plurality of forming pockets, the surgical staple cartridge comprising a cartridge body, a plurality of staple cavities, and a plurality of staples removably stored within the staple cavities, wherein each staple comprises a base and a staple leg extending from the base, wherein the staple leg comprises a staple tip comprising a piercing portion, wherein the piercing portion is configured to puncture tissue and deform against the forming pocket of the anvil, and wherein the piercing portion is configured to deform into a nested configuration such that the piercing tip is isolated from the tissue.

Example 174

The surgical staple cartridge of Example 173, wherein the nested configuration comprises a hook configuration configured to prevent the surgical staple from pulling through the tissue.

Example 175

The surgical staple cartridge of Examples 173 or 174, wherein the staple tip further comprises a cutout portion configured to receive the piercing portion when the piercing portion is deformed.

Example 176

The surgical staple cartridge of Example 175, wherein the cutout portion is concave.

Example 177

The surgical staple cartridge of Examples 175 or 176, wherein each staple comprises another staple leg extending from the base, wherein the another staple leg comprises another staple tip comprising another cutout portion, and wherein the cutout portion and the another cutout portion face each other.

Example 178

The surgical staple cartridge of Examples 173, 174, 175, 176, or 177, wherein the staple tip further comprises a curling surface configured to ride against a corresponding forming pocket of the anvil.

Example 179

The surgical staple cartridge of Examples 173, 174, 175, 176, 177, or 178, wherein each staple comprises another staple leg, wherein the staple leg and the another staple leg define a first plane, wherein the staple base defines a second plane, and wherein the first plane and the second plane are laterally offset from each other.

Example 180

A surgical staple for use with a surgical stapler including an anvil, wherein the anvil comprises a forming pocket, the surgical staple comprising a staple base portion and a staple leg extending from the staple base portion, wherein the staple leg comprises a staple tip, and wherein the staple tip comprises a piercing tip configured to contact the forming pocket to deform the staple leg and a cutout portion, wherein the piercing tip is configured to curl in toward the cutout portion upon contact with the forming pocket such that the staple tip assumes a non-piercing configuration.

Example 181

The surgical staple of Example 180, wherein the non-piercing configuration comprises a hook configuration configured to prevent the surgical staple from pulling through the tissue.

Example 182

The surgical staple of Examples 180 or 181, wherein the cutout portion is configured to receive the piercing tip when the staple tip is deformed.

Example 183

The surgical staple of Examples 180, 181, or 182, wherein the cutout portion is concave.

Example 184

The surgical staple of Examples 180, 181, 182, or 183, wherein the staple tip further comprises a deformable surface configured to form against the forming pocket of the anvil.

Example 185

A surgical staple cartridge for use with a surgical stapler including an anvil, the surgical staple cartridge comprising a cartridge body, a plurality of staple cavities, and a plurality of flat-formed staples removably stored within the staple cavities, wherein each staple comprises a staple base portion and a staple leg extending from the base portion, wherein the staple leg comprises a staple tip comprising a rounded profile and a piercing portion.

Example 186

The surgical staple cartridge of Example 185, wherein the rounded profile is attained by a cold working process.

Example 187

The surgical staple cartridge of Examples 185 or 186, wherein the staple tip comprises a coined portion.

Example 188

The surgical staple cartridge of Examples 185, 186, or 187, wherein the staple tip further comprises a deformable surface configured to form against a forming pocket of the anvil.

Example 189

The surgical staple cartridge of Examples 185, 186, 187, or 188, wherein the staple tip comprises a first hardness, and wherein the staple leg comprises a second hardness different than the first hardness.

Example 190

The surgical staple cartridge of Example 189, wherein the first hardness is greater than the second hardness.

Example 191

A surgical staple cartridge for use with a surgical stapling instrument, the surgical staple cartridge comprising a cartridge body, a plurality of staple cavities, and a plurality of staples removably stored within the staple cavities, wherein each staple comprises a staple base and a pair of staple legs extending from the staple base, wherein each staple leg comprises a staple tip, wherein the staple legs comprise a first zone comprising a first hardness, and wherein the staple tips comprise a second zone comprising a second hardness which is different than the first hardness.

Example 192

The surgical staple cartridge of Example 191, wherein the second hardness is greater than the first hardness.

Example 193

The surgical staple cartridge of Example 191, wherein the second hardness is less than the first hardness.

Example 194

The surgical staple cartridge of Examples 191, 192, or 193, wherein the staple base comprises a third zone comprising a third hardness different than the first hardness and the second hardness.

Example 195

The surgical staple cartridge of Examples 191, 192, 193, or 194, wherein the staple legs comprise corner portions that are coined to the first hardness.

Example 196

The surgical staple cartridge of Example 195, wherein the corner portions provide a preferential bending plane.

Example 197

The surgical staple cartridge of Examples 191, 192, 193, 194, 195, or 196, wherein the first zone comprises a first ductility, and wherein the second zone comprises a second ductility which is less than the first ductility.

Example 198

A surgical staple cartridge for use with a surgical stapling instrument, the surgical staple cartridge comprising a cartridge body, a plurality of staple cavities, and a plurality of staples removably stored within the staple cavities, wherein each staple comprises a staple base, a pair of staple legs extending from the staple base, a first zone comprising a first hardness, and a second zone comprising a second hardness which is different that the first hardness.

Example 199

The surgical staple cartridge of Example 198, wherein the first zone is hardened using a first method and the second zone is hardened using a second method different than the first method.

Example 200

The surgical staple cartridge of Example 198, wherein only one of the first zone and the second zone is hardened by a hardening method.

Example 201

The surgical staple cartridge of Examples 198, 199, or 200, wherein each staple further comprises bend portions intermediate the staple legs and the staple base, and wherein the bend portions comprise the first zone and the staple base comprises the second zone.

Example 202

The surgical staple cartridge of Examples 198, 199, 200, or 201, wherein the staple base comprises the first zone and the staple legs comprise the second zone.

Example 203

The surgical staple cartridge of Examples 198, 199, 200, 201, or 202, wherein the staple legs are not hardened and the staple base is hardened such that the staple legs are encouraged to assume a formed configuration and such that the staple base is configured to avoid plastic deformation.

Example 204

The surgical staple cartridge of Examples 198, 199, 200, 201, 202, or 203, wherein each staple leg comprises a transition portion extending from the staple base and a vertical leg portion extending from the transition portion, and wherein the staple base comprises the first zone and the vertical leg portion comprises the second zone.

Example 205

A surgical staple configured to be removably stored within a surgical staple cartridge in an unfired configuration, the surgical staple comprising a non-uniform hardness profile, wherein the staple comprises a first zone having a first hardness and a second zone having a second hardness, wherein the first zone is hardened to the first hardness when the staple is in a pre-load configuration, and wherein the second zone is hardened to the second hardness when the staple is in the pre-load configuration.

Example 206

A surgical staple cartridge for use with a surgical stapling instrument, the surgical staple cartridge comprising a cartridge body, a plurality of staple cavities, and a plurality of staples removably stored within the staple cavities, wherein each staple comprises a staple base, wherein the staple base defines a first zone comprising a first hardness, a plurality of bend portions extending from the staple base, wherein the bend portions define a second zone comprising a second hardness, and staple legs extending from the bend portions, wherein each staple leg defines a third zone comprising a third hardness different than the first hardness.

Example 207

The surgical staple cartridge of Example 206, wherein the first hardness is greater than the third hardness.

Example 208

The surgical staple cartridge of Example 206, wherein the first hardness is greater than the second hardness and the third hardness.

Example 209

The surgical staple cartridge of Examples 206, 207, or 208, wherein each staple leg comprises a staple tip defining a fourth zone comprising a fourth hardness which is less than the third hardness.

Example 210

A surgical staple cartridge for use with a surgical stapling instrument, the surgical staple cartridge comprising a sled, a cartridge body, a plurality of staple cavities, and a strip of staples removably stored within the staple cavities, wherein the strip of staples comprises a plurality of staples, a strip, and a plurality of connector portions joining the staples to the strip, wherein the connector portions are configured to release the staples from the strip.

Example 211

The surgical staple cartridge of Example 210, wherein each connector portion comprises a discontinuity configured to encourage the separation of the staples from the strip.

Example 212

The surgical staple cartridge of Example 210, wherein each connector portion comprises a discontinuity configured to encourage the separation of the staple from the strip when the strip of staples is loaded into the cartridge body.

Example 213

The surgical staple cartridge of Examples 210 or 211, wherein the sled is configured to separate the plurality of staples from the strip by breaking the connector portions when the sled is translated through the staple cartridge.

Example 214

The surgical staple cartridge of Examples 210, 211, 212, or 213, wherein each staple comprises a pair of outwardly biasing staple legs configured to engage the cartridge body and hold the strip of staples in the surgical staple cartridge.

Example 215

The surgical staple cartridge of Examples 210, 211, 212, 213, or 214, wherein the cartridge body comprises a bottom, and wherein the strip of staples is configured to be loaded into the bottom of the cartridge body.

Example 216

The surgical staple cartridge of Examples 210, 211, 212, 213, 214, or 215, wherein the plurality of staples are arranged in a first row and a second row, and wherein the strip is joined to the staples in the first row and the second row.

Example 217

The surgical staple cartridge of Examples 210, 211, 212, 213, 214, 215, or 216, wherein the plurality of staples comprises a first group of staples having a first configuration and a second group of staples having a second configuration different than the first configuration.

Example 218

The surgical staple cartridge of Examples 210, 211, 212, 213, 214, 215, 216, or 217, wherein the connector portion comprises a peened portion.

Example 219

The surgical staple cartridge of Examples 210, 211, 212, 213, 214, 215, 216, 217, or 218, wherein the sled comprises striking portions configured to break the connector portions.

Example 220

The surgical staple cartridge of Examples 210, 211, 212, 213, 214, 215, 216, 217, 218, or 219, wherein the staples comprise a chamfered surface configured to engage the sled when the sled is translated through the cartridge body.

Example 221

The surgical staple cartridge of Examples 210, 211, 212, 213, 214, 215, 216, 217, 218, 219, or 220, wherein the strip comprise alignment features configured to engage corresponding alignment features on the cartridge body.

Example 222

A surgical staple cartridge for use with a surgical stapling instrument, the surgical staple cartridge comprising a cartridge body, a plurality of staple cavities, and a strip of staples removably stored within the cartridge body, the strip of staples comprising a plurality of staples, a strip, and a plurality of connector portions joining the staples to the strip, wherein the connector portions are engageable to release the staples from the strip, and wherein the staples, the strip, and the connector portions are metal.

Example 223

The surgical staple cartridge of Example 222, wherein the plurality of staples comprises a first plurality of staples comprising a first crown width and a second plurality of staples comprising a second crown width which is different than the first crown width.

Example 224

The surgical staple cartridge of Examples 222 or 223, wherein the plurality of staples comprises a first group of staples comprising staple legs defining a first height and a second group of staples comprising staple legs defining a second height different than the first height.

Example 225

The surgical staple cartridge of Example 222, wherein the strip of staples comprises a uniform composition.

Example 226

The surgical staple cartridge of Examples 222, 223, 224, or 225, wherein the strip comprises alignment features configured to engage corresponding alignment features on the cartridge body.

Example 227

The surgical staple cartridge of Example 222, 223, 224, 225, or 226, further comprising a second strip of staples comprising a plurality of second staples, a second strip, and a plurality of second connector portions joining the second staples to the second strip, wherein the plurality of staples are arranged in a plurality of rows defining a first row spacing, wherein the plurality of second staples are arranged in a plurality of second rows defining a second row spacing, and wherein the first row spacing and the second row spacing are different.

Example 228

A metal strip of surgical staples configured for use with a surgical staple cartridge, the metal strip of surgical staples comprising a plurality of staples, a ribbon, and a plurality of connector portions joining the staples to the ribbon.

Example 229

The metal strip of surgical staples of Example 228, wherein the connector portions comprise a discontinuity notch.

Example 230

A surgical staple cartridge for use with a circular stapler, the surgical staple cartridge comprising a cartridge body, a plurality of staple cavities defined in the cartridge body, and a plurality of staples removably stored within the staple cavities, the plurality of staples comprising an inner row of staples comprising a quantity of first staples, wherein each first staple comprises a first staple crown defining a first staple crown width, an intermediate row of staples positioned radially outward with respect to the inner row of staples, wherein the intermediate row of staples comprises a quantity of second staples, and wherein each second staple comprises a second staple crown defining a second staple crown width, and an outer row of staples positioned radially outward with respect to the intermediate row of staples, wherein the outer row of staples comprises a quantity of third staples, wherein each third staple comprises a third staple crown defining a third staple crown width, and wherein one of the first staple crown width, the second staple crown width, and the third staple crown width is different than another of the first staple crown width, the second staple crown width, and the third staple crown width.

Example 231

The surgical staple cartridge of Example 230, wherein the inner row of staples defines a plurality of first gaps between the first staples, and wherein the second staples of the intermediate row of staples overlap the first gaps.

Example 232

The surgical staple cartridge of Example 231, wherein the intermediate row of staples defines a plurality of second gaps between the second staples, wherein the second gaps are larger than the first gaps, and wherein the third staples of the outer row of staples overlap the second gaps.

Example 233

The surgical staple cartridge of Examples 231 or 232, wherein the third staples of the outer row of staples also overlap the first gaps.

Example 234

The surgical staple cartridge of Example 230, wherein the inner row of staples defines a plurality of first gaps between the first staples, wherein the intermediate row of staples defines a plurality of second gaps between the second staples, wherein the second staples overlap the first gaps, and wherein the first gaps and the second gaps are at least substantially equal.

Example 235

The surgical staple cartridge of Example 230, wherein the inner row of staples defines a plurality of first gaps between the first staples, wherein the intermediate row of staples defines a plurality of second gaps between the second staples, wherein each first gap defines a first distance, and wherein each second gap defines a second distance which is less than the first distance.

Example 236

The surgical staple cartridge of Examples 230, 231, 232, 233, 234, or 235, wherein the first staple crown width is less than the second staple crown width.

Example 237

The surgical staple cartridge of Examples 230, 231, 232, 233, 234, or 235, wherein the first staple crown width is at least substantially equal to the second staple crown width.

Example 238

The surgical staple cartridge of Examples 230, 231, 232, 233, 234, 235, 236, or 237, wherein the third staple crown width is greater than the first staple crown width and the second staple crown width.

Example 239

A surgical staple cartridge for use with a circular stapler, the surgical staple cartridge comprising a cartridge body, a plurality of staple cavities defined in the cartridge body, and a plurality of staples removably stored within the staple cavities, the plurality of staples comprising an inner row of staples comprising a first quantity of first staples, wherein each first staple comprises a first staple crown defining a first staple crown width, an intermediate row of staples positioned radially outward with respect to the inner row of staples, wherein the intermediate row of staples comprises a second quantity of second staples, and wherein each second staple comprises a second staple crown defining a second staple crown width, and an outer row of staples positioned radially outward with respect to the intermediate row of staples, wherein the outer row of staples comprises a third quantity of third staples, wherein each third staple comprises a third staple crown defining a third staple crown width, wherein one of the first staple crown width, the second staple crown width, and the third staple crown width is different than another of the first staple crown width, the second staple crown width, and the third staple crown width, and wherein one of the first quantity, the second quantity, and the third quantity is different than another of the first quantity, the second quantity, and the third quantity.

Example 240

The surgical staple cartridge of Example 239, wherein the second quantity is less than the first quantity.

Example 241

The surgical staple cartridge of Examples 239 or 240, wherein the second quantity is less than the third quantity.

Example 242

The surgical staple cartridge of Examples 239, 240, or 241, wherein the plurality of staple cavities comprises a plurality of non-uniform cavity extenders.

Example 243

The surgical staple cartridge of Examples 239, 240, 241, or 242, wherein each first staple of the inner row of staples comprises a pair of staple legs extending radially outward from each first staple crown.

Example 244

The surgical staple cartridge of Examples 239, 240, 241, 242, or 243, wherein each second staple of the intermediate row of staples comprises a pair of staple legs extending radially inward from each second staple crown.

Example 245

The surgical staple cartridge of Examples 239, 240, 241, 242, 243, or 244, wherein each third staple of the outer row of staples comprises a pair of staple legs extending radially inward from each third staple crown.

Example 246

A surgical staple cartridge for use with a surgical stapler, the surgical staple cartridge comprising a cartridge body, a plurality of staple cavities defined in the cartridge body, and a plurality of staples removably stored within the staple cavities, the plurality of staples comprising an inner row of staples comprising a first quantity of first staples, wherein each first staple comprises a first staple crown defining a first staple crown width, an intermediate row of staples positioned outward with respect to the inner row of staples, wherein the intermediate row of staples comprises a second quantity of second staples, and wherein each second staple comprises a second staple crown defining a second staple crown width, and an outer row of staples positioned outward with respect to the intermediate row of staples, wherein the outer row of staples comprises a third quantity of third staples, wherein each third staple comprises a third staple crown defining a third staple crown width, and wherein one of the first staple crown width, the second staple crown width, and the third staple crown width is different than another of the first staple crown width, the second staple crown width, and the third staple crown width.

Example 247

The surgical staple cartridge of Example 246, wherein one of the first quantity, the second quantity, and the third quantity is different than another of the first quantity, the second quantity, and the third quantity.

Example 248

The surgical staple cartridge of Example 246, wherein the first quantity and the second quantity are equal.

Example 249

The surgical staple cartridge of Examples 246, 247, or 248, wherein the inner row of staples defines a plurality of first gaps between the first staples, wherein the intermediate row of staples defines a plurality of second gaps between the second staples, wherein each first gap defines a first distance, and wherein each second gap defines a second distance which is less than the first distance.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
U.S. Pat. No. 7,670,334, entitled SURGICAL INSTRUMENT HAVING AN ARTICULATING END EFFECTOR, which issued on Mar. 2, 2010;
U.S. Pat. No. 7,753,245, entitled SURGICAL STAPLING INSTRUMENTS, which issued on Jul. 13, 2010;
U.S. Pat. No. 8,393,514, entitled SELECTIVELY ORIENTABLE IMPLANTABLE FASTENER CARTRIDGE, which issued on Mar. 12, 2013;
U.S. patent application Ser. No. 11/343,803, entitled SURGICAL INSTRUMENT HAVING RECORDING CAPABILITIES; now U.S. Pat. No. 7,845,537;
U.S. patent application Ser. No. 12/031,573, entitled SURGICAL CUTTING AND FASTENING INSTRUMENT HAVING RF ELECTRODES, filed Feb. 14, 2008;
U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
U.S. patent application Ser. No. 12/235,782, entitled MOTOR-DRIVEN SURGICAL CUTTING INSTRUMENT, now U.S. Pat. No. 8,210,411;
U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;
U.S. patent application Ser. No. 12/893,461, entitled STAPLE CARTRIDGE, filed Sep. 29, 2012, now U.S. Pat. No. 8,733,613;
U.S. patent application Ser. No. 13/036,647, entitled SURGICAL STAPLING INSTRUMENT, filed Feb. 28, 2011, now U.S. Pat. No. 8,561,870;
U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;
U.S. patent application Ser. No. 13/800,025, entitled STAPLE CARTRIDGE TISSUE THICKNESS SENSOR SYSTEM, filed on Mar. 13, 2013, now U.S. Patent Application Publication No. 2014/0263551;
U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;
U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and
U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

By way of example only, aspects described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, plasma peroxide, or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A staple cartridge assembly, comprising:
   a cartridge body, comprising:
      a deck;
      a first longitudinal row of staple cavities;
      a second longitudinal row of staple cavities;
   a plurality of first staples, wherein each said first staple is removably stored in said first longitudinal row of staple cavities, and wherein each said first staple comprises a unitary structure including:
      a first metal base including a first metal drive surface, wherein said first metal base is not overmolded with an overmolding material; and
      a first staple leg extending from said first metal base and including a first tip, wherein a first unformed distance is defined between said first metal drive surface and said first tip;
   a plurality of second staples, wherein each said second staple is removably stored in said second longitudinal row of staple cavities, and wherein each said second staple comprises a unitary structure including:
      a second metal base including a second metal drive surface, wherein said second metal base is not overmolded with an overmolding material; and
      a second staple leg extending from said second metal base and including a second tip, wherein a second unformed distance is defined between said second metal drive surface and said second tip which is different than said first unformed distance, wherein said plurality of first staples and said plurality of second staples are stamped from sheet metal, and wherein each said first metal base of said plurality of first staples and each said second metal base of said plurality of second staples comprise substantially planar surfaces; and
   a firing member configured to directly engage said first staples and said second staples and drive said first staples and said second staples along a defined linear path toward said deck.

2. The staple cartridge assembly of claim 1, wherein each said first metal base includes a first tissue supporting surface, wherein a first tissue capture distance is defined between said first tissue supporting surface and said first tip, wherein each said second metal base includes a second tissue supporting surface, wherein a second tissue capture distance is defined between said second tissue supporting surface and said second tip, and wherein said first tissue capture distance is different than said second tissue capture distance.

3. The staple cartridge assembly of claim 1, wherein said deck comprises a first deck height along said first longitudinal row of staple cavities and a second deck height along said second longitudinal row of staple cavities which is different than said first deck height.

4. The staple cartridge assembly of claim 3, wherein said cartridge body further comprises a longitudinal slot configured to receive a cutting member, wherein said first longitudinal row of staple cavities is adjacent said longitudinal slot, wherein said second longitudinal row of staple cavities is adjacent said first longitudinal row of staple cavities, and wherein said second deck height is shorter than said first deck height.

5. The staple cartridge assembly of claim 1, wherein said cartridge body further comprises a longitudinal slot configured to receive a cutting member, wherein said first longitudinal row of staple cavities is adjacent said longitudinal slot, and wherein said second longitudinal row of staple cavities is adjacent said first longitudinal row of staple cavities.

6. The staple cartridge assembly of claim 5, wherein said first unformed distance is shorter than said second unformed distance.

7. The staple cartridge assembly of claim 6, further comprising an anvil configured to deform said first staples and said second staples.

8. The staple cartridge assembly of claim 7, wherein said anvil is configured to deform said first staples to a first deformed height and said second staples to a second deformed height which is different than said first deformed height.

9. The staple cartridge assembly of claim 7, wherein said cartridge body is movable toward said anvil to clamp tissue between said anvil and said deck of said cartridge body.

10. The staple cartridge assembly of claim 7, wherein said anvil is movable toward said cartridge body to clamp tissue between said anvil and said deck of said cartridge body.

11. The staple cartridge assembly of claim 1, further comprising staple cavity extenders extending from said deck.

12. The staple cartridge assembly of claim 11, further comprising an implantable layer positioned over said deck.

13. A staple cartridge assembly, comprising:
a cartridge body, comprising:
a deck;
a first longitudinal row of staple cavities;
a second longitudinal row of staple cavities;
a plurality of first staples, wherein each said first staple is removably stored in said first longitudinal row of staple cavities, and wherein each said first staple comprises a unitary structure including:
a first metal base including a first metal drive surface and a first tissue supporting surface, wherein said first metal base is not overmolded with an overmolding material; and
a first staple leg extending from said first metal base including a first tip, wherein a first tissue capture distance is defined between said first tissue supporting surface and said first tip;
a plurality of second staples, wherein each said second staple is removably stored in said second longitudinal row of staple cavities, and wherein each said second staple comprises a unitary structure including:
a second metal base including a second metal drive surface and a second tissue supporting surface, wherein said second metal base is not overmolded with an overmolding material; and
a second staple leg extending from said second metal base including a second tip, wherein a second tissue capture distance is defined between said second tissue supporting surface and said second tip which is different than said first tissue capture distance, wherein said plurality of first staples and said plurality of second staples are stamped from sheet metal, and wherein each said first metal base of said plurality of first staples and each said second metal base of said plurality of second staples comprise substantially planar features; and
a firing member configured to directly engage said first staples and said second staples and drive said first staples and said second staples along a defined linear path toward said deck.

14. The staple cartridge assembly of claim 13, wherein said deck comprises a first deck height along said first longitudinal row of staple cavities and a second deck height along said second longitudinal row of staple cavities which is different than said first deck height.

15. The staple cartridge assembly of claim 14, wherein said cartridge body further comprises a longitudinal slot configured to receive a cutting member, wherein said first longitudinal row of staple cavities is adjacent said longitudinal slot, wherein said second longitudinal row of staple cavities is adjacent said first longitudinal row of staple cavities, and wherein said second deck height is shorter than said first deck height.

16. The staple cartridge assembly of claim 13, further comprising an anvil configured to deform said first staples and said second staples.

17. The staple cartridge assembly of claim 16, wherein said anvil is configured to deform said first staples to a first deformed height and said second staples to a second deformed height which is different than said first deformed height.

18. The staple cartridge assembly of claim 16, wherein said cartridge body is movable toward said anvil to clamp tissue between said anvil and said deck of said cartridge body.

19. A staple cartridge assembly, comprising:
a cartridge body comprising a first longitudinal row of staple cavities and a second longitudinal row of staple cavities;
a plurality of first staples removably stored in said first longitudinal row of staple cavities, wherein each said first staple is comprised of stamped metal and includes a first base and an integrally-formed metal driver, wherein each first said base is not overmolded with an overmolding material, and wherein said first staples are deployable from said first longitudinal row of staple cavities along a defined linear path;
a plurality of second staples removably stored in said second longitudinal row of staple cavities, wherein each said second staple is comprised of stamped metal and includes a second base and an integrally-formed metal driver, wherein each said second base is not overmolded with an overmolding material, wherein said second staples are deployable from said second longitudinal row of staple cavities along a defined linear path, and wherein each first base of said plurality of first staples and each second base of said plurality of second staples comprise substantially planar surfaces; and
means for forming said first staples to a first deformed height and said second staples to a second deformed height, wherein said first deformed height is different than said second deformed height.

20. A staple cartridge assembly, comprising:
a cartridge body, comprising:
a deck;
a first longitudinal row of staple cavities;
a second longitudinal row of staple cavities;
a plurality of first staples, wherein each said first staple is removably stored in said first longitudinal row of staple cavities, and wherein each said first staple comprises a unitary structure including:
a first metal base including a first metal drive surface, wherein said first metal base is not overmolded with an overmolding material;
a first staple leg extending from said first metal base and including a first tip, wherein a first unformed distance is defined between said first metal drive surface and said first tip; and a second staple leg extending from said first metal base;
a plurality of second staples, wherein each said second staple is removably stored in said second longitudinal row of staple cavities, and wherein each said second staple comprises a unitary structure including:
  a second metal base including a second metal drive surface, wherein said second metal base is not overmolded with an overmoldinq material;
  a third staple leg extending from said second metal base and including a second tip, wherein a second unformed distance is defined between said second metal drive surface and said second tip which is different than said first unformed distance; and
  a fourth staple leg extending from said second metal base; and
a firing member configured to directly engage said first staples and said second staples and drive said first staples and said second staples along a defined linear path toward said deck, wherein said first metal drive surface of a staple of said plurality of first staples defines a first drive plane, wherein said first metal drive surface of said staple of said plurality of first staples moves relative to said cartridge body along said first drive plane, wherein said first staple leg and said second staple leg of said staple of said plurality of first staples defines a first leg plane, wherein said second metal drive surface of a staple of said plurality of second staples defines a second drive plane, wherein said second metal drive surface of said staple of said plurality of second staples moves relative to said cartridge body along said second drive plane, wherein said third staple leg and said fourth staple leg of said staple of said plurality of second staples defines a second leg plane, wherein said first drive plane is laterally offset from said first leg plane, and wherein said second drive plane is laterally offset from said second leg plane.

\* \* \* \* \*